US010434152B2

(12) United States Patent
Wei et al.

(10) Patent No.: US 10,434,152 B2
(45) Date of Patent: Oct. 8, 2019

(54) HER2 ANTIGENIC POLYPEPTIDE COMPOSITIONS, AND METHODS FOR THEIR USE IN TREATMENT AND PREVENTION OF CARCINOMAS

(71) Applicant: Wayne State University, Detroit, MI (US)

(72) Inventors: Wei-Zen Wei, Grosse Pointe Farms, MI (US); Heather Gibson, Madison Heights, MI (US); Richard Jones, Fayetteville, NY (US); Joyce Reyes, Rochester Hills, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 15/120,621

(22) PCT Filed: Feb. 19, 2015

(86) PCT No.: PCT/US2015/016542
§ 371 (c)(1),
(2) Date: Aug. 22, 2016

(87) PCT Pub. No.: WO2015/127027
PCT Pub. Date: Aug. 27, 2015

(65) Prior Publication Data

US 2017/0112909 A1 Apr. 27, 2017

Related U.S. Application Data

(60) Provisional application No. 61/942,071, filed on Feb. 20, 2014.

(51) Int. Cl.

| | |
|---|---|
| ***A61K 39/00*** | (2006.01) |
| ***A61K 39/39*** | (2006.01) |
| ***C07K 14/71*** | (2006.01) |
| ***C07K 16/28*** | (2006.01) |
| ***C07K 16/30*** | (2006.01) |
| ***C07K 16/32*** | (2006.01) |
| ***G01N 33/574*** | (2006.01) |

(52) U.S. Cl.
CPC .......... *A61K 39/0011* (2013.01); *A61K 39/39* (2013.01); *C07K 14/71* (2013.01); *C07K 16/2863* (2013.01); *C07K 16/3015* (2013.01); *C07K 16/32* (2013.01); *G01N 33/574* (2013.01); *A61K 2039/53* (2013.01); *A61K 2039/552* (2013.01); *A61K 2039/55522* (2013.01); *A61K 2039/572* (2013.01); *A61K 2039/575* (2013.01); *G01N 2800/52* (2013.01)

(58) Field of Classification Search
None
See application file for complete search history.

(56) References Cited

PUBLICATIONS

Pupa et al (Cancer research, 2005, 65:1071-1078).*
Santos et al (Dec. 2013, 8:e83673, p. 1-17).*
Chen et al (Clinical Cancer Research, 2000, 6:4381-4388).*

* cited by examiner

*Primary Examiner* — Laura B Goddard
(74) *Attorney, Agent, or Firm* — Kohn & Associates, PLLC

(57) ABSTRACT

Antigenic polypeptides of the growth factor receptor HER2, for breaking the tolerance of a host against self HER2. The antigenic polypeptides include HER2 polypeptides with single amino acid substitutions of lysine for glutamine, arginine for glutamine, or aspartic acid for asparagine. Gene expression constructs, vaccine compositions, and immunization methods including the substituted HER2 polypeptides. Methods for immunizing mammalian subjects with heterologous unsubstituted HER2 antigenic polypeptides, including polypeptides of feline and bear HER2. A diagnostic method of determining whether a mammalian subject is sufficiently immunocompetent to respond to immunotherapies directed at breaking tolerance to self HER2.

6 Claims, 23 Drawing Sheets

Specification includes a Sequence Listing.

Fig. 1

| Gene | STR Repeat | Forward Primer (5' to 3') | Reverse Primer (5' to 3') | Size |
|---|---|---|---|---|
| FCA733 | (GATA)11 | AGGCTCCTCTAGGTTTACTG D (SEQ ID NO: 61) | CCACCGATAAGTGAAATGGTAT GG (SEQ ID NO: 62) | 379 |
| FCA749 | (GATA)10/(GATA) 6 | GGGTGATGTGACCTCTTGTA G (SEQ ID NO: 63) | GGACAGAGGCTCCTTAAACAG (SEQ ID NO: 64) | 568 |
| MACROD 2 | (ACAC)10 | TCTTCCCTCCTCCGTGTATG (SEQ ID NO: 65) | AGACGCTCAATCAACTGAGCC ATC (SEQ ID NO: 66) | 519 |
| mtCR | (CACACGTA)35 | TCTTCTCGCTCCGGGCCCATT TC (SEQ ID NO: 67) | AGTCTGGCGACTCATCTAGG (SEQ ID NO: 68) | 1057 |

Fig. 2

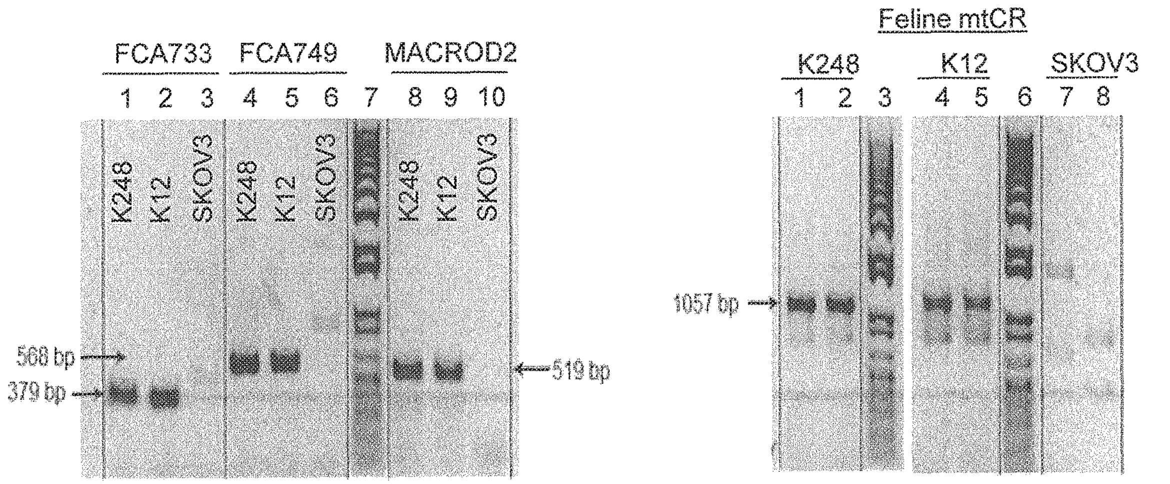

Lipinski MJ, Froenicke L, Baysac KC, Billings NC, Leutenegger CM, Alon M. et al. The ascent of cat breeds: Genetic evaluations of breeds and worldwide random-bred populations. Genomics 2008; 91:12–21.

Menotti-Raymond MA, David VA, Wachter LL, Butler JM, O'Brien SJ. An STR Forensic Typing System for Genetic Individualization of Domestic Cat (*Felis catus*) Samples. J Forensic Sci 2005; 50:1061-9.

OVRS-2
CSU-133
CSU-418
CSU-1646
PBL
HER2
pHER2 Y1248
AKT
pAKT S473
Actin

Sensitivity to Gefitinib
Sensitivity to Lapatinib
% Proliferative activity
120
100
80
60
40
20
0
0.25
1
4
μM
*
K12
K248
SKOV3
MCF7

Fig. 6A

Sequence alignment of HER2 extracellular and transmembrane regions (ECTM) from 5 mammalian species Signal peptide

```
Human    1 MELAALCRWGLLLALLPPGAASTQVCTGTDMKLRLPASPETHLDMLRHLYQGCQVVQGNLELTYLPTNASLSFLQDIQEVQGYVLIAHNQVRQVPLQRLR
Cat      1 MELAAWCRWGLLLALLPSGATGTQVCTGTDMKLRLPASPETHLDMLRHLYQGCQVVQGNLELTYLHANASLSFLQDIQEVQGYVLIAHNQVKQVPLQRLR
Bear     1 MELAAWCRWGLLLALLPSGAAGTQVCTGTDMKLRLPASPETHLDMLRHLYQACQVVQGNLELTYLPANASLSFLQDIQEVQGYVLIAHSQVRQVPLQRLR
Rat      4 MELAAWCRWGFLLALLPPGIAGTQVCTGTDMKLRLPASPETHLDMLRHLYQGCQVVQGNLELTYVPANASLSFLQDIQEVQGYMLIAHNQVKRVPLQRLR
Mouse    1 MELAAWCRWGFLLALLSPGAAGTQVCTGTDMKLRLPASPETHLDMLRHLYQGCQVVQGNLELTYLPANASLSFLQDIQEVQGYMLIAHNRVKHVPLQRLR

Human  101 IVRGTQLFEDNYALAVLDNGDPLNN-TTPVT-GASPGGLRELQLRSLTEILKGGVLIQRNPQLCYQDTILWKDIFHKNNQLALTLIDTNRSRACHPCSPM
Cat    101 IVRGTQLFEDNYALAVLDNGDPLDS-GTPAT-GAALGGLRELQLRSLTEILKGGVLIQRNPQLCHQDTILWKDIFHKNNQLALMLIDTNRSRACQPCSPA
Bear   101 IVRGTQLFEDNYALAVLDNGEPPKG-DTSVA-GATPGGLRELQLRSLTEILKGGVLIQRNPQLCHQDTILWKDIFHKNNQLALTLIDTNRSRACQPCSPA
Rat    104 IVRGTQLFEDKYALAVLDNRDPQDN-VAASTPGRTPEGLRELQLRSLTEILKGGVLIRGNPQLCYQDMVLWKDVFRKNNQLAPVDIDTNRSRACPPCAPA
Mouse  101 IVRGTQLFEDKYALAVLDNRDPLDNVTTAAP-GRTPEGLRELQLRSLTEILKGGVLIRGNPQLCYQDMVLWKDVLRKNNQLAPVDMDTNRSRACPPCAPT

Human  199 CKGSRCWGESSEDCQSLTRTVCAGGCARCKGPLPTDCCHEQCAAGCTGPKHSDCLACLHFNHSGICELHCPALVTYNTDTFESMPNPEGRYTFGASCVTA
Cat    199 CKDSHCWGASSGDCQSLTRTVCAGGCARCKGPQPTDCCHEQCAAGCTGPKHSDCLACLHFNHSGICELHCPALVTYNTDTFESMPNPEGRYTFGASCVTA
Bear   199 CKDPHCWGASSGDCQSLTRTVCAGGCARCKGPKPTDCCHEQCAAGCTGPKHSDCLACLHFNHSGICELHCPALVTYNTDTFESMPNPEGRYTFGASCVTA
Rat    203 CKDNHCWGESPEDCQILTGTICTSGCARCKGRLPTDCCHEQCAAGCTGPKHSDCLACLHFNHSGICELHCPALVTYNTDTFESMHNPEGRYTFGASCVTT
Mouse  200 CKDNHCWGESPEDCQILTGTICTSGCARCKGRLPTDCCHEQCAAGCTGPKHSDCLACLHFNHSGICELHCPALITYNTDTFESMLNPEGRYTFGASCVTT

Human  299 CPYNYLSTDVGSCTLVCPLHNQEVTAEDGTQRCEKCSKPCARVCYGLGMEHLREVRAVTSANIQEFAGCKKIFGSLAFLPESFDGDPASNTAPLQPEQLQ
Cat    299 CPYNYLSTDVGSCTLVCPLNNQEVTAEDGTQRCEKCSKPCARVCYGLGMEHLREARAVTSANIQEFVGCKKIFGSLAFLPESFEGDPASNTAPLQPEQLR
Bear   299 CPYNYLSTDVGSCTLVCPLNNQEVTAEDGTQRCEKCSRPCARVCYGLGMEHLREARAVTSANIQEFAGCKKIFGSLAFLPESFEGDPASNTAPLQPEQLR
Rat    303 CPYNYLSTEVGSCTLVCPPNNQEVTAEDGTQRCEKCSKPCARVCYGLGMEHLRGARAITSDNVQEFDGCKKIFGSLAFLPESFDGDPSSGIAPLRPEQLQ
Mouse  300 CPYNYLSTEVGSCTLVCPPNNQEVTAEDGTQRCEKCSKPCAGVCYGLGMEHLRGARAITSDNIQEFAGCKKIFGSLAFLPESFDGNPSSGVAPLKPEHLQ

Human  399 VFETLEEITGYLYISAWPDSLPDLSVFQNLQVIRGRILHNGAYSLTLQGLGISWLGLRSLRELGSGLALIHHNTHLCFVHTVPWDQLFRNPHQALLHTAN
Cat    399 VFEALEEITGYLYISAWPDSLPNLSVFQNLRVIRGRVLHDGAYSLTLQGLGISWLGLRSLRELGSGLALIHRNSRLCFVHTVPWDQLFRNPHQALLHSAN
Bear   399 VFEALEEITGYLYISAWPDSLPNLSVFQNLRVIRGRVLHDGAYSLTLQGLGISWLGLRSLRELGSGLALIHRNARLCFIHTVPWEQLFRNPHQALLHSAN
Rat    403 VFETLEEITGYLYISAWPDSLRDLSVFQNLRIIRGRILHDGAYSLTLQGLGIHSLGLRSLRELGSGLALIHRNAHLCFVHTVPWDQLFRNPHQALLHSGN
Mouse  400 VFETLEEITGYLYISAWPESFQDLSVFQNLRVIRGRILHDGAYSLTLQGLGIHSLGLRSLRELGSGLALIHRNTHLCFVNTVPWDQLFRNPHQALLHSGN

Human  499 RPEDE-CVGEGLACHQLCARGHCWGPGPTQCVNCSQFLRGQECVEECRVLQGLPREYVNARHCLPCHPECQPQNGSVTCFGPEADQCVACAHYKDPPFCV
Cat    499 RPEDE-CAGEGLACYPLCAHGHCWGPGPTQCVNCSQFLRGQECVEECRVLQGLPREYVKDRFCLPCHPECQPQNGSVTCLGSEADQCVACAHYKDPPFCV
Bear   499 RPEAE-CVGEGLACYPLCAHGHCWGPGPTQCVNCSQFLRGQECVEECRELHGLPREYVKDRYCLPCHPECRPQNGSVTCFGSEADQCVACAHYKDPPSCV
Rat    503 RPEEDLCVSSGLVCNSLCAHGHCWGPGPTQCVNCSHFLRGQECVEECRVWKGLPREYVSDKRCLPCHPECQPQNSSETCFGSEADQCAACAHYKDSSSCV
Mouse  500 RPEEA-CGLEGLVCNSLCARGHCWGPGPTQCVNCSQFLRGQECVEECRVWKGLPREYVRGKHCLPCHPECQPQNSSETCYGSEADQCEACAHYKDSSSCV

Human  598 ARCPSGVKPDLSYMPIWKFPDEEGACQPCPINCTHSCVDLDDKGCPAEQRASPLTSIISAVVGILLVVVLGVVFGILIKRRQQKIRKYTM (SEQ ID NO: 45)
Cat    598 ARCPSGVKPDLSFMPIWKFADEEGTCQPCPINCTHSCADLDEKGCPAEQRASPVTSIIAAVVGILLVVVVGLVLGILIKRRRQKIRKYTM (SEQ ID NO: 39)
Bear   588 ARCPSGVKPDLSFMPIWKFADEEGTCQPCPINCTHSCGDLDERGCPAEQRASPVTSIIAAVVGILLAVVMGLVLGILIKRRRQKIRKYTM (SEQ ID NO: 37)
Rat    603 ARCPSGVKPDLSYMPIWKYPDEEGICQPCPINCTHSCVDLDERGCPAEQRASPVTFIIATVEGVLLFLILVVVVGILIKRRRQKIRKYTM (SEQ ID NO: 49)
Mouse  599 ARCPSGVKPDLSYMPIWKYPDEEGICQPCPINCTHSCVDLDERGCPAEQRASPVTFIIATVVGVLLFLIIVVVIGILIKRRRQKIRKYTM (SEQ ID NO: 47)
```

Transmembrane domain

Full-length HER2 BLAST analysis [%Identities / %Positives / %Gaps]

| | Cat | Human | Mouse | Rat |
|---|---|---|---|---|
| Black Bear | 96 / 98 / 0 | 92 / 95 / 0 | 87 / 91 / 0 | 88 / 91 / 1 |
| Cat | | 93 / 96 / 0 | 88 / 92 / 0 | 88 / 92 / 1 |
| Human | | | 88 / 92 / 0 | 88 / 92 / 0 |
| Mouse | | | | 95 / 97 / 0 |

Fig. 6D

MELAAWCRWGLLLALLPSGATGTQVCTGTDMKLRLPASPETHLDMLRHLYQGCQVVQGNLELTYLHA
NASLSFLQDIQEVQGYVLIAHNQVKQVPLQRLRIVRGTQLFEDNYALAVLDNGDPLKNTTPVTGASPG
GLRELQLRSLTEILKGGVLIQRNPQLCYQDTILWKDIFHKNNQLALTLIDTNRSRACHPCSPMCEGSRCW
GESSEDCQSLTRTVCAGGCARCKGPLPTDCCHEQCAAGCTGPKHSDCLACLHFNHSGICELHCPALVTY
NTDTFESMPNPEGRYTFGASCVTACPYNYLSTDVGSCTLVCPLNNQEVTAEDGTQRCEKCSKPCARVC
YGLGMEHLREARAVTSANIQEFVGCKKIFGSLAFLPGSFEGDPASNTAPLQPEQLRVFEALEEITGYLYISA
WPDSLPNLSVFQNLRVIRGRVLHDGAYSLTLQGLGISWLGLRSLRELGSGLALIHRNSRLCFVHTVPWD
QLFRNPHQALLHSANRPEDECPGEGLACYPLCAHGHCWGPGPTHCVNCSQFLPGQECVEECRVLQG
LPREYVKDRFCLPCHPECQPQNGSVTCLGSEADQCVACAHYKDPPFCVARCSSGVKPDLSFMPIWKFA
DEEGTCQPCPINCTHSCADLDEKGCPAEQRASPVTSIIAAVVGILLVVVVGLVLGILIKRRRQKIRKYTMR
RLLQETELVEPLTPSGAMPNQAQMRILKETELRKVKVLGSGAFGTVYKGIWIPDGENVKIPVAIKVLREN
TSPKANKEILDEAYVMAGVGSPYVSRLLGICLTSTVQLVTQLMPYGCLLDHVREHRGRLGSQDLLNWCV
QIAKGMSYLEDVRLVHRDLAARNVLVKSPNHVKITDFGLARLLDIDETEYHADGGKVPIKWMALESILR
RRFTHQSDVWSYGVTVWELMTFGAKPYDGIPAREIPDLLEKGERLPQPPICTIDVYMIMVKCWMIDSE
CRPRFRELVAEFSRMARDPQRFVVIQNEDLGPASPLDSTFYRSLLEDEDMGDLVDAEEYLVPQQGFFCP
DPAPGAGGTAHRRHRSSSTRSGGGELTLGLEPSEEEPPKSPLAPSEGAGSDVFDGDLGMGAAKGLQSL
SPQDPSPLQRYSEDPTVPLPPETDGYVAPLTCSPQPEYVNQPEVWPKPPSPLEGPLPPSRPAGATLERP
KTLSPKTLSPGKNGVVKDVFAFGGAVENPEYLAPRGRAAPQPHPPPAFSPAFDNLYYWDQDTSERGSP
PSTFEGTPTAENPEYLGLDVPV (SEQ ID NO: 39)

In the mutant form, (SEQ ID NO: 7), the highlighted Q (glutamine) is substituted with a K (lysine). It is amino acid 141, within extracellular sub-domain I of the full-length Her2 protein. The signal peptide is single underlined; the transmembrane domain is double underlined

Fig. 8A

(SEQ ID NO: 69)

```
  1 MELAAWCRWG LLLALLPSGA TGTQVCTGTD MKLRLPASPE THLDMLRHLY QGCQVVQGNL
 61 ELTYLHANAS LSFLQDIQEV QGYVLIAHNQ VKQVPLQRLR IVRGTQLFED NYALAVLDNG
121 DPLDSGTPAT GAALGGLREL QLRSLTEILK GGVLIQRNPQ LCHQDTILWK DIFHKNNQLA
181 LMLIDTNRSR ACQPCSPACK DSHCWGASSG DCQSLTRTVC AGGCARCKGP QPTDCCHEQC
241 AAGCTGPKHS DCLACLHFNH SGICELHCPA LVTYNTDTFE SMPNPEGRYT FGASCVTACP
301 YNYLSTDVGS CTLVCPLNNQ EVTAEDGTQR CEKCSKPCAR VCYGLGMEHL REARAVTSAN
361 IQEFVGCKKI FGSLAFLPES FEGDPASNTA PLQPEQLRVF EALEEITGYL YISAWPDSLP
421 NLSVFQNLRV IRGRVLHDGA YSLTLQGLGI SWLGLRSLRE LGSGLALIHR NSRLCFVHTV
481 PWDQLFRNPH QALLHSANRP EDECAGEGLA CYPLCAHGHC WGPGPTQCVN CSQFLRGQEC
541 VEECRVLQGL PREYVKDRFC LPCHPECQPQ NGSVTCLGSE ADQCVACAHY KDPPFCVARC
601 PSGVKPDLSF MPIWKFADEE GTCQPCPINC THSCADLDEK GCPAEQRASP VTSepkscdk
661 thtcppcpap ellggpsvfl fppkpkdtlm isrtpevtcv vvdvshedpe vkfnwyvdgv
721 evhnaktkpr eeqynstyrv vsvltvlhqd wlngkeykck vsnkalpapi ektiskakgq
781 prepqvytlp psrdeltknq vsltclvkgf ypsdiavewe sngqpennyk ttppvldsdg
841 sfflyskltv dksrwqqgnv fscsvmheal hnhytqksls lspgk
```

Fig. 8B

Recombinant Feline HER2-Ig Fusion Protein

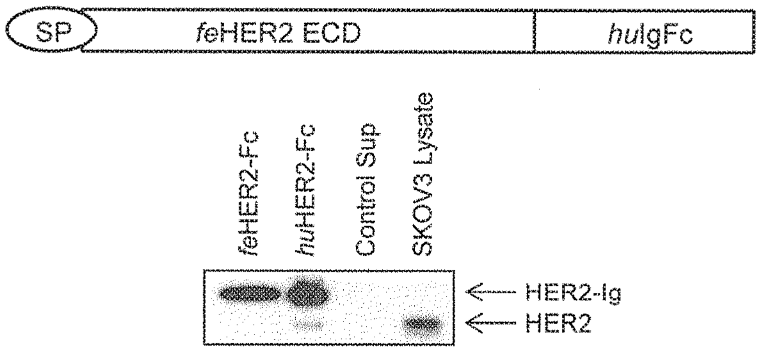

Cat vaccination with pE2Neu
3T3/huHER2
α-huHER2 IgG Titer
3T3/neu
α-neu IgG Titer
3T3/feHER2
α-feHER2 IgG Titer
Vaccine: Pre 1 2 3 4
Cat 1
Cat 2
Cat 3

3T3/huHER2
3T3/feHER2-K
3T3/feHER2
IgG titer
pfeHER2 (n=3)
pfeHER2-K (n=3)
pbearHER2 (n=3)
pE2Neu (n=3)
pE2Neu + pfeHER2-K (n=3)

Feline serum binding to 3T3

Fig. 12A

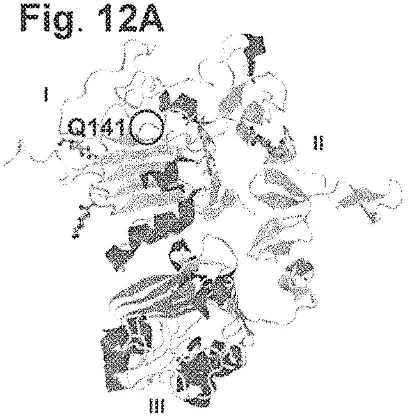

Fig. 12B

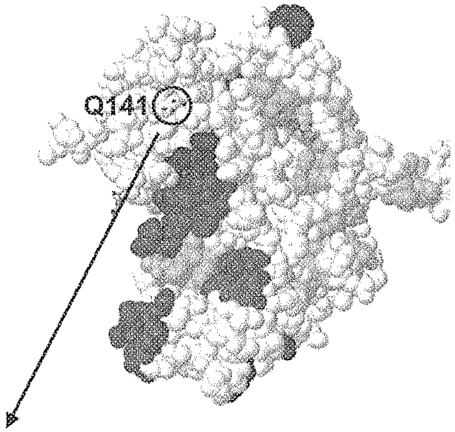

Fig. 12C

*hu*HER2 Q141 region: surface electrostatic model

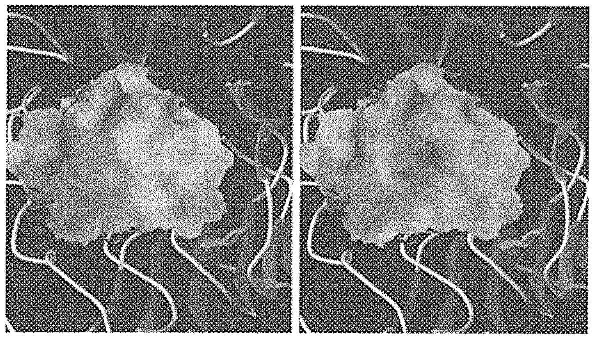

wt Q141 region 141K variant

*Visualized with SYBYL-X 2.1.1*
*Tripos (Certara LP)*

Q141K substitution in feline HER2. The 3D structure of HER2 domains I-III (a.a. 23-510; RCSB 2A91) are shown in (A) cartoon and (B) space-filling models as derived with Jmol molecule viewer. The position of Q141 in domain I is circled in both models; moieties of Q141 are indicated. (C) The predicted effect on the region of the Q141K substitution is portrayed by an electrostatic surface model (using SYBYL-X 2.1.1 software; Tripos), where the electropositive side chain of K is indicated by red (positive charge), while Q is shown in blue (neutral). The model is based on RCSB 2A91 (Garrett 2003). Q141K is on the outer surface of domain I in a 15 aa region without conventionally assigned secondary structure, but overlays residues 111-118 which form a highly-structured beta strand in the ligand binding region in ERBB homologs 1, 3 and 4.

Garrett TP, McKern NM, Lou M, Elleman TC, Adams TE, Lovrecz GO, Kofler M, Jorissen RN, Nice EC, Burgess AW, et al. The crystal structure of a truncated ErbB2 ectodomain reveals an active conformation, poised to interact with other ErbB receptors. *Molecular cell.* 2003;11(2):495-505.

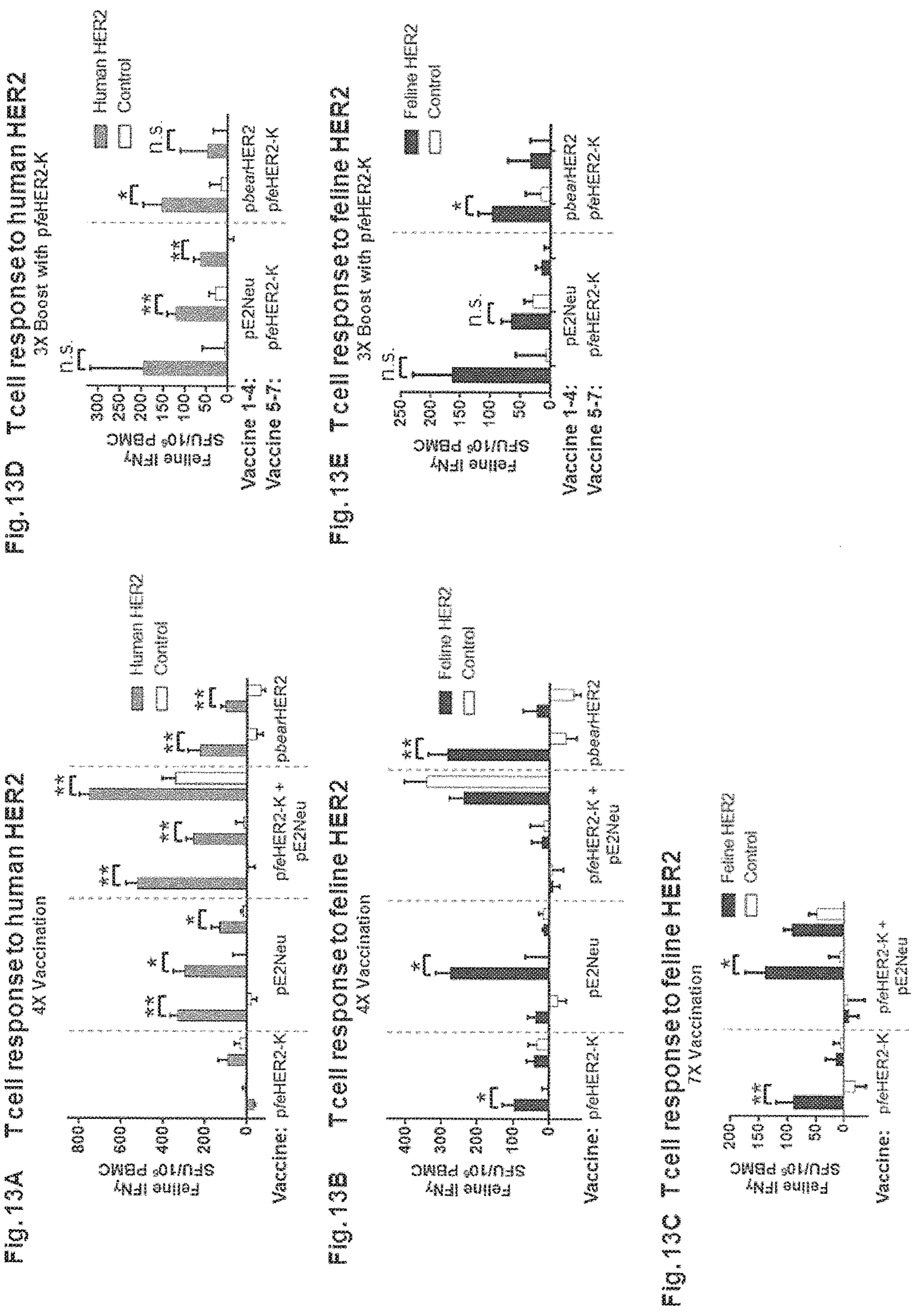
Fig. 13A T cell response to human HER2
4X Vaccination
Feline IFNγ SFU/10⁶ PBMC
Vaccine: pfeHER2-K pE2Neu pfeHER2-K + pE2Neu pbearHER2
Human HER2
Control
Fig. 13B T cell response to feline HER2
4X Vaccination
Feline IFNγ SFU/10⁶ PBMC
Vaccine: pfeHER2-K pE2Neu pfeHER2-K + pE2Neu pbearHER2
Feline HER2
Control
Fig. 13C T cell response to feline HER2
7X Vaccination
Feline IFNγ SFU/10⁶ PBMC
Vaccine: pfeHER2-K pfeHER2-K + pE2Neu
Feline HER2
Control
Fig. 13D T cell response to human HER2
3X Boost with pfeHER2-K
Feline IFNγ SFU/10⁶ PBMC
Vaccine 1-4: pE2Neu pbearHER2
Vaccine 5-7: pfeHER2-K pfeHER2-K
Human HER2
Control
n.s.
Fig. 13E T cell response to feline HER2
3X Boost with pfeHER2-K
Feline IFNγ SFU/10⁶ PBMC
Vaccine 1-4: pE2Neu pbearHER2
Vaccine 5-7: pfeHER2-K pfeHER2-K
Feline HER2
Control
n.s.

FIG. 14B Human HER2 ECD-TM
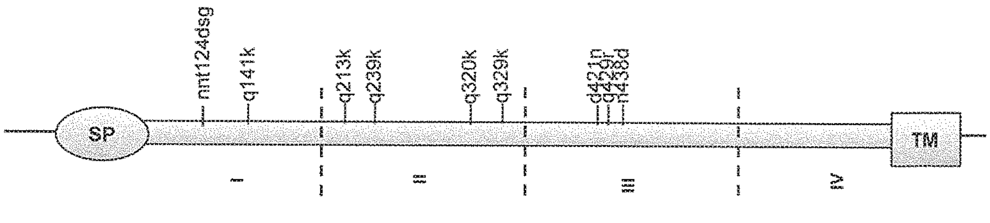
Fig. 14A Transient Transfection of 3T3 cells with human HER2 ECTM mutants
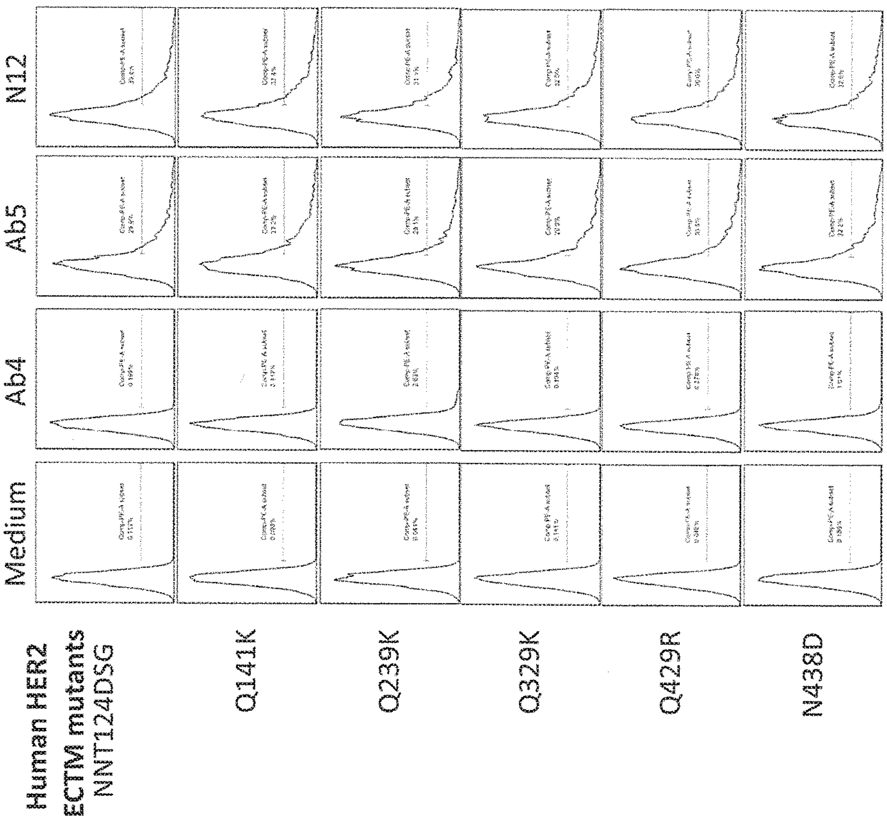

Fig. 15 Humoral Immune Response to Human Her2 ECTM Mutants in WT BALB/c Mice
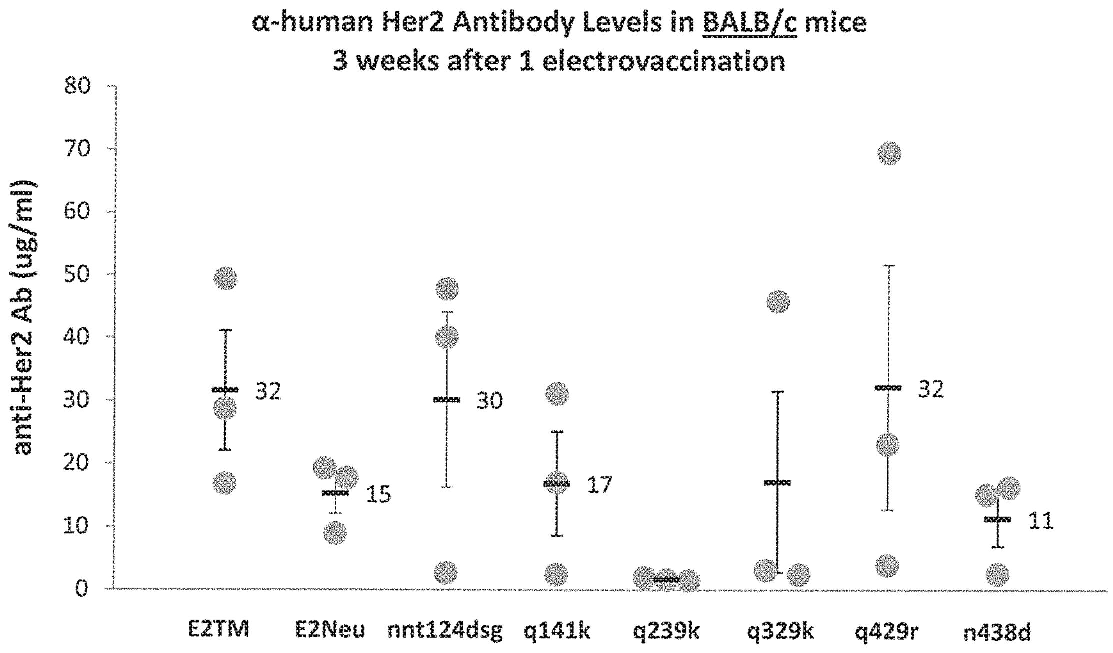

Binding of HER2Tg mouse immune serum to
3T3 EKB cells transfected to express WT human HER2

Fig. 17 HER2 and EGFR expression in human cancer cell lines
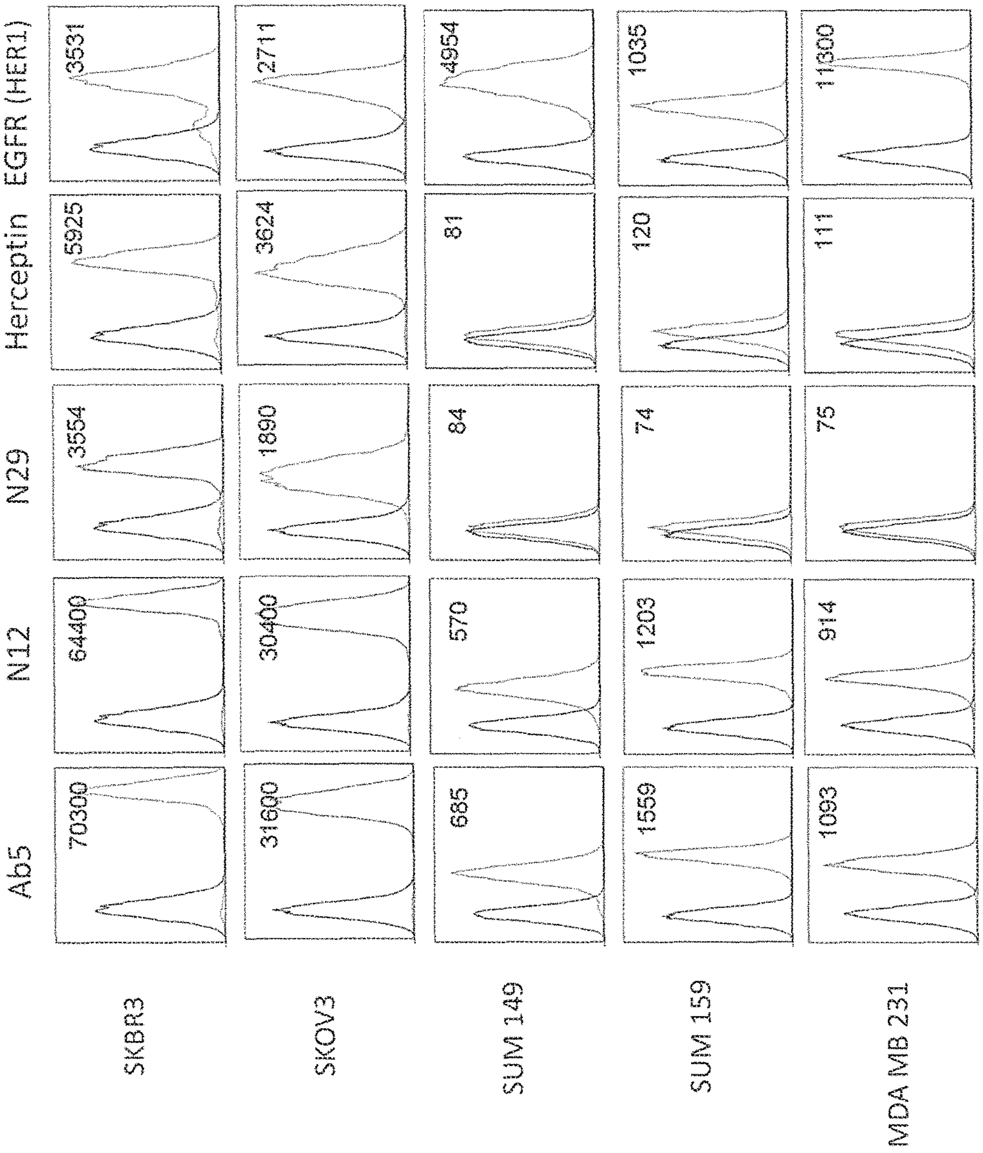

Fig. 18 Anti-Human Her2 Ab induced in BALB Her2Tg mice by HER2 mutant DNA 2 weeks after 2X electrovaccinations
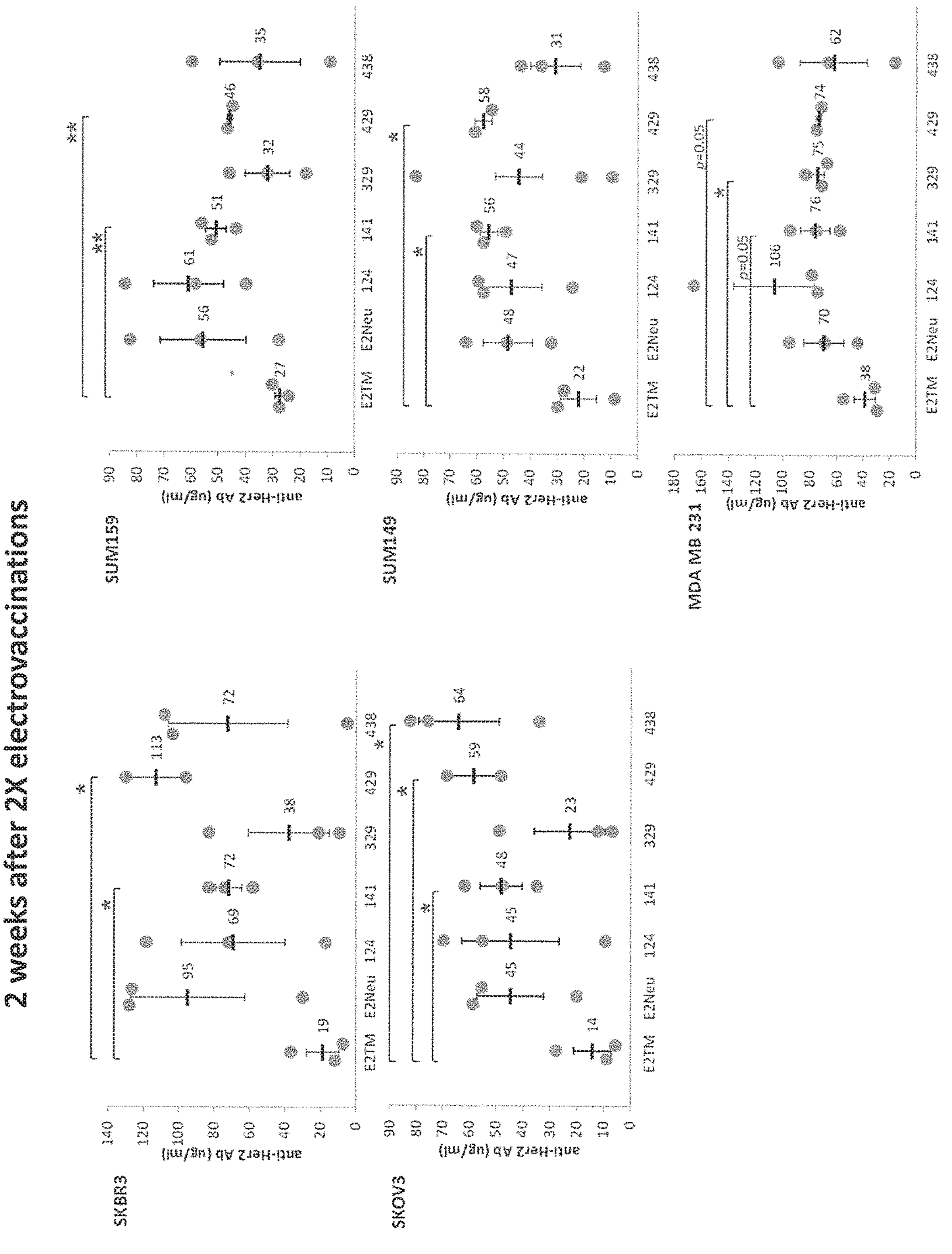

Fig. 19 Humoral Immune Response to Human Her2 ECTM Mutants in BALB Her2Tg Mice
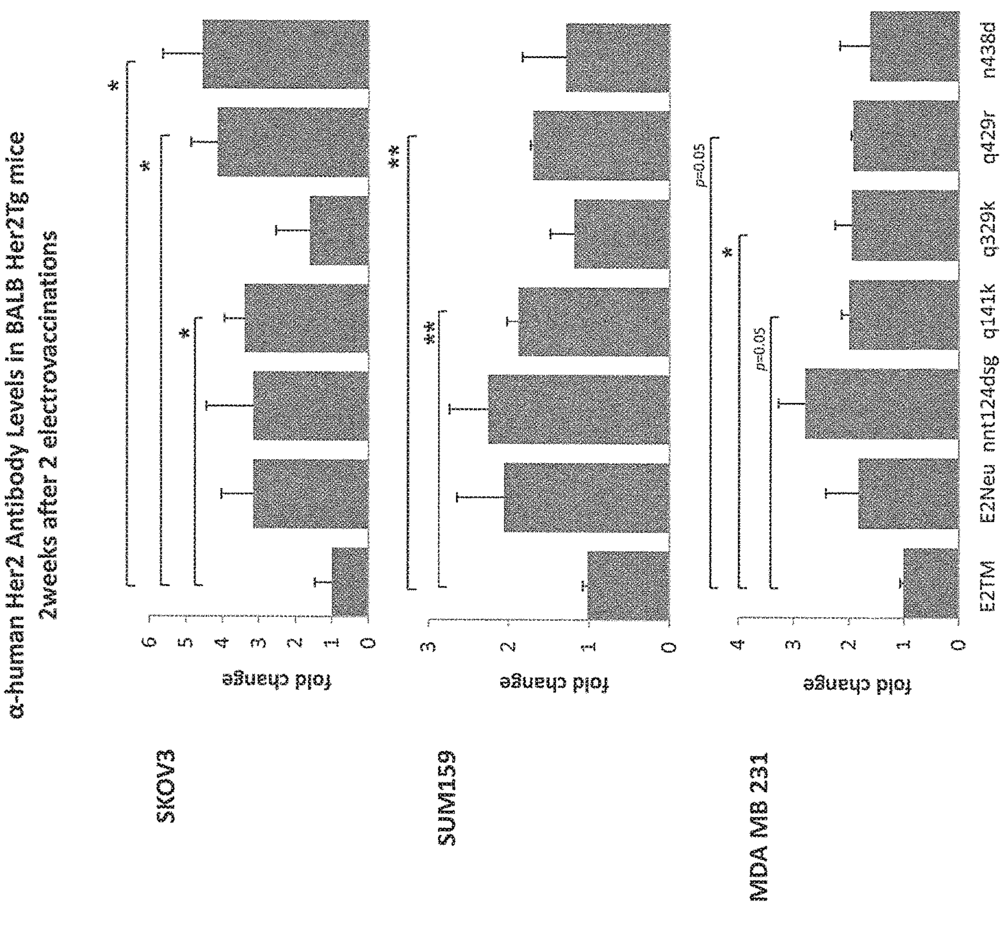

SEQUENCE LISTING

```
<160> NUMBER OF SEQ ID NOS: 118

<210> SEQ ID NO 1
<211> LENGTH: 665
<212> TYPE: PRT
<213> ORGANISM: Felis catus

<400> SEQUENCE: 1

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu His Ala Asn Ala Ser
        35                  40                  45

Leu Ser Phe Leu Gln Asp Ile Gln Glu Val Gln Gly Tyr Val Leu Ile
    50                  55                  60

Ala His Asn Gln Val Lys Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asp Ser Gly Thr Pro Ala Thr Gly Ala Ala Leu
            100                 105                 110

Gly Gly Leu Arg Glu Leu Lys Leu Arg Ser Leu Thr Glu Ile Leu Lys
        115                 120                 125

Gly Gly Val Leu Ile Gln Arg Asn Pro Gln Leu Cys His Gln Asp Thr
    130                 135                 140

Ile Leu Trp Lys Asp Ile Phe His Lys Asn Asn Gln Leu Ala Leu Met
145                 150                 155                 160

Leu Ile Asp Thr Asn Arg Ser Arg Ala Cys Gln Pro Cys Ser Pro Ala
                165                 170                 175

Cys Lys Asp Ser His Cys Trp Gly Ala Ser Ser Gly Asp Cys Gln Ser
            180                 185                 190

Leu Thr Arg Thr Val Cys Ala Gly Gly Cys Ala Arg Cys Lys Gly Pro
        195                 200                 205

Gln Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255
```

```
Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu Asn Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Ala Arg Ala Val Thr Ser
                325                 330                 335

Ala Asn Ile Gln Glu Phe Val Gly Cys Lys Lys Ile Phe Gly Ser Leu
            340                 345                 350

Ala Phe Leu Pro Glu Ser Phe Glu Gly Asp Pro Ala Ser Asn Thr Ala
        355                 360                 365

Pro Leu Gln Pro Glu Gln Leu Arg Val Phe Glu Ala Leu Glu Glu Ile
    370                 375                 380

Thr Gly Tyr Leu Tyr Ile Ser Ala Trp Pro Asp Ser Leu Pro Asn Leu
385                 390                 395                 400

Ser Val Phe Gln Asn Leu Arg Val Ile Arg Gly Arg Val Leu His Asp
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His Arg
        435                 440                 445

Asn Ser Arg Leu Cys Phe Val His Thr Val Pro Trp Asp Gln Leu Phe
    450                 455                 460

Arg Asn Pro His Gln Ala Leu Leu His Ser Ala Asn Arg Pro Glu Asp
465                 470                 475                 480

Glu Cys Ala Gly Glu Gly Leu Ala Cys Tyr Pro Leu Cys Ala His Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Lys Asp Arg Phe Cys Leu Pro Cys His Pro Glu
    530                 535                 540

Cys Gln Pro Gln Asn Gly Ser Val Thr Cys Leu Gly Ser Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Phe Met Pro Ile Trp
            580                 585                 590

Lys Phe Ala Asp Glu Glu Gly Thr Cys Gln Pro Cys Pro Ile Asn Cys
        595                 600                 605

Thr His Ser Cys Ala Asp Leu Asp Glu Lys Gly Cys Pro Ala Glu Gln
    610                 615                 620

Arg Ala Ser Pro Val Thr Ser Ile Ile Ala Ala Val Val Gly Ile Leu
625                 630                 635                 640

Leu Val Val Val Val Gly Leu Val Leu Gly Ile Leu Ile Lys Arg Arg
                645                 650                 655

Arg Gln Lys Ile Arg Lys Tyr Thr Met
            660                 665
```

-continued

<210> SEQ ID NO 2
<211> LENGTH: 665
<212> TYPE: PRT
<213> ORGANISM: Ursus americanus

<400> SEQUENCE: 2

Thr Gln Val Cys Thr Gly Thr Asp Met Lys Leu Arg Leu Pro Ala Ser
1 5 10 15

Pro Glu Thr His Leu Asp Met Leu Arg His Leu Tyr Gln Ala Cys Gln
20 25 30

Val Val Gln Gly Asn Leu Glu Leu Thr Tyr Leu Pro Ala Asn Ala Ser
35 40 45

Leu Ser Phe Leu Gln Asp Ile Gln Glu Val Gln Gly Tyr Val Leu Ile
50 55 60

Ala His Ser Gln Val Arg Gln Val Pro Leu Gln Arg Leu Arg Ile Val
65 70 75 80

Arg Gly Thr Gln Leu Phe Glu Asp Asn Tyr Ala Leu Ala Val Leu Asp
85 90 95

Asn Gly Glu Pro Pro Lys Gly Asp Thr Ser Val Ala Gly Ala Thr Pro
100 105 110

Gly Gly Leu Arg Glu Leu Lys Leu Arg Ser Leu Thr Glu Ile Leu Lys
115 120 125

Gly Gly Val Leu Ile Gln Arg Asn Pro Gln Leu Cys His Gln Asp Thr
130 135 140

Ile Leu Trp Lys Asp Ile Phe His Lys Asn Asn Gln Leu Ala Leu Thr
145 150 155 160

Leu Ile Asp Thr Asn Arg Ser Arg Ala Cys Gln Pro Cys Ser Pro Ala
165 170 175

Cys Lys Asp Pro His Cys Trp Gly Ala Ser Ser Gly Asp Cys Gln Ser
180 185 190

Leu Thr Arg Thr Val Cys Ala Gly Gly Cys Ala Arg Cys Lys Gly Pro
195 200 205

Lys Pro Thr Asp Cys Cys His Glu Gln Cys Ala Ala Gly Cys Thr Gly
210 215 220

Pro Lys His Ser Asp Cys Leu Ala Cys Leu His Phe Asn His Ser Gly
225 230 235 240

Ile Cys Glu Leu His Cys Pro Ala Leu Val Thr Tyr Asn Thr Asp Thr
245 250 255

Phe Glu Ser Met Pro Asn Pro Glu Gly Arg Tyr Thr Phe Gly Ala Ser
260 265 270

Cys Val Thr Ala Cys Pro Tyr Asn Tyr Leu Ser Thr Asp Val Gly Ser
275 280 285

Cys Thr Leu Val Cys Pro Leu Asn Asn Gln Glu Val Thr Ala Glu Asp
290 295 300

Gly Thr Gln Arg Cys Glu Lys Cys Ser Arg Pro Cys Ala Arg Val Cys
305 310 315 320

Tyr Gly Leu Gly Met Glu His Leu Arg Glu Ala Arg Ala Val Thr Ser
325 330 335

Ala Asn Ile Gln Glu Phe Ala Gly Cys Lys Lys Ile Phe Gly Ser Leu
340 345 350

Ala Phe Leu Pro Glu Ser Phe Glu Gly Asp Pro Ala Ser Asn Thr Ala
355 360 365

Pro Leu Gln Pro Glu Gln Leu Arg Val Phe Glu Ala Leu Glu Glu Ile
370 375 380

-continued

Thr Gly Tyr Leu Tyr Ile Ser Ala Trp Pro Asp Ser Leu Pro Asn Leu
385 390 395 400

Ser Val Phe Gln Asn Leu Arg Val Ile Arg Gly Arg Val Leu His Asp
405 410 415

Gly Ala Tyr Ser Leu Thr Leu Gln Gly Leu Gly Ile Ser Trp Leu Gly
420 425 430

Leu Arg Ser Leu Arg Glu Leu Gly Ser Gly Leu Ala Leu Ile His Arg
435 440 445

Asn Ala Arg Leu Cys Phe Ile His Thr Val Pro Trp Glu Gln Leu Phe
450 455 460

Arg Asn Pro His Gln Ala Leu Leu His Ser Ala Asn Arg Pro Glu Ala
465 470 475 480

Glu Cys Val Gly Glu Gly Leu Ala Cys Tyr Pro Leu Cys Ala His Gly
485 490 495

His Cys Trp Gly Pro Gly Pro Thr Gln Cys Val Asn Cys Ser Gln Phe
500 505 510

Leu Arg Gly Gln Glu Cys Val Glu Glu Cys Arg Glu Leu His Gly Leu
515 520 525

Pro Arg Glu Tyr Val Lys Asp Arg Tyr Cys Leu Pro Cys His Pro Glu
530 535 540

Cys Arg Pro Gln Asn Gly Ser Val Thr Cys Phe Gly Ser Glu Ala Asp
545 550 555 560

Gln Cys Val Ala Cys Ala His Tyr Lys Asp Pro Pro Ser Cys Val Ala
565 570 575

Arg Cys Pro Ser Gly Val Lys Pro Asp Leu Ser Phe Met Pro Ile Trp
580 585 590

Lys Phe Ala Asp Glu Glu Gly Thr Cys Gln Pro Cys Pro Ile Asn Cys
595 600 605

Thr His Ser Cys Gly Asp Leu Asp Glu Arg Gly Cys Pro Ala Glu Gln
610 615 620

Arg Ala Ser Pro Val Thr Ser Ile Ile Ala Ala Val Val Gly Ile Leu
625 630 635 640

Leu Ala Val Val Met Gly Leu Val Leu Gly Ile Leu Ile Lys Arg Arg
645 650 655

Arg Gln Lys Ile Arg Lys Tyr Thr Met
660 665

<210> SEQ ID NO 3
<211> LENGTH: 665
<212> TYPE: PRT
<213> ORGANISM: Homo sapiens

<400> SEQUENCE: 3

Thr Gln Val Cys Thr Gly Thr Asp Met Lys Leu Arg Leu Pro Ala Ser
1 5 10 15

Pro Glu Thr His Leu Asp Met Leu Arg His Leu Tyr Gln Gly Cys Gln
20 25 30

Val Val Gln Gly Asn Leu Glu Leu Thr Tyr Leu Pro Thr Asn Ala Ser
35 40 45

Leu Ser Phe Leu Gln Asp Ile Gln Glu Val Gln Gly Tyr Val Leu Ile
50 55 60

Ala His Asn Gln Val Arg Gln Val Pro Leu Gln Arg Leu Arg Ile Val
65 70 75 80

Arg Gly Thr Gln Leu Phe Glu Asp Asn Tyr Ala Leu Ala Val Leu Asp

```
                85                  90                  95

Asn Gly Asp Pro Leu Asn Asn Thr Thr Pro Val Thr Gly Ala Ser Pro
            100                 105                 110

Gly Gly Leu Arg Glu Leu Lys Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510
```

```
Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met
            660                 665


<210> SEQ ID NO 4
<211> LENGTH: 666
<212> TYPE: PRT
<213> ORGANISM: Mus musculus

<400> SEQUENCE: 4

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Ala Asn Ala Ser
        35                  40                  45

Leu Ser Phe Leu Gln Asp Ile Gln Glu Val Gln Gly Tyr Met Leu Ile
    50                  55                  60

Ala His Asn Arg Val Lys His Val Pro Leu Gln Arg Leu Arg Ile Val
65                  70                  75                  80

Arg Gly Thr Gln Leu Phe Glu Asp Lys Tyr Ala Leu Ala Val Leu Asp
                85                  90                  95

Asn Arg Asp Pro Leu Asp Asn Val Thr Thr Ala Ala Pro Gly Arg Thr
            100                 105                 110

Pro Glu Gly Leu Arg Glu Leu Lys Leu Arg Ser Leu Thr Glu Ile Leu
        115                 120                 125

Lys Gly Gly Val Leu Ile Arg Gly Asn Pro Gln Leu Cys Tyr Gln Asp
    130                 135                 140

Met Val Leu Trp Lys Asp Val Leu Arg Lys Asn Asn Gln Leu Ala Pro
145                 150                 155                 160

Val Asp Met Asp Thr Asn Arg Ser Arg Ala Cys Pro Pro Cys Ala Pro
                165                 170                 175

Thr Cys Lys Asp Asn His Cys Trp Gly Glu Ser Pro Glu Asp Cys Gln
            180                 185                 190

Ile Leu Thr Gly Thr Ile Cys Thr Ser Gly Cys Ala Arg Cys Lys Gly
        195                 200                 205

Arg Leu Pro Thr Asp Cys Cys His Glu Gln Cys Ala Ala Gly Cys Thr
```

-continued

```
    210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Ile Thr Tyr Asn Thr Asp
                245                 250                 255

Thr Phe Glu Ser Met Leu Asn Pro Glu Gly Arg Tyr Thr Phe Gly Ala
            260                 265                 270

Ser Cys Val Thr Thr Cys Pro Tyr Asn Tyr Leu Ser Thr Glu Val Gly
        275                 280                 285

Ser Cys Thr Leu Val Cys Pro Pro Asn Asn Gln Glu Val Thr Ala Glu
    290                 295                 300

Asp Gly Thr Gln Arg Cys Glu Lys Cys Ser Lys Pro Cys Ala Gly Val
305                 310                 315                 320

Cys Tyr Gly Leu Gly Met Glu His Leu Arg Gly Ala Arg Ala Ile Thr
                325                 330                 335

Ser Asp Asn Ile Gln Glu Phe Ala Gly Cys Lys Lys Ile Phe Gly Ser
            340                 345                 350

Leu Ala Phe Leu Pro Glu Ser Phe Asp Gly Asn Pro Ser Ser Gly Val
        355                 360                 365

Ala Pro Leu Lys Pro Glu His Leu Gln Val Phe Glu Thr Leu Glu Glu
    370                 375                 380

Ile Thr Gly Tyr Leu Tyr Ile Ser Ala Trp Pro Glu Ser Phe Gln Asp
385                 390                 395                 400

Leu Ser Val Phe Gln Asn Leu Arg Val Ile Arg Gly Arg Ile Leu His
                405                 410                 415

Asp Gly Ala Tyr Ser Leu Thr Leu Gln Gly Leu Gly Ile His Ser Leu
            420                 425                 430

Gly Leu Arg Ser Leu Arg Glu Leu Gly Ser Gly Leu Ala Leu Ile His
        435                 440                 445

Arg Asn Thr His Leu Cys Phe Val Asn Thr Val Pro Trp Asp Gln Leu
    450                 455                 460

Phe Arg Asn Pro His Gln Ala Leu Leu His Ser Gly Asn Arg Pro Glu
465                 470                 475                 480

Glu Ala Cys Gly Leu Glu Gly Leu Val Cys Asn Ser Leu Cys Ala Arg
                485                 490                 495

Gly His Cys Trp Gly Pro Gly Pro Thr Gln Cys Val Asn Cys Ser Gln
            500                 505                 510

Phe Leu Arg Gly Gln Glu Cys Val Glu Glu Cys Arg Val Trp Lys Gly
        515                 520                 525

Leu Pro Arg Glu Tyr Val Arg Gly Lys His Cys Leu Pro Cys His Pro
    530                 535                 540

Glu Cys Gln Pro Gln Asn Ser Ser Glu Thr Cys Tyr Gly Ser Glu Ala
545                 550                 555                 560

Asp Gln Cys Glu Ala Cys Ala His Tyr Lys Asp Ser Ser Ser Cys Val
                565                 570                 575

Ala Arg Cys Pro Ser Gly Val Lys Pro Asp Leu Ser Tyr Met Pro Ile
            580                 585                 590

Trp Lys Tyr Pro Asp Glu Glu Gly Ile Cys Gln Pro Cys Pro Ile Asn
        595                 600                 605

Cys Thr His Ser Cys Val Asp Leu Asp Glu Arg Gly Cys Pro Ala Glu
    610                 615                 620

Gln Arg Ala Ser Pro Val Thr Phe Ile Ile Ala Thr Val Val Gly Val
625                 630                 635                 640
```

```
Leu Leu Phe Leu Ile Ile Val Val Val Ile Gly Ile Leu Ile Lys Arg
                645                 650                 655

Arg Arg Gln Lys Ile Arg Lys Tyr Thr Met
            660                 665


<210> SEQ ID NO 5
<211> LENGTH: 666
<212> TYPE: PRT
<213> ORGANISM: Rattus norvegicus

<400> SEQUENCE: 5

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Val Pro Ala Asn Ala Ser
        35                  40                  45

Leu Ser Phe Leu Gln Asp Ile Gln Glu Val Gln Gly Tyr Met Leu Ile
    50                  55                  60

Ala His Asn Gln Val Lys Arg Val Pro Leu Gln Arg Leu Arg Ile Val
65                  70                  75                  80

Arg Gly Thr Gln Leu Phe Glu Asp Lys Tyr Ala Leu Ala Val Leu Asp
                85                  90                  95

Asn Arg Asp Pro Gln Asp Asn Val Ala Ala Ser Thr Pro Gly Arg Thr
            100                 105                 110

Pro Glu Gly Leu Arg Glu Leu Lys Leu Arg Ser Leu Thr Glu Ile Leu
        115                 120                 125

Lys Gly Gly Val Leu Ile Arg Gly Asn Pro Gln Leu Cys Tyr Gln Asp
    130                 135                 140

Met Val Leu Trp Lys Asp Val Phe Arg Lys Asn Asn Gln Leu Ala Pro
145                 150                 155                 160

Val Asp Ile Asp Thr Asn Arg Ser Arg Ala Cys Pro Pro Cys Ala Pro
                165                 170                 175

Ala Cys Lys Asp Asn His Cys Trp Gly Glu Ser Pro Glu Asp Cys Gln
            180                 185                 190

Ile Leu Thr Gly Thr Ile Cys Thr Ser Gly Cys Ala Arg Cys Lys Gly
        195                 200                 205

Arg Leu Pro Thr Asp Cys Cys His Glu Gln Cys Ala Ala Gly Cys Thr
    210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Val Thr Tyr Asn Thr Asp
                245                 250                 255

Thr Phe Glu Ser Met His Asn Pro Glu Gly Arg Tyr Thr Phe Gly Ala
            260                 265                 270

Ser Cys Val Thr Thr Cys Pro Tyr Asn Tyr Leu Ser Thr Glu Val Gly
        275                 280                 285

Ser Cys Thr Leu Val Cys Pro Pro Asn Asn Gln Glu Val Thr Ala Glu
    290                 295                 300

Asp Gly Thr Gln Arg Cys Glu Lys Cys Ser Lys Pro Cys Ala Arg Val
305                 310                 315                 320

Cys Tyr Gly Leu Gly Met Glu His Leu Arg Gly Ala Arg Ala Ile Thr
                325                 330                 335

Ser Asp Asn Val Gln Glu Phe Asp Gly Cys Lys Lys Ile Phe Gly Ser
```

```
            340                 345                 350

Leu Ala Phe Leu Pro Glu Ser Phe Asp Gly Asp Pro Ser Ser Gly Ile
        355                 360                 365

Ala Pro Leu Arg Pro Glu Gln Leu Gln Val Phe Glu Thr Leu Glu Glu
    370                 375                 380

Ile Thr Gly Tyr Leu Tyr Ile Ser Ala Trp Pro Asp Ser Leu Arg Asp
385                 390                 395                 400

Leu Ser Val Phe Gln Asn Leu Arg Ile Ile Arg Gly Arg Ile Leu His
                405                 410                 415

Asp Gly Ala Tyr Ser Leu Thr Leu Gln Gly Leu Gly Ile His Ser Leu
            420                 425                 430

Gly Leu Arg Ser Leu Arg Glu Leu Gly Ser Gly Leu Ala Leu Ile His
        435                 440                 445

Arg Asn Ala His Leu Cys Phe Val His Thr Val Pro Trp Asp Gln Leu
    450                 455                 460

Phe Arg Asn Pro His Gln Ala Leu Leu His Ser Gly Asn Arg Pro Glu
465                 470                 475                 480

Glu Asp Cys Gly Leu Glu Gly Leu Val Cys Asn Ser Leu Cys Ala His
                485                 490                 495

Gly His Cys Trp Gly Pro Gly Pro Thr Gln Cys Val Asn Cys Ser His
            500                 505                 510

Phe Leu Arg Gly Gln Glu Cys Val Glu Glu Cys Arg Val Trp Lys Gly
        515                 520                 525

Leu Pro Arg Glu Tyr Val Ser Asp Lys Arg Cys Leu Pro Cys His Pro
    530                 535                 540

Glu Cys Gln Pro Gln Asn Ser Ser Glu Thr Cys Phe Gly Ser Glu Ala
545                 550                 555                 560

Asp Gln Cys Ala Ala Cys Ala His Tyr Lys Asp Ser Ser Ser Cys Val
                565                 570                 575

Ala Arg Cys Pro Ser Gly Val Lys Pro Asp Leu Ser Tyr Met Pro Ile
            580                 585                 590

Trp Lys Tyr Pro Asp Glu Glu Gly Ile Cys Gln Pro Cys Pro Ile Asn
        595                 600                 605

Cys Thr His Ser Cys Val Asp Leu Asp Glu Arg Gly Cys Pro Ala Glu
    610                 615                 620

Gln Arg Ala Ser Pro Val Thr Phe Ile Ile Ala Thr Val Val Gly Val
625                 630                 635                 640

Leu Leu Phe Leu Ile Leu Val Val Val Val Gly Ile Leu Ile Lys Arg
                645                 650                 655

Arg Arg Gln Lys Ile Arg Lys Tyr Thr Met
            660                 665


<210> SEQ ID NO 6
<211> LENGTH: 668
<212> TYPE: PRT
<213> ORGANISM: Artificial Sequence
<220> FEATURE:
<223> OTHER INFORMATION: Chimeric human-rat E2Neu (HER2)

<400> SEQUENCE: 6

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
```

```
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Lys Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Glu Phe Ala Pro Leu Arg Pro Glu Gln Leu Gln Val Phe Glu Thr Leu
    370                 375                 380

Glu Glu Ile Thr Gly Tyr Leu Tyr Ile Ser Ala Trp Pro Asp Ser Leu
385                 390                 395                 400

Arg Asp Leu Ser Val Phe Gln Asn Leu Arg Ile Ile Arg Gly Arg Ile
                405                 410                 415

Leu His Asp Gly Ala Tyr Ser Leu Thr Leu Gln Gly Leu Gly Ile His
            420                 425                 430

Ser Leu Gly Leu Arg Ser Leu Arg Glu Leu Gly Ser Gly Leu Ala Leu
        435                 440                 445

Ile His Arg Asn Ala His Leu Cys Phe Val His Thr Val Pro Trp Asp
    450                 455                 460
```

```
Gln Leu Phe Arg Asn Pro His Gln Ala Leu Leu His Ser Gly Asn Arg
465                 470                 475                 480

Pro Glu Glu Asp Cys Gly Leu Glu Gly Leu Val Cys Asn Ser Leu Cys
                485                 490                 495

Ala His Gly His Cys Trp Gly Pro Gly Pro Thr Gln Cys Val Asn Cys
            500                 505                 510

Ser His Phe Leu Arg Gly Gln Glu Cys Val Glu Glu Cys Arg Val Trp
        515                 520                 525

Lys Gly Leu Pro Arg Glu Tyr Val Ser Asp Lys Arg Cys Leu Pro Cys
    530                 535                 540

His Pro Glu Cys Gln Pro Gln Asn Ser Ser Glu Thr Cys Phe Gly Ser
545                 550                 555                 560

Glu Ala Asp Gln Cys Ala Ala Cys Ala His Tyr Lys Asp Ser Ser Ser
                565                 570                 575

Cys Val Ala Arg Cys Pro Ser Gly Val Lys Pro Asp Leu Ser Tyr Met
            580                 585                 590

Pro Ile Trp Lys Tyr Pro Asp Glu Glu Gly Ile Cys Gln Pro Cys Pro
        595                 600                 605

Ile Asn Cys Thr His Ser Cys Val Asp Leu Asp Glu Arg Gly Cys Pro
    610                 615                 620

Ala Glu Gln Arg Ala Ser Pro Val Thr Phe Ile Ile Ala Thr Val Val
625                 630                 635                 640

Gly Val Leu Leu Phe Leu Ile Leu Val Val Val Val Gly Ile Leu Ile
                645                 650                 655

Lys Arg Arg Arg Gln Lys Ile Arg Lys Tyr Thr Met
            660                 665


<210> SEQ ID NO 7
<211> LENGTH: 687
<212> TYPE: PRT
<213> ORGANISM: Felis catus

<400> SEQUENCE: 7

Met Glu Leu Ala Ala Trp Cys Arg Trp Gly Leu Leu Leu Ala Leu Leu
1               5                   10                  15

Pro Ser Gly Ala Thr Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu His Ala Asn Ala Ser Leu Ser Phe Leu Gln Asp Ile Gln Glu Val
65                  70                  75                  80

Gln Gly Tyr Val Leu Ile Ala His Asn Gln Val Lys Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asp Ser Gly Thr Pro
        115                 120                 125

Ala Thr Gly Ala Ala Leu Gly Gly Leu Arg Glu Leu Lys Leu Arg Ser
    130                 135                 140

Leu Thr Glu Ile Leu Lys Gly Gly Val Leu Ile Gln Arg Asn Pro Gln
145                 150                 155                 160

Leu Cys His Gln Asp Thr Ile Leu Trp Lys Asp Ile Phe His Lys Asn
```

-continued

```
                165                 170                 175

Asn Gln Leu Ala Leu Met Leu Ile Asp Thr Asn Arg Ser Arg Ala Cys
            180                 185                 190

Gln Pro Cys Ser Pro Ala Cys Lys Asp Ser His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Gln Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Ala Arg Ala Val Thr Ser Ala Asn Ile Gln Glu Phe Val Gly Cys Lys
        355                 360                 365

Lys Ile Phe Gly Ser Leu Ala Phe Leu Pro Glu Ser Phe Glu Gly Asp
    370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ser Arg Leu Cys Phe Val His Thr Val
465                 470                 475                 480

Pro Trp Asp Gln Leu Phe Arg Asn Pro His Gln Ala Leu Leu His Ser
                485                 490                 495

Ala Asn Arg Pro Glu Asp Glu Cys Ala Gly Glu Gly Leu Ala Cys Tyr
            500                 505                 510

Pro Leu Cys Ala His Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Lys Asp Arg Phe Cys
545                 550                 555                 560

Leu Pro Cys His Pro Glu Cys Gln Pro Gln Asn Gly Ser Val Thr Cys
                565                 570                 575

Leu Gly Ser Glu Ala Asp Gln Cys Val Ala Cys Ala His Tyr Lys Asp
            580                 585                 590
```

```
Pro Pro Phe Cys Val Ala Arg Cys Pro Ser Gly Val Lys Pro Asp Leu
        595                 600                 605

Ser Phe Met Pro Ile Trp Lys Phe Ala Asp Glu Glu Gly Thr Cys Gln
    610                 615                 620

Pro Cys Pro Ile Asn Cys Thr His Ser Cys Ala Asp Leu Asp Glu Lys
625                 630                 635                 640

Gly Cys Pro Ala Glu Gln Arg Ala Ser Pro Val Thr Ser Ile Ile Ala
                645                 650                 655

Ala Val Val Gly Ile Leu Leu Val Val Val Val Gly Leu Val Leu Gly
            660                 665                 670

Ile Leu Ile Lys Arg Arg Arg Gln Lys Ile Arg Lys Tyr Thr Met
        675                 680                 685


<210> SEQ ID NO 8
<211> LENGTH: 687
<212> TYPE: PRT
<213> ORGANISM: Ursus americanus

<400> SEQUENCE: 8

Met Glu Leu Ala Ala Trp Cys Arg Trp Gly Leu Leu Leu Ala Leu Leu
1               5                   10                  15

Pro Ser Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Ala Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80

Gln Gly Tyr Val Leu Ile Ala His Ser Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Glu Pro Pro Lys Gly Asp Thr Ser
        115                 120                 125

Val Ala Gly Ala Thr Pro Gly Gly Leu Arg Glu Leu Lys Leu Arg Ser
    130                 135                 140

Leu Thr Glu Ile Leu Lys Gly Gly Val Leu Ile Gln Arg Asn Pro Gln
145                 150                 155                 160

Leu Cys His Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

Gln Pro Cys Ser Pro Ala Cys Lys Asp Pro His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Lys Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
```

```
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Arg
                325                 330                 335

Pro Cys Ala Arg Val Cys Tyr Gly Leu Gly Met Glu His Leu Arg Glu
            340                 345                 350

Ala Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Glu Gly Asp
    370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ala Arg Leu Cys Phe Ile His Thr Val
465                 470                 475                 480

Pro Trp Glu Gln Leu Phe Arg Asn Pro His Gln Ala Leu Leu His Ser
                485                 490                 495

Ala Asn Arg Pro Glu Ala Glu Cys Val Gly Glu Gly Leu Ala Cys Tyr
            500                 505                 510

Pro Leu Cys Ala His Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Glu Leu His Gly Leu Pro Arg Glu Tyr Val Lys Asp Arg Tyr Cys
545                 550                 555                 560

Leu Pro Cys His Pro Glu Cys Arg Pro Gln Asn Gly Ser Val Thr Cys
                565                 570                 575

Phe Gly Ser Glu Ala Asp Gln Cys Val Ala Cys Ala His Tyr Lys Asp
            580                 585                 590

Pro Pro Ser Cys Val Ala Arg Cys Pro Ser Gly Val Lys Pro Asp Leu
        595                 600                 605

Ser Phe Met Pro Ile Trp Lys Phe Ala Asp Glu Glu Gly Thr Cys Gln
    610                 615                 620

Pro Cys Pro Ile Asn Cys Thr His Ser Cys Gly Asp Leu Asp Glu Arg
625                 630                 635                 640

Gly Cys Pro Ala Glu Gln Arg Ala Ser Pro Val Thr Ser Ile Ile Ala
                645                 650                 655

Ala Val Val Gly Ile Leu Leu Ala Val Val Met Gly Leu Val Leu Gly
            660                 665                 670

Ile Leu Ile Lys Arg Arg Arg Gln Lys Ile Arg Lys Tyr Thr Met
        675                 680                 685
```

<210> SEQ ID NO 9

<211> LENGTH: 687
<212> TYPE: PRT
<213> ORGANISM: Homo sapiens

<400> SEQUENCE: 9

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Lys Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
```

-continued

```
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 10
<211> LENGTH: 688
<212> TYPE: PRT
<213> ORGANISM: Mus Musculus

<400> SEQUENCE: 10

Met Glu Leu Ala Ala Trp Cys Arg Trp Gly Phe Leu Leu Ala Leu Leu
1               5                   10                  15

Ser Pro Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80
```

-continued

```
Gln Gly Tyr Met Leu Ile Ala His Asn Arg Val Lys His Val Pro Leu
                85                  90                  95

Gln Arg Leu Arg Ile Val Arg Gly Thr Gln Leu Phe Glu Asp Lys Tyr
            100                 105                 110

Ala Leu Ala Val Leu Asp Asn Arg Asp Pro Leu Asp Asn Val Thr Thr
        115                 120                 125

Ala Ala Pro Gly Arg Thr Pro Glu Gly Leu Arg Glu Leu Lys Leu Arg
    130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
            180                 185                 190

Cys Pro Pro Cys Ala Pro Thr Cys Lys Asp Asn His Cys Trp Gly Glu
        195                 200                 205

Ser Pro Glu Asp Cys Gln Ile Leu Thr Gly Thr Ile Cys Thr Ser Gly
    210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
            260                 265                 270

Ile Thr Tyr Asn Thr Asp Thr Phe Glu Ser Met Leu Asn Pro Glu Gly
        275                 280                 285

Arg Tyr Thr Phe Gly Ala Ser Cys Val Thr Thr Cys Pro Tyr Asn Tyr
    290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
            340                 345                 350

Gly Ala Arg Ala Ile Thr Ser Asp Asn Ile Gln Glu Phe Ala Gly Cys
        355                 360                 365

Lys Lys Ile Phe Gly Ser Leu Ala Phe Leu Pro Glu Ser Phe Asp Gly
    370                 375                 380

Asn Pro Ser Ser Gly Val Ala Pro Leu Lys Pro Glu His Leu Gln Val
385                 390                 395                 400

Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
            420                 425                 430

Arg Gly Arg Ile Leu His Asp Gly Ala Tyr Ser Leu Thr Leu Gln Gly
        435                 440                 445

Leu Gly Ile His Ser Leu Gly Leu Arg Ser Leu Arg Glu Leu Gly Ser
    450                 455                 460

Gly Leu Ala Leu Ile His Arg Asn Thr His Leu Cys Phe Val Asn Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Ala Cys Gly Leu Glu Gly Leu Val Cys
```

```
            500                 505                 510

Asn Ser Leu Cys Ala Arg Gly His Cys Trp Gly Pro Gly Pro Thr Gln
        515                 520                 525

Cys Val Asn Cys Ser Gln Phe Leu Arg Gly Gln Glu Cys Val Glu Glu
    530                 535                 540

Cys Arg Val Trp Lys Gly Leu Pro Arg Glu Tyr Val Arg Gly Lys His
545                 550                 555                 560

Cys Leu Pro Cys His Pro Glu Cys Gln Pro Gln Asn Ser Ser Glu Thr
                565                 570                 575

Cys Tyr Gly Ser Glu Ala Asp Gln Cys Glu Ala Cys Ala His Tyr Lys
            580                 585                 590

Asp Ser Ser Ser Cys Val Ala Arg Cys Pro Ser Gly Val Lys Pro Asp
        595                 600                 605

Leu Ser Tyr Met Pro Ile Trp Lys Tyr Pro Asp Glu Glu Gly Ile Cys
    610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Phe Ile Ile
                645                 650                 655

Ala Thr Val Val Gly Val Leu Leu Phe Leu Ile Ile Val Val Val Ile
            660                 665                 670

Gly Ile Leu Ile Lys Arg Arg Arg Gln Lys Ile Arg Lys Tyr Thr Met
        675                 680                 685


<210> SEQ ID NO 11
<211> LENGTH: 691
<212> TYPE: PRT
<213> ORGANISM: Rattus norvegicus

<400> SEQUENCE: 11

Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
            20                  25                  30

Asp Met Lys Leu Arg Leu Pro Ala Ser Pro Glu Thr His Leu Asp Met
        35                  40                  45

Leu Arg His Leu Tyr Gln Gly Cys Gln Val Val Gln Gly Asn Leu Glu
    50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
        115                 120                 125

Val Ala Ala Ser Thr Pro Gly Arg Thr Pro Glu Gly Leu Arg Glu Leu
    130                 135                 140

Lys Leu Arg Ser Leu Thr Glu Ile Leu Lys Gly Gly Val Leu Ile Arg
145                 150                 155                 160

Gly Asn Pro Gln Leu Cys Tyr Gln Asp Met Val Leu Trp Lys Asp Val
                165                 170                 175

Phe Arg Lys Asn Asn Gln Leu Ala Pro Val Asp Ile Asp Thr Asn Arg
            180                 185                 190
```

-continued

```
Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
                245                 250                 255

Leu Ala Cys Leu His Phe Asn His Ser Gly Ile Cys Glu Leu His Cys
            260                 265                 270

Pro Ala Leu Val Thr Tyr Asn Thr Asp Thr Phe Glu Ser Met His Asn
        275                 280                 285

Pro Glu Gly Arg Tyr Thr Phe Gly Ala Ser Cys Val Thr Thr Cys Pro
    290                 295                 300

Tyr Asn Tyr Leu Ser Thr Glu Val Gly Ser Cys Thr Leu Val Cys Pro
305                 310                 315                 320

Pro Asn Asn Gln Glu Val Thr Ala Glu Asp Gly Thr Gln Arg Cys Glu
                325                 330                 335

Lys Cys Ser Lys Pro Cys Ala Arg Val Cys Tyr Gly Leu Gly Met Glu
            340                 345                 350

His Leu Arg Gly Ala Arg Ala Ile Thr Ser Asp Asn Val Gln Glu Phe
        355                 360                 365

Asp Gly Cys Lys Lys Ile Phe Gly Ser Leu Ala Phe Leu Pro Glu Ser
    370                 375                 380

Phe Asp Gly Asp Pro Ser Ser Gly Ile Ala Pro Leu Arg Pro Glu Gln
385                 390                 395                 400

Leu Gln Val Phe Glu Thr Leu Glu Glu Ile Thr Gly Tyr Leu Tyr Ile
                405                 410                 415

Ser Ala Trp Pro Asp Ser Leu Arg Asp Leu Ser Val Phe Gln Asn Leu
            420                 425                 430

Arg Ile Ile Arg Gly Arg Ile Leu His Asp Gly Ala Tyr Ser Leu Thr
        435                 440                 445

Leu Gln Gly Leu Gly Ile His Ser Leu Gly Leu Arg Ser Leu Arg Glu
    450                 455                 460

Leu Gly Ser Gly Leu Ala Leu Ile His Arg Asn Ala His Leu Cys Phe
465                 470                 475                 480

Val His Thr Val Pro Trp Asp Gln Leu Phe Arg Asn Pro His Gln Ala
                485                 490                 495

Leu Leu His Ser Gly Asn Arg Pro Glu Glu Asp Cys Gly Leu Glu Gly
            500                 505                 510

Leu Val Cys Asn Ser Leu Cys Ala His Gly His Cys Trp Gly Pro Gly
        515                 520                 525

Pro Thr Gln Cys Val Asn Cys Ser His Phe Leu Arg Gly Gln Glu Cys
    530                 535                 540

Val Glu Glu Cys Arg Val Trp Lys Gly Leu Pro Arg Glu Tyr Val Ser
545                 550                 555                 560

Asp Lys Arg Cys Leu Pro Cys His Pro Glu Cys Gln Pro Gln Asn Ser
                565                 570                 575

Ser Glu Thr Cys Phe Gly Ser Glu Ala Asp Gln Cys Ala Ala Cys Ala
            580                 585                 590

His Tyr Lys Asp Ser Ser Ser Cys Val Ala Arg Cys Pro Ser Gly Val
        595                 600                 605

Lys Pro Asp Leu Ser Tyr Met Pro Ile Trp Lys Tyr Pro Asp Glu Glu
```

```
    610                 615                 620

Gly Ile Cys Gln Pro Cys Pro Ile Asn Cys Thr His Ser Cys Val Asp
625                 630                 635                 640

Leu Asp Glu Arg Gly Cys Pro Ala Glu Gln Arg Ala Ser Pro Val Thr
                645                 650                 655

Phe Ile Ile Ala Thr Val Val Gly Val Leu Leu Phe Leu Ile Leu Val
            660                 665                 670

Val Val Val Gly Ile Leu Ile Lys Arg Arg Arg Gln Lys Ile Arg Lys
        675                 680                 685

Tyr Thr Met
    690


<210> SEQ ID NO 12
<211> LENGTH: 690
<212> TYPE: PRT
<213> ORGANISM: Artificial Sequence
<220> FEATURE:
<223> OTHER INFORMATION: Chimeric human-rat E2Neu (HER2)

<400> SEQUENCE: 12

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Lys Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
```

-continued

```
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Glu Phe Ala Pro Leu Arg Pro Glu Gln Leu
385                 390                 395                 400

Gln Val Phe Glu Thr Leu Glu Glu Ile Thr Gly Tyr Leu Tyr Ile Ser
                405                 410                 415

Ala Trp Pro Asp Ser Leu Arg Asp Leu Ser Val Phe Gln Asn Leu Arg
            420                 425                 430

Ile Ile Arg Gly Arg Ile Leu His Asp Gly Ala Tyr Ser Leu Thr Leu
        435                 440                 445

Gln Gly Leu Gly Ile His Ser Leu Gly Leu Arg Ser Leu Arg Glu Leu
    450                 455                 460

Gly Ser Gly Leu Ala Leu Ile His Arg Asn Ala His Leu Cys Phe Val
465                 470                 475                 480

His Thr Val Pro Trp Asp Gln Leu Phe Arg Asn Pro His Gln Ala Leu
                485                 490                 495

Leu His Ser Gly Asn Arg Pro Glu Glu Asp Cys Gly Leu Glu Gly Leu
            500                 505                 510

Val Cys Asn Ser Leu Cys Ala His Gly His Cys Trp Gly Pro Gly Pro
        515                 520                 525

Thr Gln Cys Val Asn Cys Ser His Phe Leu Arg Gly Gln Glu Cys Val
    530                 535                 540

Glu Glu Cys Arg Val Trp Lys Gly Leu Pro Arg Glu Tyr Val Ser Asp
545                 550                 555                 560

Lys Arg Cys Leu Pro Cys His Pro Glu Cys Gln Pro Gln Asn Ser Ser
                565                 570                 575

Glu Thr Cys Phe Gly Ser Glu Ala Asp Gln Cys Ala Ala Cys Ala His
            580                 585                 590

Tyr Lys Asp Ser Ser Ser Cys Val Ala Arg Cys Pro Ser Gly Val Lys
        595                 600                 605

Pro Asp Leu Ser Tyr Met Pro Ile Trp Lys Tyr Pro Asp Glu Glu Gly
    610                 615                 620

Ile Cys Gln Pro Cys Pro Ile Asn Cys Thr His Ser Cys Val Asp Leu
625                 630                 635                 640

Asp Glu Arg Gly Cys Pro Ala Glu Gln Arg Ala Ser Pro Val Thr Phe
                645                 650                 655

Ile Ile Ala Thr Val Val Gly Val Leu Leu Phe Leu Ile Leu Val Val
            660                 665                 670

Val Val Gly Ile Leu Ile Lys Arg Arg Arg Gln Lys Ile Arg Lys Tyr
        675                 680                 685

Thr Met
    690
```

<210> SEQ ID NO 13
<211> LENGTH: 1995
<212> TYPE: DNA
<213> ORGANISM: Felis catus

<400> SEQUENCE: 13
acccaagtgt gcaccggcac agacatgaag ctgcggctcc cagccagtcc cgagacccac 60
ctggacatgc tccgccacct ctaccagggc tgtcaagtgg tacagggcaa cctggagctc 120
acctacctgc atgccaatgc cagcctctcc ttcctgcagg atatccagga ggtgcaaggc 180
tatgtgctca ttgcccacaa ccaagtgaaa caggtcccac tgcagaggct acgaatcgtg 240
cgaggcaccc agctctttga ggacaactac gccctggccg tgctggacaa cggagaccca 300
ctggacagtg gcacccctgc tacaggggct gccctaggag ggctgcggga gctgaagctc 360
cgaagcctca cagagatcct gaagggaggg gtcctcattc agcggaaccc gcagctctgc 420
caccaggaca cgattctgtg gaaggacatc ttccacaaga acaaccagct ggccctcatg 480
ctgatagaca ccaaccgctc tcgggcctgc caaccctgtt ctccagcttg taaagactcc 540
cactgctggg gagcaagttc cggggactgt cagagcttga ctcgaactgt ctgtgctggc 600
ggctgtgccc gctgcaaggg cccgcagccc accgactgct gccacgagca atgtgctgct 660
ggctgcacgg gccccaagca ttctgactgc ctggcctgcc tccacttcaa ccacagtggc 720
atctgtgagc tgcactgccc agccctggtc acctacaaca cggacacctt cgaatccatg 780
cccaaccctg agggccgtta taccttcggt gccagctgtg tgactgcctg tccctacaac 840
tacctgtcta cggacgtggg atcctgcacc ctggtctgtc ccctgaacaa ccaagaggtg 900
acagctgagg atggaacaca gcggtgtgag aaatgcagca agccctgtgc ccgagtgtgc 960
tacggcctag gcatggagca cctgcgggag gcgagggcag tcaccagtgc caacatccaa 1020
gaatttgtcg gctgcaagaa gatctttggg agcctggcgt ttctgccaga gagctttgag 1080
ggggacccag cctccaacac tgcccccctg cagcctgagc agctcagagt gtttgaggct 1140
ctggaggaga ttacaggtta cctgtacatc tcagcgtggc cagacagctt gcctaacctc 1200
agtgtcttcc agaacctcag agtgatccgg ggccgagttc tgcatgacgg tgcttactcg 1260
ctgacccttc aagggctggg catcagctgg ctggggctgc gctcgctgcg ggagctgggc 1320
agtgggctgg ccctcatcca ccgcaactcc cgcctctgct tcgtacacac ggtgccctgg 1380
gaccagctct tccggaaccc ccaccaggcc ctgctccaca gcgccaaccg gccagaggac 1440
gagtgcgcgg gtgagggcct ggcctgctat ccgctgtgtg cccacgggca ctgctggggt 1500
ccgggaccca cccagtgtgt caactgcagc cagttccttc ggggccagga gtgcgtggag 1560
gaatgccgag tattgcaggg gcttccccgg gagtatgtga aggataggtt ctgtctgcca 1620
tgccacccgg agtgtcagcc ccagaatggc tcagtgacct gcttgggctc ggaagctgac 1680
cagtgtgtgg cctgtgccca ctacaaggac cctcctttct gtgtggctcg ctgccccagt 1740
ggggtgaaac ctgacctctc cttcatgccc atctggaagt tcgcagatga ggagggcacg 1800
tgccagccat gccccatcaa ctgcacccac tcctgtgcgg acctggacga gaagggctgc 1860
cccgccgagc agagagccag ccctgtgacg tccatcattg ctgctgtggt gggcattctg 1920
ctggtcgtgg ttgtggggct ggtccttggc atcctaatca agcgaaggcg gcagaagatc 1980
cggaagtaca cgatg 1995

<210> SEQ ID NO 14

<211> LENGTH: 1995
<212> TYPE: DNA
<213> ORGANISM: Ursus americanus

<400> SEQUENCE: 14

```
acccaagtgt gcaccggcac agacatgaag ctgcggctcc ctgccagtcc cgagacccac     60

ctggatatgc tccgccacct ctaccaggcc tgtcaagtgg tacagggtaa cctggagctc    120

acctacctgc ccgccaatgc cagcctgtcc ttcctgcagg atatccagga ggtacagggc    180

tatgtgctca ttgctcacag ccaagtgaga caggtcccgc tgcagaggct ccgaatcgtg    240

cgaggcaccc agctctttga ggacaactac gccctggccg tgctggacaa tggagagccg    300

cccaaggggg acacctctgt ggcaggggct accccaggag ggctgcggga gctgaagctt    360

cgaagcctca cagagatcct gaagggaggg gtcttgattc agcggaaccc acagctctgc    420

caccaggaca cgattttgtg gaaggacatc ttccacaaga acaaccagct ggccctcacg    480

ctgatagaca ccaaccgctc tcgggcctgc caaccctgtt ctccagcctg taaagacccc    540

cactgctggg gagcaagttc cggggactgt cagagcttga cacgaaccgt ctgtgccggc    600

ggctgtgccc gctgcaaggg cccaaaaccc actgactgct gccatgagca gtgcgcggct    660

ggctgcacgg gccccaagca ctcggactgc ctggcctgcc ttcacttcaa ccacagtggc    720

atctgtgagc tgcactgccc agccctggtc acctacaaca cggacacgtt cgaatccatg    780

cccaaccctg agggccgata caccttcggt gccagctgtg tgaccgcctg tccctacaac    840

tacctgtcca cggacgtggg atcctgcacc ctggtctgtc ccctgaacaa ccaagaggtg    900

acggctgagg atggcaccca gcggtgtgag aaatgcagca gaccctgtgc ccgagtgtgc    960

tatggtctgg gcatggagca cctgcgggag gcgagggcgg tcaccagcgc caacatccaa   1020

gagttcgccg gctgcaagaa gatctttggg agcctggcgt ttctgccaga gagcttcgag   1080

ggagacccag cctccaacac tgccccccctg cagcctgaac agctcagagt gttcgaggcc   1140

ctggaggaga tcacaggtta cctgtatatc tcagcgtggc cggacagctt gcctaacctc   1200

agtgtcttcc agaacctgcg agtaatccgg ggacgagttc tgcatgatgg cgcctactcg   1260

ctgaccctgc aagggctggg catcagctgg ctggggctgc gctcgctgcg ggaactgggc   1320

agcgggctgg ccctcatcca ccgcaacgcc cgcctctgct tcatccacac ggtgccctgg   1380

gagcagctct tccggaaccc ccaccaagcc ctgctgcaca gtgccaaccg gccggaggcc   1440

gagtgcgtgg gcgagggcct ggcctgctac ccgctgtgcg cccatgggca ctgctggggt   1500

ccggggccca cccagtgcgt caactgcagc caattccttc ggggccagga gtgcgtggag   1560

gaatgccgag aactgcacgg gctaccccgg gaatatgtga aggacagata ctgtctgcca   1620

tgccaccccg agtgtcggcc ccagaatggc tcagtgacct gctttgggtc ggaggctgac   1680

cagtgtgtgg cctgcgccca ctacaaggac cctccctcct gcgtggctcg ctgccccagt   1740

ggtgtgaaac ccgacctctc tttcatgccc atttggaagt ttgcagatga ggagggcaca   1800

tgccagccgt gccccatcaa ctgcacccac tcctgtgggg acctggacga gaggggctgc   1860

cccgccgaac agagagccag ccctgtgaca tccatcattg ccgctgtggt gggcattctg   1920

ctggccgtgg tcatggggct ggtcctcggc atcctgatca agcgaaggcg acagaagatc   1980

cggaagtaca cgatg                                                    1995
```

<210> SEQ ID NO 15
<211> LENGTH: 1998
<212> TYPE: DNA
<213> ORGANISM: Homo sapiens -continued

<400> SEQUENCE: 15

```
acccaagtgt gcaccggcac agacatgaag ctgcggctcc ctgccagtcc cgagacccac     60
ctggacatgc tccgccacct ctaccagggc tgccaggtgg tgcagggaaa cctggaactc    120
acctacctgc ccaccaatgc cagcctgtcc ttcctgcagg atatccagga ggtgcagggc    180
tacgtgctca tcgctcacaa ccaagtgagg caggtcccac tgcagaggct gcggattgtg    240
cgaggcaccc agctctttga ggacaactat gccctggccg tgctagacaa tggagacccg    300
ctgaacaata ccacccctgt cacaggggcc tccccaggag gcctgcggga gctgaagctt    360
cgaagcctca cagagatctt gaaaggaggg gtcttgatcc agcggaaccc ccagctctgc    420
taccaggaca cgattttgtg gaaggacatc ttccacaaga acaaccagct ggctctcaca    480
ctgatagaca ccaaccgctc tcgggcctgc cacccctgtt ctccgatgtg taagggctcc    540
cgctgctggg gagagagttc tgaggattgt cagagcctga cgcgcactgt ctgtgccggt    600
ggctgtgccc gctgcaaggg gccactgccc actgactgct gccatgagca gtgtgctgcc    660
ggctgcacgg gccccaagca ctctgactgc ctggcctgcc tccacttcaa ccacagtggc    720
atctgtgagc tgcactgccc agccctggtc acctacaaca cagacacgtt tgagtccatg    780
cccaatcccg agggccggta tacattcggc gccagctgtg tgactgcctg tccctacaac    840
tacctttcta cggacgtggg atcctgcacc ctcgtctgcc ccctgcacaa ccaagaggtg    900
acagcagagg atggaacaca gcggtgtgag aagtgcagca agccctgtgc ccgagtgtgc    960
tatggtctgg gcatggagca cttgcgagag gtgagggcag ttaccagtgc caatatccag   1020
gagtttgctg gctgcaagaa gatctttggg agcctggcat ttctgccgga gagctttgat   1080
ggggacccag cctccaacac tgccccgctc cagccagagc agctccaagt gtttgagact   1140
ctggaagaga tcacaggtta cctatacatc tcagcatggc cggacagcct gcctgacctc   1200
agcgtcttcc agaacctgca agtaatccgg ggacgaattc tgcacaatgg cgcctactcg   1260
ctgaccctgc aagggctggg catcagctgg ctggggctgc gctcactgag ggaactgggc   1320
agtggactgg ccctcatcca ccataacacc cacctctgct tcgtgcacac ggtgccctgg   1380
gaccagctct ttcggaaccc gcaccaagct ctgctccaca ctgccaaccg gccagaggac   1440
gagtgtgtgg gcgagggcct ggcctgccac cagctgtgcg cccgagggca ctgctggggt   1500
ccagggccca cccagtgtgt caactgcagc cagttccttc ggggccagga gtgcgtggag   1560
gaatgccgag tactgcaggg gctccccagg gagtatgtga atgccaggca ctgtttgccg   1620
tgccaccctg agtgtcagcc ccagaatggc tcagtgacct gttttggacc ggaggctgac   1680
cagtgtgtgg cctgtgccca ctataaggac cctcccttct gcgtggcccg ctgccccagc   1740
ggtgtgaaac ctgacctctc ctacatgccc atctggaagt ttccagatga ggagggcgca   1800
tgccagcctt gccccatcaa ctgcacccac tcctgtgtgg acctggatga caagggctgc   1860
cccgccgagc agagagccag ccctctgacg tccatcatct ctgcggtggt tggcattctg   1920
ctggtcgtgg tcttgggggt ggtctttggg atcctcatca agcgacggca gcagaagatc   1980
cggaagtaca cgatgtag                                                 1998
```

<210> SEQ ID NO 16
<211> LENGTH: 1998
<212> TYPE: DNA
<213> ORGANISM: Mus musculus

<400> SEQUENCE: 16

-continued

```
acccaagtgt gtaccggtac cgacatgaag ttgcgactcc ctgccagtcc tgagacccac     60
ctggacatgc ttcgccacct ctaccagggc tgtcaggtgg tgcagggcaa tttggagctt    120
acctacctgc ccgccaatgc cagcctctca ttcctgcagg acatccagga agtccaggga    180
tacatgctca tcgctcacaa ccgagtgaaa cacgtcccac tgcagaggtt gcgcatcgtg    240
agagggactc agctctttga ggacaagtat gccctggctg tgctagacaa ccgagaccct    300
ttggacaacg tcaccaccgc cgccccaggc agaaccccag aagggctgcg ggagctgaag    360
cttcgaagtc tcacagagat cttgaaggga ggagttttga tccgtgggaa ccctcagctc    420
tgctaccagg acatggtttt gtggaaggat gtcctccgta agaataacca gctggctcct    480
gtcgacatgg acaccaatcg ttcccgggcc tgtccacctt gtgccccaac ctgcaaagac    540
aatcactgtt ggggtgagag tcctgaagac tgtcagatct tgactggcac catctgtact    600
agtggctgtg cccggtgcaa gggccggctg cccactgact gttgccatga gcagtgtgct    660
gcaggctgca cgggtcccaa gcattctgac tgcctggcct gcctccactt caatcatagt    720
ggtatctgtg agctgcactg cccggccctc atcacctaca acacagacac cttcgagtcc    780
atgctcaacc ctgagggtcg ctacaccttt ggtgccagct gtgtgaccac ctgcccctac    840
aactacctct ccacggaagt gggatcctgc actctggtct gtcccccgaa caaccaagag    900
gtcacagctg aggacggaac acagcggtgt gagaaatgca gcaagccctg tgctggagta    960
tgctatggtc tgggcatgga gcacctccga ggggcgaggg ccatcaccag tgacaatatc   1020
caggagtttg ctggctgcaa gaagatcttt gggagcctgg catttttgcc ggagagcttt   1080
gatgggaacc cctcctccgg cgttgcccca ctgaagccag agcatctcca agtgttcgaa   1140
accctggagg agatcacagg ttacctatac atttcagcat ggccagagag cttccaagac   1200
ctcagtgtct tccagaacct tcgggtcatt cggggacgga ttctccatga tggtgcttac   1260
tcattgacgt tgcaaggcct ggggattcac tcactggggc tacgctcact gcgggagctg   1320
ggcagtggat tggctctcat tcaccgcaac acccatctct gctttgtaaa cactgtacct   1380
tgggaccagc tcttccggaa cccgcaccag gccctactcc acagtgggaa ccggccagaa   1440
gaggcatgtg gtcttgaggg cttggtctgt aactcactgt gtgcccgtgg gcactgctgg   1500
gggccagggc ccacccagtg tgtcaactgc agtcagttcc tccggggcca ggagtgtgtg   1560
gaggagtgcc gagtatggaa ggggctcccc agggagtatg tgaggggcaa gcactgtctg   1620
ccatgccacc ccgagtgtca gcctcaaaac agctcggaga cctgctatgg atcggaggct   1680
gaccagtgtg aggcttgtgc ccactacaag gactcatctt cctgtgtggc tcgctgcccc   1740
agtggtgtga agccagacct ctcctacatg cctatctgga agtacccgga tgaggagggc   1800
atatgtcagc catgccccat caactgcacc cactcatgtg tggacctgga cgaacgaggc   1860
tgcccagcag agcagagagc cagcccagtg acattcatca ttgcaactgt ggtgggcgtc   1920
ctgttgttcc tgatcatagt ggtggtcatt ggaatcctaa tcaaacgaag gcgacagaag   1980
atccggaagt ataccatg                                                 1998
```

<210> SEQ ID NO 17
<211> LENGTH: 1998
<212> TYPE: DNA
<213> ORGANISM: Rattus norvegicus

<400> SEQUENCE: 17

```
acccaagtgt gtaccggcac agacatgaag ttgcggctcc ctgccagtcc tgagacccac     60
ctggacatgc tccgccacct gtaccagggc tgtcaggtag tgcagggcaa cttggagctt    120
```

-continued acctacgtgc ctgccaatgc cagcctctca ttcctgcagg acatccagga agttcagggt 180
tacatgctca tcgctcacaa ccaggtgaag cgcgtcccac tgcaaaggct gcgcatcgtg 240
agagggaccc agctctttga ggacaagtat gccctggctg tgctagacaa ccgagatcct 300
caggacaatg tcgccgcctc caccccaggc agaaccccag aggggctgcg ggagctgaag 360
cttcgaagtc tcacagagat cctgaaggga ggagttttga tccgtgggaa ccctcagctc 420
tgctaccagg acatggtttt gtggaaggac gtcttccgca agaataacca actggctcct 480
gtcgatatag acaccaatcg ttcccgggcc tgtccacctt gtgcccccgc ctgcaaagac 540
aatcactgtt ggggtgagag tccggaagac tgtcagatct tgactggcac catctgtacc 600
agtggttgtg cccggtgcaa gggccggctg cccactgact gctgccatga gcagtgtgcc 660
gcaggctgca cgggccccaa gcattctgac tgcctggcct gcctccactt caatcatagt 720
ggtatctgtg agctgcactg cccagccctc gtcacctaca acacagacac ctttgagtcc 780
atgcacaacc ctgagggtcg ctacaccttt ggtgccagct gcgtgaccac ctgcccctac 840
aactacctgt ctacggaagt gggatcctgc actctggtgt gtcccccgaa taaccaagag 900
gtcacagctg aggacggaac acagcgttgt gagaaatgca gcaagccctg tgctcgagtg 960
tgctatggtc tgggcatgga gcaccttcga ggggcgaggg ccatcaccag tgacaatgtc 1020
caggagtttg atggctgcaa gaagatcttt gggagcctgg catttttgcc ggagagcttt 1080
gatggggacc cctcctccgg cattgctccg ctgaggcctg agcagctcca agtgttcgaa 1140
accctggagg agatcacagg ttacctgtac atctcagcat ggccagacag tctccgtgac 1200
ctcagtgtct tccagaacct tcgaatcatt cggggacgga ttctccacga tggcgcgtac 1260
tcattgacac tgcaaggcct ggggatccac tcgctggggc tgcgctcact gcgggagctg 1320
ggcagtggat tggctctgat tcaccgcaac gcccatctct gctttgtaca cactgtacct 1380
tgggaccagc tcttccggaa cccacatcag gccctgctcc acagtgggaa ccggccggaa 1440
gaggattgtg gtctcgaggg cttggtctgt aactcactgt gtgcccacgg gcactgctgg 1500
gggccagggc ccacccagtg tgtcaactgc agtcatttcc ttcggggcca ggagtgtgtg 1560
gaggagtgcc gagtatggaa ggggctcccc cgggagtatg tgagtgacaa gcgctgtctg 1620
ccgtgtcacc ccgagtgtca gcctcaaaac agctcagaga cctgctttgg atcggaggct 1680
gatcagtgtg cagcctgcgc ccactacaag gactcgtcct cctgtgtggc tcgctgcccc 1740
agtggtgtga aaccggacct ctcctacatg cccatctgga agtacccgga tgaggagggc 1800
atatgccagc cgtgccccat caactgcacc cactcctgtg tggatctgga tgaacgaggc 1860
tgcccagcag agcagagagc cagcccggtg acattcatca ttgcaactgt agtgggcgtc 1920
ctgctgttcc tgatcttagt ggtggtcgtt ggaatcctaa tcaaacgaag gagacagaag 1980
atccggaagt atacgatg 1998

<210> SEQ ID NO 18
<211> LENGTH: 2004
<212> TYPE: DNA
<213> ORGANISM: Artificial Sequence
<220> FEATURE:
<223> OTHER INFORMATION: Chimeric human-rat E2Neu (HER2)

<400> SEQUENCE: 18
acccaagtgt gcaccggcac agacatgaag ctgcggctcc ctgccagtcc cgagacccac 60
ctggacatgc tccgccacct ctaccagggc tgccaggtgg tgcagggaaa cctggaactc 120

```
acctacctgc ccaccaatgc cagcctgtcc ttcctgcagg atatccagga ggtgcagggc    180
tacgtgctca tcgctcacaa ccaagtgagg caggtcccac tgcagaggct gcggattgtg    240
cgaggcaccc agctctttga ggacaactat gccctggccg tgctagacaa tggagacccg    300
ctgaacaata ccacccctgt cacaggggcc tccccaggag gcctgcggga gctgaagctt    360
cgaagcctca cagagatctt gaaaggaggg gtcttgatcc agcggaaccc ccagctctgc    420
taccaggaca cgattttgtg gaaggacatc ttccacaaga acaaccagct ggctctcaca    480
ctgatagaca ccaaccgctc tcgggcctgc cacccctgtt ctccgatgtg taagggctcc    540
cgctgctggg gagagagttc tgaggattgt cagagcctga cgcgcactgt ctgtgccggt    600
ggctgtgccc gctgcaaggg gccactgccc actgactgct gccatgagca gtgtgctgcc    660
ggctgcacgg gccccaagca ctctgactgc ctggcctgcc tccacttcaa ccacagtggc    720
atctgtgagc tgcactgccc agccctggtc acctacaaca cagacacgtt tgagtccatg    780
cccaatcccg agggccggta tacattcggc gccagctgtg tgactgcctg tccctacaac    840
tacctttcta cggacgtggg atcctgcacc ctcgtctgcc ccctgcacaa ccaagaggtg    900
acagcagagg atggaacaca gcggtgtgag aagtgcagca agccctgtgc ccgagtgtgc    960
tatggtctgg gcatggagca cttgcgagag gtgagggcag ttaccagtgc caatatccag   1020
gagtttgctg gctgcaagaa gatctttggg agcctggcat ttctgccgga gagctttgat   1080
ggggacccag cctccaacac tgccgaattc gctccgctga ggcctgagca gctccaagtg   1140
ttcgaaaccc tggaggagat cacaggttac ctgtacatct cagcatggcc agacagtctc   1200
cgtgacctca gtgtcttcca gaaccttcga atcattcggg gacggattct ccacgatggc   1260
gcgtactcat tgacactgca aggcctgggg atccactcgc tggggctgcg ctcactgcgg   1320
gagctgggca gtggattggc tctgattcac cgcaacgccc atctctgctt tgtacacact   1380
gtaccttggg accagctctt ccggaaccca catcaggccc tgctccacag tgggaaccgg   1440
ccggaagagg attgtggtct cgagggcttg gtctgtaact cactgtgtgc ccacgggcac   1500
tgctgggggc cagggcccac ccagtgtgtc aactgcagtc atttccttcg gggccaggag   1560
tgtgtggagg agtgccgagt atggaagggg ctcccccggg agtatgtgag tgacaagcgc   1620
tgtctgccgt gtcaccccga gtgtcagcct caaaacagct cagagacctg ctttggatcg   1680
gaggctgatc agtgtgcagc ctgcgcccac tacaaggact cgtcctcctg tgtggctcgc   1740
tgccccagtg gtgtgaaacc ggacctctcc tacatgccca tctggaagta cccggatgag   1800
gagggcatat gccagccgtg ccccatcaac tgcacccact cctgtgtgga tctggatgaa   1860
cgaggctgcc cagcagagca gagagccagc ccggtgacat tcatcattgc aactgtagtg   1920
ggcgtcctgc tgttcctgat cttagtggtg gtcgttggaa tcctaatcaa acgaaggaga   1980
cagaagatcc ggaagtatac gatg                                          2004
```

```
<210> SEQ ID NO 19
<211> LENGTH: 2061
<212> TYPE: DNA
<213> ORGANISM: Felis catus

<400> SEQUENCE: 19
```

```
atggagctgg cggcctggtg ccgctggggg ctcctcctcg ccctcctgcc ctccggagcc     60
acgggcaccc aagtgtgcac cggcacagac atgaagctgc ggctcccagc cagtcccgag    120
acccacctgg acatgctccg ccacctctac cagggctgtc aagtggtaca gggcaacctg    180
gagctcacct acctgcatgc caatgccagc ctctccttcc tgcaggatat ccaggaggtg    240
```

caaggctatg tgctcattgc ccacaaccaa gtgaaacagg tcccactgca gaggctacga 300
atcgtgcgag gcacccagct ctttgaggac aactacgccc tggccgtgct ggacaacgga 360
gacccactgg acagtggcac ccctgctaca ggggctgccc taggagggct gcgggagctg 420
aagctccgaa gcctcacaga gatcctgaag ggaggggtcc tcattcagcg gaacccgcag 480
ctctgccacc aggacacgat tctgtggaag gacatcttcc acaagaacaa ccagctggcc 540
ctcatgctga tagacaccaa ccgctctcgg gcctgccaac cctgttctcc agcttgtaaa 600
gactcccact gctggggagc aagttccggg gactgtcaga gcttgactcg aactgtctgt 660
gctggcggct gtgcccgctg caagggcccg cagcccaccg actgctgcca cgagcaatgt 720
gctgctggct gcacgggccc caagcattct gactgcctgg cctgcctcca cttcaaccac 780
agtggcatct gtgagctgca ctgcccagcc ctggtcacct acaacacgga caccttcgaa 840
tccatgccca accctgaggg ccgttatacc ttcggtgcca gctgtgtgac tgcctgtccc 900
tacaactacc tgtctacgga cgtgggatcc tgcaccctgg tctgtcccct gaacaaccaa 960
gaggtgacag ctgaggatgg aacacagcgg tgtgagaaat gcagcaagcc ctgtgcccga 1020
gtgtgctacg gcctaggcat ggagcacctg cgggaggcga gggcagtcac cagtgccaac 1080
atccaagaat ttgtcggctg caagaagatc tttgggagcc tggcgtttct gccagagagc 1140
tttgaggggg acccagcctc caacactgcc cccctgcagc ctgagcagct cagagtgttt 1200
gaggctctgg aggagattac aggttacctg tacatctcag cgtggccaga cagcttgcct 1260
aacctcagtg tcttccagaa cctcagagtg atccggggcc gagttctgca tgacggtgct 1320
tactcgctga cccttcaagg gctgggcatc agctggctgg ggctgcgctc gctgcgggag 1380
ctgggcagtg ggctggccct catccaccgc aactcccgcc tctgcttcgt acacacggtg 1440
ccctgggacc agctcttccg gaacccccac caggccctgc tccacagcgc caaccggcca 1500
gaggacgagt gcgcgggtga gggcctggcc tgctatccgc tgtgtgccca cgggcactgc 1560
tggggtccgg gacccaccca gtgtgtcaac tgcagccagt tccttcgggg ccaggagtgc 1620
gtggaggaat gccgagtatt gcaggggctt ccccgggagt atgtgaagga taggttctgt 1680
ctgccatgcc acccggagtg tcagccccag aatggctcag tgacctgctt gggctcggaa 1740
gctgaccagt gtgtggcctg tgcccactac aaggaccctc ctttctgtgt ggctcgctgc 1800
cccagtgggg tgaaacctga cctctccttc atgcccatct ggaagttcgc agatgaggag 1860
ggcacgtgcc agccatgccc catcaactgc acccactcct gtgcggacct ggacgagaag 1920
ggctgccccg ccgagcagag agccagccct gtgacgtcca tcattgctgc tgtggtgggc 1980
attctgctgg tcgtggttgt ggggctggtc cttggcatcc taatcaagcg aaggcggcag 2040
aagatccgga agtacacgat g 2061

<210> SEQ ID NO 20
<211> LENGTH: 2061
<212> TYPE: DNA
<213> ORGANISM: Ursus americanus

<400> SEQUENCE: 20
atggagctgg cggcctggtg ccgctggggg ctcctcctcg ccctcctgcc ctccggagcc 60
gcgggcaccc aagtgtgcac cggcacagac atgaagctgc ggctccctgc cagtcccgag 120
acccacctgg atatgctccg ccacctctac caggcctgtc aagtggtaca gggtaacctg 180
gagctcacct acctgcccgc caatgccagc ctgtccttcc tgcaggatat ccaggaggta 240

-continued

```
cagggctatg tgctcattgc tcacagccaa gtgagacagg tcccgctgca gaggctccga    300

atcgtgcgag gcacccagct ctttgaggac aactacgccc tggccgtgct ggacaatgga    360

gagccgccca agggggacac ctctgtggca ggggctaccc caggagggct gcgggagctg    420

aagcttcgaa gcctcacaga gatcctgaag ggaggggtct tgattcagcg gaacccacag    480

ctctgccacc aggacacgat tttgtggaag gacatcttcc acaagaacaa ccagctggcc    540

ctcacgctga tagacaccaa ccgctctcgg gcctgccaac cctgttctcc agcctgtaaa    600

gacccccact gctggggagc aagttccggg gactgtcaga gcttgacacg aaccgtctgt    660

gccggcggct gtgcccgctg caagggccca aaacccactg actgctgcca tgagcagtgc    720

gcggctggct gcacgggccc caagcactcg gactgcctgg cctgccttca cttcaaccac    780

agtggcatct gtgagctgca ctgcccagcc ctggtcacct acaacacgga cacgttcgaa    840

tccatgccca accctgaggg ccgatacacc ttcggtgcca gctgtgtgac cgcctgtccc    900

tacaactacc tgtccacgga cgtgggatcc tgcaccctgg tctgtcccct gaacaaccaa    960

gaggtgacgg ctgaggatgg cacccagcgg tgtgagaaat gcagcagacc ctgtgcccga   1020

gtgtgctatg gtctgggcat ggagcacctg cgggaggcga gggcggtcac cagcgccaac   1080

atccaagagt tcgccggctg caagaagatc tttgggagcc tggcgtttct gccagagagc   1140

ttcgagggag acccagcctc caacactgcc cccctgcagc ctgaacagct cagagtgttc   1200

gaggccctgg aggagatcac aggttacctg tatatctcag cgtggccgga cagcttgcct   1260

aacctcagtg tcttccagaa cctgcgagta atccggggac gagttctgca tgatggcgcc   1320

tactcgctga ccctgcaagg gctgggcatc agctggctgg ggctgcgctc gctgcgggaa   1380

ctgggcagcg ggctggccct catccaccgc aacgcccgcc tctgcttcat ccacacggtg   1440

ccctgggagc agctcttccg gaacccccac caagccctgc tgcacagtgc caaccggccg   1500

gaggccgagt gcgtgggcga gggcctggcc tgctacccgc tgtgcgccca tgggcactgc   1560

tggggtccgg ggcccaccca gtgcgtcaac tgcagccaat tccttcgggg ccaggagtgc   1620

gtggaggaat gccgagaact gcacgggcta ccccgggaat atgtgaagga cagatactgt   1680

ctgccatgcc accccgagtg tcggccccag aatggctcag tgacctgctt tgggtcggag   1740

gctgaccagt gtgtggcctg cgcccactac aaggaccctc cctcctgcgt ggctcgctgc   1800

cccagtggtg tgaaacccga cctctctttc atgcccattt ggaagtttgc agatgaggag   1860

ggcacatgcc agccgtgccc catcaactgc acccactcct gtggggacct ggacgagagg   1920

ggctgccccg ccgaacagag agccagccct gtgacatcca tcattgccgc tgtggtgggc   1980

attctgctgg ccgtggtcat ggggctggtc ctcggcatcc tgatcaagcg aaggcgacag   2040

aagatccgga agtacacgat g                                              2061
```

<210> SEQ ID NO 21
<211> LENGTH: 2064
<212> TYPE: DNA
<213> ORGANISM: Homo sapiens

<400> SEQUENCE: 21

```
atggagctgg cggccttgtg ccgctggggg ctcctcctcg ccctcttgcc ccccggagcc     60

gcgagcaccc aagtgtgcac cggcacagac atgaagctgc ggctccctgc cagtcccgag    120

acccacctgg acatgctccg ccacctctac cagggctgcc aggtggtgca gggaaacctg    180

gaactcacct acctgcccac caatgccagc ctgtccttcc tgcaggatat ccaggaggtg    240

cagggctacg tgctcatcgc tcacaaccaa gtgaggcagg tcccactgca gaggctgcgg    300
```

attgtgcgag gcacccagct ctttgaggac aactatgccc tggccgtgct agacaatgga 360
gacccgctga acaataccac ccctgtcaca ggggcctccc caggaggcct gcgggagctg 420
aagcttcgaa gcctcacaga gatcttgaaa ggaggggtct tgatccagcg gaaccccccag 480 ctctgctacc aggacacgat tttgtggaag gacatcttcc acaagaacaa ccagctggct 540
ctcacactga tagacaccaa ccgctctcgg gcctgccacc cctgttctcc gatgtgtaag 600
ggctcccgct gctggggaga gagttctgag gattgtcaga gcctgacgcg cactgtctgt 660
gccggtggct gtgcccgctg caaggggcca ctgcccactg actgctgcca tgagcagtgt 720
gctgccggct gcacgggccc caagcactct gactgcctgg cctgcctcca cttcaaccac 780
agtggcatct gtgagctgca ctgcccagcc ctggtcacct acaacacaga cacgtttgag 840
tccatgccca atcccgaggg ccggtataca ttcggcgcca gctgtgtgac tgcctgtccc 900
tacaactacc tttctacgga cgtgggatcc tgcaccctcg tctgccccct gcacaaccaa 960
gaggtgacag cagaggatgg aacacagcgg tgtgagaagt gcagcaagcc ctgtgcccga 1020
gtgtgctatg gtctgggcat ggagcacttg cgagaggtga gggcagttac cagtgccaat 1080
atccaggagt ttgctggctg caagaagatc tttgggagcc tggcatttct gccggagagc 1140
tttgatgggg acccagcctc caacactgcc ccgctccagc cagagcagct ccaagtgttt 1200
gagactctgg aagagatcac aggttaccta tacatctcag catggccgga cagcctgcct 1260
gacctcagcg tcttccagaa cctgcaagta atccggggac gaattctgca caatggcgcc 1320
tactcgctga ccctgcaagg gctgggcatc agctggctgg ggctgcgctc actgagggaa 1380
ctgggcagtg gactggccct catccaccat aacacccacc tctgcttcgt gcacacggtg 1440
ccctgggacc agctctttcg gaacccgcac caagctctgc tccacactgc caaccggcca 1500
gaggacgagt gtgtgggcga gggcctggcc tgccaccagc tgtgcgcccg agggcactgc 1560
tggggtccag ggcccaccca gtgtgtcaac tgcagccagt tccttcgggg ccaggagtgc 1620
gtggaggaat gccgagtact gcaggggctc cccagggagt atgtgaatgc caggcactgt 1680
ttgccgtgcc accctgagtg tcagccccag aatggctcag tgacctgttt tggaccggag 1740
gctgaccagt gtgtggcctg tgcccactat aaggaccctc ccttctgcgt ggcccgctgc 1800
cccagcggtg tgaaacctga cctctcctac atgcccatct ggaagtttcc agatgaggag 1860
ggcgcatgcc agccttgccc catcaactgc acccactcct gtgtggacct ggatgacaag 1920
ggctgccccg ccgagcagag agccagccct ctgacgtcca tcatctctgc ggtggttggc 1980
attctgctgg tcgtggtctt gggggtggtc tttgggatcc tcatcaagcg acggcagcag 2040
aagatccgga agtacacgat gtag 2064

<210> SEQ ID NO 22
<211> LENGTH: 2064
<212> TYPE: DNA
<213> ORGANISM: Mus musculus

<400> SEQUENCE: 22
atggagctgg cggcctggtg ccgttggggg ttcctcctcg ccctcctgtc cccccggagcc 60 gcgggtaccc aagtgtgtac cggtaccgac atgaagttgc gactccctgc cagtcctgag 120
acccacctgg acatgcttcg ccacctctac cagggctgtc aggtggtgca gggcaatttg 180
gagcttacct acctgcccgc caatgccagc ctctcattcc tgcaggacat ccaggaagtc 240
cagggataca tgctcatcgc tcacaaccga gtgaaacacg tcccactgca gaggttgcgc 300

-continued

```
atcgtgagag ggactcagct ctttgaggac aagtatgccc tggctgtgct agacaaccga    360
gacccctttgg acaacgtcac caccgccgcc ccaggcagaa ccccagaagg gctgcgggag    420
ctgaagcttc gaagtctcac agagatcttg aagggaggag ttttgatccg tgggaaccct    480
cagctctgct accaggacat ggttttgtgg aaggatgtcc tccgtaagaa taaccagctg    540
gctcctgtcg acatggacac caatcgttcc cgggcctgtc caccttgtgc cccaacctgc    600
aaagacaatc actgttgggg tgagagtcct gaagactgtc agatcttgac tggcaccatc    660
tgtactagtg gctgtgcccg gtgcaagggc cggctgccca ctgactgttg ccatgagcag    720
tgtgctgcag gctgcacggg tcccaagcat tctgactgcc tggcctgcct ccacttcaat    780
catagtggta tctgtgagct gcactgcccg gccctcatca cctacaacac agacaccttc    840
gagtccatgc tcaaccctga gggtcgctac acctttggtg ccagctgtgt gaccacctgc    900
ccctacaact acctctccac ggaagtggga tcctgcactc tggtctgtcc cccgaacaac    960
caagaggtca cagctgagga cggaacacag cggtgtgaga aatgcagcaa gccctgtgct   1020
ggagtatgct atggtctggg catggagcac ctccgagggg cgagggccat caccagtgac   1080
aatatccagg agtttgctgg ctgcaagaag atctttggga gcctggcatt tttgccggag   1140
agctttgatg ggaacccctc ctccggcgtt gccccactga agccagagca tctccaagtg   1200
ttcgaaaccc tggaggagat cacaggttac ctatacattt cagcatggcc agagagcttc   1260
caagacctca gtgtcttcca gaaccttcgg gtcattcggg gacggattct ccatgatggt   1320
gcttactcat tgacgttgca aggcctgggg attcactcac tggggctacg ctcactgcgg   1380
gagctgggca gtggattggc tctcattcac cgcaacaccc atctctgctt tgtaaacact   1440
gtaccttggg accagctctt ccggaacccg caccaggccc tactccacag tgggaaccgg   1500
ccagaagagg catgtggtct tgagggcttg gtctgtaact cactgtgtgc ccgtgggcac   1560
tgctgggggc cagggcccac ccagtgtgtc aactgcagtc agttcctccg gggccaggag   1620
tgtgtggagg agtgccgagt atggaagggg ctccccaggg agtatgtgag gggcaagcac   1680
tgtctgccat gccaccccga gtgtcagcct caaaacagct cggagacctg ctatggatcg   1740
gaggctgacc agtgtgaggc ttgtgcccac tacaaggact catcttcctg tgtggctcgc   1800
tgccccagtg gtgtgaagcc agacctctcc tacatgccta tctggaagta cccggatgag   1860
gagggcatat gtcagccatg ccccatcaac tgcacccact catgtgtgga cctggacgaa   1920
cgaggctgcc cagcagagca gagagccagc ccagtgacat tcatcattgc aactgtggtg   1980
ggcgtcctgt tgttcctgat catagtggtg gtcattggaa tcctaatcaa acgaaggcga   2040
cagaagatcc ggaagtatac catg                                           2064
```

<210> SEQ ID NO 23
<211> LENGTH: 2073
<212> TYPE: DNA
<213> ORGANISM: Rattus norvegicus

<400> SEQUENCE: 23

```
atgatcatca tggagctggc ggcctggtgc cgctgggggt tcctcctcgc cctcctgccc     60
cccggaatcg cgggcaccca agtgtgtacc ggcacagaca tgaagttgcg gctccctgcc    120
agtcctgaga cccacctgga catgctccgc cacctgtacc agggctgtca ggtagtgcag    180
ggcaacttgg agcttaccta cgtgcctgcc aatgccagcc tctcattcct gcaggacatc    240
caggaagttc agggttacat gctcatcgct cacaaccagg tgaagcgcgt cccactgcaa    300
aggctgcgca tcgtgagagg gacccagctc tttgaggaca agtatgccct ggctgtgcta    360
```

gacaaccgag atcctcagga caatgtcgcc gcctccaccc caggcagaac cccagagggg 420
ctgcgggagc tgaagcttcg aagtctcaca gagatcctga agggaggagt tttgatccgt 480
gggaaccctc agctctgcta ccaggacatg gttttgtgga aggacgtctt ccgcaagaat 540
aaccaactgg ctcctgtcga tatagacacc aatcgttccc gggcctgtcc accttgtgcc 600
cccgcctgca aagacaatca ctgttggggt gagagtccgg aagactgtca gatcttgact 660
ggcaccatct gtaccagtgg ttgtgcccgg tgcaagggcc ggctgcccac tgactgctgc 720
catgagcagt gtgccgcagg ctgcacgggc cccaagcatt ctgactgcct ggcctgcctc 780
cacttcaatc atagtggtat ctgtgagctg cactgcccag ccctcgtcac ctacaacaca 840
gacacctttg agtccatgca caaccctgag ggtcgctaca cctttggtgc cagctgcgtg 900
accacctgcc cctacaacta cctgtctacg gaagtgggat cctgcactct ggtgtgtccc 960
ccgaataacc aagaggtcac agctgaggac ggaacacagc gttgtgagaa atgcagcaag 1020
ccctgtgctc gagtgtgcta tggtctgggc atggagcacc ttcgaggggc gagggccatc 1080
accagtgaca atgtccagga gtttgatggc tgcaagaaga tctttgggag cctggcattt 1140
ttgccggaga gctttgatgg ggacccctcc tccggcattg ctccgctgag gcctgagcag 1200
ctccaagtgt tcgaaaccct ggaggagatc acaggttacc tgtacatctc agcatggcca 1260
gacagtctcc gtgacctcag tgtcttccag aaccttcgaa tcattcgggg acggattctc 1320
cacgatggcg cgtactcatt gacactgcaa ggcctgggga tccactcgct ggggctgcgc 1380
tcactgcggg agctgggcag tggattggct ctgattcacc gcaacgccca tctctgcttt 1440
gtacacactg taccttggga ccagctcttc cggaacccac atcaggccct gctccacagt 1500
gggaaccggc cggaagagga ttgtggtctc gagggcttgg tctgtaactc actgtgtgcc 1560
cacgggcact gctgggggcc agggcccacc cagtgtgtca actgcagtca tttccttcgg 1620
ggccaggagt gtgtggagga gtgccgagta tggaaggggc tcccccggga gtatgtgagt 1680
gacaagcgct gtctgccgtg tcaccccgag tgtcagcctc aaaacagctc agagacctgc 1740
tttggatcgg aggctgatca gtgtgcagcc tgcgcccact acaaggactc gtcctcctgt 1800
gtggctcgct gccccagtgg tgtgaaaccg gacctctcct acatgcccat ctggaagtac 1860
ccggatgagg agggcatatg ccagccgtgc cccatcaact gcacccactc ctgtgtggat 1920
ctggatgaac gaggctgccc agcagagcag agagccagcc cggtgacatt catcattgca 1980
actgtagtgg gcgtcctgct gttcctgatc ttagtggtgg tcgttggaat cctaatcaaa 2040
cgaaggagac agaagatccg gaagtatacg atg 2073

<210> SEQ ID NO 24
<211> LENGTH: 2070
<212> TYPE: DNA
<213> ORGANISM: Artificial Sequence
<220> FEATURE:
<223> OTHER INFORMATION: Chimeric human-rat E2Neu (HER2)

<400> SEQUENCE: 24
atggagctgg cggccttgtg ccgctggggg ctcctcctcg ccctcttgcc ccccggagcc 60
gcgagcaccc aagtgtgcac cggcacagac atgaagctgc ggctccctgc cagtcccgag 120
acccacctgg acatgctccg ccacctctac cagggctgcc aggtggtgca gggaaacctg 180
gaactcacct acctgcccac caatgccagc ctgtccttcc tgcaggatat ccaggaggtg 240
cagggctacg tgctcatcgc tcacaaccaa gtgaggcagg tcccactgca gaggctgcgg 300

-continued

```
attgtgcgag gcacccagct ctttgaggac aactatgccc tggccgtgct agacaatgga    360
gacccgctga acaataccac ccctgtcaca ggggcctccc caggaggcct gcgggagctg    420
aagcttcgaa gcctcacaga gatcttgaaa ggaggggtct tgatccagcg gaacccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc gaattcgctc cgctgaggcc tgagcagctc   1200
caagtgttcg aaaccctgga ggagatcaca ggttacctgt acatctcagc atggccagac   1260
agtctccgtg acctcagtgt cttccagaac cttcgaatca ttcggggacg gattctccac   1320
gatggcgcgt actcattgac actgcaaggc ctggggatcc actcgctggg gctgcgctca   1380
ctgcgggagc tgggcagtgg attggctctg attcaccgca acgcccatct ctgctttgta   1440
cacactgtac cttgggacca gctcttccgg aacccacatc aggccctgct ccacagtggg   1500
aaccggccgg aagaggattg tggtctcgag ggcttggtct gtaactcact gtgtgcccac   1560
gggcactgct gggggccagg gcccacccag tgtgtcaact gcagtcattt ccttcggggc   1620
caggagtgtg tggaggagtg ccgagtatgg aaggggctcc cccgggagta tgtgagtgac   1680
aagcgctgtc tgccgtgtca ccccgagtgt cagcctcaaa acagctcaga gacctgcttt   1740
ggatcggagg ctgatcagtg tgcagcctgc gcccactaca aggactcgtc ctcctgtgtg   1800
gctcgctgcc ccagtggtgt gaaaccggac ctctcctaca tgcccatctg gaagtacccg   1860
gatgaggagg gcatatgcca gccgtgcccc atcaactgca cccactcctg tgtggatctg   1920
gatgaacgag gctgcccagc agagcagaga gccagcccgg tgacattcat cattgcaact   1980
gtagtgggcg tcctgctgtt cctgatctta gtggtggtcg ttggaatcct aatcaaacga   2040
aggagacaga agatccggaa gtatacgatg                                    2070
```

```
<210> SEQ ID NO 25
<211> LENGTH: 665
<212> TYPE: PRT
<213> ORGANISM: Homo sapiens

<400> SEQUENCE: 25

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60
```

-continued

```
Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Lys Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480
```

```
Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met
            660                 665


<210> SEQ ID NO 26
<211> LENGTH: 665
<212> TYPE: PRT
<213> ORGANISM: Homo sapiens

<400> SEQUENCE: 26

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190
```

-continued

```
Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Arg Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605
```

-continued

```
Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met
            660                 665


<210> SEQ ID NO 27
<211> LENGTH: 665
<212> TYPE: PRT
<213> ORGANISM: Homo sapiens

<400> SEQUENCE: 27

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320
```

```
Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asp
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640

Leu Val Val Val Leu Gly Val Val Phe Gly Ile Leu Ile Lys Arg Arg
                645                 650                 655

Gln Gln Lys Ile Arg Lys Tyr Thr Met
            660                 665


<210> SEQ ID NO 28
<211> LENGTH: 687
<212> TYPE: PRT
<213> ORGANISM: Homo sapiens

<400> SEQUENCE: 28

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
```

-continued

```
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Lys Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445
```

```
Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 29
<211> LENGTH: 687
<212> TYPE: PRT
<213> ORGANISM: Homo sapiens

<400> SEQUENCE: 29

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
```

-continued

```
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Arg Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560
```

```
Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 30
<211> LENGTH: 687
<212> TYPE: PRT
<213> ORGANISM: Homo sapiens

<400> SEQUENCE: 30

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
```

```
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670
```

```
Ile Leu Ile Lys Arg Arg Gln Gln Lys Ile Arg Lys Tyr Thr Met
        675                 680                 685


<210> SEQ ID NO 31
<211> LENGTH: 1998
<212> TYPE: DNA
<213> ORGANISM: Homo sapiens

<400> SEQUENCE: 31

acccaagtgt gcaccggcac agacatgaag ctgcggctcc ctgccagtcc cgagacccac      60

ctggacatgc tccgccacct ctaccagggc tgccaggtgg tgcagggaaa cctggaactc     120

acctacctgc ccaccaatgc cagcctgtcc ttcctgcagg atatccagga ggtgcagggc     180

tacgtgctca tcgctcacaa ccaagtgagg caggtcccac tgcagaggct gcggattgtg     240

cgaggcaccc agctctttga ggacaactat gccctggccg tgctagacaa tggagacccg     300

ctgaacaata ccacccctgt cacaggggcc tccccaggag gcctgcggga gctgcagctt     360

cgaagcctca cagagatctt gaaaggaggg gtcttgatcc agcggaaccc ccagctctgc     420

taccaggaca cgattttgtg gaaggacatc ttccacaaga acaaccagct ggctctcaca     480

ctgatagaca ccaaccgctc tcgggcctgc cacccctgtt ctccgatgtg taagggctcc     540

cgctgctggg gagagagttc tgaggattgt cagagcctga cgcgcactgt ctgtgccggt     600

ggctgtgccc gctgcaaggg gccactgccc actgactgct gccatgagca gtgtgctgcc     660

ggctgcacgg gccccaagca ctctgactgc ctggcctgcc tccacttcaa ccacagtggc     720

atctgtgagc tgcactgccc agccctggtc acctacaaca cagacacgtt tgagtccatg     780

cccaatcccg agggccggta tacattcggc gccagctgtg tgactgcctg tccctacaac     840

tacctttcta cggacgtggg atcctgcacc ctcgtctgcc ccctgcacaa ccaagaggtg     900

acagcagagg atggaacaaa gcggtgtgag aagtgcagca agccctgtgc ccgagtgtgc     960

tatggtctgg gcatggagca cttgcgagag gtgagggcag ttaccagtgc caatatccag    1020

gagtttgctg gctgcaagaa gatctttggg agcctggcat ttctgccgga gagctttgat    1080

ggggacccag cctccaacac tgccccgctc cagccagagc agctccaagt gtttgagact    1140

ctggaagaga tcacaggtta cctatacatc tcagcatggc cggacagcct gcctgacctc    1200

agcgtcttcc agaacctgca agtaatccgg ggacgaattc tgcacaatgg cgcctactcg    1260

ctgaccctgc aagggctggg catcagctgg ctggggctgc gctcactgag ggaactgggc    1320

agtggactgg ccctcatcca ccataacacc cacctctgct tcgtgcacac ggtgccctgg    1380

gaccagctct ttcggaaccc gcaccaagct ctgctccaca ctgccaaccg gccagaggac    1440

gagtgtgtgg gcgagggcct ggcctgccac cagctgtgcg cccgagggca ctgctggggt    1500

ccagggccca cccagtgtgt caactgcagc cagttccttc ggggccagga gtgcgtggag    1560

gaatgccgag tactgcaggg gctccccagg gagtatgtga atgccaggca ctgtttgccg    1620

tgccaccctg agtgtcagcc ccagaatggc tcagtgacct gttttggacc ggaggctgac    1680

cagtgtgtgg cctgtgccca ctataaggac cctcccttct gcgtggcccg ctgccccagc    1740

ggtgtgaaac ctgacctctc ctacatgccc atctggaagt ttccagatga ggagggcgca    1800

tgccagcctt gccccatcaa ctgcacccac tcctgtgtgg acctggatga caagggctgc    1860

cccgccgagc agagagccag ccctctgacg tccatcatct ctgcggtggt tggcattctg    1920

ctggtcgtgg tcttgggggt ggtctttggg atcctcatca agcgacggca gcagaagatc    1980

cggaagtaca cgatgtga                                                  1998
```

<210> SEQ ID NO 32
<211> LENGTH: 1998
<212> TYPE: DNA
<213> ORGANISM: Homo sapiens

<400> SEQUENCE: 32
acccaagtgt gcaccggcac agacatgaag ctgcggctcc ctgccagtcc cgagacccac 60
ctggacatgc tccgccacct ctaccagggc tgccaggtgg tgcagggaaa cctggaactc 120
acctacctgc ccaccaatgc cagcctgtcc ttcctgcagg atatccagga ggtgcagggc 180
tacgtgctca tcgctcacaa ccaagtgagg caggtcccac tgcagaggct gcggattgtg 240
cgaggcaccc agctctttga ggacaactat gccctggccg tgctagacaa tggagacccg 300
ctgaacaata ccacccctgt cacaggggcc tccccaggag gcctgcggga gctgcagctt 360
cgaagcctca cagagatctt gaaaggaggg gtcttgatcc agcggaaccc ccagctctgc 420
taccaggaca cgattttgtg gaaggacatc ttccacaaga acaaccagct ggctctcaca 480
ctgatagaca ccaaccgctc tcgggcctgc cacccctgtt ctccgatgtg taagggctcc 540
cgctgctggg gagagagttc tgaggattgt cagagcctga cgcgcactgt ctgtgccggt 600
ggctgtgccc gctgcaaggg gccactgccc actgactgct gccatgagca gtgtgctgcc 660
ggctgcacgg gccccaagca ctctgactgc ctggcctgcc tccacttcaa ccacagtggc 720
atctgtgagc tgcactgccc agccctggtc acctacaaca cagacacgtt tgagtccatg 780
cccaatcccg agggccggta tacattcggc gccagctgtg tgactgcctg tccctacaac 840
tacctttcta cggacgtggg atcctgcacc ctcgtctgcc ccctgcacaa ccaagaggtg 900
acagcagagg atggaacaca gcggtgtgag aagtgcagca agccctgtgc ccgagtgtgc 960
tatggtctgg gcatggagca cttgcgagag gtgagggcag ttaccagtgc caatatccag 1020
gagtttgctg gctgcaagaa gatctttggg agcctggcat ttctgccgga gagctttgat 1080
ggggacccag cctccaacac tgccccgctc cagccagagc agctccaagt gtttgagact 1140
ctggaagaga tcacaggtta cctatacatc tcagcatggc cggacagcct gcctgacctc 1200
agcgtcttcc agaacctgag agtaatccgg ggacgaattc tgcacaatgg cgcctactcg 1260
ctgaccctgc aagggctggg catcagctgg ctggggctgc gctcactgag ggaactgggc 1320
agtggactgg ccctcatcca ccataacacc cacctctgct tcgtgcacac ggtgccctgg 1380
gaccagctct ttcggaaccc gcaccaagct ctgctccaca ctgccaaccg gccagaggac 1440
gagtgtgtgg gcgagggcct ggcctgccac cagctgtgcg cccgagggca ctgctggggt 1500
ccagggccca cccagtgtgt caactgcagc cagttccttc ggggccagga gtgcgtggag 1560
gaatgccgag tactgcaggg gctccccagg gagtatgtga atgccaggca ctgtttgccg 1620
tgccaccctg agtgtcagcc ccagaatggc tcagtgacct gttttggacc ggaggctgac 1680
cagtgtgtgg cctgtgccca ctataaggac cctcccttct gcgtggcccg ctgccccagc 1740
ggtgtgaaac ctgacctctc ctacatgccc atctggaagt ttccagatga ggagggcgca 1800
tgccagcctt gccccatcaa ctgcacccac tcctgtgtgg acctggatga caagggctgc 1860
cccgccgagc agagagccag ccctctgacg tccatcatct ctgcggtggt tggcattctg 1920
ctggtcgtgg tcttgggggt ggtctttggg atcctcatca agcgacggca gcagaagatc 1980
cggaagtaca cgatgtga 1998

<210> SEQ ID NO 33

<211> LENGTH: 1998
<212> TYPE: DNA
<213> ORGANISM: Homo sapiens

<400> SEQUENCE: 33
acccaagtgt gcaccggcac agacatgaag ctgcggctcc ctgccagtcc cgagacccac 60
ctggacatgc tccgccacct ctaccagggc tgccaggtgg tgcagggaaa cctggaactc 120
acctacctgc ccaccaatgc cagcctgtcc ttcctgcagg atatccagga ggtgcagggc 180
tacgtgctca tcgctcacaa ccaagtgagg caggtcccac tgcagaggct gcggattgtg 240
cgaggcaccc agctctttga ggacaactat gccctggccg tgctagacaa tggagacccg 300
ctgaacaata ccacccctgt cacaggggcc tccccaggag gcctgcggga gctgcagctt 360
cgaagcctca cagagatctt gaaaggaggg gtcttgatcc agcggaaccc ccagctctgc 420
taccaggaca cgattttgtg gaaggacatc ttccacaaga acaaccagct ggctctcaca 480
ctgatagaca ccaaccgctc tcgggcctgc cacccctgtt ctccgatgtg taagggctcc 540
cgctgctggg gagagagttc tgaggattgt cagagcctga cgcgcactgt ctgtgccggt 600
ggctgtgccc gctgcaaggg gccactgccc actgactgct gccatgagca gtgtgctgcc 660
ggctgcacgg gccccaagca ctctgactgc ctggcctgcc tccacttcaa ccacagtggc 720
atctgtgagc tgcactgccc agccctggtc acctacaaca cagacacgtt tgagtccatg 780
cccaatcccg agggccggta tacattcggc gccagctgtg tgactgcctg tccctacaac 840
tacctttcta cggacgtggg atcctgcacc ctcgtctgcc ccctgcacaa ccaagaggtg 900
acagcagagg atggaacaca gcggtgtgag aagtgcagca agccctgtgc ccgagtgtgc 960
tatggtctgg gcatggagca cttgcgagag gtgagggcag ttaccagtgc caatatccag 1020
gagtttgctg gctgcaagaa gatctttggg agcctggcat ttctgccgga gagctttgat 1080
ggggacccag cctccaacac tgccccgctc cagccagagc agctccaagt gtttgagact 1140
ctggaagaga tcacaggtta cctatacatc tcagcatggc cggacagcct gcctgacctc 1200
agcgtcttcc agaacctgca agtaatccgg ggacgaattc tgcacgatgg cgcctactcg 1260
ctgaccctgc aagggctggg catcagctgg ctggggctgc gctcactgag ggaactgggc 1320
agtggactgg ccctcatcca ccataacacc cacctctgct tcgtgcacac ggtgccctgg 1380
gaccagctct ttcggaaccc gcaccaagct ctgctccaca ctgccaaccg gccagaggac 1440
gagtgtgtgg gcgagggcct ggcctgccac cagctgtgcg cccgagggca ctgctggggt 1500
ccagggccca cccagtgtgt caactgcagc cagttccttc ggggccagga gtgcgtggag 1560
gaatgccgag tactgcaggg gctccccagg gagtatgtga atgccaggca ctgtttgccg 1620
tgccaccctg agtgtcagcc ccagaatggc tcagtgacct gttttggacc ggaggctgac 1680
cagtgtgtgg cctgtgccca ctataaggac cctcccttct gcgtggcccg ctgccccagc 1740
ggtgtgaaac ctgacctctc ctacatgccc atctggaagt ttccagatga ggagggcgca 1800
tgccagcctt gccccatcaa ctgcacccac tcctgtgtgg acctggatga caagggctgc 1860
cccgccgagc agagagccag ccctctgacg tccatcatct ctgcggtggt tggcattctg 1920
ctggtcgtgg tcttgggggt ggtctttggg atcctcatca agcgacggca gcagaagatc 1980
cggaagtaca cgatgtga 1998

<210> SEQ ID NO 34
<211> LENGTH: 2064
<212> TYPE: DNA
<213> ORGANISM: Homo sapiens

<400> SEQUENCE: 34

```
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaacccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacaaagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga agtacacgat gtga                                          2064
```

<210> SEQ ID NO 35
<211> LENGTH: 2064
<212> TYPE: DNA
<213> ORGANISM: Homo sapiens

<400> SEQUENCE: 35

```
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaacccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgagagta atccggggac gaattctgca caatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga agtacacgat gtga                                           2064
```

<210> SEQ ID NO 36
<211> LENGTH: 2064
<212> TYPE: DNA
<213> ORGANISM: Homo sapiens

<400> SEQUENCE: 36

-continued

```
atggagctgg cggccttgtg ccgctggggg ctcctcctcg ccctcttgcc ccccggagcc     60
gcgagcaccc aagtgtgcac cggcacagac atgaagctgc ggctccctgc cagtcccgag    120
acccacctgg acatgctccg ccacctctac cagggctgcc aggtggtgca gggaaacctg    180
gaactcacct acctgcccac caatgccagc ctgtccttcc tgcaggatat ccaggaggtg    240
cagggctacg tgctcatcgc tcacaaccaa gtgaggcagg tcccactgca gaggctgcgg    300
attgtgcgag gcacccagct ctttgaggac aactatgccc tggccgtgct agacaatgga    360
gacccgctga acaataccac ccctgtcaca ggggcctccc caggaggcct gcgggagctg    420
cagcttcgaa gcctcacaga gatcttgaaa ggaggggtct tgatccagcg gaacccccag    480
ctctgctacc aggacacgat tttgtggaag gacatcttcc acaagaacaa ccagctggct    540
ctcacactga tagacaccaa ccgctctcgg gcctgccacc cctgttctcc gatgtgtaag    600
ggctcccgct gctggggaga gagttctgag gattgtcaga gcctgacgcg cactgtctgt    660
gccggtggct gtgcccgctg caaggggcca ctgcccactg actgctgcca tgagcagtgt    720
gctgccggct gcacgggccc caagcactct gactgcctgg cctgcctcca cttcaaccac    780
agtggcatct gtgagctgca ctgcccagcc ctggtcacct acaacacaga cacgtttgag    840
tccatgccca atcccgaggg ccggtataca ttcggcgcca gctgtgtgac tgcctgtccc    900
tacaactacc tttctacgga cgtgggatcc tgcaccctcg tctgccccct gcacaaccaa    960
gaggtgacag cagaggatgg aacacagcgg tgtgagaagt gcagcaagcc ctgtgcccga   1020
gtgtgctatg gtctgggcat ggagcacttg cgagaggtga gggcagttac cagtgccaat   1080
atccaggagt ttgctggctg caagaagatc tttgggagcc tggcatttct gccggagagc   1140
tttgatgggg acccagcctc caacactgcc ccgctccagc cagagcagct ccaagtgttt   1200
gagactctgg aagagatcac aggttaccta tacatctcag catggccgga cagcctgcct   1260
gacctcagcg tcttccagaa cctgcaagta atccggggac gaattctgca cgatggcgcc   1320
tactcgctga ccctgcaagg gctgggcatc agctggctgg ggctgcgctc actgagggaa   1380
ctgggcagtg gactggccct catccaccat aacacccacc tctgcttcgt gcacacggtg   1440
ccctgggacc agctctttcg gaacccgcac caagctctgc tccacactgc caaccggcca   1500
gaggacgagt gtgtgggcga gggcctggcc tgccaccagc tgtgcgcccg agggcactgc   1560
tggggtccag ggcccaccca gtgtgtcaac tgcagccagt tccttcgggg ccaggagtgc   1620
gtggaggaat gccgagtact gcaggggctc cccagggagt atgtgaatgc caggcactgt   1680
ttgccgtgcc accctgagtg tcagccccag aatggctcag tgacctgttt tggaccggag   1740
gctgaccagt gtgtggcctg tgcccactat aaggaccctc ccttctgcgt ggcccgctgc   1800
cccagcggtg tgaaacctga cctctcctac atgcccatct ggaagtttcc agatgaggag   1860
ggcgcatgcc agccttgccc catcaactgc acccactcct gtgtggacct ggatgacaag   1920
ggctgccccg ccgagcagag agccagccct ctgacgtcca tcatctctgc ggtggttggc   1980
attctgctgg tcgtggtctt gggggtggtc tttgggatcc tcatcaagcg acggcagcag   2040
aagatccgga agtacacgat gtga                                          2064
```

<210> SEQ ID NO 37
<211> LENGTH: 687
<212> TYPE: PRT
<213> ORGANISM: Ursus americanus

<400> SEQUENCE: 37

-continued

```
Met Glu Leu Ala Ala Trp Cys Arg Trp Gly Leu Leu Leu Ala Leu Leu
1               5                   10                  15

Pro Ser Gly Ala Ala Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Ala Cys Gln Val Val Gln Gly Asn Leu Glu Leu Thr Tyr
    50                  55                  60

Leu Pro Ala Asn Ala Ser Leu Ser Phe Leu Gln Asp Ile Gln Glu Val
65                  70                  75                  80

Gln Gly Tyr Val Leu Ile Ala His Ser Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Glu Pro Pro Lys Gly Asp Thr Ser
        115                 120                 125

Val Ala Gly Ala Thr Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys His Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

Gln Pro Cys Ser Pro Ala Cys Lys Asp Pro His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Lys Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Arg
                325                 330                 335

Pro Cys Ala Arg Val Cys Tyr Gly Leu Gly Met Glu His Leu Arg Glu
            340                 345                 350

Ala Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Glu Gly Asp
    370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
```

-continued

```
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ala Arg Leu Cys Phe Ile His Thr Val
465                 470                 475                 480

Pro Trp Glu Gln Leu Phe Arg Asn Pro His Gln Ala Leu Leu His Ser
                485                 490                 495

Ala Asn Arg Pro Glu Ala Glu Cys Val Gly Glu Gly Leu Ala Cys Tyr
            500                 505                 510

Pro Leu Cys Ala His Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Glu Leu His Gly Leu Pro Arg Glu Tyr Val Lys Asp Arg Tyr Cys
545                 550                 555                 560

Leu Pro Cys His Pro Glu Cys Arg Pro Gln Asn Gly Ser Val Thr Cys
                565                 570                 575

Phe Gly Ser Glu Ala Asp Gln Cys Val Ala Cys Ala His Tyr Lys Asp
            580                 585                 590

Pro Pro Ser Cys Val Ala Arg Cys Pro Ser Gly Val Lys Pro Asp Leu
        595                 600                 605

Ser Phe Met Pro Ile Trp Lys Phe Ala Asp Glu Glu Gly Thr Cys Gln
    610                 615                 620

Pro Cys Pro Ile Asn Cys Thr His Ser Cys Gly Asp Leu Asp Glu Arg
625                 630                 635                 640

Gly Cys Pro Ala Glu Gln Arg Ala Ser Pro Val Thr Ser Ile Ile Ala
                645                 650                 655

Ala Val Val Gly Ile Leu Leu Ala Val Val Met Gly Leu Val Leu Gly
            660                 665                 670

Ile Leu Ile Lys Arg Arg Arg Gln Lys Ile Arg Lys Tyr Thr Met
        675                 680                 685


<210> SEQ ID NO 38
<211> LENGTH: 665
<212> TYPE: PRT
<213> ORGANISM: Ursus americanus

<400> SEQUENCE: 38

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Ala Cys Gln
            20                  25                  30

Val Val Gln Gly Asn Leu Glu Leu Thr Tyr Leu Pro Ala Asn Ala Ser
        35                  40                  45

Leu Ser Phe Leu Gln Asp Ile Gln Glu Val Gln Gly Tyr Val Leu Ile
    50                  55                  60

Ala His Ser Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Glu Pro Pro Lys Gly Asp Thr Ser Val Ala Gly Ala Thr Pro
            100                 105                 110
```

```
Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys His Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys Gln Pro Cys Ser Pro Ala
                165                 170                 175

Cys Lys Asp Pro His Cys Trp Gly Ala Ser Ser Gly Asp Cys Gln Ser
            180                 185                 190

Leu Thr Arg Thr Val Cys Ala Gly Gly Cys Ala Arg Cys Lys Gly Pro
        195                 200                 205

Lys Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu Asn Asn Gln Glu Val Thr Ala Glu Asp
    290                 295                 300

Gly Thr Gln Arg Cys Glu Lys Cys Ser Arg Pro Cys Ala Arg Val Cys
305                 310                 315                 320

Tyr Gly Leu Gly Met Glu His Leu Arg Glu Ala Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Glu Gly Asp Pro Ala Ser Asn Thr Ala
        355                 360                 365

Pro Leu Gln Pro Glu Gln Leu Arg Val Phe Glu Ala Leu Glu Glu Ile
    370                 375                 380

Thr Gly Tyr Leu Tyr Ile Ser Ala Trp Pro Asp Ser Leu Pro Asn Leu
385                 390                 395                 400

Ser Val Phe Gln Asn Leu Arg Val Ile Arg Gly Arg Val Leu His Asp
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His Arg
        435                 440                 445

Asn Ala Arg Leu Cys Phe Ile His Thr Val Pro Trp Glu Gln Leu Phe
    450                 455                 460

Arg Asn Pro His Gln Ala Leu Leu His Ser Ala Asn Arg Pro Glu Ala
465                 470                 475                 480

Glu Cys Val Gly Glu Gly Leu Ala Cys Tyr Pro Leu Cys Ala His Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Glu Leu His Gly Leu
        515                 520                 525

Pro Arg Glu Tyr Val Lys Asp Arg Tyr Cys Leu Pro Cys His Pro Glu
```

```
    530                 535                 540

Cys Arg Pro Gln Asn Gly Ser Val Thr Cys Phe Gly Ser Glu Ala Asp
545                 550                 555                 560

Gln Cys Val Ala Cys Ala His Tyr Lys Asp Pro Pro Ser Cys Val Ala
                565                 570                 575

Arg Cys Pro Ser Gly Val Lys Pro Asp Leu Ser Phe Met Pro Ile Trp
            580                 585                 590

Lys Phe Ala Asp Glu Glu Gly Thr Cys Gln Pro Cys Pro Ile Asn Cys
        595                 600                 605

Thr His Ser Cys Gly Asp Leu Asp Glu Arg Gly Cys Pro Ala Glu Gln
    610                 615                 620

Arg Ala Ser Pro Val Thr Ser Ile Ile Ala Ala Val Val Gly Ile Leu
625                 630                 635                 640

Leu Ala Val Val Met Gly Leu Val Leu Gly Ile Leu Ile Lys Arg Arg
                645                 650                 655

Arg Gln Lys Ile Arg Lys Tyr Thr Met
            660                 665


<210> SEQ ID NO 39
<211> LENGTH: 687
<212> TYPE: PRT
<213> ORGANISM: Felis catus

<400> SEQUENCE: 39

Met Glu Leu Ala Ala Trp Cys Arg Trp Gly Leu Leu Leu Ala Leu Leu
1               5                   10                  15

Pro Ser Gly Ala Thr Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu His Ala Asn Ala Ser Leu Ser Phe Leu Gln Asp Ile Gln Glu Val
65                  70                  75                  80

Gln Gly Tyr Val Leu Ile Ala His Asn Gln Val Lys Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asp Ser Gly Thr Pro
        115                 120                 125

Ala Thr Gly Ala Ala Leu Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys His Gln Asp Thr Ile Leu Trp Lys Asp Ile Phe His Lys Asn
                165                 170                 175

Asn Gln Leu Ala Leu Met Leu Ile Asp Thr Asn Arg Ser Arg Ala Cys
            180                 185                 190

Gln Pro Cys Ser Pro Ala Cys Lys Asp Ser His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Gln Pro Thr Asp Cys Cys His Glu Gln Cys
225                 230                 235                 240
```

-continued

```
Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Ala Arg Ala Val Thr Ser Ala Asn Ile Gln Glu Phe Val Gly Cys Lys
        355                 360                 365

Lys Ile Phe Gly Ser Leu Ala Phe Leu Pro Glu Ser Phe Glu Gly Asp
    370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ser Arg Leu Cys Phe Val His Thr Val
465                 470                 475                 480

Pro Trp Asp Gln Leu Phe Arg Asn Pro His Gln Ala Leu Leu His Ser
                485                 490                 495

Ala Asn Arg Pro Glu Asp Glu Cys Ala Gly Glu Gly Leu Ala Cys Tyr
            500                 505                 510

Pro Leu Cys Ala His Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Lys Asp Arg Phe Cys
545                 550                 555                 560

Leu Pro Cys His Pro Glu Cys Gln Pro Gln Asn Gly Ser Val Thr Cys
                565                 570                 575

Leu Gly Ser Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Phe Met Pro Ile Trp Lys Phe Ala Asp Glu Glu Gly Thr Cys Gln
    610                 615                 620

Pro Cys Pro Ile Asn Cys Thr His Ser Cys Ala Asp Leu Asp Glu Lys
625                 630                 635                 640

Gly Cys Pro Ala Glu Gln Arg Ala Ser Pro Val Thr Ser Ile Ile Ala
                645                 650                 655

Ala Val Val Gly Ile Leu Leu Val Val Val Val Gly Leu Val Leu Gly
```

```
            660                 665                 670

Ile Leu Ile Lys Arg Arg Arg Gln Lys Ile Arg Lys Tyr Thr Met
        675                 680                 685


<210> SEQ ID NO 40
<211> LENGTH: 665
<212> TYPE: PRT
<213> ORGANISM: Felis catus

<400> SEQUENCE: 40

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu His Ala Asn Ala Ser
        35                  40                  45

Leu Ser Phe Leu Gln Asp Ile Gln Glu Val Gln Gly Tyr Val Leu Ile
    50                  55                  60

Ala His Asn Gln Val Lys Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asp Ser Gly Thr Pro Ala Thr Gly Ala Ala Leu
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys His Gln Asp Thr
    130                 135                 140

Ile Leu Trp Lys Asp Ile Phe His Lys Asn Asn Gln Leu Ala Leu Met
145                 150                 155                 160

Leu Ile Asp Thr Asn Arg Ser Arg Ala Cys Gln Pro Cys Ser Pro Ala
                165                 170                 175

Cys Lys Asp Ser His Cys Trp Gly Ala Ser Ser Gly Asp Cys Gln Ser
            180                 185                 190

Leu Thr Arg Thr Val Cys Ala Gly Gly Cys Ala Arg Cys Lys Gly Pro
        195                 200                 205

Gln Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu Asn Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Ala Arg Ala Val Thr Ser
                325                 330                 335

Ala Asn Ile Gln Glu Phe Val Gly Cys Lys Lys Ile Phe Gly Ser Leu
            340                 345                 350
```

-continued

```
Ala Phe Leu Pro Glu Ser Phe Glu Gly Asp Pro Ala Ser Asn Thr Ala
        355                 360                 365

Pro Leu Gln Pro Glu Gln Leu Arg Val Phe Glu Ala Leu Glu Glu Ile
    370                 375                 380

Thr Gly Tyr Leu Tyr Ile Ser Ala Trp Pro Asp Ser Leu Pro Asn Leu
385                 390                 395                 400

Ser Val Phe Gln Asn Leu Arg Val Ile Arg Gly Arg Val Leu His Asp
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His Arg
        435                 440                 445

Asn Ser Arg Leu Cys Phe Val His Thr Val Pro Trp Asp Gln Leu Phe
    450                 455                 460

Arg Asn Pro His Gln Ala Leu Leu His Ser Ala Asn Arg Pro Glu Asp
465                 470                 475                 480

Glu Cys Ala Gly Glu Gly Leu Ala Cys Tyr Pro Leu Cys Ala His Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Lys Asp Arg Phe Cys Leu Pro Cys His Pro Glu
    530                 535                 540

Cys Gln Pro Gln Asn Gly Ser Val Thr Cys Leu Gly Ser Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Phe Met Pro Ile Trp
            580                 585                 590

Lys Phe Ala Asp Glu Glu Gly Thr Cys Gln Pro Cys Pro Ile Asn Cys
        595                 600                 605

Thr His Ser Cys Ala Asp Leu Asp Glu Lys Gly Cys Pro Ala Glu Gln
    610                 615                 620

Arg Ala Ser Pro Val Thr Ser Ile Ile Ala Ala Val Val Gly Ile Leu
625                 630                 635                 640

Leu Val Val Val Val Gly Leu Val Leu Gly Ile Leu Ile Lys Arg Arg
                645                 650                 655

Arg Gln Lys Ile Arg Lys Tyr Thr Met
            660                 665


<210> SEQ ID NO 41
<211> LENGTH: 2061
<212> TYPE: DNA
<213> ORGANISM: Ursus americanus

<400> SEQUENCE: 41

atggagctgg cggcctggtg ccgctggggg ctcctcctcg ccctcctgcc ctccggagcc      60

gcgggcaccc aagtgtgcac cggcacagac atgaagctgc ggctccctgc cagtcccgag     120

acccacctgg atatgctccg ccacctctac caggcctgtc aagtggtaca gggtaacctg     180

gagctcacct acctgcccgc caatgccagc ctgtccttcc tgcaggatat ccaggaggta     240

cagggctatg tgctcattgc tcacagccaa gtgagacagg tcccgctgca gaggctccga     300

atcgtgcgag gcacccagct ctttgaggac aactacgccc tggccgtgct ggacaatgga     360
```

```
gagccgccca agggggacac ctctgtggca ggggctaccc caggagggct gcgggagctg    420

cagcttcgaa gcctcacaga gatcctgaag ggaggggtct tgattcagcg gaacccacag    480

ctctgccacc aggacacgat tttgtggaag gacatcttcc acaagaacaa ccagctggcc    540

ctcacgctga tagacaccaa ccgctctcgg gcctgccaac cctgttctcc agcctgtaaa    600

gacccccact gctggggagc aagttccggg gactgtcaga gcttgacacg aaccgtctgt    660

gccggcggct gtgcccgctg caagggccca aaacccactg actgctgcca tgagcagtgc    720

gcggctggct gcacgggccc caagcactcg gactgcctgg cctgccttca cttcaaccac    780

agtggcatct gtgagctgca ctgcccagcc ctggtcacct acaacacgga cacgttcgaa    840

tccatgccca accctgaggg ccgatacacc ttcggtgcca gctgtgtgac cgcctgtccc    900

tacaactacc tgtccacgga cgtgggatcc tgcaccctgg tctgtcccct gaacaaccaa    960

gaggtgacgg ctgaggatgg cacccagcgg tgtgagaaat gcagcagacc ctgtgcccga   1020

gtgtgctatg gtctgggcat ggagcacctg cgggaggcga gggcggtcac cagcgccaac   1080

atccaagagt tcgccggctg caagaagatc tttgggagcc tggcgtttct gccagagagc   1140

ttcgagggag acccagcctc caacactgcc cccctgcagc ctgaacagct cagagtgttc   1200

gaggccctgg aggagatcac aggttacctg tatatctcag cgtggccgga cagcttgcct   1260

aacctcagtg tcttccagaa cctgcgagta atccggggac gagttctgca tgatggcgcc   1320

tactcgctga ccctgcaagg gctgggcatc agctggctgg ggctgcgctc gctgcgggaa   1380

ctgggcagcg ggctggccct catccaccgc aacgcccgcc tctgcttcat ccacacggtg   1440

ccctgggagc agctcttccg gaacccccac caagccctgc tgcacagtgc caaccggccg   1500

gaggccgagt gcgtgggcga gggcctggcc tgctacccgc tgtgcgccca tgggcactgc   1560

tggggtccgg ggcccaccca gtgcgtcaac tgcagccaat tccttcgggg ccaggagtgc   1620

gtggaggaat gccgagaact gcacgggcta ccccgggaat atgtgaagga cagatactgt   1680

ctgccatgcc accccgagtg tcggccccag aatggctcag tgacctgctt tgggtcggag   1740

gctgaccagt gtgtggcctg cgcccactac aaggaccctc cctcctgcgt ggctcgctgc   1800

cccagtggtg tgaaacccga cctctctttc atgcccattt ggaagtttgc agatgaggag   1860

ggcacatgcc agccgtgccc catcaactgc acccactcct gtggggacct ggacgagagg   1920

ggctgccccg ccgaacagag agccagccct gtgacatcca tcattgccgc tgtggtgggc   1980

attctgctgg ccgtggtcat ggggctggtc ctcggcatcc tgatcaagcg aaggcgacag   2040

aagatccgga agtacacgat g                                             2061
```

<210> SEQ ID NO 42
<211> LENGTH: 1995
<212> TYPE: DNA
<213> ORGANISM: Ursus americanus

<400> SEQUENCE: 42

```
acccaagtgt gcaccggcac agacatgaag ctgcggctcc ctgccagtcc cgagacccac     60

ctggatatgc tccgccacct ctaccaggcc tgtcaagtgg tacagggtaa cctggagctc    120

acctacctgc ccgccaatgc cagcctgtcc ttcctgcagg atatccagga ggtacagggc    180

tatgtgctca ttgctcacag ccaagtgaga caggtcccgc tgcagaggct ccgaatcgtg    240

cgaggcaccc agctctttga ggacaactac gccctggccg tgctggacaa tggagagccg    300

cccaaggggg acacctctgt ggcaggggct accccaggag ggctgcggga gctgcagctt    360
```

```
cgaagcctca cagagatcct gaagggaggg gtcttgattc agcggaaccc acagctctgc    420
caccaggaca cgattttgtg gaaggacatc ttccacaaga acaaccagct ggccctcacg    480
ctgatagaca ccaaccgctc tcgggcctgc caaccctgtt ctccagcctg taaagacccc    540
cactgctggg gagcaagttc cggggactgt cagagcttga cacgaaccgt ctgtgccggc    600
ggctgtgccc gctgcaaggg cccaaaaccc actgactgct gccatgagca gtgcgcggct    660
ggctgcacgg gccccaagca ctcggactgc ctggcctgcc ttcacttcaa ccacagtggc    720
atctgtgagc tgcactgccc agccctggtc acctacaaca cggacacgtt cgaatccatg    780
cccaaccctg agggccgata caccttcggt gccagctgtg tgaccgcctg tccctacaac    840
tacctgtcca cggacgtggg atcctgcacc ctggtctgtc ccctgaacaa ccaagaggtg    900
acggctgagg atggcaccca gcggtgtgag aaatgcagca gaccctgtgc ccgagtgtgc    960
tatggtctgg gcatggagca cctgcgggag gcgagggcgg tcaccagcgc caacatccaa   1020
gagttcgccg gctgcaagaa gatctttggg agcctggcgt ttctgccaga gagcttcgag   1080
ggagacccag cctccaacac tgcccccctg cagcctgaac agctcagagt gttcgaggcc   1140
ctggaggaga tcacaggtta cctgtatatc tcagcgtggc cggacagctt gcctaacctc   1200
agtgtcttcc agaacctgcg agtaatccgg ggacgagttc tgcatgatgg cgcctactcg   1260
ctgaccctgc aagggctggg catcagctgg ctggggctgc gctcgctgcg ggaactgggc   1320
agcgggctgg ccctcatcca ccgcaacgcc cgcctctgct tcatccacac ggtgccctgg   1380
gagcagctct tccggaaccc ccaccaagcc ctgctgcaca gtgccaaccg gccggaggcc   1440
gagtgcgtgg gcgagggcct ggcctgctac ccgctgtgcg cccatgggca ctgctggggt   1500
ccggggccca cccagtgcgt caactgcagc caattccttc ggggccagga gtgcgtggag   1560
gaatgccgag aactgcacgg gctaccccgg gaatatgtga aggacagata ctgtctgcca   1620
tgccaccccg agtgtcggcc ccagaatggc tcagtgacct gctttgggtc ggaggctgac   1680
cagtgtgtgg cctgcgccca ctacaaggac cctccctcct gcgtggctcg ctgccccagt   1740
ggtgtgaaac ccgacctctc tttcatgccc atttggaagt ttgcagatga ggagggcaca   1800
tgccagccgt gccccatcaa ctgcacccac tcctgtgggg acctggacga gaggggctgc   1860
cccgccgaac agagagccag ccctgtgaca tccatcattg ccgctgtggt gggcattctg   1920
ctggccgtgg tcatggggct ggtcctcggc atcctgatca agcgaaggcg acagaagatc   1980
cggaagtaca cgatg                                                    1995
```

<210> SEQ ID NO 43
<211> LENGTH: 2061
<212> TYPE: DNA
<213> ORGANISM: Felis catus

<400> SEQUENCE: 43

```
atggagctgg cggcctggtg ccgctggggg ctcctcctcg ccctcctgcc ctccggagcc     60
acgggcaccc aagtgtgcac cggcacagac atgaagctgc ggctcccagc cagtcccgag    120
acccacctgg acatgctccg ccacctctac cagggctgtc aagtggtaca gggcaacctg    180
gagctcacct acctgcatgc caatgccagc ctctccttcc tgcaggatat ccaggaggtg    240
caaggctatg tgctcattgc ccacaaccaa gtgaaacagg tcccactgca gaggctacga    300
atcgtgcgag gcacccagct ctttgaggac aactacgccc tggccgtgct ggacaacgga    360
gacccactgg acagtggcac ccctgctaca ggggctgccc taggagggct gcgggagctg    420
cagctccgaa gcctcacaga gatcctgaag ggaggggtcc tcattcagcg gaacccgcag    480
```

```
ctctgccacc aggacacgat tctgtggaag gacatcttcc acaagaacaa ccagctggcc    540
ctcatgctga tagacaccaa ccgctctcgg gcctgccaac cctgttctcc agcttgtaaa    600
gactcccact gctggggagc aagttccggg gactgtcaga gcttgactcg aactgtctgt    660
gctggcggct gtgcccgctg caagggcccg cagcccaccg actgctgcca cgagcaatgt    720
gctgctggct gcacgggccc caagcattct gactgcctgg cctgcctcca cttcaaccac    780
agtggcatct gtgagctgca ctgcccagcc ctggtcacct acaacacgga caccttcgaa    840
tccatgccca accctgaggg ccgttatacc ttcggtgcca gctgtgtgac tgcctgtccc    900
tacaactacc tgtctacgga cgtgggatcc tgcaccctgg tctgtcccct gaacaaccaa    960
gaggtgacag ctgaggatgg aacacagcgg tgtgagaaat gcagcaagcc ctgtgcccga   1020
gtgtgctacg gcctaggcat ggagcacctg cgggaggcga gggcagtcac cagtgccaac   1080
atccaagaat ttgtcggctg caagaagatc tttgggagcc tggcgtttct gccagagagc   1140
tttgaggggg acccagcctc caacactgcc cccctgcagc ctgagcagct cagagtgttt   1200
gaggctctgg aggagattac aggttacctg tacatctcag cgtggccaga cagcttgcct   1260
aacctcagtg tcttccagaa cctcagagtg atccggggcc gagttctgca tgacggtgct   1320
tactcgctga cccttcaagg gctgggcatc agctggctgg ggctgcgctc gctgcgggag   1380
ctgggcagtg ggctggccct catccaccgc aactcccgcc tctgcttcgt acacacggtg   1440
ccctgggacc agctcttccg gaacccccac caggccctgc tccacagcgc caaccggcca   1500
gaggacgagt gcgcgggtga gggcctggcc tgctatccgc tgtgtgccca cgggcactgc   1560
tggggtccgg gacccaccca gtgtgtcaac tgcagccagt tccttcgggg ccaggagtgc   1620
gtggaggaat gccgagtatt gcaggggctt ccccgggagt atgtgaagga taggttctgt   1680
ctgccatgcc acccggagtg tcagccccag aatggctcag tgacctgctt gggctcggaa   1740
gctgaccagt gtgtggcctg tgcccactac aaggaccctc ctttctgtgt ggctcgctgc   1800
cccagtgggg tgaaacctga cctctccttc atgcccatct ggaagttcgc agatgaggag   1860
ggcacgtgcc agccatgccc catcaactgc acccactcct gtgcggacct ggacgagaag   1920
ggctgccccg ccgagcagag agccagccct gtgacgtcca tcattgctgc tgtggtgggc   1980
attctgctgg tcgtggttgt ggggctggtc cttggcatcc taatcaagcg aaggcggcag   2040
aagatccgga agtacacgat g                                               2061
```

<210> SEQ ID NO 44
<211> LENGTH: 1995
<212> TYPE: DNA
<213> ORGANISM: Felis catus

<400> SEQUENCE: 44

```
acccaagtgt gcaccggcac agacatgaag ctgcggctcc cagccagtcc cgagacccac     60
ctggacatgc tccgccacct ctaccagggc tgtcaagtgg tacagggcaa cctggagctc    120
acctacctgc atgccaatgc cagcctctcc ttcctgcagg atatccagga ggtgcaaggc    180
tatgtgctca ttgcccacaa ccaagtgaaa caggtcccac tgcagaggct acgaatcgtg    240
cgaggcaccc agctctttga ggacaactac gccctggccg tgctggacaa cggagaccca    300
ctggacagtg gcacccctgc tacaggggct gccctaggag ggctgcggga gctgcagctc    360
cgaagcctca cagagatcct gaagggaggg gtcctcattc agcggaaccc gcagctctgc    420
caccaggaca cgattctgtg gaaggacatc ttccacaaga acaaccagct ggccctcatg    480
```

-continued

```
ctgatagaca ccaaccgctc tcgggcctgc caaccctgtt ctccagcttg taaagactcc    540

cactgctggg gagcaagttc cggggactgt cagagcttga ctcgaactgt ctgtgctggc    600

ggctgtgccc gctgcaaggg cccgcagccc accgactgct gccacgagca atgtgctgct    660

ggctgcacgg gccccaagca ttctgactgc ctggcctgcc tccacttcaa ccacagtggc    720

atctgtgagc tgcactgccc agccctggtc acctacaaca cggacacctt cgaatccatg    780

cccaaccctg agggccgtta taccttcggt gccagctgtg tgactgcctg tccctacaac    840

tacctgtcta cggacgtggg atcctgcacc ctggtctgtc ccctgaacaa ccaagaggtg    900

acagctgagg atggaacaca gcggtgtgag aaatgcagca agccctgtgc ccgagtgtgc    960

tacggcctag gcatggagca cctgcgggag gcgagggcag tcaccagtgc caacatccaa   1020

gaatttgtcg gctgcaagaa gatctttggg agcctggcgt ttctgccaga gagctttgag   1080

ggggacccag cctccaacac tgcccccctg cagcctgagc agctcagagt gtttgaggct   1140

ctggaggaga ttacaggtta cctgtacatc tcagcgtggc cagacagctt gcctaacctc   1200

agtgtcttcc agaacctcag agtgatccgg ggccgagttc tgcatgacgg tgcttactcg   1260

ctgacccttc aagggctggg catcagctgg ctggggctgc gctcgctgcg ggagctgggc   1320

agtgggctgg ccctcatcca ccgcaactcc cgcctctgct tcgtacacac ggtgccctgg   1380

gaccagctct tccggaaccc ccaccaggcc ctgctccaca gcgccaaccg gccagaggac   1440

gagtgcgcgg gtgagggcct ggcctgctat ccgctgtgtg cccacgggca ctgctggggt   1500

ccgggaccca cccagtgtgt caactgcagc cagttccttc ggggccagga gtgcgtggag   1560

gaatgccgag tattgcaggg gcttccccgg gagtatgtga aggataggtt ctgtctgcca   1620

tgccacccgg agtgtcagcc ccagaatggc tcagtgacct gcttgggctc ggaagctgac   1680

cagtgtgtgg cctgtgccca ctacaaggac cctccctttct gtgtggctcg ctgccccagt   1740

ggggtgaaac ctgacctctc cttcatgccc atctggaagt tcgcagatga ggagggcacg   1800

tgccagccat gccccatcaa ctgcacccac tcctgtgcgg acctggacga gaagggctgc   1860

cccgccgagc agagagccag ccctgtgacg tccatcattg ctgctgtggt gggcattctg   1920

ctggtcgtgg ttgtggggct ggtccttggc atcctaatca agcgaaggcg gcagaagatc   1980

cggaagtaca cgatg                                                    1995
```

<210> SEQ ID NO 45
<211> LENGTH: 687
<212> TYPE: PRT
<213> ORGANISM: Homo sapiens

<400> SEQUENCE: 45

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
```

-continued

```
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525
```

```
Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 46
<211> LENGTH: 665
<212> TYPE: PRT
<213> ORGANISM: Homo sapiens

<400> SEQUENCE: 46

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
```

-continued

```
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
    450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr Ser Ile Ile Ser Ala Val Val Gly Ile Leu
625                 630                 635                 640
```

Leu Val Val Val Leu Gly Val Val Phe Gly Ile Leu Ile Lys Arg Arg
645 650 655

Gln Gln Lys Ile Arg Lys Tyr Thr Met
660 665

<210> SEQ ID NO 47
<211> LENGTH: 688
<212> TYPE: PRT
<213> ORGANISM: Mus musculus

<400> SEQUENCE: 47

Met Glu Leu Ala Ala Trp Cys Arg Trp Gly Phe Leu Leu Ala Leu Leu
1 5 10 15

Ser Pro Gly Ala Ala Gly Thr Gln Val Cys Thr Gly Thr Asp Met Lys
20 25 30

Leu Arg Leu Pro Ala Ser Pro Glu Thr His Leu Asp Met Leu Arg His
35 40 45

Leu Tyr Gln Gly Cys Gln Val Val Gln Gly Asn Leu Glu Leu Thr Tyr
50 55 60

Leu Pro Ala Asn Ala Ser Leu Ser Phe Leu Gln Asp Ile Gln Glu Val
65 70 75 80

Gln Gly Tyr Met Leu Ile Ala His Asn Arg Val Lys His Val Pro Leu
85 90 95

Gln Arg Leu Arg Ile Val Arg Gly Thr Gln Leu Phe Glu Asp Lys Tyr
100 105 110

Ala Leu Ala Val Leu Asp Asn Arg Asp Pro Leu Asp Asn Val Thr Thr
115 120 125

Ala Ala Pro Gly Arg Thr Pro Glu Gly Leu Arg Glu Leu Gln Leu Arg
130 135 140

Ser Leu Thr Glu Ile Leu Lys Gly Gly Val Leu Ile Arg Gly Asn Pro
145 150 155 160

Gln Leu Cys Tyr Gln Asp Met Val Leu Trp Lys Asp Val Leu Arg Lys
165 170 175

Asn Asn Gln Leu Ala Pro Val Asp Met Asp Thr Asn Arg Ser Arg Ala
180 185 190

Cys Pro Pro Cys Ala Pro Thr Cys Lys Asp Asn His Cys Trp Gly Glu
195 200 205

Ser Pro Glu Asp Cys Gln Ile Leu Thr Gly Thr Ile Cys Thr Ser Gly
210 215 220

Cys Ala Arg Cys Lys Gly Arg Leu Pro Thr Asp Cys Cys His Glu Gln
225 230 235 240

Cys Ala Ala Gly Cys Thr Gly Pro Lys His Ser Asp Cys Leu Ala Cys
245 250 255

Leu His Phe Asn His Ser Gly Ile Cys Glu Leu His Cys Pro Ala Leu
260 265 270

Ile Thr Tyr Asn Thr Asp Thr Phe Glu Ser Met Leu Asn Pro Glu Gly
275 280 285

Arg Tyr Thr Phe Gly Ala Ser Cys Val Thr Thr Cys Pro Tyr Asn Tyr
290 295 300

Leu Ser Thr Glu Val Gly Ser Cys Thr Leu Val Cys Pro Pro Asn Asn
305 310 315 320

Gln Glu Val Thr Ala Glu Asp Gly Thr Gln Arg Cys Glu Lys Cys Ser
325 330 335

Lys Pro Cys Ala Gly Val Cys Tyr Gly Leu Gly Met Glu His Leu Arg

-continued

```
            340                 345                 350

Gly Ala Arg Ala Ile Thr Ser Asp Asn Ile Gln Glu Phe Ala Gly Cys
        355                 360                 365

Lys Lys Ile Phe Gly Ser Leu Ala Phe Leu Pro Glu Ser Phe Asp Gly
    370                 375                 380

Asn Pro Ser Ser Gly Val Ala Pro Leu Lys Pro Glu His Leu Gln Val
385                 390                 395                 400

Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
            420                 425                 430

Arg Gly Arg Ile Leu His Asp Gly Ala Tyr Ser Leu Thr Leu Gln Gly
        435                 440                 445

Leu Gly Ile His Ser Leu Gly Leu Arg Ser Leu Arg Glu Leu Gly Ser
    450                 455                 460

Gly Leu Ala Leu Ile His Arg Asn Thr His Leu Cys Phe Val Asn Thr
465                 470                 475                 480

Val Pro Trp Asp Gln Leu Phe Arg Asn Pro His Gln Ala Leu Leu His
                485                 490                 495

Ser Gly Asn Arg Pro Glu Glu Ala Cys Gly Leu Glu Gly Leu Val Cys
            500                 505                 510

Asn Ser Leu Cys Ala Arg Gly His Cys Trp Gly Pro Gly Pro Thr Gln
        515                 520                 525

Cys Val Asn Cys Ser Gln Phe Leu Arg Gly Gln Glu Cys Val Glu Glu
    530                 535                 540

Cys Arg Val Trp Lys Gly Leu Pro Arg Glu Tyr Val Arg Gly Lys His
545                 550                 555                 560

Cys Leu Pro Cys His Pro Glu Cys Gln Pro Gln Asn Ser Ser Glu Thr
                565                 570                 575

Cys Tyr Gly Ser Glu Ala Asp Gln Cys Glu Ala Cys Ala His Tyr Lys
            580                 585                 590

Asp Ser Ser Ser Cys Val Ala Arg Cys Pro Ser Gly Val Lys Pro Asp
        595                 600                 605

Leu Ser Tyr Met Pro Ile Trp Lys Tyr Pro Asp Glu Glu Gly Ile Cys
    610                 615                 620

Gln Pro Cys Pro Ile Asn Cys Thr His Ser Cys Val Asp Leu Asp Glu
625                 630                 635                 640

Arg Gly Cys Pro Ala Glu Gln Arg Ala Ser Pro Val Thr Phe Ile Ile
                645                 650                 655

Ala Thr Val Val Gly Val Leu Leu Phe Leu Ile Ile Val Val Val Ile
            660                 665                 670

Gly Ile Leu Ile Lys Arg Arg Arg Gln Lys Ile Arg Lys Tyr Thr Met
        675                 680                 685


<210> SEQ ID NO 48
<211> LENGTH: 666
<212> TYPE: PRT
<213> ORGANISM: Mus musculus

<400> SEQUENCE: 48

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30
```

-continued

```
Val Val Gln Gly Asn Leu Glu Leu Thr Tyr Leu Pro Ala Asn Ala Ser
        35                  40                  45

Leu Ser Phe Leu Gln Asp Ile Gln Glu Val Gln Gly Tyr Met Leu Ile
    50                  55                  60

Ala His Asn Arg Val Lys His Val Pro Leu Gln Arg Leu Arg Ile Val
65                  70                  75                  80

Arg Gly Thr Gln Leu Phe Glu Asp Lys Tyr Ala Leu Ala Val Leu Asp
                85                  90                  95

Asn Arg Asp Pro Leu Asp Asn Val Thr Thr Ala Ala Pro Gly Arg Thr
            100                 105                 110

Pro Glu Gly Leu Arg Glu Leu Gln Leu Arg Ser Leu Thr Glu Ile Leu
        115                 120                 125

Lys Gly Gly Val Leu Ile Arg Gly Asn Pro Gln Leu Cys Tyr Gln Asp
    130                 135                 140

Met Val Leu Trp Lys Asp Val Leu Arg Lys Asn Asn Gln Leu Ala Pro
145                 150                 155                 160

Val Asp Met Asp Thr Asn Arg Ser Arg Ala Cys Pro Pro Cys Ala Pro
                165                 170                 175

Thr Cys Lys Asp Asn His Cys Trp Gly Glu Ser Pro Glu Asp Cys Gln
            180                 185                 190

Ile Leu Thr Gly Thr Ile Cys Thr Ser Gly Cys Ala Arg Cys Lys Gly
        195                 200                 205

Arg Leu Pro Thr Asp Cys Cys His Glu Gln Cys Ala Ala Gly Cys Thr
    210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Ile Thr Tyr Asn Thr Asp
                245                 250                 255

Thr Phe Glu Ser Met Leu Asn Pro Glu Gly Arg Tyr Thr Phe Gly Ala
            260                 265                 270

Ser Cys Val Thr Thr Cys Pro Tyr Asn Tyr Leu Ser Thr Glu Val Gly
        275                 280                 285

Ser Cys Thr Leu Val Cys Pro Pro Asn Asn Gln Glu Val Thr Ala Glu
    290                 295                 300

Asp Gly Thr Gln Arg Cys Glu Lys Cys Ser Lys Pro Cys Ala Gly Val
305                 310                 315                 320

Cys Tyr Gly Leu Gly Met Glu His Leu Arg Gly Ala Arg Ala Ile Thr
                325                 330                 335

Ser Asp Asn Ile Gln Glu Phe Ala Gly Cys Lys Lys Ile Phe Gly Ser
            340                 345                 350

Leu Ala Phe Leu Pro Glu Ser Phe Asp Gly Asn Pro Ser Ser Gly Val
        355                 360                 365

Ala Pro Leu Lys Pro Glu His Leu Gln Val Phe Glu Thr Leu Glu Glu
    370                 375                 380

Ile Thr Gly Tyr Leu Tyr Ile Ser Ala Trp Pro Glu Ser Phe Gln Asp
385                 390                 395                 400

Leu Ser Val Phe Gln Asn Leu Arg Val Ile Arg Gly Arg Ile Leu His
                405                 410                 415

Asp Gly Ala Tyr Ser Leu Thr Leu Gln Gly Leu Gly Ile His Ser Leu
            420                 425                 430

Gly Leu Arg Ser Leu Arg Glu Leu Gly Ser Gly Leu Ala Leu Ile His
        435                 440                 445

Arg Asn Thr His Leu Cys Phe Val Asn Thr Val Pro Trp Asp Gln Leu
```

```
    450                 455                 460

Phe Arg Asn Pro His Gln Ala Leu Leu His Ser Gly Asn Arg Pro Glu
465                 470                 475                 480

Glu Ala Cys Gly Leu Glu Gly Leu Val Cys Asn Ser Leu Cys Ala Arg
                485                 490                 495

Gly His Cys Trp Gly Pro Gly Pro Thr Gln Cys Val Asn Cys Ser Gln
            500                 505                 510

Phe Leu Arg Gly Gln Glu Cys Val Glu Glu Cys Arg Val Trp Lys Gly
        515                 520                 525

Leu Pro Arg Glu Tyr Val Arg Gly Lys His Cys Leu Pro Cys His Pro
    530                 535                 540

Glu Cys Gln Pro Gln Asn Ser Ser Glu Thr Cys Tyr Gly Ser Glu Ala
545                 550                 555                 560

Asp Gln Cys Glu Ala Cys Ala His Tyr Lys Asp Ser Ser Ser Cys Val
                565                 570                 575

Ala Arg Cys Pro Ser Gly Val Lys Pro Asp Leu Ser Tyr Met Pro Ile
            580                 585                 590

Trp Lys Tyr Pro Asp Glu Glu Gly Ile Cys Gln Pro Cys Pro Ile Asn
        595                 600                 605

Cys Thr His Ser Cys Val Asp Leu Asp Glu Arg Gly Cys Pro Ala Glu
    610                 615                 620

Gln Arg Ala Ser Pro Val Thr Phe Ile Ile Ala Thr Val Val Gly Val
625                 630                 635                 640

Leu Leu Phe Leu Ile Ile Val Val Val Ile Gly Ile Leu Ile Lys Arg
                645                 650                 655

Arg Arg Gln Lys Ile Arg Lys Tyr Thr Met
            660                 665


<210> SEQ ID NO 49
<211> LENGTH: 691
<212> TYPE: PRT
<213> ORGANISM: Rattus norvegicus

<400> SEQUENCE: 49

Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
            20                  25                  30

Asp Met Lys Leu Arg Leu Pro Ala Ser Pro Glu Thr His Leu Asp Met
        35                  40                  45

Leu Arg His Leu Tyr Gln Gly Cys Gln Val Val Gln Gly Asn Leu Glu
    50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
        115                 120                 125

Val Ala Ala Ser Thr Pro Gly Arg Thr Pro Glu Gly Leu Arg Glu Leu
    130                 135                 140

Gln Leu Arg Ser Leu Thr Glu Ile Leu Lys Gly Gly Val Leu Ile Arg
145                 150                 155                 160
```

-continued

```
Gly Asn Pro Gln Leu Cys Tyr Gln Asp Met Val Leu Trp Lys Asp Val
                165                 170                 175

Phe Arg Lys Asn Asn Gln Leu Ala Pro Val Asp Ile Asp Thr Asn Arg
            180                 185                 190

Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
                245                 250                 255

Leu Ala Cys Leu His Phe Asn His Ser Gly Ile Cys Glu Leu His Cys
            260                 265                 270

Pro Ala Leu Val Thr Tyr Asn Thr Asp Thr Phe Glu Ser Met His Asn
        275                 280                 285

Pro Glu Gly Arg Tyr Thr Phe Gly Ala Ser Cys Val Thr Thr Cys Pro
    290                 295                 300

Tyr Asn Tyr Leu Ser Thr Glu Val Gly Ser Cys Thr Leu Val Cys Pro
305                 310                 315                 320

Pro Asn Asn Gln Glu Val Thr Ala Glu Asp Gly Thr Gln Arg Cys Glu
                325                 330                 335

Lys Cys Ser Lys Pro Cys Ala Arg Val Cys Tyr Gly Leu Gly Met Glu
            340                 345                 350

His Leu Arg Gly Ala Arg Ala Ile Thr Ser Asp Asn Val Gln Glu Phe
        355                 360                 365

Asp Gly Cys Lys Lys Ile Phe Gly Ser Leu Ala Phe Leu Pro Glu Ser
    370                 375                 380

Phe Asp Gly Asp Pro Ser Ser Gly Ile Ala Pro Leu Arg Pro Glu Gln
385                 390                 395                 400

Leu Gln Val Phe Glu Thr Leu Glu Glu Ile Thr Gly Tyr Leu Tyr Ile
                405                 410                 415

Ser Ala Trp Pro Asp Ser Leu Arg Asp Leu Ser Val Phe Gln Asn Leu
            420                 425                 430

Arg Ile Ile Arg Gly Arg Ile Leu His Asp Gly Ala Tyr Ser Leu Thr
        435                 440                 445

Leu Gln Gly Leu Gly Ile His Ser Leu Gly Leu Arg Ser Leu Arg Glu
    450                 455                 460

Leu Gly Ser Gly Leu Ala Leu Ile His Arg Asn Ala His Leu Cys Phe
465                 470                 475                 480

Val His Thr Val Pro Trp Asp Gln Leu Phe Arg Asn Pro His Gln Ala
                485                 490                 495

Leu Leu His Ser Gly Asn Arg Pro Glu Glu Asp Cys Gly Leu Glu Gly
            500                 505                 510

Leu Val Cys Asn Ser Leu Cys Ala His Gly His Cys Trp Gly Pro Gly
        515                 520                 525

Pro Thr Gln Cys Val Asn Cys Ser His Phe Leu Arg Gly Gln Glu Cys
    530                 535                 540

Val Glu Glu Cys Arg Val Trp Lys Gly Leu Pro Arg Glu Tyr Val Ser
545                 550                 555                 560

Asp Lys Arg Cys Leu Pro Cys His Pro Glu Cys Gln Pro Gln Asn Ser
                565                 570                 575

Ser Glu Thr Cys Phe Gly Ser Glu Ala Asp Gln Cys Ala Ala Cys Ala
```

```
            580                 585                 590

His Tyr Lys Asp Ser Ser Ser Cys Val Ala Arg Cys Pro Ser Gly Val
        595                 600                 605

Lys Pro Asp Leu Ser Tyr Met Pro Ile Trp Lys Tyr Pro Asp Glu Glu
    610                 615                 620

Gly Ile Cys Gln Pro Cys Pro Ile Asn Cys Thr His Ser Cys Val Asp
625                 630                 635                 640

Leu Asp Glu Arg Gly Cys Pro Ala Glu Gln Arg Ala Ser Pro Val Thr
                645                 650                 655

Phe Ile Ile Ala Thr Val Val Gly Val Leu Leu Phe Leu Ile Leu Val
                660                 665                 670

Val Val Val Gly Ile Leu Ile Lys Arg Arg Arg Gln Lys Ile Arg Lys
        675                 680                 685

Tyr Thr Met
    690


<210> SEQ ID NO 50
<211> LENGTH: 666
<212> TYPE: PRT
<213> ORGANISM: Rattus norvegicus

<400> SEQUENCE: 50

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Val Pro Ala Asn Ala Ser
        35                  40                  45

Leu Ser Phe Leu Gln Asp Ile Gln Glu Val Gln Gly Tyr Met Leu Ile
    50                  55                  60

Ala His Asn Gln Val Lys Arg Val Pro Leu Gln Arg Leu Arg Ile Val
65                  70                  75                  80

Arg Gly Thr Gln Leu Phe Glu Asp Lys Tyr Ala Leu Ala Val Leu Asp
                85                  90                  95

Asn Arg Asp Pro Gln Asp Asn Val Ala Ala Ser Thr Pro Gly Arg Thr
            100                 105                 110

Pro Glu Gly Leu Arg Glu Leu Gln Leu Arg Ser Leu Thr Glu Ile Leu
        115                 120                 125

Lys Gly Gly Val Leu Ile Arg Gly Asn Pro Gln Leu Cys Tyr Gln Asp
    130                 135                 140

Met Val Leu Trp Lys Asp Val Phe Arg Lys Asn Asn Gln Leu Ala Pro
145                 150                 155                 160

Val Asp Ile Asp Thr Asn Arg Ser Arg Ala Cys Pro Pro Cys Ala Pro
                165                 170                 175

Ala Cys Lys Asp Asn His Cys Trp Gly Glu Ser Pro Glu Asp Cys Gln
            180                 185                 190

Ile Leu Thr Gly Thr Ile Cys Thr Ser Gly Cys Ala Arg Cys Lys Gly
        195                 200                 205

Arg Leu Pro Thr Asp Cys Cys His Glu Gln Cys Ala Ala Gly Cys Thr
    210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Val Thr Tyr Asn Thr Asp
                245                 250                 255
```

-continued

```
Thr Phe Glu Ser Met His Asn Pro Glu Gly Arg Tyr Thr Phe Gly Ala
            260                 265                 270

Ser Cys Val Thr Thr Cys Pro Tyr Asn Tyr Leu Ser Thr Glu Val Gly
        275                 280                 285

Ser Cys Thr Leu Val Cys Pro Pro Asn Asn Gln Glu Val Thr Ala Glu
    290                 295                 300

Asp Gly Thr Gln Arg Cys Glu Lys Cys Ser Lys Pro Cys Ala Arg Val
305                 310                 315                 320

Cys Tyr Gly Leu Gly Met Glu His Leu Arg Gly Ala Arg Ala Ile Thr
                325                 330                 335

Ser Asp Asn Val Gln Glu Phe Asp Gly Cys Lys Lys Ile Phe Gly Ser
            340                 345                 350

Leu Ala Phe Leu Pro Glu Ser Phe Asp Gly Asp Pro Ser Ser Gly Ile
        355                 360                 365

Ala Pro Leu Arg Pro Glu Gln Leu Gln Val Phe Glu Thr Leu Glu Glu
    370                 375                 380

Ile Thr Gly Tyr Leu Tyr Ile Ser Ala Trp Pro Asp Ser Leu Arg Asp
385                 390                 395                 400

Leu Ser Val Phe Gln Asn Leu Arg Ile Ile Arg Gly Arg Ile Leu His
                405                 410                 415

Asp Gly Ala Tyr Ser Leu Thr Leu Gln Gly Leu Gly Ile His Ser Leu
            420                 425                 430

Gly Leu Arg Ser Leu Arg Glu Leu Gly Ser Gly Leu Ala Leu Ile His
        435                 440                 445

Arg Asn Ala His Leu Cys Phe Val His Thr Val Pro Trp Asp Gln Leu
    450                 455                 460

Phe Arg Asn Pro His Gln Ala Leu Leu His Ser Gly Asn Arg Pro Glu
465                 470                 475                 480

Glu Asp Cys Gly Leu Glu Gly Leu Val Cys Asn Ser Leu Cys Ala His
                485                 490                 495

Gly His Cys Trp Gly Pro Gly Pro Thr Gln Cys Val Asn Cys Ser His
            500                 505                 510

Phe Leu Arg Gly Gln Glu Cys Val Glu Glu Cys Arg Val Trp Lys Gly
        515                 520                 525

Leu Pro Arg Glu Tyr Val Ser Asp Lys Arg Cys Leu Pro Cys His Pro
    530                 535                 540

Glu Cys Gln Pro Gln Asn Ser Ser Glu Thr Cys Phe Gly Ser Glu Ala
545                 550                 555                 560

Asp Gln Cys Ala Ala Cys Ala His Tyr Lys Asp Ser Ser Ser Cys Val
                565                 570                 575

Ala Arg Cys Pro Ser Gly Val Lys Pro Asp Leu Ser Tyr Met Pro Ile
            580                 585                 590

Trp Lys Tyr Pro Asp Glu Glu Gly Ile Cys Gln Pro Cys Pro Ile Asn
        595                 600                 605

Cys Thr His Ser Cys Val Asp Leu Asp Glu Arg Gly Cys Pro Ala Glu
    610                 615                 620

Gln Arg Ala Ser Pro Val Thr Phe Ile Ile Ala Thr Val Val Gly Val
625                 630                 635                 640

Leu Leu Phe Leu Ile Leu Val Val Val Val Gly Ile Leu Ile Lys Arg
                645                 650                 655

Arg Arg Gln Lys Ile Arg Lys Tyr Thr Met
            660                 665
```

-continued

<210> SEQ ID NO 51
<211> LENGTH: 690
<212> TYPE: PRT
<213> ORGANISM: Artificial Sequence
<220> FEATURE:
<223> OTHER INFORMATION: Chimeric human-rat E2Neu (HER2)

<400> SEQUENCE: 51

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
```

```
    370                 375                 380

Pro Ala Ser Asn Thr Ala Glu Phe Ala Pro Leu Arg Pro Glu Gln Leu
385                 390                 395                 400

Gln Val Phe Glu Thr Leu Glu Glu Ile Thr Gly Tyr Leu Tyr Ile Ser
                405                 410                 415

Ala Trp Pro Asp Ser Leu Arg Asp Leu Ser Val Phe Gln Asn Leu Arg
            420                 425                 430

Ile Ile Arg Gly Arg Ile Leu His Asp Gly Ala Tyr Ser Leu Thr Leu
        435                 440                 445

Gln Gly Leu Gly Ile His Ser Leu Gly Leu Arg Ser Leu Arg Glu Leu
    450                 455                 460

Gly Ser Gly Leu Ala Leu Ile His Arg Asn Ala His Leu Cys Phe Val
465                 470                 475                 480

His Thr Val Pro Trp Asp Gln Leu Phe Arg Asn Pro His Gln Ala Leu
                485                 490                 495

Leu His Ser Gly Asn Arg Pro Glu Glu Asp Cys Gly Leu Glu Gly Leu
            500                 505                 510

Val Cys Asn Ser Leu Cys Ala His Gly His Cys Trp Gly Pro Gly Pro
        515                 520                 525

Thr Gln Cys Val Asn Cys Ser His Phe Leu Arg Gly Gln Glu Cys Val
    530                 535                 540

Glu Glu Cys Arg Val Trp Lys Gly Leu Pro Arg Glu Tyr Val Ser Asp
545                 550                 555                 560

Lys Arg Cys Leu Pro Cys His Pro Glu Cys Gln Pro Gln Asn Ser Ser
                565                 570                 575

Glu Thr Cys Phe Gly Ser Glu Ala Asp Gln Cys Ala Ala Cys Ala His
            580                 585                 590

Tyr Lys Asp Ser Ser Ser Cys Val Ala Arg Cys Pro Ser Gly Val Lys
        595                 600                 605

Pro Asp Leu Ser Tyr Met Pro Ile Trp Lys Tyr Pro Asp Glu Glu Gly
    610                 615                 620

Ile Cys Gln Pro Cys Pro Ile Asn Cys Thr His Ser Cys Val Asp Leu
625                 630                 635                 640

Asp Glu Arg Gly Cys Pro Ala Glu Gln Arg Ala Ser Pro Val Thr Phe
                645                 650                 655

Ile Ile Ala Thr Val Val Gly Val Leu Leu Phe Leu Ile Leu Val Val
            660                 665                 670

Val Val Gly Ile Leu Ile Lys Arg Arg Arg Gln Lys Ile Arg Lys Tyr
        675                 680                 685

Thr Met
    690


<210> SEQ ID NO 52
<211> LENGTH: 668
<212> TYPE: PRT
<213> ORGANISM: Artificial Sequence
<220> FEATURE:
<223> OTHER INFORMATION: Chimeric human-rat E2Neu (HER2)

<400> SEQUENCE: 52

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
```

-continued

```
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Glu Phe Ala Pro Leu Arg Pro Glu Gln Leu Gln Val Phe Glu Thr Leu
    370                 375                 380

Glu Glu Ile Thr Gly Tyr Leu Tyr Ile Ser Ala Trp Pro Asp Ser Leu
385                 390                 395                 400

Arg Asp Leu Ser Val Phe Gln Asn Leu Arg Ile Ile Arg Gly Arg Ile
                405                 410                 415

Leu His Asp Gly Ala Tyr Ser Leu Thr Leu Gln Gly Leu Gly Ile His
            420                 425                 430

Ser Leu Gly Leu Arg Ser Leu Arg Glu Leu Gly Ser Gly Leu Ala Leu
        435                 440                 445

Ile His Arg Asn Ala His Leu Cys Phe Val His Thr Val Pro Trp Asp
    450                 455                 460
```

```
Gln Leu Phe Arg Asn Pro His Gln Ala Leu Leu His Ser Gly Asn Arg
465                 470                 475                 480

Pro Glu Glu Asp Cys Gly Leu Glu Gly Leu Val Cys Asn Ser Leu Cys
                485                 490                 495

Ala His Gly His Cys Trp Gly Pro Gly Pro Thr Gln Cys Val Asn Cys
            500                 505                 510

Ser His Phe Leu Arg Gly Gln Glu Cys Val Glu Glu Cys Arg Val Trp
        515                 520                 525

Lys Gly Leu Pro Arg Glu Tyr Val Ser Asp Lys Arg Cys Leu Pro Cys
    530                 535                 540

His Pro Glu Cys Gln Pro Gln Asn Ser Ser Glu Thr Cys Phe Gly Ser
545                 550                 555                 560

Glu Ala Asp Gln Cys Ala Ala Cys Ala His Tyr Lys Asp Ser Ser Ser
                565                 570                 575

Cys Val Ala Arg Cys Pro Ser Gly Val Lys Pro Asp Leu Ser Tyr Met
            580                 585                 590

Pro Ile Trp Lys Tyr Pro Asp Glu Glu Gly Ile Cys Gln Pro Cys Pro
        595                 600                 605

Ile Asn Cys Thr His Ser Cys Val Asp Leu Asp Glu Arg Gly Cys Pro
    610                 615                 620

Ala Glu Gln Arg Ala Ser Pro Val Thr Phe Ile Ile Ala Thr Val Val
625                 630                 635                 640

Gly Val Leu Leu Phe Leu Ile Leu Val Val Val Val Gly Ile Leu Ile
                645                 650                 655

Lys Arg Arg Arg Gln Lys Ile Arg Lys Tyr Thr Met
            660                 665
```

<210> SEQ ID NO 53
<211> LENGTH: 2064
<212> TYPE: DNA
<213> ORGANISM: Homo sapiens

<400> SEQUENCE: 53

```
atggagctgg cggccttgtg ccgctggggg ctcctcctcg ccctcttgcc ccccggagcc      60

gcgagcaccc aagtgtgcac cggcacagac atgaagctgc ggctccctgc cagtcccgag     120

acccacctgg acatgctccg ccacctctac cagggctgcc aggtggtgca gggaaacctg     180

gaactcacct acctgcccac caatgccagc ctgtccttcc tgcaggatat ccaggaggtg     240

cagggctacg tgctcatcgc tcacaaccaa gtgaggcagg tcccactgca gaggctgcgg     300

attgtgcgag gcacccagct ctttgaggac aactatgccc tggccgtgct agacaatgga     360

gacccgctga acaataccac ccctgtcaca ggggcctccc caggaggcct gcgggagctg     420

cagcttcgaa gcctcacaga gatcttgaaa ggaggggtct tgatccagcg gaacccccag     480

ctctgctacc aggacacgat tttgtggaag gacatcttcc acaagaacaa ccagctggct     540

ctcacactga tagacaccaa ccgctctcgg gcctgccacc cctgttctcc gatgtgtaag     600

ggctcccgct gctggggaga gagttctgag gattgtcaga gcctgacgcg cactgtctgt     660

gccggtggct gtgcccgctg caaggggcca ctgcccactg actgctgcca tgagcagtgt     720

gctgccggct gcacgggccc caagcactct gactgcctgg cctgcctcca cttcaaccac     780

agtggcatct gtgagctgca ctgcccagcc ctggtcacct acaacacaga cacgtttgag     840

tccatgccca atcccgaggg ccggtataca ttcggcgcca gctgtgtgac tgcctgtccc     900

tacaactacc tttctacgga cgtgggatcc tgcaccctcg tctgccccct gcacaaccaa     960
```

gaggtgacag cagaggatgg aacacagcgg tgtgagaagt gcagcaagcc ctgtgcccga 1020
gtgtgctatg gtctgggcat ggagcacttg cgagaggtga gggcagttac cagtgccaat 1080
atccaggagt ttgctggctg caagaagatc tttgggagcc tggcatttct gccggagagc 1140
tttgatgggg acccagcctc caacactgcc ccgctccagc cagagcagct ccaagtgttt 1200
gagactctgg aagagatcac aggttaccta tacatctcag catggccgga cagcctgcct 1260
gacctcagcg tcttccagaa cctgcaagta atccggggac gaattctgca caatggcgcc 1320
tactcgctga ccctgcaagg gctgggcatc agctggctgg ggctgcgctc actgagggaa 1380
ctgggcagtg gactggccct catccaccat aacacccacc tctgcttcgt gcacacggtg 1440
ccctgggacc agctctttcg gaacccgcac caagctctgc tccacactgc caaccggcca 1500
gaggacgagt gtgtgggcga gggcctggcc tgccaccagc tgtgcgcccg agggcactgc 1560
tggggtccag ggcccaccca gtgtgtcaac tgcagccagt tccttcgggg ccaggagtgc 1620
gtggaggaat gccgagtact gcaggggctc cccagggagt atgtgaatgc caggcactgt 1680
ttgccgtgcc accctgagtg tcagccccag aatggctcag tgacctgttt tggaccggag 1740
gctgaccagt gtgtggcctg tgcccactat aaggaccctc ccttctgcgt ggcccgctgc 1800
cccagcggtg tgaaacctga cctctcctac atgcccatct ggaagtttcc agatgaggag 1860
ggcgcatgcc agccttgccc catcaactgc acccactcct gtgtggacct ggatgacaag 1920
ggctgccccg ccgagcagag agccagccct ctgacgtcca tcatctctgc ggtggttggc 1980
attctgctgg tcgtggtctt gggggtggtc tttgggatcc tcatcaagcg acggcagcag 2040
aagatccgga agtacacgat gtga 2064

<210> SEQ ID NO 54
<211> LENGTH: 1998
<212> TYPE: DNA
<213> ORGANISM: Homo sapiens

<400> SEQUENCE: 54
acccaagtgt gcaccggcac agacatgaag ctgcggctcc ctgccagtcc cgagacccac 60
ctggacatgc tccgccacct ctaccagggc tgccaggtgg tgcagggaaa cctggaactc 120
acctacctgc ccaccaatgc cagcctgtcc ttcctgcagg atatccagga ggtgcagggc 180
tacgtgctca tcgctcacaa ccaagtgagg caggtcccac tgcagaggct gcggattgtg 240
cgaggcaccc agctctttga ggacaactat gccctggccg tgctagacaa tggagacccg 300
ctgaacaata ccacccctgt cacaggggcc tccccaggag gcctgcggga gctgcagctt 360
cgaagcctca cagagatctt gaaaggaggg gtcttgatcc agcggaaccc ccagctctgc 420
taccaggaca cgattttgtg gaaggacatc ttccacaaga acaaccagct ggctctcaca 480
ctgatagaca ccaaccgctc tcgggcctgc cacccctgtt ctccgatgtg taagggctcc 540
cgctgctggg gagagagttc tgaggattgt cagagcctga cgcgcactgt ctgtgccggt 600
ggctgtgccc gctgcaaggg gccactgccc actgactgct gccatgagca gtgtgctgcc 660
ggctgcacgg gccccaagca ctctgactgc ctggcctgcc tccacttcaa ccacagtggc 720
atctgtgagc tgcactgccc agccctggtc acctacaaca cagacacgtt tgagtccatg 780
cccaatcccg agggccggta tacattcggc gccagctgtg tgactgcctg tccctacaac 840
tacctttcta cggacgtggg atcctgcacc ctcgtctgcc ccctgcacaa ccaagaggtg 900
acagcagagg atggaacaca gcggtgtgag aagtgcagca agccctgtgc ccgagtgtgc 960
tatggtctgg gcatggagca cttgcgagag gtgagggcag ttaccagtgc caatatccag 1020
gagtttgctg gctgcaagaa gatctttggg agcctggcat ttctgccgga gagctttgat 1080
ggggacccag cctccaacac tgccccgctc cagccagagc agctccaagt gtttgagact 1140
ctggaagaga tcacaggtta cctatacatc tcagcatggc cggacagcct gcctgacctc 1200
agcgtcttcc agaacctgca agtaatccgg ggacgaattc tgcacaatgg cgcctactcg 1260
ctgaccctgc aagggctggg catcagctgg ctggggctgc gctcactgag ggaactgggc 1320
agtggactgg ccctcatcca ccataacacc cacctctgct tcgtgcacac ggtgccctgg 1380
gaccagctct ttcggaaccc gcaccaagct ctgctccaca ctgccaaccg gccagaggac 1440
gagtgtgtgg gcgagggcct ggcctgccac cagctgtgcg cccgagggca ctgctggggt 1500
ccagggccca cccagtgtgt caactgcagc cagttccttc ggggccagga gtgcgtggag 1560
gaatgccgag tactgcaggg gctccccagg gagtatgtga atgccaggca ctgtttgccg 1620
tgccaccctg agtgtcagcc ccagaatggc tcagtgacct gttttggacc ggaggctgac 1680
cagtgtgtgg cctgtgccca ctataaggac cctcccttct gcgtggcccg ctgccccagc 1740
ggtgtgaaac ctgacctctc ctacatgccc atctggaagt ttccagatga ggagggcgca 1800
tgccagcctt gccccatcaa ctgcacccac tcctgtgtgg acctggatga caagggctgc 1860
cccgccgagc agagagccag ccctctgacg tccatcatct ctgcggtggt tggcattctg 1920
ctggtcgtgg tcttgggggt ggtctttggg atcctcatca agcgacggca gcagaagatc 1980
cggaagtaca cgatgtga 1998

<210> SEQ ID NO 55
<211> LENGTH: 2064
<212> TYPE: DNA
<213> ORGANISM: Mus musculus

<400> SEQUENCE: 55
atggagctgg cggcctggtg ccgttggggg ttcctcctcg ccctcctgtc ccccggagcc 60
gcgggtaccc aagtgtgtac cggtaccgac atgaagttgc gactccctgc cagtcctgag 120
acccacctgg acatgcttcg ccacctctac cagggctgtc aggtggtgca gggcaatttg 180
gagcttacct acctgcccgc caatgccagc ctctcattcc tgcaggacat ccaggaagtc 240
cagggataca tgctcatcgc tcacaaccga gtgaaacacg tcccactgca gaggttgcgc 300
atcgtgagag ggactcagct ctttgaggac aagtatgccc tggctgtgct agacaaccga 360 gacccctttgg acaacgtcac caccgccgcc ccaggcagaa ccccagaagg gctgcgggag 420
ctgcagcttc gaagtctcac agagatcttg aagggaggag ttttgatccg tgggaaccct 480
cagctctgct accaggacat ggttttgtgg aaggatgtcc tccgtaagaa taaccagctg 540
gctcctgtcg acatggacac caatcgttcc cgggcctgtc caccttgtgc cccaacctgc 600
aaagacaatc actgttgggg tgagagtcct gaagactgtc agatcttgac tggcaccatc 660
tgtactagtg gctgtgcccg gtgcaagggc cggctgccca ctgactgttg ccatgagcag 720
tgtgctgcag gctgcacggg tcccaagcat tctgactgcc tggcctgcct ccacttcaat 780
catagtggta tctgtgagct gcactgcccg gccctcatca cctacaacac agacaccttc 840
gagtccatgc tcaaccctga gggtcgctac acctttggtg ccagctgtgt gaccacctgc 900
ccctacaact acctctccac ggaagtggga tcctgcactc tggtctgtcc cccgaacaac 960
caagaggtca cagctgagga cggaacacag cggtgtgaga aatgcagcaa gccctgtgct 1020
ggagtatgct atggtctggg catggagcac ctccgagggg cgagggccat caccagtgac 1080

```
aatatccagg agtttgctgg ctgcaagaag atctttggga gcctggcatt tttgccggag   1140
agctttgatg ggaacccctc ctccggcgtt gccccactga agccagagca tctccaagtg   1200
ttcgaaaccc tggaggagat cacaggttac ctatacattt cagcatggcc agagagcttc   1260
caagacctca gtgtcttcca gaaccttcgg gtcattcggg gacggattct ccatgatggt   1320
gcttactcat tgacgttgca aggcctgggg attcactcac tggggctacg ctcactgcgg   1380
gagctgggca gtggattggc tctcattcac cgcaacaccc atctctgctt tgtaaacact   1440
gtaccttggg accagctctt ccggaacccg caccaggccc tactccacag tgggaaccgg   1500
ccagaagagg catgtggtct tgagggcttg gtctgtaact cactgtgtgc ccgtgggcac   1560
tgctgggggc cagggcccac ccagtgtgtc aactgcagtc agttcctccg gggccaggag   1620
tgtgtggagg agtgccgagt atggaagggg ctccccaggg agtatgtgag ggcaagcac   1680
tgtctgccat gccaccccga gtgtcagcct caaaacagct cggagacctg ctatggatcg   1740
gaggctgacc agtgtgaggc ttgtgcccac tacaaggact catcttcctg tgtggctcgc   1800
tgccccagtg gtgtgaagcc agacctctcc tacatgccta tctggaagta cccggatgag   1860
gagggcatat gtcagccatg ccccatcaac tgcacccact catgtgtgga cctggacgaa   1920
cgaggctgcc cagcagagca gagagccagc ccagtgacat tcatcattgc aactgtggtg   1980
ggcgtcctgt tgttcctgat catagtggtg gtcattggaa tcctaatcaa acgaaggcga   2040
cagaagatcc ggaagtatac catg                                          2064
```

<210> SEQ ID NO 56
<211> LENGTH: 1998
<212> TYPE: DNA
<213> ORGANISM: Mus musculus

<400> SEQUENCE: 56

```
acccaagtgt gtaccggtac cgacatgaag ttgcgactcc ctgccagtcc tgagacccac     60
ctggacatgc ttcgccacct ctaccagggc tgtcaggtgg tgcagggcaa tttggagctt    120
acctacctgc ccgccaatgc cagcctctca ttcctgcagg acatccagga agtccaggga    180
tacatgctca tcgctcacaa ccgagtgaaa cacgtcccac tgcagaggtt gcgcatcgtg    240
agagggactc agctctttga ggacaagtat gccctggctg tgctagacaa ccgagaccct    300
ttggacaacg tcaccaccgc cgccccaggc agaaccccag aagggctgcg ggagctgcag    360
cttcgaagtc tcacagagat cttgaaggga ggagttttga tccgtgggaa ccctcagctc    420
tgctaccagg acatggtttt gtggaaggat gtcctccgta agaataacca gctggctcct    480
gtcgacatgg acaccaatcg ttcccgggcc tgtccacctt gtgccccaac ctgcaaagac    540
aatcactgtt ggggtgagag tcctgaagac tgtcagatct tgactggcac catctgtact    600
agtggctgtg cccggtgcaa gggccggctg cccactgact gttgccatga gcagtgtgct    660
gcaggctgca cgggtcccaa gcattctgac tgcctggcct gcctccactt caatcatagt    720
ggtatctgtg agctgcactg cccggccctc atcacctaca acacagacac cttcgagtcc    780
atgctcaacc ctgagggtcg ctacaccttt ggtgccagct gtgtgaccac ctgcccctac    840
aactacctct ccacggaagt gggatcctgc actctggtct gtcccccgaa caaccaagag    900
gtcacagctg aggacggaac acagcggtgt gagaaatgca gcaagccctg tgctggagta    960
tgctatggtc tgggcatgga gcacctccga ggggcgaggg ccatcaccag tgacaatatc   1020
caggagtttg ctggctgcaa gaagatcttt gggagcctgg catttttgcc ggagagcttt   1080
```

gatgggaacc cctcctccgg cgttgcccca ctgaagccag agcatctcca agtgttcgaa 1140
accctggagg agatcacagg ttacctatac atttcagcat ggccagagag cttccaagac 1200
ctcagtgtct tccagaacct tcgggtcatt cggggacgga ttctccatga tggtgcttac 1260
tcattgacgt tgcaaggcct ggggattcac tcactggggc tacgctcact gcgggagctg 1320
ggcagtggat tggctctcat tcaccgcaac acccatctct gctttgtaaa cactgtacct 1380
tgggaccagc tcttccggaa cccgcaccag gccctactcc acagtgggaa ccggccagaa 1440
gaggcatgtg gtcttgaggg cttggtctgt aactcactgt gtgcccgtgg gcactgctgg 1500
gggccagggc ccacccagtg tgtcaactgc agtcagttcc tccggggcca ggagtgtgtg 1560
gaggagtgcc gagtatggaa ggggctcccc agggagtatg tgaggggcaa gcactgtctg 1620
ccatgccacc ccgagtgtca gcctcaaaac agctcggaga cctgctatgg atcggaggct 1680
gaccagtgtg aggcttgtgc ccactacaag gactcatctt cctgtgtggc tcgctgcccc 1740
agtggtgtga agccagacct ctcctacatg cctatctgga agtacccgga tgaggagggc 1800
atatgtcagc catgccccat caactgcacc cactcatgtg tggacctgga cgaacgaggc 1860
tgcccagcag agcagagagc cagcccagtg acattcatca ttgcaactgt ggtgggcgtc 1920
ctgttgttcc tgatcatagt ggtggtcatt ggaatcctaa tcaaacgaag gcgacagaag 1980
atccggaagt ataccatg 1998

<210> SEQ ID NO 57
<211> LENGTH: 2073
<212> TYPE: DNA
<213> ORGANISM: Rattus norvegicus

<400> SEQUENCE: 57
atgatcatca tggagctggc ggcctggtgc cgctgggggt tcctcctcgc cctcctgccc 60
cccggaatcg cgggcaccca agtgtgtacc ggcacagaca tgaagttgcg gctccctgcc 120
agtcctgaga cccacctgga catgctccgc cacctgtacc agggctgtca ggtagtgcag 180
ggcaacttgg agcttaccta cgtgcctgcc aatgccagcc tctcattcct gcaggacatc 240
caggaagttc agggttacat gctcatcgct cacaaccagg tgaagcgcgt cccactgcaa 300
aggctgcgca tcgtgagagg gacccagctc tttgaggaca agtatgccct ggctgtgcta 360
gacaaccgag atcctcagga caatgtcgcc gcctccaccc caggcagaac cccagagggg 420
ctgcgggagc tgcagcttcg aagtctcaca gagatcctga agggaggagt tttgatccgt 480
gggaaccctc agctctgcta ccaggacatg gttttgtgga aggacgtctt ccgcaagaat 540
aaccaactgg ctcctgtcga tatagacacc aatcgttccc gggcctgtcc accttgtgcc 600
cccgcctgca aagacaatca ctgttggggt gagagtccgg aagactgtca gatcttgact 660
ggcaccatct gtaccagtgg ttgtgcccgg tgcaagggcc ggctgcccac tgactgctgc 720
catgagcagt gtgccgcagg ctgcacgggc cccaagcatt ctgactgcct ggcctgcctc 780
cacttcaatc atagtggtat ctgtgagctg cactgcccag ccctcgtcac ctacaacaca 840
gacacctttg agtccatgca caaccctgag ggtcgctaca cctttggtgc cagctgcgtg 900
accacctgcc cctacaacta cctgtctacg gaagtgggat cctgcactct ggtgtgtccc 960
ccgaataacc aagaggtcac agctgaggac ggaacacagc gttgtgagaa atgcagcaag 1020
ccctgtgctc gagtgtgcta tggtctgggc atggagcacc ttcgaggggc gagggccatc 1080
accagtgaca atgtccagga gtttgatggc tgcaagaaga tctttgggag cctggcattt 1140
ttgccggaga gctttgatgg ggacccctcc tccggcattg ctccgctgag gcctgagcag 1200

-continued

```
ctccaagtgt tcgaaaccct ggaggagatc acaggttacc tgtacatctc agcatggcca   1260

gacagtctcc gtgacctcag tgtcttccag aaccttcgaa tcattcgggg acggattctc   1320

cacgatggcg cgtactcatt gacactgcaa ggcctgggga tccactcgct ggggctgcgc   1380

tcactgcggg agctgggcag tggattggct ctgattcacc gcaacgccca tctctgcttt   1440

gtacacactg taccttggga ccagctcttc cggaacccac atcaggccct gctccacagt   1500

gggaaccggc cggaagagga ttgtggtctc gagggcttgg tctgtaactc actgtgtgcc   1560

cacgggcact gctgggggcc agggcccacc cagtgtgtca actgcagtca tttccttcgg   1620

ggccaggagt gtgtggagga gtgccgagta tggaaggggc tcccccggga gtatgtgagt   1680

gacaagcgct gtctgccgtg tcaccccgag tgtcagcctc aaaacagctc agagacctgc   1740

tttggatcgg aggctgatca gtgtgcagcc tgcgcccact acaaggactc gtcctcctgt   1800

gtggctcgct gccccagtgg tgtgaaaccg gacctctcct acatgcccat ctggaagtac   1860

ccggatgagg agggcatatg ccagccgtgc cccatcaact gcacccactc ctgtgtggat   1920

ctggatgaac gaggctgccc agcagagcag agagccagcc cggtgacatt catcattgca   1980

actgtagtgg gcgtcctgct gttcctgatc ttagtggtgg tcgttggaat cctaatcaaa   2040

cgaaggagac agaagatccg gaagtatacg atg                                 2073
```

<210> SEQ ID NO 58
<211> LENGTH: 1998
<212> TYPE: DNA
<213> ORGANISM: Rattus norvegicus

<400> SEQUENCE: 58

```
acccaagtgt gtaccggcac agacatgaag ttgcggctcc ctgccagtcc tgagacccac     60

ctggacatgc tccgccacct gtaccagggc tgtcaggtag tgcagggcaa cttggagctt    120

acctacgtgc ctgccaatgc cagcctctca ttcctgcagg acatccagga agttcagggt    180

tacatgctca tcgctcacaa ccaggtgaag cgcgtcccac tgcaaaggct gcgcatcgtg    240

agagggaccc agctctttga ggacaagtat gccctggctg tgctagacaa ccgagatcct    300

caggacaatg tcgccgcctc caccccaggc agaaccccag aggggctgcg ggagctgcag    360

cttcgaagtc tcacagagat cctgaaggga ggagttttga tccgtgggaa ccctcagctc    420

tgctaccagg acatggtttt gtggaaggac gtcttccgca agaataacca actggctcct    480

gtcgatatag acaccaatcg ttcccgggcc tgtccacctt gtgcccccgc ctgcaaagac    540

aatcactgtt ggggtgagag tccggaagac tgtcagatct tgactggcac catctgtacc    600

agtggttgtg cccggtgcaa gggccggctg cccactgact gctgccatga gcagtgtgcc    660

gcaggctgca cgggccccaa gcattctgac tgcctggcct gcctccactt caatcatagt    720

ggtatctgtg agctgcactg cccagccctc gtcacctaca acacagacac ctttgagtcc    780

atgcacaacc ctgagggtcg ctacaccttt ggtgccagct gcgtgaccac ctgcccctac    840

aactacctgt ctacggaagt gggatcctgc actctggtgt gtcccccgaa taaccaagag    900

gtcacagctg aggacggaac acagcgttgt gagaaatgca gcaagccctg tgctcgagtg    960

tgctatggtc tgggcatgga gcaccttcga ggggcgaggg ccatcaccag tgacaatgtc   1020

caggagtttg atggctgcaa gaagatcttt gggagcctgg catttttgcc ggagagcttt   1080

gatggggacc cctcctccgg cattgctccg ctgaggcctg agcagctcca agtgttcgaa   1140

accctggagg agatcacagg ttacctgtac atctcagcat ggccagacag tctccgtgac   1200
```

-continued

```
ctcagtgtct tccagaacct tcgaatcatt cggggacgga ttctccacga tggcgcgtac   1260

tcattgacac tgcaaggcct ggggatccac tcgctggggc tgcgctcact gcgggagctg   1320

ggcagtggat tggctctgat tcaccgcaac gcccatctct gctttgtaca cactgtacct   1380

tgggaccagc tcttccggaa cccacatcag gccctgctcc acagtgggaa ccggccggaa   1440

gaggattgtg gtctcgaggg cttggtctgt aactcactgt gtgcccacgg gcactgctgg   1500

gggccagggc ccacccagtg tgtcaactgc agtcatttcc ttcggggcca ggagtgtgtg   1560

gaggagtgcc gagtatggaa ggggctcccc cgggagtatg tgagtgacaa gcgctgtctg   1620

ccgtgtcacc ccgagtgtca gcctcaaaac agctcagaga cctgctttgg atcggaggct   1680

gatcagtgtg cagcctgcgc ccactacaag gactcgtcct cctgtgtggc tcgctgcccc   1740

agtggtgtga aaccggacct ctcctacatg cccatctgga agtacccgga tgaggagggc   1800

atatgccagc cgtgccccat caactgcacc cactcctgtg tggatctgga tgaacgaggc   1860

tgcccagcag agcagagagc cagcccggtg acattcatca ttgcaactgt agtgggcgtc   1920

ctgctgttcc tgatcttagt ggtggtcgtt ggaatcctaa tcaaacgaag gagacagaag   1980

atccggaagt atacgatg                                                 1998
```

<210> SEQ ID NO 59
<211> LENGTH: 2070
<212> TYPE: DNA
<213> ORGANISM: Artificial Sequence
<220> FEATURE:
<223> OTHER INFORMATION: Chimeric human-rat E2Neu (HER2)

<400> SEQUENCE: 59

```
atggagctgg cggccttgtg ccgctggggg ctcctcctcg ccctcttgcc ccccggagcc     60

gcgagcaccc aagtgtgcac cggcacagac atgaagctgc ggctccctgc cagtcccgag    120

acccacctgg acatgctccg ccacctctac cagggctgcc aggtggtgca gggaaacctg    180

gaactcacct acctgcccac caatgccagc ctgtccttcc tgcaggatat ccaggaggtg    240

cagggctacg tgctcatcgc tcacaaccaa gtgaggcagg tcccactgca gaggctgcgg    300

attgtgcgag gcacccagct ctttgaggac aactatgccc tggccgtgct agacaatgga    360

gacccgctga acaataccac ccctgtcaca ggggcctccc caggaggcct gcgggagctg    420

cagcttcgaa gcctcacaga gatcttgaaa ggaggggtct tgatccagcg gaaccccccag    480

ctctgctacc aggacacgat tttgtggaag gacatcttcc acaagaacaa ccagctggct    540

ctcacactga tagacaccaa ccgctctcgg gcctgccacc cctgttctcc gatgtgtaag    600

ggctcccgct gctggggaga gagttctgag gattgtcaga gcctgacgcg cactgtctgt    660

gccggtggct gtgcccgctg caaggggcca ctgcccactg actgctgcca tgagcagtgt    720

gctgccggct gcacgggccc caagcactct gactgcctgg cctgcctcca cttcaaccac    780

agtggcatct gtgagctgca ctgcccagcc ctggtcacct acaacacaga cacgtttgag    840

tccatgccca atcccgaggg ccggtataca ttcggcgcca gctgtgtgac tgcctgtccc    900

tacaactacc tttctacgga cgtgggatcc tgcaccctcg tctgccccct gcacaaccaa    960

gaggtgacag cagaggatgg aacacagcgg tgtgagaagt gcagcaagcc ctgtgcccga   1020

gtgtgctatg gtctgggcat ggagcacttg cgagaggtga gggcagttac cagtgccaat   1080

atccaggagt ttgctggctg caagaagatc tttgggagcc tggcatttct gccggagagc   1140

tttgatgggg acccagcctc caacactgcc gaattcgctc cgctgaggcc tgagcagctc   1200

caagtgttcg aaaccctgga ggagatcaca ggttacctgt acatctcagc atggccagac   1260
```

agtctccgtg acctcagtgt cttccagaac cttcgaatca ttcggggacg gattctccac 1320
gatggcgcgt actcattgac actgcaaggc ctggggatcc actcgctggg gctgcgctca 1380
ctgcgggagc tgggcagtgg attggctctg attcaccgca acgcccatct ctgctttgta 1440
cacactgtac cttgggacca gctcttccgg aacccacatc aggccctgct ccacagtggg 1500
aaccggccgg aagaggattg tggtctcgag ggcttggtct gtaactcact gtgtgcccac 1560
gggcactgct gggggccagg gcccacccag tgtgtcaact gcagtcattt ccttcggggc 1620
caggagtgtg tggaggagtg ccgagtatgg aaggggctcc cccgggagta tgtgagtgac 1680
aagcgctgtc tgccgtgtca ccccgagtgt cagcctcaaa acagctcaga gacctgcttt 1740
ggatcggagg ctgatcagtg tgcagcctgc gcccactaca aggactcgtc ctcctgtgtg 1800
gctcgctgcc ccagtggtgt gaaaccggac ctctcctaca tgcccatctg gaagtacccg 1860
gatgaggagg gcatatgcca gccgtgcccc atcaactgca cccactcctg tgtggatctg 1920
gatgaacgag gctgcccagc agagcagaga gccagcccgg tgacattcat cattgcaact 1980
gtagtgggcg tcctgctgtt cctgatctta gtggtggtcg ttggaatcct aatcaaacga 2040
aggagacaga agatccggaa gtatacgatg 2070

<210> SEQ ID NO 60
<211> LENGTH: 2004
<212> TYPE: DNA
<213> ORGANISM: Artificial Sequence
<220> FEATURE:
<223> OTHER INFORMATION: Chimeric human-rat E2Neu (HER2)

<400> SEQUENCE: 60
acccaagtgt gcaccggcac agacatgaag ctgcggctcc ctgccagtcc cgagacccac 60
ctggacatgc tccgccacct ctaccagggc tgccaggtgg tgcagggaaa cctggaactc 120
acctacctgc ccaccaatgc cagcctgtcc ttcctgcagg atatccagga ggtgcagggc 180
tacgtgctca tcgctcacaa ccaagtgagg caggtcccac tgcagaggct gcggattgtg 240
cgaggcaccc agctctttga ggacaactat gccctggccg tgctagacaa tggagacccg 300
ctgaacaata ccacccctgt cacaggggcc tccccaggag gcctgcggga gctgcagctt 360
cgaagcctca cagagatctt gaaaggaggg gtcttgatcc agcggaaccc ccagctctgc 420
taccaggaca cgattttgtg gaaggacatc ttccacaaga acaaccagct ggctctcaca 480
ctgatagaca ccaaccgctc tcgggcctgc caccccctgtt ctccgatgtg taagggctcc 540
cgctgctggg gagagagttc tgaggattgt cagagcctga cgcgcactgt ctgtgccggt 600
ggctgtgccc gctgcaaggg gccactgccc actgactgct gccatgagca gtgtgctgcc 660
ggctgcacgg gccccaagca ctctgactgc ctggcctgcc tccacttcaa ccacagtggc 720
atctgtgagc tgcactgccc agccctggtc acctacaaca cagacacgtt tgagtccatg 780
cccaatcccg agggccggta tacattcggc gccagctgtg tgactgcctg tccctacaac 840
tacctttcta cggacgtggg atcctgcacc ctcgtctgcc ccctgcacaa ccaagaggtg 900
acagcagagg atggaacaca gcggtgtgag aagtgcagca agccctgtgc ccgagtgtgc 960
tatggtctgg gcatggagca cttgcgagag gtgagggcag ttaccagtgc caatatccag 1020
gagtttgctg gctgcaagaa gatctttggg agcctggcat ttctgccgga gagctttgat 1080
ggggacccag cctccaacac tgccgaattc gctccgctga ggcctgagca gctccaagtg 1140
ttcgaaaccc tggaggagat cacaggttac ctgtacatct cagcatggcc agacagtctc 1200

-continued

```
cgtgacctca gtgtcttcca gaaccttcga atcattcggg gacggattct ccacgatggc   1260

gcgtactcat tgacactgca aggcctgggg atccactcgc tggggctgcg ctcactgcgg   1320

gagctgggca gtggattggc tctgattcac cgcaacgccc atctctgctt tgtacacact   1380

gtaccttggg accagctctt ccggaaccca catcaggccc tgctccacag tgggaaccgg   1440

ccggaagagg attgtggtct cgagggcttg gtctgtaact cactgtgtgc ccacgggcac   1500

tgctgggggc cagggcccac ccagtgtgtc aactgcagtc atttccttcg gggccaggag   1560

tgtgtggagg agtgccgagt atggaagggg ctcccccggg agtatgtgag tgacaagcgc   1620

tgtctgccgt gtcaccccga gtgtcagcct caaaacagct cagagacctg ctttggatcg   1680

gaggctgatc agtgtgcagc ctgcgcccac tacaaggact cgtcctcctg tgtggctcgc   1740

tgccccagtg gtgtgaaacc ggacctctcc tacatgccca tctggaagta cccggatgag   1800

gagggcatat gccagccgtg ccccatcaac tgcacccact cctgtgtgga tctggatgaa   1860

cgaggctgcc cagcagagca gagagccagc ccggtgacat tcatcattgc aactgtagtg   1920

ggcgtcctgc tgttcctgat cttagtggtg gtcgttggaa tcctaatcaa acgaaggaga   1980

cagaagatcc ggaagtatac gatg                                          2004


<210> SEQ ID NO 61
<211> LENGTH: 21
<212> TYPE: DNA
<213> ORGANISM: Artificial Sequence
<220> FEATURE:
<223> OTHER INFORMATION: FCA733 forward primer

<400> SEQUENCE: 61

aggctcctct aggtttactg d                                               21


<210> SEQ ID NO 62
<211> LENGTH: 24
<212> TYPE: DNA
<213> ORGANISM: Artificial Sequence
<220> FEATURE:
<223> OTHER INFORMATION: FCA733 reverse primer

<400> SEQUENCE: 62

ccaccgataa gtgaaatggt atgg                                            24


<210> SEQ ID NO 63
<211> LENGTH: 21
<212> TYPE: DNA
<213> ORGANISM: Artificial Sequence
<220> FEATURE:
<223> OTHER INFORMATION: FCA749 forward primer

<400> SEQUENCE: 63

gggtgatgtg acctcttgta g                                               21


<210> SEQ ID NO 64
<211> LENGTH: 21
<212> TYPE: DNA
<213> ORGANISM: Artificial Sequence
<220> FEATURE:
<223> OTHER INFORMATION: FCA749 reverse primer

<400> SEQUENCE: 64

ggacagaggc tccttaaaca g                                               21


<210> SEQ ID NO 65
<211> LENGTH: 20
```

<212> TYPE: DNA
<213> ORGANISM: Artificial Sequence
<220> FEATURE:
<223> OTHER INFORMATION: MACROD2 foward primer

<400> SEQUENCE: 65
tcttccctcc tccgtgtatg 20

<210> SEQ ID NO 66
<211> LENGTH: 24
<212> TYPE: DNA
<213> ORGANISM: Artificial Sequence
<220> FEATURE:
<223> OTHER INFORMATION: MACROD2 reverse primer

<400> SEQUENCE: 66
agacgctcaa tcaactgagc catc 24

<210> SEQ ID NO 67
<211> LENGTH: 23
<212> TYPE: DNA
<213> ORGANISM: Artificial Sequence
<220> FEATURE:
<223> OTHER INFORMATION: mtCR forward primer

<400> SEQUENCE: 67
tcttctcgct ccgggcccat ttc 23

<210> SEQ ID NO 68
<211> LENGTH: 20
<212> TYPE: DNA
<213> ORGANISM: Artificial Sequence
<220> FEATURE:
<223> OTHER INFORMATION: mtCR reverse primer

<400> SEQUENCE: 68
agtctggcga ctcatctagg 20

<210> SEQ ID NO 69
<211> LENGTH: 885
<212> TYPE: PRT
<213> ORGANISM: Artificial Sequence
<220> FEATURE:
<223> OTHER INFORMATION: fusion protein feHER2ecd-hFc

<400> SEQUENCE: 69

```
Met Glu Leu Ala Ala Trp Cys Arg Trp Gly Leu Leu Leu Ala Leu Leu
1               5                   10                  15

Pro Ser Gly Ala Thr Gly Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu His Ala Asn Ala Ser Leu Ser Phe Leu Gln Asp Ile Gln Glu Val
65                  70                  75                  80

Gln Gly Tyr Val Leu Ile Ala His Asn Gln Val Lys Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asp Ser Gly Thr Pro
        115                 120                 125
```

-continued

```
Ala Thr Gly Ala Ala Leu Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys His Gln Asp Thr Ile Leu Trp Lys Asp Ile Phe His Lys Asn
                165                 170                 175

Asn Gln Leu Ala Leu Met Leu Ile Asp Thr Asn Arg Ser Arg Ala Cys
            180                 185                 190

Gln Pro Cys Ser Pro Ala Cys Lys Asp Ser His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Gln Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Ala Arg Ala Val Thr Ser Ala Asn Ile Gln Glu Phe Val Gly Cys Lys
        355                 360                 365

Lys Ile Phe Gly Ser Leu Ala Phe Leu Pro Glu Ser Phe Glu Gly Asp
    370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ser Arg Leu Cys Phe Val His Thr Val
465                 470                 475                 480

Pro Trp Asp Gln Leu Phe Arg Asn Pro His Gln Ala Leu Leu His Ser
                485                 490                 495

Ala Asn Arg Pro Glu Asp Glu Cys Ala Gly Glu Gly Leu Ala Cys Tyr
            500                 505                 510

Pro Leu Cys Ala His Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Lys Asp Arg Phe Cys
```

```
545                 550                 555                 560

Leu Pro Cys His Pro Glu Cys Gln Pro Gln Asn Gly Ser Val Thr Cys
                565                 570                 575

Leu Gly Ser Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Phe Met Pro Ile Trp Lys Phe Ala Asp Glu Glu Gly Thr Cys Gln
    610                 615                 620

Pro Cys Pro Ile Asn Cys Thr His Ser Cys Ala Asp Leu Asp Glu Lys
625                 630                 635                 640

Gly Cys Pro Ala Glu Gln Arg Ala Ser Pro Val Thr Ser Glu Pro Lys
                645                 650                 655

Ser Cys Asp Lys Thr His Thr Cys Pro Pro Cys Pro Ala Pro Glu Leu
            660                 665                 670

Leu Gly Gly Pro Ser Val Phe Leu Phe Pro Pro Lys Pro Lys Asp Thr
        675                 680                 685

Leu Met Ile Ser Arg Thr Pro Glu Val Thr Cys Val Val Val Asp Val
    690                 695                 700

Ser His Glu Asp Pro Glu Val Lys Phe Asn Trp Tyr Val Asp Gly Val
705                 710                 715                 720

Glu Val His Asn Ala Lys Thr Lys Pro Arg Glu Glu Gln Tyr Asn Ser
                725                 730                 735

Thr Tyr Arg Val Val Ser Val Leu Thr Val Leu His Gln Asp Trp Leu
            740                 745                 750

Asn Gly Lys Glu Tyr Lys Cys Lys Val Ser Asn Lys Ala Leu Pro Ala
        755                 760                 765

Pro Ile Glu Lys Thr Ile Ser Lys Ala Lys Gly Gln Pro Arg Glu Pro
    770                 775                 780

Gln Val Tyr Thr Leu Pro Pro Ser Arg Asp Glu Leu Thr Lys Asn Gln
785                 790                 795                 800

Val Ser Leu Thr Cys Leu Val Lys Gly Phe Tyr Pro Ser Asp Ile Ala
                805                 810                 815

Val Glu Trp Glu Ser Asn Gly Gln Pro Glu Asn Asn Tyr Lys Thr Thr
            820                 825                 830

Pro Pro Val Leu Asp Ser Asp Gly Ser Phe Phe Leu Tyr Ser Lys Leu
        835                 840                 845

Thr Val Asp Lys Ser Arg Trp Gln Gln Gly Asn Val Phe Ser Cys Ser
    850                 855                 860

Val Met His Glu Ala Leu His Asn His Tyr Thr Gln Lys Ser Leu Ser
865                 870                 875                 880

Leu Ser Pro Gly Lys
                885
```

<210> SEQ ID NO 70
<211> LENGTH: 39
<212> TYPE: DNA
<213> ORGANISM: Artificial Sequence
<220> FEATURE:
<223> OTHER INFORMATION: Feline HER2 ECTM (prefeHER2) FORWARD PRIMER

<400> SEQUENCE: 70
attactacaa gcttgagacc atggagctgg cggcctggt 39

<210> SEQ ID NO 71

<211> LENGTH: 39
<212> TYPE: DNA
<213> ORGANISM: Artificial Sequence
<220> FEATURE:
<223> OTHER INFORMATION: Feline HER2 ECTM (prefeHER2) Reverse PRIMER

<400> SEQUENCE: 71
tactaatcta gatcacatcg tgtacttccg gatcttctg 39

<210> SEQ ID NO 72
<211> LENGTH: 26
<212> TYPE: DNA
<213> ORGANISM: Artificial Sequence
<220> FEATURE:
<223> OTHER INFORMATION: Feline HER2 ECD-Fc ECD FORWARD PRIMER

<400> SEQUENCE: 72
caccaagctt gagaccatgg agctgg 26

<210> SEQ ID NO 73
<211> LENGTH: 28
<212> TYPE: DNA
<213> ORGANISM: Artificial Sequence
<220> FEATURE:
<223> OTHER INFORMATION: Feline HER2 ECD-Fc ECD Reverse PRIMER

<400> SEQUENCE: 73
gatttgggct cggacgtcac agggctgg 28

<210> SEQ ID NO 74
<211> LENGTH: 29
<212> TYPE: DNA
<213> ORGANISM: Artificial Sequence
<220> FEATURE:
<223> OTHER INFORMATION: Feline HER2 ECD-Fc tag FORWARD PRIMER

<400> SEQUENCE: 74
ctgtgacgtc cgagcccaaa tcttgtgac 29

<210> SEQ ID NO 75
<211> LENGTH: 34
<212> TYPE: DNA
<213> ORGANISM: Artificial Sequence
<220> FEATURE:
<223> OTHER INFORMATION: Feline HER2 ECD-Fc tag Reverse PRIMER

<400> SEQUENCE: 75
tctagattat ttacccggag acagggagag gctc 34

<210> SEQ ID NO 76
<211> LENGTH: 33
<212> TYPE: DNA
<213> ORGANISM: Artificial Sequence
<220> FEATURE:
<223> OTHER INFORMATION: Black bear HER2 ECTM (prebearHER2) FORWARD
PRIMER

<400> SEQUENCE: 76
taagcttgag accatggagc tggcggcctg gtg 33

<210> SEQ ID NO 77
<211> LENGTH: 33
<212> TYPE: DNA
<213> ORGANISM: Artificial Sequence
<220> FEATURE:
<223> OTHER INFORMATION: Black bear HER2 ECTM (prebearHER2) Reverse
PRIMER

<400> SEQUENCE: 77
ctctagattc acatcgtgta cttccggatc ttc 33

<210> SEQ ID NO 78
<211> LENGTH: 31
<212> TYPE: DNA
<213> ORGANISM: Artificial Sequence
<220> FEATURE:
<223> OTHER INFORMATION: Feline GM-CSF FORWARD PRIMER

<400> SEQUENCE: 78
caccatgtgg ctgcagaacc tgcttttcct g 31

<210> SEQ ID NO 79
<211> LENGTH: 27
<212> TYPE: DNA
<213> ORGANISM: Artificial Sequence
<220> FEATURE:
<223> OTHER INFORMATION: Feline GM-CSF Reverse PRIMER

<400> SEQUENCE: 79
ttacttctgg tctggtcccc agcagtc 27

<210> SEQ ID NO 80
<211> LENGTH: 27
<212> TYPE: DNA
<213> ORGANISM: Artificial Sequence
<220> FEATURE:
<223> OTHER INFORMATION: feCSF2 1-67 FORWARD PRIMER

<400> SEQUENCE: 80
atgtggctgc agaacctgct tttcctg 27

<210> SEQ ID NO 81
<211> LENGTH: 24
<212> TYPE: DNA
<213> ORGANISM: Artificial Sequence
<220> FEATURE:
<223> OTHER INFORMATION: feCSF2 1-67 Reverse PRIMER

<400> SEQUENCE: 81
ctcagggtca aacatttcag agac 24

<210> SEQ ID NO 82
<211> LENGTH: 25
<212> TYPE: DNA
<213> ORGANISM: Artificial Sequence
<220> FEATURE:
<223> OTHER INFORMATION: feCSF2 60-145 FORWARD PRIMER

<400> SEQUENCE: 82
gtctctgaaa tgtttgaccc tgagg 25

<210> SEQ ID NO 83
<211> LENGTH: 27
<212> TYPE: DNA
<213> ORGANISM: Artificial Sequence
<220> FEATURE:
<223> OTHER INFORMATION: feCSF2 60-145 Reverse PRIMER

<400> SEQUENCE: 83
ttacttctgg tctggtcccc agcagtc 27

<210> SEQ ID NO 84

```
<211> LENGTH: 687
<212> TYPE: PRT
<213> ORGANISM: Homo sapiens

<400> SEQUENCE: 84

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Lys Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
```

```
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 85
<211> LENGTH: 687
<212> TYPE: PRT
<213> ORGANISM: Homo sapiens

<400> SEQUENCE: 85

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80
```

-continued

```
Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Lys Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
```

```
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 86
<211> LENGTH: 687
<212> TYPE: PRT
<213> ORGANISM: Homo sapiens

<400> SEQUENCE: 86

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asp Ser Gly Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190
```

-continued

```
His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
```

```
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met
        675                 680                 685


<210> SEQ ID NO 87
<211> LENGTH: 25
<212> TYPE: DNA
<213> ORGANISM: Artificial Sequence
<220> FEATURE:
<223> OTHER INFORMATION: prehumHER2-Q141K FORWARD PRIMER

<400> SEQUENCE: 87

gctgaagctt cgaagcctca cagag                                         25


<210> SEQ ID NO 88
<211> LENGTH: 23
<212> TYPE: DNA
<213> ORGANISM: Artificial Sequence
<220> FEATURE:
<223> OTHER INFORMATION: prehumHER2-Q141K reverse PRIMER

<400> SEQUENCE: 88

tcccgcaggc ctcctgggga ggc                                           23


<210> SEQ ID NO 89
<211> LENGTH: 21
<212> TYPE: DNA
<213> ORGANISM: Artificial Sequence
<220> FEATURE:
<223> OTHER INFORMATION: prehumHER2-Q213K FORWARD

<400> SEQUENCE: 89

tgaggattgt aagagcctga c                                             21


<210> SEQ ID NO 90
<211> LENGTH: 18
<212> TYPE: DNA
<213> ORGANISM: Artificial Sequence
<220> FEATURE:
<223> OTHER INFORMATION: prehumHER2-Q213K reverse

<400> SEQUENCE: 90

gaactctctc cccagcag                                                 18


<210> SEQ ID NO 91
<211> LENGTH: 21
<212> TYPE: DNA
<213> ORGANISM: Artificial Sequence
<220> FEATURE:
<223> OTHER INFORMATION: prehumHER2-Q239K FORWARD

<400> SEQUENCE: 91

ctgccatgag aagtgtgctg c                                             21


<210> SEQ ID NO 92
<211> LENGTH: 18
<212> TYPE: DNA
<213> ORGANISM: Artificial Sequence
```

<220> FEATURE:
<223> OTHER INFORMATION: prehumHER2-Q239K reverse PRIMER

<400> SEQUENCE: 92
cagtcagtgg gcagtggc 18

<210> SEQ ID NO 93
<211> LENGTH: 25
<212> TYPE: DNA
<213> ORGANISM: Artificial Sequence
<220> FEATURE:
<223> OTHER INFORMATION: prehumHER2-Q320K FORWARD PRIMER

<400> SEQUENCE: 93
aagaggtgac agcagaggat ggaac 25

<210> SEQ ID NO 94
<211> LENGTH: 22
<212> TYPE: DNA
<213> ORGANISM: Artificial Sequence
<220> FEATURE:
<223> OTHER INFORMATION: prehumHER2-Q320K reverse PRIMER

<400> SEQUENCE: 94
tgttgtgcag ggggcagacg ag 22

<210> SEQ ID NO 95
<211> LENGTH: 21
<212> TYPE: DNA
<213> ORGANISM: Artificial Sequence
<220> FEATURE:
<223> OTHER INFORMATION: prehumHER2-Q329K FORWARD PRIMER

<400> SEQUENCE: 95
ggatggaaca aagcggtgtg a 21

<210> SEQ ID NO 96
<211> LENGTH: 18
<212> TYPE: DNA
<213> ORGANISM: Artificial Sequence
<220> FEATURE:
<223> OTHER INFORMATION: prehumHER2-Q329K reverse PRIMER

<400> SEQUENCE: 96
tctgctgtca cctcttgg 18

<210> SEQ ID NO 97
<211> LENGTH: 23
<212> TYPE: DNA
<213> ORGANISM: Artificial Sequence
<220> FEATURE:
<223> OTHER INFORMATION: prehumHER2-Q429R FORWARD PRIMER

<400> SEQUENCE: 97
ccagaacctg agagtaatcc ggg 23

<210> SEQ ID NO 98
<211> LENGTH: 18
<212> TYPE: DNA
<213> ORGANISM: Artificial Sequence
<220> FEATURE:
<223> OTHER INFORMATION: prehumHER2-Q429R reverse PRIMER

<400> SEQUENCE: 98
aagacgctga ggtcaggc 18

<210> SEQ ID NO 99
<211> LENGTH: 21
<212> TYPE: DNA
<213> ORGANISM: Artificial Sequence
<220> FEATURE:
<223> OTHER INFORMATION: prehumHER2-N438D FORWARD

<400> SEQUENCE: 99
aattctgcac gatggcgcct a 21

<210> SEQ ID NO 100
<211> LENGTH: 18
<212> TYPE: DNA
<213> ORGANISM: Artificial Sequence
<220> FEATURE:
<223> OTHER INFORMATION: prehumHER2-N438D reverse

<400> SEQUENCE: 100
cgtccccgga ttacttgc 18

<210> SEQ ID NO 101
<211> LENGTH: 28
<212> TYPE: DNA
<213> ORGANISM: Artificial Sequence
<220> FEATURE:
<223> OTHER INFORMATION: prehumHER2-NNT124DSG FORWARD PRIMER

<400> SEQUENCE: 101
ggcacacctg tcacaggggc ctccccag 28

<210> SEQ ID NO 102
<211> LENGTH: 30
<212> TYPE: DNA
<213> ORGANISM: Artificial Sequence
<220> FEATURE:
<223> OTHER INFORMATION: prehumHER2-NNT124DSG reverse PRIMER

<400> SEQUENCE: 102
actgtccagc gggtctccat tgtctagcac 30

<210> SEQ ID NO 103
<211> LENGTH: 21
<212> TYPE: DNA
<213> ORGANISM: Artificial Sequence
<220> FEATURE:
<223> OTHER INFORMATION: prefeHER2-Q141K FORWARD PRIMER

<400> SEQUENCE: 103
gcgggagctg aagctccgaa g 21

<210> SEQ ID NO 104
<211> LENGTH: 25
<212> TYPE: DNA
<213> ORGANISM: Artificial Sequence
<220> FEATURE:
<223> OTHER INFORMATION: prefeHER2-Q141K reverse PRIMER

<400> SEQUENCE: 104
agccctccta gggcagcccc tgtag 25

<210> SEQ ID NO 105
<211> LENGTH: 31
<212> TYPE: DNA
<213> ORGANISM: Artificial Sequence
<220> FEATURE:
<223> OTHER INFORMATION: prefeHER2-R398Q FORWARD PRIMER

<400> SEQUENCE: 105
tgagcagctc caagtgtttg aggctctgga g 31

<210> SEQ ID NO 106
<211> LENGTH: 18
<212> TYPE: DNA
<213> ORGANISM: Artificial Sequence
<220> FEATURE:
<223> OTHER INFORMATION: prefeHER2-R398Q reverse PRIMER

<400> SEQUENCE: 106
ggctgcaggg gggcagtg 18

<210> SEQ ID NO 107
<211> LENGTH: 22
<212> TYPE: DNA
<213> ORGANISM: Artificial Sequence
<220> FEATURE:
<223> OTHER INFORMATION: prefeHER2-N421D FORWARD PRIMER

<400> SEQUENCE: 107
cagcttgcct gacctcagtg tc 22

<210> SEQ ID NO 108
<211> LENGTH: 18
<212> TYPE: DNA
<213> ORGANISM: Artificial Sequence
<220> FEATURE:
<223> OTHER INFORMATION: prefeHER2-N421D reverse PRIMER

<400> SEQUENCE: 108
tctggccacg ctgagatg 18

<210> SEQ ID NO 109
<211> LENGTH: 15
<212> TYPE: PRT
<213> ORGANISM: Artificial Sequence
<220> FEATURE:
<223> OTHER INFORMATION: Conserved sequence in HER2, unsubstituted

<400> SEQUENCE: 109

Gln Leu Arg Ser Leu Thr Glu Ile Leu Lys Gly Gly Val Leu Ile
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Conserved sequence in HER2, with Q-K
substitution

<400> SEQUENCE: 110

Lys Leu Arg Ser Leu Thr Glu Ile Leu Lys Gly Gly Val Leu Ile
1 5 10 15

<210> SEQ ID NO 111
<211> LENGTH: 22
<212> TYPE: DNA
<213> ORGANISM: Artificial Sequence
<220> FEATURE:
<223> OTHER INFORMATION: prebearHER2-Q141K and mbearHER2-Q119K FORWARD
primer

<400> SEQUENCE: 111

-continued aagcctcaca gagatcctga ag 22

<210> SEQ ID NO 112
<211> LENGTH: 25
<212> TYPE: DNA
<213> ORGANISM: Artificial Sequence
<220> FEATURE:
<223> OTHER INFORMATION: prebearHER2-Q141K and mbearHER2-Q119K REVERSE primer

<400> SEQUENCE: 112
cgaagcttca gctcccgcag ccctc 25

<210> SEQ ID NO 113
<211> LENGTH: 22
<212> TYPE: DNA
<213> ORGANISM: Artificial Sequence
<220> FEATURE:
<223> OTHER INFORMATION: premouseHER2-Q142K and mmouseHER2-Q120K FORWARD primer

<400> SEQUENCE: 113
agtctcacag agatcttgaa gg 22

<210> SEQ ID NO 114
<211> LENGTH: 24
<212> TYPE: DNA
<213> ORGANISM: Artificial Sequence
<220> FEATURE:
<223> OTHER INFORMATION: premouseHER2-Q142K and mmouseHER2-Q120K REVERSE primer

<400> SEQUENCE: 114
tcgaagcttc agctcccgca gccc 24

<210> SEQ ID NO 115
<211> LENGTH: 22
<212> TYPE: DNA
<213> ORGANISM: Artificial Sequence
<220> FEATURE:
<223> OTHER INFORMATION: preratHER2-Q145K and mratHER2-Q120K FORWARD primer

<400> SEQUENCE: 115
gcttcgaagt ctcacagaga tc 22

<210> SEQ ID NO 116
<211> LENGTH: 22
<212> TYPE: DNA
<213> ORGANISM: Artificial Sequence
<220> FEATURE:
<223> OTHER INFORMATION: preratHER2-Q145K and mratHER2-Q120K REVERSE primer

<400> SEQUENCE: 116
ttcagctccc gcagcccctc tg 22

<210> SEQ ID NO 117
<211> LENGTH: 23
<212> TYPE: DNA
<213> ORGANISM: Artificial Sequence
<220> FEATURE:
<223> OTHER INFORMATION: prehumHER2-Q141K and mhumHER2-Q119K FORWARD primer

<400> SEQUENCE: 117
gctgaagctt cgaagcctca cag 23

-continued

```
<210> SEQ ID NO 118
<211> LENGTH: 22
<212> TYPE: DNA
<213> ORGANISM: Artificial Sequence
<220> FEATURE:
<223> OTHER INFORMATION: prehumHER2-Q141K and mhumHER2-Q119K REVERSE
      primer

<400> SEQUENCE: 118

tcccgcaggc ctcctgggga gg                                               22
```

HER2 ANTIGENIC POLYPEPTIDE COMPOSITIONS, AND METHODS FOR THEIR USE IN TREATMENT AND PREVENTION OF CARCINOMAS

GRANT INFORMATION

This invention was made with government support under grant No. CA076340 awarded by the National Institutes of Health and grant No. W81XWH-11-1-0050 awarded by the US ARMY/Medical Research and Materiel Command. The government has certain rights in the invention.

TECHNICAL FIELD

The invention relates to the field of antigens and vaccines for inducing a host to initiate immune response to the growth factor receptor HER2, and particularly for breaking tolerance to self HER2. The invention related particularly to the induction of anti-HER2 immunity for the treatment and prevention of mammary carcinomas and other HER2 expressing tumors in humans and other mammalian species.

BACKGROUND OF THE INVENTION

One of the foremost barriers to cancer immunotherapy and immunoprevention is the phenomenon of tolerance, the immune system's safeguard against autoimmune disease. Most tumor antigens are self antigens showing little or no difference from their normal counterparts in amino acid sequence and three dimensional structure.

The immune system generally becomes tolerant to self antigens early in life. T lymphocyte clones specifically reactive to self antigens are either deleted or anergized during thymic development, or are kept in check at the periphery, mainly by diverse populations of regulatory T cells (Treg). Especially important are natural Treg which develop in the thymus upon high affinity recognition of antigens in the thymic stroma (Colombo and Piconese, 2007). It is often impossible to predict an antigen and immunization protocol that will break tolerance to a self antigen to achieve effective vaccination. This problem has defeated the development of many vaccines intended to induce immune response against tumor antigens (Wei et al, 2004).

A most promising tumor antigen in breast and other carcinomas is HER2 (ErbB-2, neu). HER2 is amplified in ~30% of all breast cancers and is over-expressed in several other epithelial-derived neoplasms including ovarian cancer, small cell lung cancer, and cancers of the head and neck (Slamon, et al., 1989, Yu and Hung, 2000; Tzahar and Yarden. 1998).

HER2 receptors include an extracellular domain (ECD) of about 630 amino acids, a single membrane-spanning transmembrane region (TM), and an intracellular domain (ICD) including a cytoplasmic tyrosine kinase. The ECD contains four domains arranged as a tandem repeat of a two-domain unit consisting of a ~190-amino acid L domain (domains I and III) followed by a ~120-amino acid cysteine-rich domain (domains II and IV) (Witton, 2003, Roskoski, 2014).

Other members of the HER family of receptors, HER1, HER3, and HER4, bind extracellular growth factor (EGF) family ligands, but HER2 itself does not. Instead, it acts as a co-receptor, the preferred binding partner of the other HER family receptors. Ligand binding brings about heterodimerization of HER family receptors with HER2, leading to tyrosine kinase activation, and the activation of downstream signaling pathways. Overexpression of HER2, commonly seen in carcinomas, promotes spontaneous receptor dimerization and the activation of signaling pathways, in the absence of a ligand (Olayioye, 2001).

The presence of HER2 specific T cells and antibodies in breast and ovarian cancer patients indicate this molecule as a target of immunoprevention and therapy (Disis, et al., 1994; Peoples, et al., 1995; Fisk, et al., 1997; Kobayashi, et al., 2000). Passive immunotherapy, by administration of the anti-HER2 moAb (monoclonal antibody), Herceptin®, is used to treat patients with advanced breast cancer (Cobleigh, et al., 1999). Unfortunately, since ErbB-2 is a self antigen, and its sequence is typically unmodified in cancer, tumor hosts show strong immune tolerance against immune tolerance to HER2.

A HER2 tolerance breaking strategy that has shown some promise is to immunize a host with xenogeneic (heterologous) HER2, that is, HER2 from a different species than that of the immunized host. The strategy depends on the development of antigens that are sufficiently foreign to the HER2 of the host species to break tolerance to HER2, but sufficiently similar to elicit T cells and antibodies that cross react with the host HER2.

Some success has been attained with this strategy. It was found, for example, that heterologous vaccination with rat HER2 (rat neu) produced a degree of T cell response in human-HER2-tolerant transgenic mice. More complete responses were produced by vaccinating the transgenic mice with a hybrid antigen combining components of rat and human HER2 (Jacob, et al, 2006; Jacob, et al., 2010).

There is a need for more effective tolerance breaking antigens, for use in therapeutic and preventative vaccination against mammary carcinoma and other HER2-expressing cancers. There is also a need for monoclonal antibodies to such antigens, because such antibodies are themselves potential cross reacting reagents that can target HER2 expressing tumor cells.

There is also a need for antigens and methods useful for breaking tolerance to self HER2 in cats, for the treatment and prevention of mammary carcinoma in domestic feline populations. Feline mammary cancer is an important veterinary problem. The domestic cat population is estimated at 1 billion worldwide (Mullikin, et al., 2010) with approximately 95 million residing in US households (www.humanesociety.org/issues/pet_overpopulation/facts/pet_ownership_statistics.html) About 15% of unsprayed domestic cats spontaneously develop mammary tumors, 90% of which are malignant. Most of the malignancies are adenocarcinomas, with progression and histopathology similar to that of human breast cancer. HER2 expression has been reported in these tumors (Hayden, et al., 1971; Munson and Moresco, 2007; Gimenez, et al., 2010; Soares, et al., 2013; DeMaria, et al., 2005). Furthermore, successful HER2-targeted immunotherapies in outbred cat populations can lead directly to improved immunotherapies for human patients, which is not the case for immunotherapies developed with inbred rodent model populations. That is because the amino acid sequences of human and feline HER2 are more similar than those of human and mouse or rat neu (see, e.g., FIG. 6B), and because outbred cat populations exhibit a genetic diversity similar to that of human populations. There is therefore a need for antigens, vaccines, and methods for breaking tolerance to self HER2 for the therapeutic and preventative vaccination of mammary carcinomas of domestic cats.

Even with improved antigens and vaccines, a roadblock to breaking HER2 tolerance is the immunocompromised status of many cancer patients at the time of presentation for treatment. A competent immune system is required to meet the challenge of mounting a response to a self antigen. The induction of regulatory T cells, and the effects chemotherapy and radiation treatments can all contribute to a compromised immune system. There is a need for a diagnostic method for screening human and animal candidates for immunocompetence before the start of extended courses of tolerance-breaking immunotherapies.

SUMMARY OF THE INVENTION

The present invention provides antigenic HER2 polypeptides for breaking tolerance to self HER2 of an animal subject, the HER2 polypeptides including at least one point mutation in the extracellular domain of HER2.

The present invention also provides isolated HER2 antigenic polypeptides for inducing immune response against HER2 in a subject of a mammalian species. The HER2 polypeptides include an amino substitution of glutamine with lysine at position 141 of precursor feline HER2, or at position 119 of mature feline HER2, or at homologous positions of the HER2 of other species.

The present invention further provides HER2 gene expression constructs for the expression of these substituted antigenic HER2 polypeptides in living cells.

The present invention still further provides HER2 vaccine compositions for inducing immunity to HER2 in a mammalian subject, including an effective amount of one of the substituted HER2 gene expression constructs, and an effective amount of an adjuvant.

The present invention also provides methods for inducing an immune response to HER2 in a mammalian subject, including the steps of administering a substituted HER2 vaccine composition, and inducing an immune response to HER2.

The present invention further provides a method for inducing immune response to HER2 in a mammalian subject, using heterologous HER2 polypeptides. The method includes the steps of administering an effective amount of a gene expression construct encoding a heterologous unsubstituted (i.e. wild type) feline or bear HER2 polypeptide; administering an effective amount of an immunological adjuvant; expressing the gene construct in cells of the mammalian subject; and inducing an immune response against HER2 in the mammalian subject.

The present invention still further provides a method for inducing immune response to HER2 in a cat, including the steps of administering, to a cat, an effective amount of a gene expression construct encoding an antigenic polypeptide of human HER2, bear HER2, mouse HER2, rat neu, or human-rat chimeric HER2neu; administering an effective amount of an immunological adjuvant; expressing the gene construct in the cells of the cat, and inducing an immune response against HER2 in the cat.

The present invention also provides antigenic polypeptides for inducing immune response against HER2 in a mammalian subject, the antigenic polypeptides including either a substitution of glutamine with lysine at position 329 of precursor human HER2; a substitution of glutamine with lysine at position 307 of mature human HER2; a substitution of glutamine with arginine at position 429 of precursor human HER2; a substitution of glutamine with arginine at position 407 of mature human HER2; a substitution of asparagine with arginine at position 438 of precursor human HER2; and a substitution of asparagine with arginine at position 416 of mature human HER2. The invention provides these antigenic peptides as isolated peptides, gene expression vectors, and vaccine compositions.

The present invention further provides monoclonal antibodies selective for all of the previously mentioned substituted antigenic HER2 polypeptides.

The present invention still further provides a diagnostic test to determine whether a mammalian subject is sufficiently immunocompetent to respond to immunotherapy directed at self HER2.

BRIEF DESCRIPTION OF THE DRAWINGS

Other advantages of the present invention are readily appreciated as the same becomes better understood by reference to the following detailed description when considered in connection with the accompanying drawings wherein:

FIG. 1 shows a table of primer pairs used for the authentication of feline mammary tumor lines;

FIG. 2 shows the authentication of the feline mammary tumor lines K248 and K12 via short tandem repeat (STR) analysis at 4 loci: FCA733 (*Felis catus* Failed Axon Connector, human homolog), FCA 749 (Thyroglobulin), MACROD2 (MACRO Domain Containing 2), and feline mtCR (Mitochondrial Control Region/d-Loop); PCR amplification was conducted using primer pairs listed in the table above; template DNAs were prepared with a DNeasy kit (Qiagen) from cultures of cat mammary tumor lines K248 and K12 or the human ovarian cancer line SKOV3 as a negative control; the left-hand panel shows predicted product sizes of STR regions from FCA733 (lanes 1-3), FCA749 (lanes 4-6), or MACROD2 (lanes 8-10); ladder (1 kb+, Invitrogen) is in lane 7; the right-hand panel shows product sizes of the feline mtCR PCR amplified in duplicate, with ladder in lanes 3 and 6; Amplified products matched expected sizes based on the current cat genome sequence assembly (c.f. www.ncbi.nlm-.nih.gov/genome/guide/cat/) and the *Felis catus* mitochondrion (NC_001700.1); PCR products were verified by sequencing;

FIG. 6A shows the amino acid sequences of human, cat, bear, rat, and mouse HER2, compared by clustal alignment ([*], identical a.a., [:], strongly similar a.a., [·], weakly similar a.a.); the signal peptide and transmembrane region are indicated with lines;

FIG. 6D shows an annotated amino acid sequence of precursor feline HER2, highlighting the site of the 141 substitution;

FIG. 8A shows the sequence of the feHER2ecd-hFc fusion protein;

FIG. 8B shows a schematic of the feHER2ecd-hFc fusion protein (top panel) and a Western blot verifying its composition (bottom panel);

FIG. 12A shows a cartoon model of the effect of a Q141K substitution in feline HER2;

FIG. 12B shows a space filling model of the effect of a Q141K substitution in feline HER2;

FIG. 12C shows an surface electrostatic model of the effect of a Q141K substitution in feline HER2;

FIG. 13A shows the induction of human HER2-specific T cells in cats; PBMC were harvested after 4× vaccination and stimulated with 10 μg/mL rhuHER2-huFc or an IgG control; results are presented as IFNγ spot forming units (SFU)/$10^6$ PBMC; *p<0.05, **p<0.01 Mann-Whitney test;

FIG. 13B shows the induction of feline HER2-specific T cells in cats; PBMC were harvested after 4× vaccination and stimulated with 10 μg/mL rfeHER2-huFc or human IgG control; results are presented as IFNγ spot forming units (SFU)/$10^6$ PBMC; *p<0.05, **p<0.01 Mann-Whitney test;

FIG. 13C shows induction of feline HER2-specific T cells in cats; HER2 specific T cell response to feline HER2 is shown after a total of 7 vaccinations with pfeHER2-K with or without pE2Neu; *p<0.05, **p<0.01 Mann-Whitney test;

FIG. 13D shows human HER2 specific T cell response induced by pE2Neu or pbearHER2 followed by pfeHER2; *p<0.05, **p<0.01 Mann-Whitney test;

FIG. 13E shows feline HER2-specific T cell response induced by pE2Neu or pbearHER2 followed by pfeHER2; *p<0.05, **p<0.01 Mann-Whitney test;

FIG. 14A shows the binding of anti-human HER2 antibodies to 3T3 cells transiently transfected by lipofection with human HER2 mutant constructs encoding amino acid substitutions, with binding of moAb to HER2, Ab5 and N12 was measured by flow cytometry; Ab4 specific to rat neu is the negative control;

FIG. 14B shows the location of the amino acid substitutions shown in FIG. 14A on a schematic diagram of human HER2;

FIG. 15 shows a summary of results of a flow cytometric analysis of humoral immune response of wild-type BALB/c mice to human HER2 including amino acid substitutions; wild type BALB/c mice were electro-vaccinated i.m. with 60 ug HER2 construct+60 ug pmGMCSF divided in two sites; serum was collected 3 weeks after immunization and binding to Her2-expressing SKOV3 cells was assessed by flow cytometry;

FIG. 17 shows a characterization of HER2 and EGFR expression in the human cancer cell lines used to detect the presence of HER2 and EGFR antibodies in the sera of immunized mice;

FIG. 18 shows an analysis of the binding of anti-human HER2 antibodies, induced in BALB Her2Tg mice by two rounds of vaccination with HER2 mutant DNA encoding amino acid substitutions, to the human cancer cell lines characterized in FIG. 17; * $p<0.05$,  $p<0.005$, by 2-tail student's t test; and FIG. 19** shows an analysis of humoral immune response in BALB Her2Tg mice to human Her2 ECTM including amino acid substitutions; female BALB Her2Tg mice were electro-vaccinated twice at a 2-week interval; serum was collected 2 weeks after immunizations, and binding to HER2-expressing SKOV3 and TNBC SUM159 cells was assessed by flow cytometry; HER2 Ab levels elicited by each mutant construct were compared to the wild type pE2TM; * $p<0.05$, ** $p<0.005$, by 2-tail student's t test.

DETAILED DESCRIPTION OF THE INVENTION

Figure 3A:
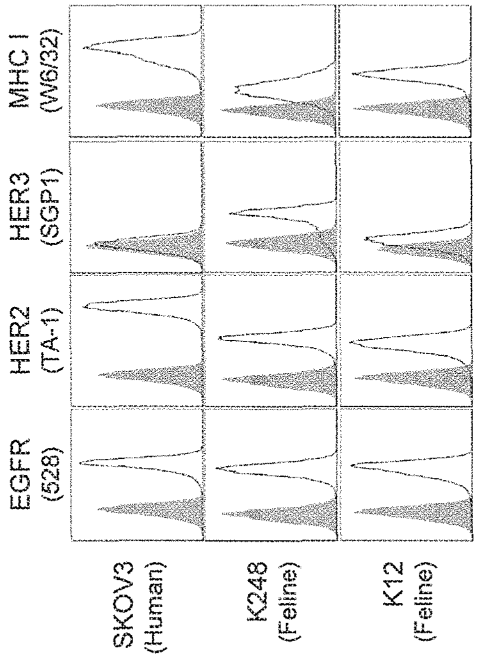
FIG. 3A shows expression of HER2 in feline mammary carcinoma by flow cytometric analysis of cell surface EGFR (HER1), HER2, HER3 and MHCI expression (open histograms) in FMC cell lines K12 and K248; human SKOV3 cells are included as controls; shaded histograms are unstained controls.

The compositions and methods according to the present invention represent solutions to the problem of immunological tolerance of tumor hosts to the HER2 antigens of their tumors. They represent the first reported examples of deliberately introduced point mutations that convert HER2 polypeptides into antigens capable of breaking tolerance to self HER2, and inducing an immune response reactive to self HER2. In an exemplary embodiment, a point mutation brings about the substitution of glutamine with lysine (Q-K) in the amino acid sequence QLRSLTEILKGGVLI (SEQ ID NO: 109) of HER2 domain I, rendering the sequence KLRSLTEILKGGVLI (SEQ ID NO: 110).

In a related embodiment, the present invention includes isolated antigenic polypeptides for breaking tolerance and inducing immune response against HER2 in a mammalian subject. The polypeptides include a substitution of glutamine with lysine with (Q-K) or a with a conservative amino acid of lysine, at position 141 (Q141K) of precursor feline HER2, or at a homologous position of the precursor HER2 of another animal species. Precursor HER2 (preHER2) is defined as HER2 including a signal peptide, an extracellular domain (ECD) and a transmembrane domain (TM). For brevity, the term Q-K substitution will refer to both a substitution of Q with K, and to a substitution of Q with a conservative amino acid, such as arginine. Also included in this embodiment are antigenic polypeptides of mature HER2 (mHER2), that is, HER2 lacking a signal peptide, and including the ECD and TM. In mHER2, the Q-K substitution is at position 119 of mfeHER2, or at a homologous position of the mature HER2 of another species.

The specification of the Q141K or Q119K substitution at a "homologous position of the HER2 of another animal species" indicates that the substitution is made to the Q that is in the lead position in a highly conserved 15 aa sequence in domain I of ErbB2, the conserved sequence being QLRSLTEILKGGVLI (see, for example, the underlined feature of SEQ ID NO: 39 as shown in FIG. 6D for precursor feline HER2. Exemplary amino acid and nucleotide sequences of HER2 polypeptides are listed in Table 4.

A standardized notation system will be used to denote specific forms of HER2 polypeptides. The notation will refer both to a polypeptide gene product, and to the gene construct employed to induce expression of the gene product in an organism. In the notation system, the animal species from which the HER2 is derived will be abbreviated and italicized and placed before HER2. The identity and location of an amino acid substitution if any, will be hyphenated after HER2. A wild-type HER2 will lack a designated substitution. The designation of a precursor or mature form will be abbreviated "pre" or "m", respectively, and placed to the left of the species. If the construct is included in a vector, the vector abbreviation will appear as the left-most term. For example:

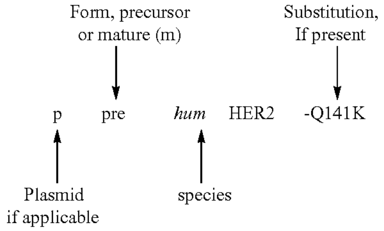

An annotated amino acid sequence of unsubstituted prefeHER2 (SEQ ID NO: 39) and prefeHER2-Q141K (SEQ ID NO: 7) is shown in FIG. 6D. Other exemplary embodiments of the antigenic HER2 polypeptides having a Q141K or homologous substitution are described in Example 2. They include precursor feline HER-2 having a Q-K substitution at position 141 (prefeHER2-Q141K), precursor bear HER-2 having a Q-K mutation at position 141 (prebearHER2-Q141K), precursor human HER-2 having a Q-K mutation at position 141 (prehumHER2-Q141K), precursor mouse HER-2 having a Q-K mutation at position 142 (premouseHER2-Q142K), precursor rat HER-2 having a Q-K mutation at position 145 (preratHER2-Q145K), and precursor human rat chimeric HER2 having a Q-K mutation at position 141 (preE2Neu-Q141K). They also include mature feline HER2 having a Q-K substitution at position 119 (mfeHER2-Q119K); mature bear HER2 having a Q-K substitution at position 119 (mbearHER2-Q119K); mature human HER2 having a Q-K substitution at position 119 (mhumHER2-Q119K); mature mouse HER-2 having a Q-K substitution at position 120 (mmouseHER2-Q120K); mature rat HER2 (rat neu) having a Q-K substitution at position 120 (mratHER2-Q120K); and mature human rat chimeric HER2 having a Q-K substitution at position 119 (mE2Neu-Q119K)

Exemplary amino acid sequences for each of the substituted antigens as follows: prefeHER2-Q141K, SEQ ID NO: 7; prebearHER2-Q141K, SEQ ID NO: 8; prehumHER2-Q141K, SEQ ID NO: 9; premouseHER2-Q142K, SEQ ID NO: 10; preratHER2-Q145K, SEQ ID NO: 11; preE2Neu-Q141K, SEQ ID NO: 12; mfeHER2-Q119K, SEQ ID NO: 1; mbearHER2-Q119K, SEQ ID NO: 2; mhumHER2-Q119K, SEQ ID NO: 3; mmouseHER2-Q120K, SEQ ID NO: 4; mratHER2-Q120K, SEQ ID NO: 5; and mE2Neu-Q119K, SEQ ID NO: 6. It will be understood that the disclosed amino acid sequences are exemplary, and that the present invention encompasses all immunologically equivalent sequences.

The development of the antigenic HER2 polypeptides of the present invention was initiated on the basis of experiments in which it was found that heterologous electrovaccination with rat neu (rat HER2) overcame T cell tolerance in human HER2 transgenic (Tg) mice. The term "heterologous", when used to refer to HER2, or another antigen, indicates that the antigen is derived from an animal species or species hybrid that is different from the species of the animal being vaccinated. Unfortunately, heterologous vaccination of human HER2 Tg mice with rat neu did not produce an effective humoral (B cell) response. The resulting immune sera did not cross react with human HER2 (Jacob, et al., 2006).

A hybrid antigen was next developed, which included portions of human HER2 and rat HER2 (rat neu), which will be referred to as E2Neu. This hybrid antigen included human HER2 extracellular domains (ECD) ½, rat neu ECD ¾ and the rat neu transmembrane domain. E2Neu was incorporated into a gene construct for expression in animals, specifically the plasmid vector pE2Neu. The vector was delivered, as a component of a vaccine, to human HER2 Tg mice. The pE2Neu vaccine was found to induce both humoral and cellular (T cell) immunity against human HER2 in human HER2 Tg mice (Jacob, et al., 2010).

Because a chimeric human/rat form of HER2 broke tolerance as well as the pure heterologous rat form, and gave a more complete immune response than the pure rat form, it was hypothesized that results can be further improved by immunization with forms of HER2 that are more minimally altered from the HER2 of a human host or experimental animal.

In one test of this hypotheses, animal hosts were immunized with self HER2 containing point mutations, to afford immunogenicity while preserving HER2 epitopes. In experiments disclosed in Examples 3 and 4, certain point mutations in HER2 were found to confer enhanced immunogenicity in vaccination experiments. Each point mutation produced a single amino acid substitution in HER2.

Figures 6B, 6C:
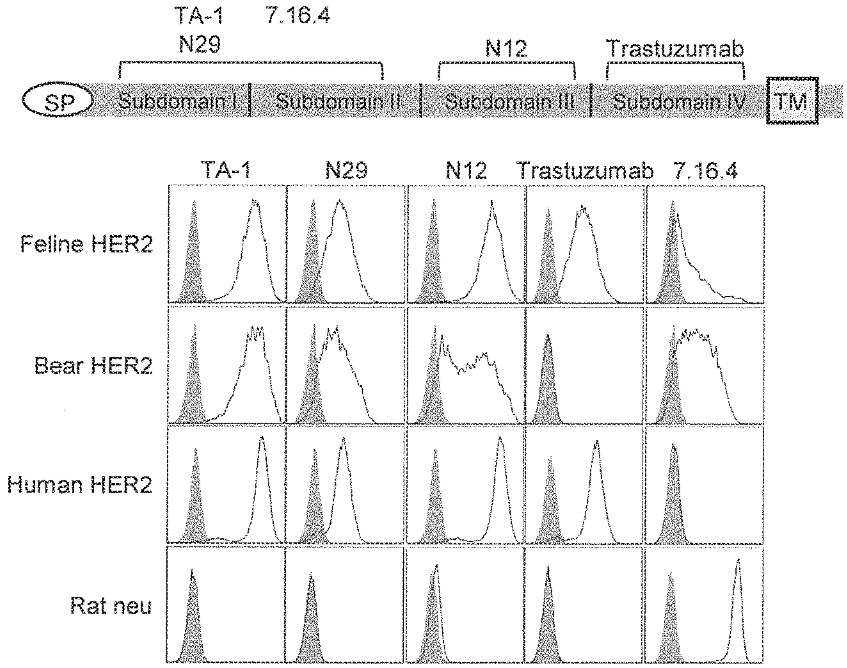
FIG. 6B summarizes the results of BLASTP analysis of full-length HER2 a.a. sequence identity.
FIG. 6C (top panel) shows a schematic of HER2 domains, and (bottom panel) flow cytometric analyses of the binding of four moAb to human HER2 (TA-1, N29, N12, Trastuzumab) and one moAb to rat neu (7.16.4); 3T3 cells transfected to express the indicated HER2 ECTM were stained with 1 μg/mL of the indicated moAb (open histogram) with detection by PE-conjugated secondary antibody; secondary antibody alone (shaded histogram) was the negative control.

Vaccination experiments with wild type and substituted forms of HER2 are described in Example 3. These vaccination experiments were performed not only in mice but also in a novel and highly realistic outbred cat tumor immunity model, which was utilized in experiments disclosed in Examples 1-4. Feline HER2 is more closely related to human HER2 than are the HER2s of mice or rats (FIG. 6B). Outbred cats show a range of genetic diversity, including MHC molecule diversity, comparable to that of humans, and not found in inbred rodent models.

In the experiments of Example 3, cats were immunized with a genetic vaccine including an expression vector which induced expression of the prefeHER2Q141K as well as wild type controls and heterologous HER2 forms. It was found that prefeHer2-Q141K was sufficiently foreign to break tolerance to self HER2 (i.e. feHER2) in outbred cats, inducing both antibodies and T cells reactive with feHer2. The antibodies and T cells were also reactive with Her2 molecules of humans and other species. Because these findings were obtained in the highly realistic outbred cat vaccine test system, it is reasonably predictable that they will also be applicable to other animal species. That is, it is predictable that HER2-K mutant antigens of cats and other animal species, in which Q141 or a homologous Q is substituted with K, will produce anti HER2 immunity in those animal species, when included in an appropriate vaccine composition. Indeed, it found, in experiments disclosed in Example 4, that the homologous substituted human HER2 polypeptide, prehumHER2-Q141K, broke tolerance to human HER2 in human HER2 transgenic mice.

Extrapolating from these findings, it is also predictable that the corresponding mature forms of HER2-Q141K, will also be effective in inducing immunity. The lack of a signal peptide is expected to have no effect on the reactivity of the Q-K substitution epitope, which is over a hundred residues distant, in the ECD. When expressed in a host cell, the mature forms of HER2 would not be processed into the secretory pathway and inserted into the cell membrane, but they would nonetheless be available to antigen presenting cells upon apoptosis or necrosis of the expressing cells. Thus, the previously enumerated mature forms of HER2, including a Q-K substitution at position 119 of feline HER2, or at a homologous position in other species, are also encompassed by the present invention.

In a related embodiment, the present invention includes gene expression constructs such as those utilized in Examples 2-4. The expression constructs include a nucleic acid sequence encoding an antigenic polypeptide of the HER2 of an animal species, and specifically encoding the Q141K substitution at position 141 of precursor feline HER2 (prefeHER2-Q141K), or at position 119 of mature feline HER2 (mfeHER2-Q119K), and at homologous positions of the precursor and mature forms of HER2 of other animal species. The expression construct additionally includes at least one promoter operatively linked to said nucleic acid sequence encoding a HER2 polypeptide, for expression of said antigenic peptide in a living cell.

The encoded constructs, and exemplary nucleic acid sequences encoding them, include: mfeHER2-Q119K, SEQ ID NO: 13; mbearHER2-Q119K, SEQ ID NO: 14; mhumHER2-Q119K, SEQ ID NO: 15; mmouseHER2-Q120K, SEQ ID NO: 16; mratHER2-Q120K, SEQ ID NO: 17; mE2Neu-Q119K, SEQ ID NO: 18; prefeHER2-Q141K; SEQ ID NO: 19; prebearHER2-Q141K, SEQ ID NO: 20; prehumHER2-Q141K, SEQ ID NO: 21; premouseHER2-Q142K, SEQ ID NO: 22; preratHER2-Q145K, SEQ ID NO: 23; and mE2Neu-Q141K, SEQ ID NO: 24. It will be understood that the recited nucleic acid sequences are only exemplary, and that each specified polypeptide can be encoded by one or more synonymous nucleic acid sequences without departing from the scope of the present invention. The nucleic acid sequences are preferably DNA sequences, but may alternatively comprise at least one RNA molecule.

The gene construct also includes at least one promoter operatively linked to the nucleic acid sequence encoding a HER2 Q-K substituted polypeptide, to promote expression of the gene product in a mammal or other organism. The promoter or other regulatory element is selected to ensure that the nucleic acid sequence is transcribed and translated into the antigenic polypeptide upon introduction into a living cell. An exemplary promoter is the cytomegalovirus (CMV) promoter, but any suitable promoter known in the art can be utilized, including, but not limited to, the cytomegalovirus (CMV) promoter, the Rous sarcoma virus (RSV) promoter; the SV40 virus promoter, and the mammalian housekeeping promoter EF1 (elongation factor 1).

A preferred expression vector is the naked DNA plasmid vector pVAX1 (Life Technologies, Grand Island, N.Y.), but any suitable vector system known in the art can be employed with routine modifications, depending on the cell type in which expression is to be obtained. In the Examples, gene constructs are expressed in mammalian hosts and in cultured mammalian cells, but with suitable expression vectors they can also be expressed in bacteria, yeasts, insect cells, and any other desired host. Appropriate techniques or references thereto can be found in Green and Sambrook (2012).

In a related embodiment, the present invention includes a vaccine composition for inducing immunity to HER2 in a mammalian subject. The vaccine composition includes an effective amount of at least one of the previously enumerated isolated HER2 polypeptide antigens or, more preferably, an effective amount of at least one of the previously mentioned gene expression constructs. The gene expression construct is expressible the living cells of the mammalian subject. The vaccine composition preferably includes an adjuvant to amplify immune response to the antigen. The present invention also includes methods for inducing immune response to HER2 in a mammalian subject, including the steps of administering an effective amount of the vaccine composition, and inducing an immune response to HER2.

An effective amount of vaccine composition is defined as one which produces an observable antigen-specific humoral and/or cellular immune response, and if administered as a therapy, a reduction in a population HER2-expressing target cells. The effective amount of a particular vaccine composition can be determined by one skilled in the art on the basis of preliminary trials in which increasing doses are given, and, as warranted, multiple courses of administration are tested. The extent of T or B cell response is measured by, for example, ELISA, cytotoxicity or growth suppression assays, and ELISPOT or other cytokine release assays. The effective amount can be adjusted to account for differences in host weight, species, or physical condition.

Exemplary gene constructs for vaccination techniques, according to the present invention, include HER2 antigens encoded into the naked DNA plasmid expression vector pVax, as described in detail in Examples 3 and 4. The preferred adjuvant is GM-CSF, administered either in soluble form or as a nucleic acid expression vector, which results in GM-CSF expression at a vaccination site. Preferably, the GM-CSF is preferably delivered as an expression plasmid.

Alternatively, the HER2 antigen gene constructs of the present invention can be cloned into any plasmid, or bacterial, or viral vector that can serve as a vaccine vector, to transfect or transduce mammalian cells. Examples include a retrovirus vector, an adenovirus vector, a lentivirus vector, a vaccinia virus vector, a pox virus vector, an adenovirus-associated vector, a virus-like particle, a *Salmonella* vector, a *Shigella* vector, a *Listeria* vector, a *Yersinia* vector, and an *Escherichia* vector. Techniques for expression of proteins using viral vectors can be found in Adolph, K. ed. "Viral Genome Methods" CRC Press, Florida (1996) and in Harrop, et al., 2006. Techniques for the use of attenuated bacterial vectors such as *Salmonella, Shigella, Listeria, Yersinia*, and *Escherichia* species are found for example in Vassaux et al., 2006. Vaccination is preferably accompanied by a cytokine adjuvant, such as −1, -2, -3, -6, -12, gamma-interferon, tumor necrosis factor, GM-CSF, or flt-3 ligand, delivered either as an expression construct, or as a cytokine protein.

Although electrovaccination is the preferred delivery mode, the gene expression constructs of the present invention can alternatively be packaged into liposomes or coated onto colloidal gold particles prior to administration. The gene expression constructs can then be administered intradermally, subcutaneously or intramuscularly by injection or by gas driven particle bombardment. Alternatively, the gene expression constructs can be administered to host cells ex vivo. Host cells, such as bone-marrow derived cells, can be induced to express the HER2 polypeptide antigens, and then reintroduced to the host to effect immunization. Appropriate techniques can be found in Sudowe, S. and Reske-Kunz, A. B. eds. "Biolistic DNA Delivery: Methods and Protocols", Humana Press, New York City (2012), and Raz, E., ed. "Gene Vaccination: Theory and Practice, Springer, New York City (1998).

The antigenic HER2 polypeptides of the present invention can also be administered as isolated polypeptides, as a component of a vaccine composition that can also include at least one adjuvant, including but not limited to incomplete or complete Freund's adjuvant, alum, QS21, TITERMAX; cytokines, and cytokines such as, interleukins-1, -2, -3, -6, -12, gamma-interferon, tumor necrosis factor, GM-CSF, or flt-3 ligand. The vaccine composition, with or without adjuvant, can be administered in a pure preparation, or admixed with a pharmaceutically acceptable carrier, diluent, or excipient, as a sterile suspension, emulsion, or in a lipid carrier such as a liposome. Delivery can be by subcutaneous, intradermal, intramuscular, intranasal, or intravenous routes.

In another embodiment, the present invention includes antibodies that selectively bind each of the substituted HER2 antigenic polypeptides disclosed herein. The term "selectively binds", when applied to an antibody of the present invention, indicates that the antibody (a) binds at a level above background to a particular substituted HER2 antigenic polypeptide, with background taken as the level of binding of a nonspecific reference agent such as a matched immunoglobulin isotype control; and (b) binds at a level at or below background to the corresponding wild type HER2 peptide.

With the amino acid sequences disclsosed herein, one skilled in the art can readily generate antibodies selective for each of the substituted HER2 polypeptides. Thus, the present invention includes monoclonal antibodies selective for substituted HER2 polypeptides, the substituted HER2 polypeptides being selected from the group consisting of: prefeHER2-Q141K mfeHER2-Q119K, prebearHER2-Q141K, mbearHER2-Q119K, prehumHER2-Q141K, mhumHER2-Q119K, premouseHER2-Q142K, mmouseHER2-Q120K, preratHER2-Q145K, mratHER2-Q120K, preE2Neu-Q141K, mE2Neu-Q119K, prehumHER2-Q329K, mhumHER2-Q307K, prehumHER2-Q429R, mhumHER2-Q407R; prehumHER2-N438D, and mhumHER2-N416D. Monoclonal antibodies according to the present invention can be obtained by using the polypeptides or their antigenic fragments as the antigens. For example, an antibody can be obtained by preparing hybridomas by fusion of myelomas, or other mammalian cells capable of infinite proliferation, with antibody-producing cells collected from mammals immunized with one of the antigens. Hybridoma clones capable of producing monoclonal antibody are cultured in vivo or in vitro. The preferred method of immunizing a mammal is by electrovaccination with expression vectors encoding mutant HER2, as described in Examples 3 and 4.

Alternatively, immunizations can be performed with purified or partially purified antigenic polypeptides. For example, the antigens can be in the form of live or killed cells expressing mutant HER2, or the partially purified culture supernatants or homogenates of such cells. In another alternative, the antigens are prepared chemically by peptide synthesis based on the amino acid sequences disclosed herein for the substituted polypeptides.

Immunization with antigenic polypeptides is performed by techniques well known in the art. For example, antigens, preferably in combination appropriate adjuvants, are injected into mammals intradermally, subcutaneously, intramuscularly, intraperitoneally, or intravenously. Rodents such as rats, mice and hamsters can be used. Depending upon species, the total dose of the antigens is generally in the range of about 5-500 pg of purified antigen or equivalent per animal.

Immunizations are performed 2-5 times at an interval of 1-2 Weeks. After the course of immunization, the animal's spleen is extracted and dispersed into a suspension of spleen cells. The antibody-producing cells and the myeloma cells obtained in the above are fused into a cell fusion mixture containing the objective hybridomas.

Suitable myeloma cells include mouse myeloma lines, such as P3-NS1-Ag4-1 cells (ATCC TIB18), P3-X63-Ag8 cells (ATCC TIB9), SP2/O-Ag14 cells (ATCC CRL1581), and other mutants which lack the HGPRT (hypoxanthine-guanine phosphoribosyltransferase) gene.

Cell fusion is carried out by techniques well known in the art, such as incubation with polyethylene glycol or Sendai virus, or by electric pulse. For example, fusion partners are suspended in fusion media containing fusion accelerators, and incubated at about 30-40° C. for about 1-5 min. Conventional serum-free media such as minimum essential medium (MEM), RPMI 1640 medium, and Iscove's Modified Dulbecco's Medium (IMDM) are preferred fusion media. To select hybridomas, the resultant cell fusion mixture is transferred to selection media such as HAT medium, and incubated at about 30-40° C. for from 3 days to 3 weeks, after which point only hybridomas are expected to survive. Detailed fusion and selection protocols are found in Harlow and Lane 1988 and Pandey, 2010.

Hybridomas are cultured as monoclonal populations, and antibodies secreted into culture are screened for reactivity with the immunizing antigen, preferably expressed on cells. Screening is preferably by immunofluorescence assays such as those described in Example 1. Alternatively, well known assays such as enzyme linked immunoassay and radioimmunoassay are used. See, for example Harlow and Lane, 1988

For selection of antibodies specifically reactive to the substituted HER2 antigens of the present invention, immunoassay screening techniques are employed to determine which of the monoclonal antibodies are reactive with the substituted antigen but not to the corresponding non-substituted antigen. Preferably, the immunoassay is an immunofluorescence assay, and the targets for immunofluorescence staining are cells transfected with either the substituted or non-substituted form of the HER2 antigen. Exemplary techniques for transfecting 3T3 cells with HER2 antigen constructs, and for assaying specific antibody binding to the transfected cells, are described in Piechocki, et al., 2001. Hybridoma clones secreting antibodies that bind specifically to the substituted form of the HER2 antigen, but not to the unsubstituted form, are producing the selective antibodies of the present invention. These clones are cultured or stored according to standard techniques. The monoclonal antibodies produced by these clones are harvested from culture in vivo, for example from animal ascites culture, or in vitro, from culture medium. The antibodies are purified by techniques such as protein A or Protein G affinity chromatography, salting out, dialysis, ultrafiltration, ion-exchange chromatography, affinity chromatography, high performance liquid chromatography (HPLC), gel electrophoresis, and isoelectrophoresis, or an appropriate combination of techniques. Once purified, the monoclonal antibodies are refrigerated, frozen, or lyophilized for storage.

Alternatively, one skilled in the art can utilize the HER2 antigens of the present invention to generate monoclonal antibodies by antibody phage display techniques. For example, cats are vaccinated with feHER2 or feHER2-Q141K, and RNA is extracted from bone marrow cells or PBLs. The RNA is used for the preparation of oligo dT-primed cDNA libraries, as described by Konthur and Walter (2002). Variable heavy (VH) and variable light (VL) chain orfs are PCR amplified based on reported sequences (www.ncbi.nlm.nih.gov/genome?term=felis%20catus), then Ig cDNA libraries are generated following the protocol described by Hammers and Stanley (2014). For screening purposes, phagemids such as pCombo3X are used to express these two chains as an scFv fused to the pill minor capsid protein of an engineered filamentous bacteriophage (originally derived from M13) (Hammers and Stanley 2014). The cognate antigen used for screening is recombinant fe HER2ecd-Fc (SEQ ID NO: 69), which is immobilized on sterile dishes via Fc binding. Screening is carried out with the pCombo3×/feHER2scFv library. A round of screening consists of binding of the feHER2scFv library to immobilized feHER2ecd-Fc to capture clones with high-affinity binding ("biopanning"), washing to remove background non-binding phage, elution of bound phage/scFv, infection of competent *E. coli*, expression and recovery via addition of helper phage, and preparation of recovered phage/scFv library for another round of screening. Several rounds of such screening are required to achieve sufficient purity of the aHER2 fe-scFv for functional and genetic analysis. Affinities of ~1 nMolar are readily achievable (Hammers and Stanley 2014; Carmen and Jemutus 2002). The cloned aHER2-fe-scFv can be 1) used directly as a recombinant scFv, 2) stabilized by fusion to an Fc domain (as in SEQ ID NO: 69) for use in vivo, or 3) reconstructed into full-length IgG light and heavy chains for production of aHER2 monoclonal Ab's of interest.

Human anti-HER2 mAb's are engineered by the same protocol using human PBLs for generating the initial Ig cDNA libraries.

In another embodiment, the present invention includes methods for immunizing a mammalian subject against HER2, using heterologous, unsubstituted ("wild type") antigenic polypeptides of bear HER2 or feline HER2. While these HER2 polypeptides are known, naturally occurring polypeptides, their inclusion in a method to induce immunity against HER2 represents a novel use. The methods include vaccination with an effective amount of expression construct, as previously described for the methods involving Q to K mutants of HER2. The unsubstituted bear and feline HER2 polypeptides were found to be effective antigens in experiments testing the hypothesis that anti-HER2 response can be achieved by immunization of a host with HER2 that is heterologous, but relatively closely matched to self HER2. Cat and bear HER2 are more closely related to human HER2 than is, for example, rodent HER2 (FIG. 6B). As disclosed in Example 3, bear HER2 broke the HER2 tolerance of cats, and induced both antibodies and T cells that reacted against feline HER2.

Therefore, the present invention includes a method for inducing immune response to HER2 in a mammalian subject, beginning with the step of administering, to a mammalian subject, an effective amount of a gene construct comprising a nucleic acid sequence encoding a heterologous antigenic polypeptide selected from the group consisting of precursor unsubstituted bear HER2 (prebearHER2); mature unsubstituted bear HER2 (mbearHER2); precursor unsubstituted feline HER2 (prefeHER2); and mature unsubstituted feline HER2 (mfeHER2). The gene construct additionally includes at least one promoter for expression of said antigenic peptide in a living cell. The step of administering the gene construct is followed by the steps of administering an effective amount of an immunological adjuvant, expressing the gene construct in cells of the mammalian subject, and inducing an immune response against HER2 in the mammalian subject.

In another embodiment, the present invention includes methods for immunizing cats against self HER2 with vaccines including antigenic polypeptides including the ECD and TM domains of wild type human, mouse, rat, or bear, HER2, and the human-rat hybrid E2neu. Both the precursor and mature forms are included. Use of these antigens for the immunization in experimental rodent models is known, but their administration to cats as an effective anti-HER2 vaccine in cats is a novel use. These antigens are known but their use in methods of inducing immunity to self HER2 in cats is novel. Again, the methods include vaccination with an effective amount of expression construct, as previously described. Exemplary antigenic polypeptides included in the HER2 antigens include: prebearHER2, SEQ ID NO: 37; mbearHER2, SEQ ID NO: 38; prefeHER2. SEQ ID NO: 39; mfeHER2, SEQ ID NO: 40; prehumHER, SEQ ID NO: 45; mhumHER2, SEQ ID NO: 46; premouseHER2, SEQ ID NO: 47; mmouseHER2, SEQ ID NO: 48; preratHER2, SEQ ID NO: 49; mratHER2, SEQ ID NO: 50; preE2Neu, SEQ ID NO: 51; and mE2Neu, SEQ ID NO: 52. Where the antigenic polypeptides are administered in the form of expression constructs, they can be encoded in the following exemplary polynucleotide sequences, or in synonymous sequences thereof: prebearHER2, SEQ ID NO: 41; mbearHER2, SEQ ID NO: 42; prefeHER2, SEQ ID NO: 43; mfeHER2, SEQ ID NO: 44; prehumHER, SEQ ID NO: 53; mhumHER2, SEQ ID NO: 54; premouseHER2, SEQ ID NO: 55; mmouseHER2, SEQ ID NO: 56; preratHER2, SEQ ID NO: 57; mratHER2, SEQ ID NO: 58; preE2Neu, SEQ ID NO: 59; and mE2Neu, SEQ ID NO: 60.

An additional panel of substituted human HER2 polypeptides was also found to break tolerance to human HER2 in mice transgenically expressing human HER2 (human Tg mice), in experiments described in Example 4. Human HER2 is self HER2 in human HER2 Tg mice, and these mice are well known to exhibit strong tolerance to human HER2 (Piechocki, et al., 2003). The additional HER2 polypeptides found to be effective tolerance-breakers included precursor human HER2 having a Q-K substitution at amino acid 329, or a substitution of arginine for glutamine (Q-R) at amino acid 429, or a substitution of aspartic acid for asparagine (N-D) at position 438. The mature forms of these substituted HER2 antigens are reasonably predicted to be equivalently immunogenic to the precursor forms, for reasons previously stated.

Therefore, the present invention provides antigenic polypeptides for inducing immune response against HER2 in a mammalian subject, The polypeptides include at least the extracellular and transmembrane domains of human HER2, the extracellular domain including at least one of the following amino acid substitutions: glutamine with lysine (Q-K) or a conservative amino acid of lysine, at position 141 of precursor humanHER2 (prehumHER2-Q141K); glutamine with lysine (Q-K) or a conservative amino acid of lysine, at position 119 of mature humanHER2 (mhumHER2-Q119K); glutamine with lysine (Q-K) or a conservative amino acid of lysine, at position 329 of precursor humanHER2 (prehumHER2-Q329K); glutamine with lysine (Q-K) or a conservative amino acid of lysine, at position 307 of mature humanHER2 (mhumHER2-Q307K); glutamine with arginine (Q-R), or a conservative amino acid of arginine, at position 429 of precursor human HER2 (prehumHER2-Q429R); glutamine with arginine (Q-R), or a conservative amino acid of arginine, at position 407 of mature human HER2 (mhumHER2-Q407R); asparagine with aspartic acid (N-D), or a conservative amino acid of aspartic acid, at position 438 of precursor human HER2 (prehumHER2-N438D); and asparagine with aspartic acid (N-D), or a conservative amino acid of aspartic acid, at position 416 of mature human HER2 (mhumHER2-N416D).

Exemplary amino acid sequences for each of the substituted antigens as follows: prehumHER2-Q141K (SEQ ID NO: 9); mhumHER2-Q119K (SEQ ID NO: 3;); prehumHER2-Q329K (SEQ ID NO: 28); mhumHER2-Q307K (SEQ ID NO: 25); prehumHER2-Q429R (SEQ ID NO: 29); mhumHER2-Q407R (SEQ ID NO: 26); prehumHER2-N438D (SEQ ID NO: 30); and mhumHER2-N416D (SEQ ID NO: 27). It will be understood that the disclosed amino acid sequences are exemplary, and that the present invention encompasses all immunologically equivalent sequences.

The antigenic peptides are provided as isolated polypeptides, and also as polypeptides encoded as nucleic acid sequences in gene constructs. Each gene construct additionally includes at least one promoter operatively linked to the nucleic acid sequence, with the promoter inducing the expression of the encoded antigenic polypeptide in a living cell.

The encoded constructs, and exemplary nucleic acid sequences encoding them, include: prehumHER2-Q141K, SEQ ID NO: 21; mhumHER2-Q119K, SEQ ID NO: 15; prehumHER2-Q329K, SEQ ID NO: 34; mhumHER2-Q307K, SEQ ID NO: 231; prehumHER2-Q429R, SEQ ID NO: 35; mhumHER2-Q407R, SEQ ID NO: 32; prehumHER2-N438D, SEQ ID NO: 36; and mhumHER2-N416D, SEQ ID NO: 33. It will be understood that the recited nucleic acid sequences are only exemplary, and that each specified polypeptide can be encoded by one or more synonymous nucleic acid sequences without departing from the scope of the present invention. The nucleic acid sequences are preferably DNA sequences, but may alternatively comprise at least one RNA molecule.

In a related embodiment, the present invention provides the additional panel of HER2 antigen constructs in a vaccine composition for inducing immunity to HER2 in a mammalian subject, the vaccine composition including an effective amount of at least one of the gene constructs and an effective amount of an adjuvant. An exemplary use of these vaccine compositions is disclosed in Example 4.

In another related embodiment, the present invention includes monoclonal antibodies selective for each member of the additional panel of substituted human HER2 polypeptides. As previously stated, with the amino acid sequences disclosed herein, one skilled in the art can readily generate antibodies selective for each of the substituted HER2 polypeptides.

In order to respond to vaccines against self HER2, a host must possess an immune system sufficiently competent to overcome tolerance in response to vaccination. The immunodepression characteristic of mammary carcinomas and other cancers can prevent the success of even the most potent vaccine. In one embodiment, the present invention includes a diagnostic method for determining whether a host is capable of making a response to self HER2.

In the diagnostic method, a sufficient amount of vaccine known to break tolerance to the HER2 of host species is administered to a candidate host for anti-HER2 immunotherapy. A vaccine "known to induce immune response" is a vaccine which has been shown to produce a measurable benefit to at least a subset of similarly disposed mammalian hosts, for example in a clinical or preclinical trial. The vaccines include those that incorporate the substituted HER2 polypeptide antigens of the present invention, which are shown to induce immunity in Examples 3 and 4. After the vaccine has been administered, the subject is monitored for the development of cellular and/or humoral immunity to self HER2, for example by means of the immunoassays described in Example 3. If detectable immune response is detected, then the candidate host is recognized as being sufficiently immunocompetent to respond to immunotherapy directed at self HER2. Ideally, the diagnostic test represents a minimal, initial course of vaccination, with the results determining whether a more extensive course of vaccination will next be administered.

The invention is further described in detail in reference to the following examples, which are provided for the purpose of illustration only, and are not intended to be limiting. Thus, the present invention should in no way be construed as being limited to the following examples, but rather, be construed to encompass any and all variations which become evident as a result of the teaching provided herein.

Example 1

Expression and Function of HER-2 in Feline Mammary Carcinoma Cell Lines and Explants Materials and Methods Animals and tissues BALB/c mice were purchased from Charles River Laboratory. Pathogen free (SPF) purpose bred domestic shorthair cats aged 6 months-2 years were obtained from Liberty Research, Inc (Liberty, N.Y.). Animals were housed and maintained in the Department of Laboratory Animal Resource (DLAR) facility at the Wayne State University School of Medicine in accordance with Institutional Animal Care and Use Committee guidelines. The experimental cats were adopted as domestic pets by the care taker community after completion of the study. A black bear legally harvested in Ontario, Canada was the donor of the liver tissue.

Feline mammary carcinoma (FMC) samples were obtained from mastectomy tissues of two feline patients treated at Oakland Veterinary Referral Services (OVRS) in Michigan with consent from the cat owners (Table 1).

TABLE 1

Feline Mammary Carcinoma Patients

| Cat | Breed | Sex | Spayed | Age |
|---|---|---|---|---|
| OVRS-1A | Rex | F | Y | 8 |
| OVRS-1B | | | | 9 |
| OVRS-2 | DSH | F | Y | 13 |
| CSU-133 | Persian | F | N | 12 |
| CSU-418 | DLH | F | Y | 5 |
| CSU-1646 | DSH | F | Y | 5 |

OVRS-1A and OVRS-1B are two independent primary tumors from the same cat. Three additional mammary tumor samples with paired, uninvolved stromal tissues were purchased from Colorado State University (CSU-133, 418, and 1646).

Cell Lines

K248 established from a pulmonary metastasis of a Siamese cat mammary carcinoma was provided by Dr. John Hilkens and the late Dr. Wim Misdorp at the Netherland Cancer Institute (Minke, et al., 2010). Mammary carcinoma line K12 from a 14 year old cat was established by Dr. William Hardy, Jr. and provided by Dr. Jaime Modiano of the University of Pennsylvania, Pa. (Modiano, et al., 1991). SKOV3 cells were purchased from the American Type Culture Collection. MCF7 cells were obtained from Lisa Polin of the Karmanos Cancer Institute. All cells were maintained in Dulbecco's Modified Eagle's Medium supplemented with fetal bovine sera, penicillin and streptomycin. The feline origin of K248 and K12 cells was authenticated by short tandem repeat (STR) analysis of four loci (FIGS. 1 and 2.).

Immunohistochemical Analysis

Pathological diagnoses were performed according to the WHO classification for tumors in domestic animals. For feline HER2 detection, epitopes were retrieved with sodium citrate buffer (pH 6.0) and histological grade primary antibodies were applied according to manufacturer's recommendation (HER2, clone Z4881, Invitrogen) followed by broad-spectrum HRP polymer conjugate (SuperPicTure™ Polymer Detection Kit, Zymed) and DAB substrate (Pierce Biotech). Feline mammary tumor cells, K248, were injected subcutaneously in SCID mice. Tumor explants were used as controls.

Cell Proliferation Assay

Cells were plated at 2-5,000/well in 96-well plates and treated with gefitinib or lapatinib in quintuplicate for 48 h. Alamar Blue reagent (Life Technologies) was added and fluorescence measured after 3-4 h. The % proliferative activity was determined relative to the average of untreated samples.

Western Blot Analysis

Cells or tissues were lysed in a non-ionic detergent lysis buffer (Gibson, et al., 2013) with protease inhibitor cocktail (Roche Diagnostics) immediately after the addition of phosphatase inhibitors (NEB). Total protein was quantified by BCA assay (Pierce Biotech). Ten pg protein was boiled in Laemmli buffer, separated with 8% SDS-polyacrylamide (PAGE) gel and transferred onto PVDF membrane for overnight incubation with antibody to HER2 (42/c-erbB-2, BD Biosciences), phospho-HER2 Y1248 (polyclonal, Cell Signaling Technology), Akt (polyclonal, Cell Signaling Technology), phospho-Akt S473 (587F11, Cell Signaling Technology) or b-Actin (1-19, Santa Cruz Biotech). After washing in TBS-Tween, membranes were incubated with horseradish peroxidase (HRP)-conjugated secondary antibody before washing and development using enhanced chemiluminescent reagents (Thermo Scientific).

Flow Cytometric Analysis

HER2/neu epitopes were detected by moAb TA-1 (Calbiochem), Trastuzumab (Genentech), 7.16.4 (Calbiochem), N12, and N29 (hybridoma lines were generous gifts of Dr. Yosef Yarden, Weissman Institute, Isreal). moAb to human EGFR (528, Santa Cruz Biotech), HER3 (SGP1, eBioscience) and HLA-ABC (W6/32, eBioscience) were used as indicated. Phycoerythrin-conjugated goat anti-mouse or anti-human IgG was the secondary antibody (Jackson ImmunoResearch). Flow cytometric analysis was performed using FACS Canto II and data analyzed with FlowJo (Tree Star).

To measure antibody level in immune sera, mouse or feline sera were incubated with 3T3 cells transfected to express the designated antigen and detected by PE-conjugated anti-mouse or feline IgG secondary antibody (Santa-Cruz). Mouse antibody concentrations were extrapolated from a standard curve of HER2 moAb TA-1. Feline antibody titers were determined by serial dilution until binding was no longer detected above isotype control.

Results

In a step toward establishing an outbred cat model of HER2 immunity, the expression and signaling functions of HER2 in feline mammary carcinoma cell lines was characterized. These HER2 properties were also compared those of spontaneous feline mammary carcinomas and known HER2-expressing cell lines.

Expression of HER2 in feline mammary carcinoma (FMC)

Figure 3B:
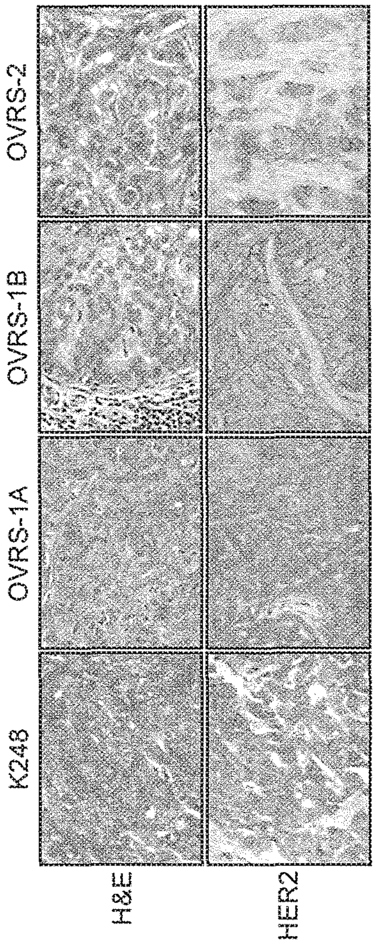
FIG. 3B shows expression of HER2 in feline mammary carcinoma by immunohistochemical analysis of three primary FMC samples and FMC line K248 outgrowth in SCID mice using polyclonal Ab to huHER2; H&E stains are shown in parallel.

Expression of ERBB family receptor tyrosine kinase (RTK) in FMC was measured by flow cytometry. Surface expression of HER1 (EGFR), HER2, and HER3 was detected in K12 and K248 cells, using moAbs to their human homologs (FIG. 3A) (FIG. 3A). MHC I expression was also detected with moAb W6/32 to a constant region of human MHC I. Control human ovarian cancer cell line SKOV3 showed elevated HER2, while lacking HER3 expression (Gostring, et al., 2012). Feline HER2 expression in primary FMC clinical samples (Table 1) was detected by IHC staining (FIG. 3B). Membrane staining of HER2 was detected in all three primary FMC samples and in K248 explant, consistent with membrane staining of K248 cells by flow cytometry (FIG. 3A). Membranous expression of HER2 in FMC would be expected to permit recognition by effectors of both humoral and cellular immunity. Cytoplasmic staining was also detected in OVRS-1A and the K248 explant and may indicate accumulation of incompletely or incorrectly processed HER2. The clinical significance of cytoplasmic HER2 remains unclear but T cells would be expected to recognize cytoplasmically derived peptides in the context of MHC I and II molecules.

Receptor Tyrosine Kinase (RTK) Activity in FMC

Figure 4B:
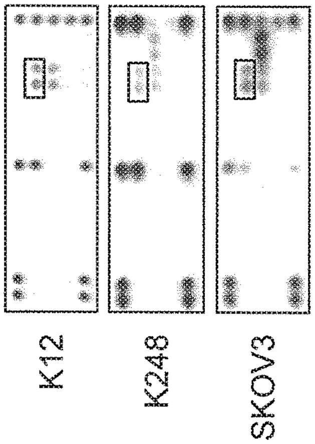
FIG. 4B shows RTK analysis of FMC cell lines K12 and K248 were analyzed by PathScan RTK signaling array (Cell Signaling Technology). Phospho-Akt (S473) detection is indicated with a box; human SKOV3 was the control.
Figure 4A:
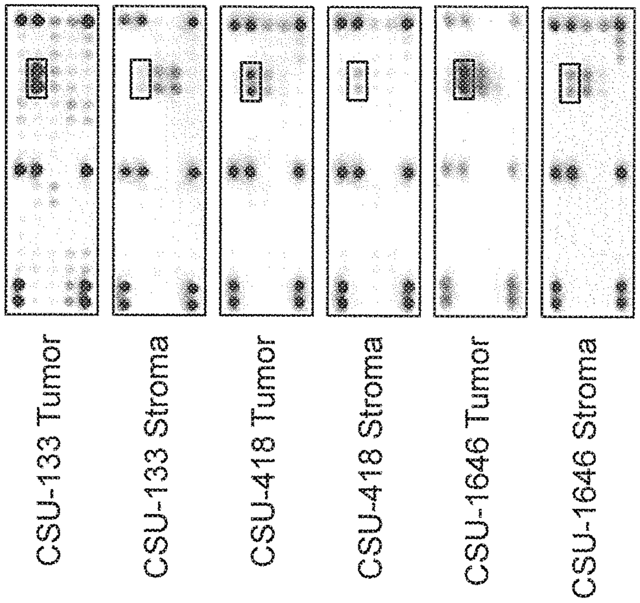
FIG. 4A shows RTK (receptor tyrosine kinase) analysis of protein lysates from primary FMC tumor with paired uninvolved stromal tissue; phospho-Akt (S473) detection is indicated with a box.
Figures 5A, 5B:
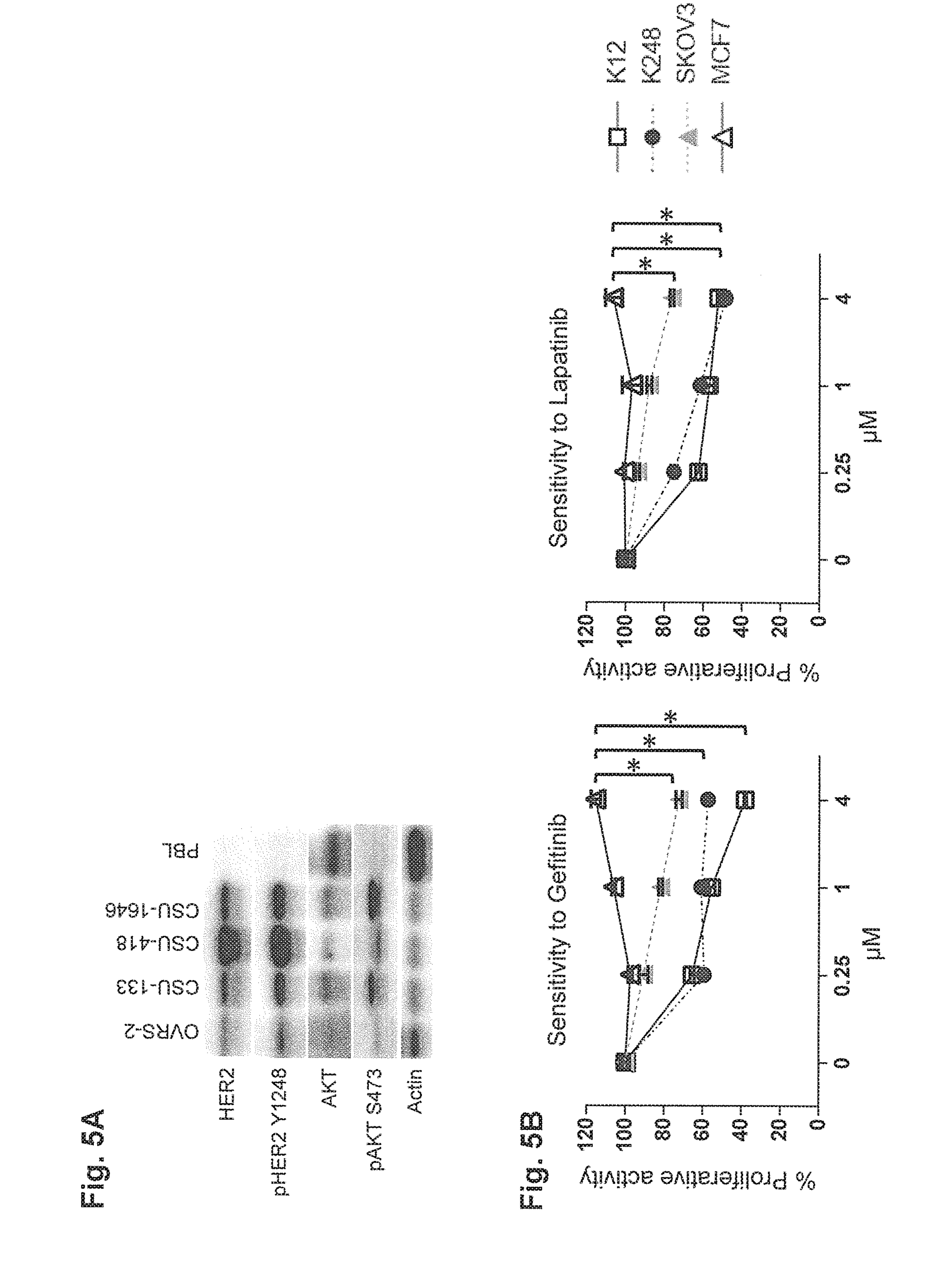
FIG. 5A shows RTK activity in FMC, as determined by Western blot analysis of total HER2, pHER2 (Y1248), total Akt and pAkt (S473) in primary FMC samples; feline PBL (peripheral blood leukocytes) was the negative control.
FIG. 5B shows the sensitivity of FMC cell lines to receptor tyrosine kinase inhibitors; cells were cultured in gefitinib or lapatinib for 48 h and the percentage of proliferative cells was measured with Alamar Blue by comparison to untreated controls; *p<0.001 two-way ANOVA with Dunnet's posttest.

Activation of RTK signaling in FMC was tested using a human RTK array (R&D Systems), FIGS. 4A and 4B. Although cross-reactivity with feline antigens by all antibodies in this array was not verified, AKT phosphorylation (S473) was elevated in 3/3 FMC tissue samples CSU-133, 418, and 1646, compared to their paired, uninvolved stromal tissue. AKT phosphorylation was also observed in K12 and K248 cells consistent with RTK pathway activation in FMC. HER2 (Y1248) and downstream AKT (S473) phosphorylation in primary FMC tissue was further tested by Western blotting (FIG. 5A). Total and phosphorylated HER2 and AKT were detected in FMC OVRS-2, CSU-133, CSU-418 and CSU-1646, demonstrating activation of HER2 and downstream RTK signaling events.

To further test if ERRB RTK signaling is required for FMC cell proliferation, FMC cell lines K12 and K248 were cultured with or without ERRB family tyrosine kinase inhibitors gefitinib or lapatinib. Both K12 and K248 exhibited dose-dependent inhibition of cell proliferation. SKOV3 and MCF7 cells were the positive and negative control, respectively (FIG. 5B). Therefore, FMC express functional tyrosine kinase receptors which trigger downstream signaling and cell proliferation.

The results show that the FMC cell lines are useful models for the induction and effects of anti-HER2 immune response.

Example 2

Cloning and Characterization of Substituted Feline HER2, and HER2 of Other Species Materials and Methods DNA cloning and construction Cloning primer sequences are shown in Table 2.

TABLE 2

CLONING PRIMERS

| cDNA product | Primer | Sequence (5' to 3') | SEQ ID NO |
|---|---|---|---|
| Feline HER2 ECTM (prefeHER2) | Forward | ATTAC TACAA GCTTG AGACC ATGGA GCTGG CGGCC TGGT | SEQ ID NO: 70 |
| Feline HER2 ECTM (prefeHER2) | Reverse | TACTA ATCTA GATCA CATCG TGTAC TTCCG GATCT TCTG | SEQ ID NO: 71 |
| Feline HER2 ECD-Fc | Forward (HER2 ECD) | CACCA AGCTT GAGAC CATGG AGCTG G | SEQ ID NO: 72 |
| Feline HER2 ECD-Fc | Reverse (HER2 ECD) | GATTT GGGCT CGGAC GTCAC AGGGC TGG | SEQ ID NO: 73 |
| Feline HER2 ECD-Fc | Forward (Fc tag) | CTGTG ACGTC CGAGC CCAAA TCTTG TGAC | SEQ ID NO: 74 |
| Feline HER2 ECD-Fc | Reverse (Fc tag) | TCTAG ATTAT TTACC CGGAG ACAGG GAGAG GCTC | SEQ ID NO: 75 |
| Black bear HER2 ECTM (prebearHER2) | Forward | TAAGC TTGAG ACCAT GGAGC TGGCG GCCTG GTG | SEQ ID NO: 76 |
| Black bear HER2 ECTM (prebearHER2) | Reverse | CTCTA GATTC ACATC GTGTA CTTCC GGATC TTC | SEQ ID NO: 77 |
| Feline GM-CSF | Forward | CACCA TGTGG CTGCA GAACC TGCTT TTCCT G | SEQ ID NO: 78 |
| Feline GM-CSF | Reverse | TTACT TCTGG TCTGG TCCCC AGCAG TC | SEQ ID NO: 79 |
| prefeHER2-Q141-K and mfeHER2-Q119-K | Forward | GCGGGAGCTGaAGCTCCGAAG | SEQ ID NO: 103 |
| prefeHER2-Q141-K and mfeHER2-Q119-K | Reverse | *AGCCCTCCTAGGGCAGCCCCTGTAG* | SEQ ID NO: 104 |

TABLE 2 -continued

CLONING PRIMERS

| cDNA product | Primer | Sequence (5' to 3') | SEQ ID NO |
|---|---|---|---|
| prebearher2-0141K and mbearher2-Q119K | Forward | AAGCCTCACAGAGATCCTGAAG | SEQ ID NO: 111 |
| prebearher2-0141K and mbearher2-Q119K | Reverse | CGAAGCTTCAGCTCCCGCAGCCCTC | SEQ ID NO: 112 |
| premouseHE R2-Q142K and mmouseHER2-Q120K | Forward | AGTCTCACAGAGATCTTGAAGG | SEQ ID NO: 113 |
| premouseHER2-Q142K and mmouseHER2-Q120K | Reverse | TCGAAGCTTCAGCTCCCGCAGCCC | SEQ ID NO: 114 |
| preratHER2-Q145K and mratHER2-Q120K | Forward | GCTTCGAAGTCTCACAGAGATC | SEQ ID NO: 115 |
| preratHER2-Q145K and mratHER2-Q120K | Reverse | TTCAGCTCCCGCAGCCCCTCTG | SEQ ID NO: 116 |
| prehumHER2-Q141K, pre E2Neu-Q141K, mhumHER2-Q119K, and mE2Neu-Q119K | Forward | GCTGAAGCTTCGAAGCCTCACAG | SEQ ID NO: 117 |
| prehumHER2-Q141K, preE2Neu-Q141K, mhumHER2-Q119K, and mE2Neu-Q119K | Reverse | TCCCGCAGGCCTCCTGGGGAGG | SEQ ID NO: 118 |

Figure 7:
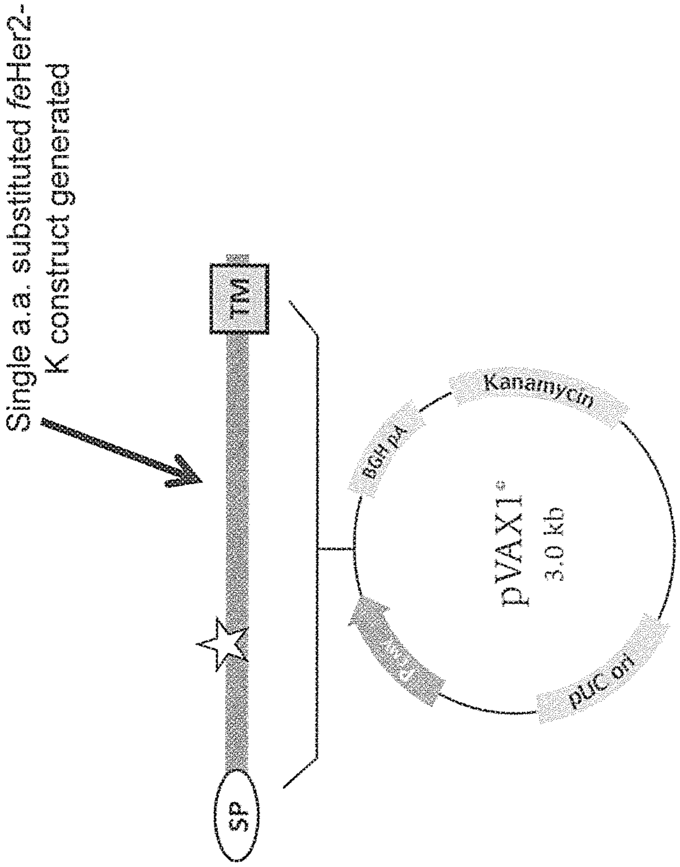
FIG. 7 shows a construct for the expression of prefeHer2-Q141K ("feHER2-K") in a host animal.

Feline HER2 (ERBB2) cDNA was cloned from cell line K248 (39), K12 (40), and the ovary of a domestic shorthair cat using a Protoscript kit (New England Biolabs) which showed identical sequences for all three sources. The confirmed full-length precursor feline ERBB2 (prefeHER2) cDNA sequence has been submitted to Genbank (#JN990983). For vaccination, a stop codon was introduced after codon 687 to delete the oncogenic intracellular domain, then subcloned into pVax1, giving pprefeHER2 which contains the signal peptide, extracellular and transmembrane domains of feline HER2 (FIG. 7). The pprefeHER2-K nucleotide substitution in codon 141 of extracellular domain I was cag→aag, based on our reported sequence of feline ERBB2 (Genbank JN990983) and was generated by PCR-based methods and verified by DNA sequencing. Homologous Q-K substituted antigens for bear, mouse, and other species of HER2 are similarly generated, using the primers given in Table 2.

Black bear HER2 cDNA was similarly cloned from the liver tissue of a black bear. The cDNA sequence was submitted to Genbank (#JQ040508). DNA vaccine pprebearHER2 encoding the signal peptide, extracellular and transmembrane domains was constructed by PCR similar to pprefeHER2.

Results

Feline HER2 (ERBB2) cDNA cloned from K12, K248 and normal feline ovary showed identical sequences (GenBank Accession JN990983). The amino acid. translate of full-length feline HER2 shared 93% sequence identity with human HER2 (FIGS. 6A and 6B). Black bear HER2 (GenBank Accession JQ040508) had 96% and 92% a.a. sequence identity with feline and human HER2, respectively. The comparative data in FIG. 6B also show that human HER2 is more closely related to the HER2 of cats and black bears than they are to the HER2 of experimental rodents.

The feline, black bear, human and rat HER2 (rat neu) extracellular and transmembrane regions (ECTM) were individually transfected into 3T3 cells. Epitope expression was compared by staining with moAbs to human HER2 (TA-1, N12, N29 and trastuzumab) or rat neu (7.16.4) (McKenzie, et al., 1989; Stancovski, et al., 1991; Hudziak, et al., 1989; Drebin, et al., 1984) (FIG. 6C). Feline HER2 was recognized by all five moAbs. The closely related black bear HER2 was recognized by four moAbs, except trastuzumab, signifying structural disparity at this epitope. moAb 7.16.4 identifies a rat neu epitope which is present in feline and black bear, but not human HER2. Overall, there are high levels of epitope sharing among HER2 molecules from these 4 species, with cat HER2 expressing all 5 epitopes recognized by the panel of moAbs.

Example 3

Immunogenicity of Substituted and Heterologous HER Antigenic Polypeptides

Materials and Methods

Generation of recombinant feline HER2 and human Fc fusion protein-feHER2ecd-Fc

The secreted fusion protein feHER2ecd-hFc (SEQ ID NO: 69) was generated to serve as a stimulator for T cells in vitro. feHER2ecd-hFc was synthesized by fusing the 3' end of the signal peptide-extracellular domain region of feHER2 (codons 1-653) to the hinge-CH2-CH3 region of human IGHG1. This codon 1-653 region of feHER2 (Genbank JN990983) was PCR amplified with forward primer 5' CACCA AGCTT GAGAC CATGG AGCTG G (SEQ ID NO: 72) and reverse primer 5'-GATTT GGGCT CGGAC GTCAC AGGGC TGG (SEQ ID NO: 73), giving a 1986 bp product. IGHG1 cDNA (BC080557; Openbiosystems) was PCR amplified with primers 5'-CTGTG ACGTC CGAGC CCAAA TCTTG TGAC (SEQ ID NO: 74) and 5'-TCTAG ATTAT TTACC CGGAG ACAGG GAGAG GCTC (SEQ ID NO: 75), giving a 716 bp product consisting of codons 248-479. These two DNAs, which overlap by 22 bases, were fused by overlap extension-primed DNA synthesis giving 2676 bp product, which was then cloned into the HindIII and XbaI sites of the mammalian expression vector pVax1. The sequence coded by this feHER2ecd-hFc fusion cDNA, confirmed by DNA sequence analysis, is shown in FIG. 8A (feHER2ecd in uppercase, hFc in lowercase).

A schematic of feHER2ecd-hFc is shown in the upper panel of FIG. 8B. A Western blot verifying the fusion protein is shown in the lower panel of FIG. 8B. For production of feHER2ecd-hFc, murine 3T3 cells were transfected with the pVax/feHER2-hFc vector, and recombinant feHER2-Fc in culture supernatant was quantified by ELISA using mouse anti-human HER2 capture moAb (clone TA-1, Calbiochem), which cross-reacts with feline HER2. Rabbit anti-human IgG was the detection antibody (Jackson lmmunoresearch). huHER2-¬ fc was purchased from Sino Biologicals.

Stimulation of T Cells in vitro with Recombinant HER2ecd-Fc.

Feline PBMC were isolated by ficoll separation (GE Healthcare). Cells were plated at 2×105/well in round bottom 96-well plates and cultured with 10 μg/mL feHER2Fc (3T3 supernatant equivalent as described above), huHER2Fc, human IgG control or control 3T3 conditioned medium for 72 h. Total well contents were then transferred to feline IFNγ ELISPOT plates (R&D Systems) and incubated for an additional 48 h prior to enumeration.

Analysis of T cell response by ELISPOT

Mouse splenocytes or feline PBMC isolated by Ficoll separation (GE Healthcare) were maintained in Roswell Park Memorial Institute Medium supplemented with fetal bovine sera, penicillin/streptomycin. Feline PBMC were supplemented with 0.5 ng/mL feline IL-2 (R&D Systems). Cells were plated at $2\times10^5$/well in round bottom 96-well plates and cultured with 10 μg/mL feHER2Fc (3T3 supernatant equivalent as described above), huHER2Fc, human IgG control (Jackson Immunolabs) or control 3T3 conditioned medium for 48 (mouse) or 72 (feline) hours. Total well contents were then transferred to mouse or or feline (R&D Systems) $IFN_\gamma$ ELISPOT plates and incubated for an additional 48 hours prior to detection and enumeration as per manufacturer protocol. Visualized cytokine spots were enumerated using the ImmunoSpot analyzer (CTL, Shaker Heights, Ohio) and expressed as the number of cytokine-producing cells per $10^6$ splenocytes or PBMC.

Feline GM-CSF (CSF2) cDNA was amplified from a randomly-primed cDNA library (Protoscript kit from New England Biolabs) prepared from ConA-stimulated feline peripheral blood mononuclear cells (PBMC). Codons 1 through 67 were PCR amplified with forward primer 5'-ATGTG GCTGC AGAAC CTGCT TTTCC TG (SEQ ID NO: 80) and reverse primer 5'-CTCAG GGTCA AACAT TTCAG AGAC (SEQ ID NO: 81). Codons 60 through 145 were amplified with primers 5'-GTCTC TGAAA TGTTT GACCC TGAGG (SEQ ID NO: 82) and 5'-TTACT TCTGG TCTGG TCCCC AGCAG TC (SEQ ID NO: 83). These two PCR products with fused by overlap extension priming PCR, giving a 435 bp full-length CSF2 orf, which was cloned into expression vector pcDNA3.1 blunt Topo (Invitrogen). The orf sequence from a clone in the correct orientation was in accord with the consensus of feline CSF2 cDNAs in Genbank (AY878357, NM001009840, AF053007 and AF138140).

Electrovaccination of Mice and Cats

Mice were injected with an admix of 50 μg each of vaccine plasmid and plasmid encoding murine GM-CSF (pmuGM-CSF) in 50 μl PBS in the gastrocnemius muscle (Jacob, et al., 2006). Conductive gel was applied on the skin over the injection sites. Electroporation was conducted with NEPA21 electroporator (Napagene) using a tweezer electrode. Three 50 msec degenerating bipolar pulses of 100 V were administered at each site. Cats were injected with 1.5 mg each of HER2 vaccine plasmid and pfeGM-CSF in 1.5 mL PBS, divided equally over three injection sites in the biceps femoris or quadriceps. Two rounds of electroporation were applied to each site as described using a 1.5 cm2 caliper electrode (BTX).

Results

Note that in FIGS. 9-13, an abbreviated notation is used for the HER2 polypeptides. The term Q141K is shortened to "K". The prefix "pre" is omitted. For example, the plasmid "pprefeHER2-Q141K" is given as pfeHER2.

Immunogenicity of Substituted and Heterologous Forms of HER2.

Figure 9A:
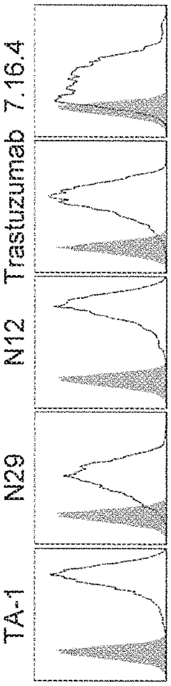
FIG. 9A shows a flow cytometric analysis of the binding of 3T3/prefeHER2-Q141K by moAb to HER2/neu, with staining and analysis conducted as in FIG. 6C.

Recombinant prefeHER2-Q141K was expressed in 3T3 cells and characterized by flow cytometry (FIG. 9A). Positive staining by the panel of five moAbs indicated preservation of 5 HER2/neu epitopes after Q→K substitution. Improved binding of feHER2-K by neu specific moAb 7.16.4 compared to WT prefeHER2 (compare to FIG. 6C) suggests a possible structural alteration of this epitope.

Figure 11A:
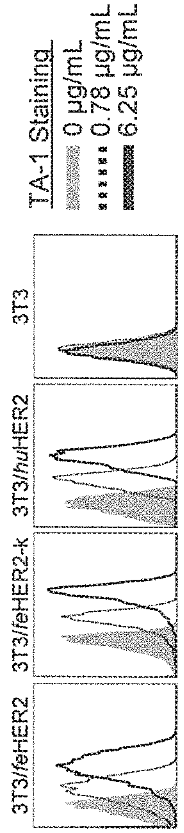
FIG. 11A shows a specificity control of mouse immune serum: binding of moAb TA-1 at indicated concentrations to 3T3 cells expressing prefeHER2, prefeHER2-Q141K, or prehuHER2; un-transfected 3T3 cells were the control.
Figure 11B:
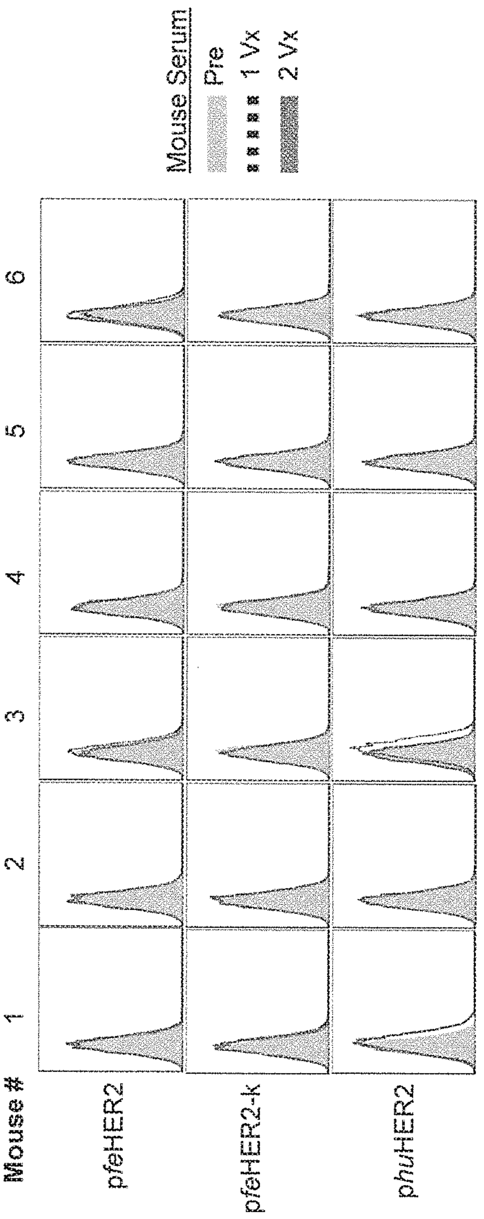
FIG. 11B shows a specificity control of mouse immune serum: binding of immune serum from vaccinated mice to un-transfected 3T3 cells; each panel depicts the binding of pre-, post 1× and post 2× vaccination serum from an individual mouse.

The immunogenicity of prefeHER2 and prefeHER2-Q141K was initially characterized in BALB/c mice by electrovaccination with pprefeHER2, prefeHER2-Q141K, or control pprehuHER2 (encoding human HER2 ECTM), each of which were admixed with pmuGM-CSF encoding murine GM-CSF (Jacob, et al., 2010; Radkevich-Brown, et al., 2009; Jacob, et al., 2006; Jacob, et al., 2007) Antisera of vaccinated mice were tested for reactivity against 3T3 cells transfected with pprefeHER2 ("3T3/HER2"), pprefeHer2-Q141K ("3T3/HER2-K"), or control pprehuHER2 ("3T3/huHER2"). Expression of with pprefeHER2, pprefeHer2-Q141K, or control pprehuHER2. on individually transfected 3T3 cells was comparable, as verified with moAb TA-1 binding at 2 different concentrations (FIG. 11A).

Figure 9B:
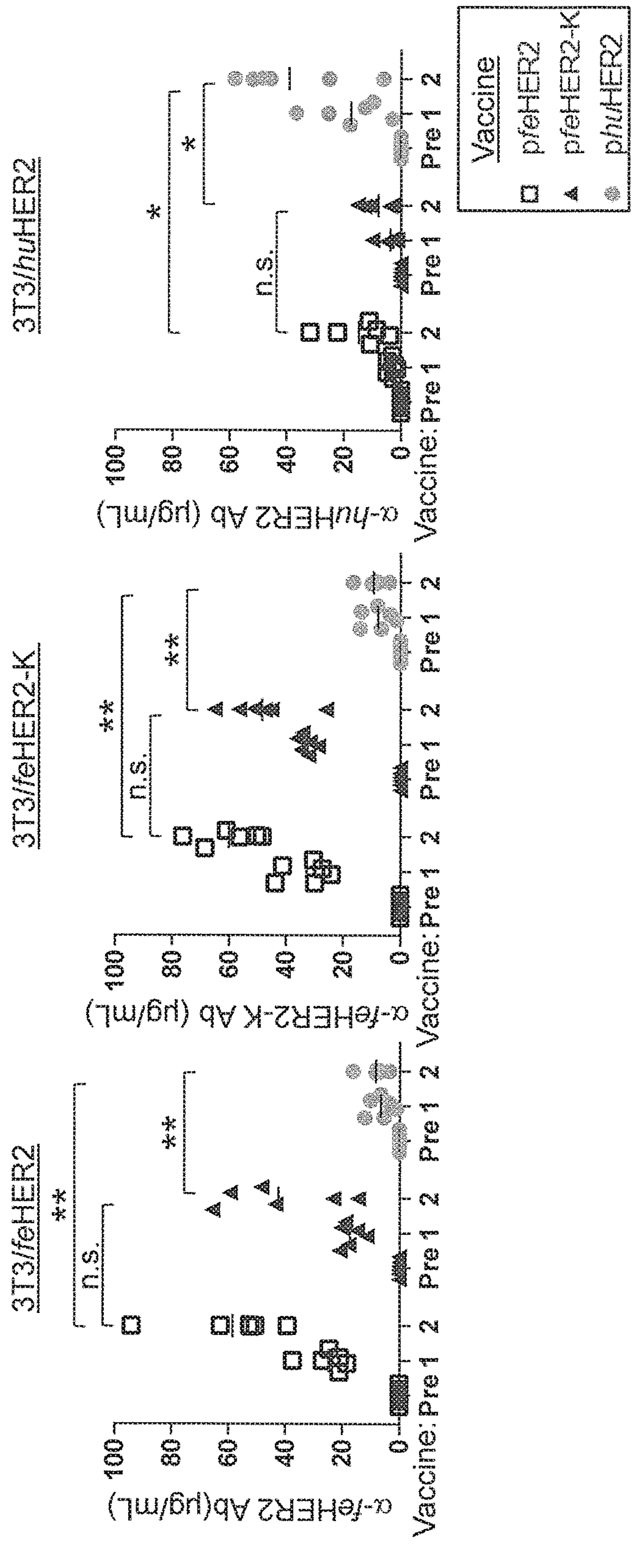
FIG. 9B shows antibody response to pprefeHER2, pprefeHER2-Q141K and pprehuHER2 in BALB/c mice before (Pre) and two weeks after 1× and 2× vaccination given in 2 wk intervals; horizontal lines depict the mean for each group (*p<0.05, **p<0.005 one-way ANOVA with Tukey's post-test)
Figure 9C:
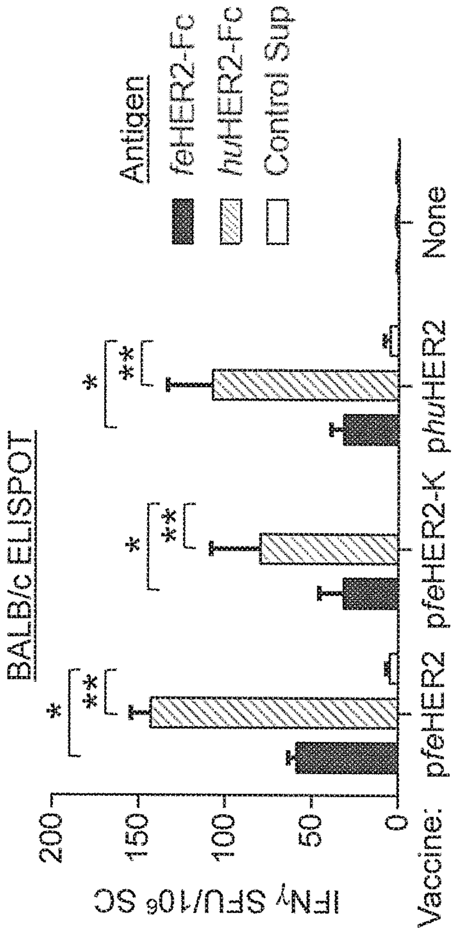
FIG. 9C shows T cell response to feline and human HER2 in 2× vaccinated mouse splenocytes (n=4) or naïve mouse splenocytes (n=3) as measured by ELISPOT in triplicates using 10 μg recombinant antigen (*p<0.05, **p<0.01 two-way ANOVA with Dunnet's posttest)

After 2× immunization, mice produced 59±19, 49±13 and 39±20 μg/mL IgG to their cognate antigens, respectively, as measured with 3T3 cells transfected with individual test antigens (FIG. 9B). The results indicate that antibodies induced by vaccination with pprefeHER2 or pprefeHER2-Q141K are highly cross-reactive, with both antibodies recognizing dominant foreign epitopes on feline HER2 (FIG.

9B left and middle panels). Therefore, the Q141K substitution appears to create only subtle changes which did not alter the immune response to the dominant foreign epitopes. Modest cross-reactivity between feline and human HER2 immune sera was also observed. Neither pre-, nor post-vaccination mouse serum bound un-transfected 3T3 cells (FIG. 11B), supporting HER2 specificity of the immune sera.

To measure T cell response after vaccination, a feline HER2 extracellular domain (ECD) and human Ig Fc fusion protein, feHER2-Fc, was generated as the test antigen, as previously described and shown in FIG. 8B. Splenocytes from immunized BALB/c mice were stimulated by incubation with feHER2-Fc or control huHER2-Fc, and IFNγ-producing T cells were enumerated by ELISPOT.

The results (FIG. 9C) show that T cell responses to feline HER2 were induced by vaccination with pprefeHER2 ("pfeHER2"), pprefeHER2-Q141K ("pfeHER2-K") or pprehuHER2 ("phuHER2"). This finding indicates cross-reactivity between feline and human HER2 antigen. This finding also indicates that the Q141K substitution does not alter mouse T cell response to the WT HER2 protein. The greater responses produced by in vitro stimulation with huHER2-Fc, relative to feHER2-Fc, probably reflects the different forms of the stimulating preparations, with purified huHER2-Fc protein stimulating more effectively than secreted feHER2-Fc in culture supernatant.

Anti-HER2 Vaccinations in the Feline Model System

The feasibility of DNA electrovaccination in cats was initially tested with ppreE2Neu encoding a fusion protein of human HER2 and rat neu. This construct was previously found to be effective at inducing both humoral and cellular immunity in HER2 Tg mice (Jacob, et al., 2010).

Three healthy purpose-bred, pathogen-free domestic shorthair cats 12-24 months of age (Liberty Research Inc. Liberty, N.Y.) were injected with ppreE2Neu and pfeGM-CSF in three legs in the biceps femoralis or quadriceps. Each injection site was subjected to 2 rounds of electroporation. Vaccination was administered 4× at 3 week intervals. Blood was collected through the jugular vein 2 weeks after each vaccination.

Humoral Response of Cats to ppreE2Neu

Antibodies to huHER2, rat neu, and feHER2 were quantitated by flow cytometric analysis of feline antibody binding to 3T3 cells transfected with prehuHER2, rat neu, or prefeHER2, as previously described.

Figures 10A, 10B:
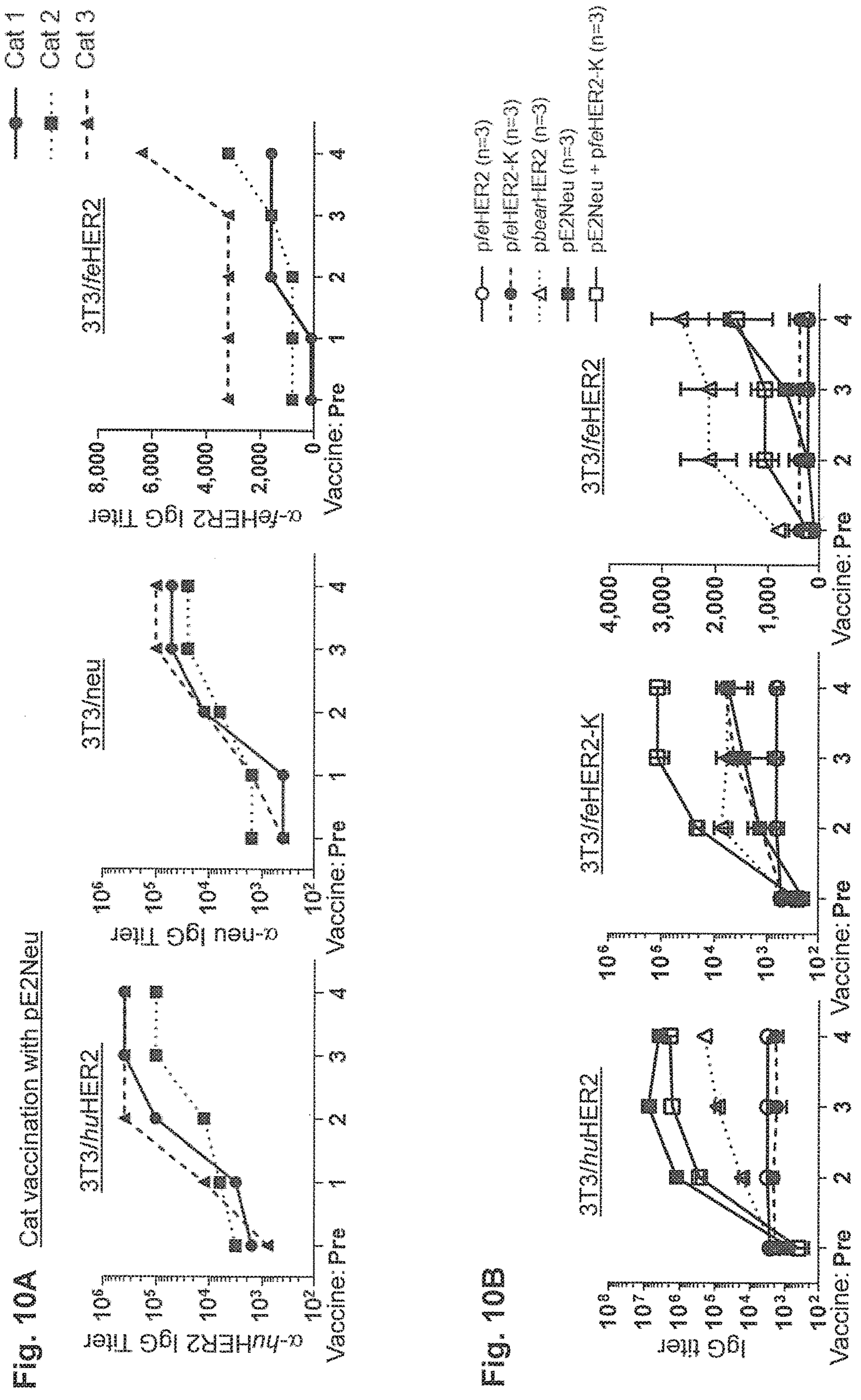
FIG. 10A shows induction of anti-HER2 antibody in cats including feline anti-huHER2 (left panel), rat neu (rat HER2) (middle panel) or feHER2 (right panel) IgG titer induced by pE2Neu and pfeGM-CSF vaccination; serum samples were collected just before and 2 weeks after each of 4 vaccinations given in 3 week intervals. Antigen binding was analyzed by flow cytometry using transfected 3T3 cells.
FIG. 10B shows induction of anti-HER2 antibody in cats, including feline anti-huHER2 (left), feHER2-K (middle) or feHER2 (right) IgG titer induced by the indicated vaccines; serum samples were collected just before and 2 weeks after each of 4 vaccinations given in 3 week intervals; antigen binding was analyzed by flow cytometry using transfected 3T3 cells.

Human HER2 binding IgG reached a titer of 1:400,000 in two of three cats and 1:100,000 in the third (FIG. 10A, left panel). Rat neu binding Ab ranged from 1:25,000 to 1:100,000 (FIG. 10A, middle panel). The robust response validated the effectiveness of DNA electrovaccination in cats.

Figure 11C:
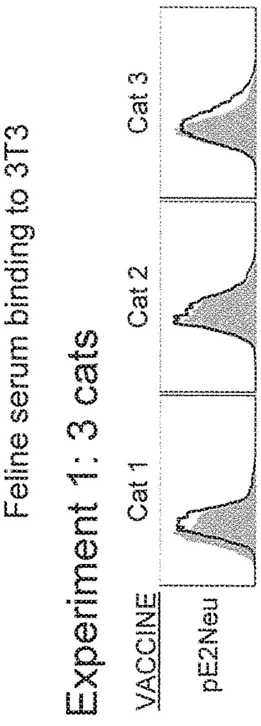
FIG. 11C shows a specificity control of feline immune serum, based on an experiment with 3 cats; pre-vaccination (gray shaded) and two weeks post 4× vaccination (open histogram); serum was incubated at a 1:50 dilution with untransfected 3T3 cells followed by PE-anti-feline IgG; each panel represents an individual cat.

Vaccination with ppreE2Neu induced antibody that cross reacted with wild type feline HER2 as determined by binding to 3T3 cells expressing prefeHER2 ("3T3/feHER2" in FIG. 10A, right panel). Neither pre-, nor post $4^{th}$-vaccination feline serum stained non-transfected 3T3 cells, illustrating the HER2/neu-specific reactivity of the immune sera (FIG. 11C).

Humoral Responses of Cats to Vaccines Including Bear and Substituted Feline HER2

A panel of HER2 vaccines were tested in fifteen additional healthy cats between 5-8 months of age. Cats were electrovaccinated four times with pprefeHER2, pprefeHER2-K, pprebearHER2, ppreE2Neu, or an admixture of pprefeHER2-K and ppreE2Neu. Results are shown in FIG. 10B. In each panel of FIG. 10B, the antibody target-binding cell type is listed at the top of the panel. The graphs show IgG titers obtained with each of five vaccines, which are listed in the FIG. 10B legend.

Consistent with the results shown previously in FIG. 10A, the six cats that received ppreE2Neu either alone or in combination with pprefeHER2-K developed high levels of IgG antibody to human HER2 (FIG. 10B, left panel). Peak titers were achieved after three vaccinations. Immune sera induced by pprebearHER2 cross-reacted with human HER2, and the titers increased after each booster immunization. pprefeHER2 or pprefeHER2-K immunization did not induce significant antibody response to human HER2.

Recognition of prefeHER2-Q141K by immune sera was measured by their binding to 3T3/prefeHER2-Q141K (FIG. 10B, middle panel, "3T3/feHER2-K"). A prominent response (~1:120,000) was induced by pfeHER2-K+pE2Neu. Individually, pfeHER2-K, pE2Neu or pbearHER2 induced moderate titers averaging ~1:6,000. The enhancement of immune response to pprefeHER2-K and to pbearHER2 by admixture with pE2Neu suggests a synergistic or adjuvant effect of the heterologous pE2Neu. Vaccination with pprefeHER2 did not generate a significant antibody response to prefeHER2-Q141K.

Figure 11D:
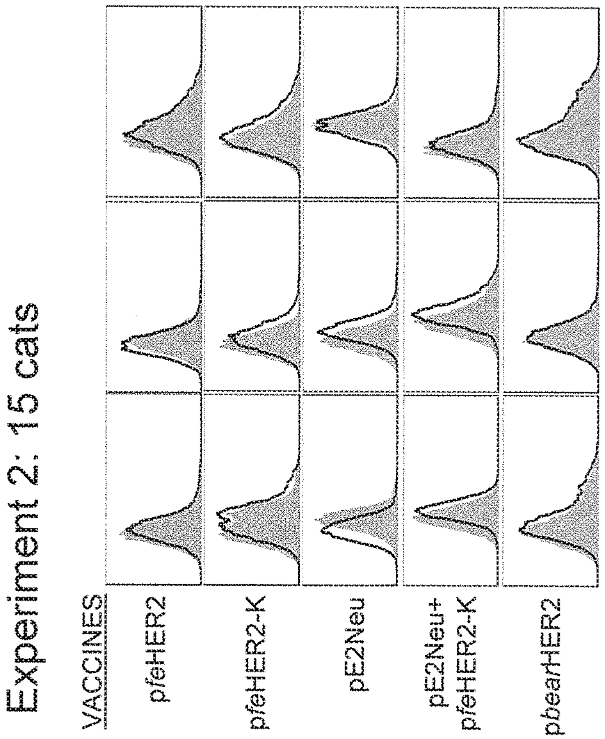
FIG. 11D shows a specificity control of feline immune serum, based on an experiment with 15 cats; pre-vaccination (gray shaded) and two weeks post 4× vaccination (open histogram); serum was incubated at a 1:50 dilution with untransfected 3T3 cells followed by PE-anti-feline IgG. Each panel represents an individual cat.

Antibodies binding to 3T3 cells expressing wild type prefeHER2 ("3T3/feHER2") were detected at a dilution of between 1:1,600-1:3,200 of immune sera from pE2Neu, pfeHER2-K+pE2Neu, or pbearHER2 vaccinated cats (FIG. 10B, right panel). These results show that these heterologous vaccines break tolerance to self feHER2, and induce antibodies which cross react with self feHER2. The specificity of HER2 antigen recognition was validated by the absence of binding to un-transfected 3T3 cells after 4× vaccination (FIG. 11D).

Immune sera from mice immunized only with pprefeHER2 or pprefeHER2-K showed negligible antibody binding to 3T3/feHER2 (FIG. 10B, right panel). The pprefeHER2-K vaccine showed much greater effect, however, when the immune sera were tested against feline mammary carcinoma cells. These cells constitute a much more realistic system, for the carcinoma cells express not only HER2 but also HER1 and HER3, which are capable of heterodimerizing with HER2 (Olayioye, 2001).

Figure 10C:
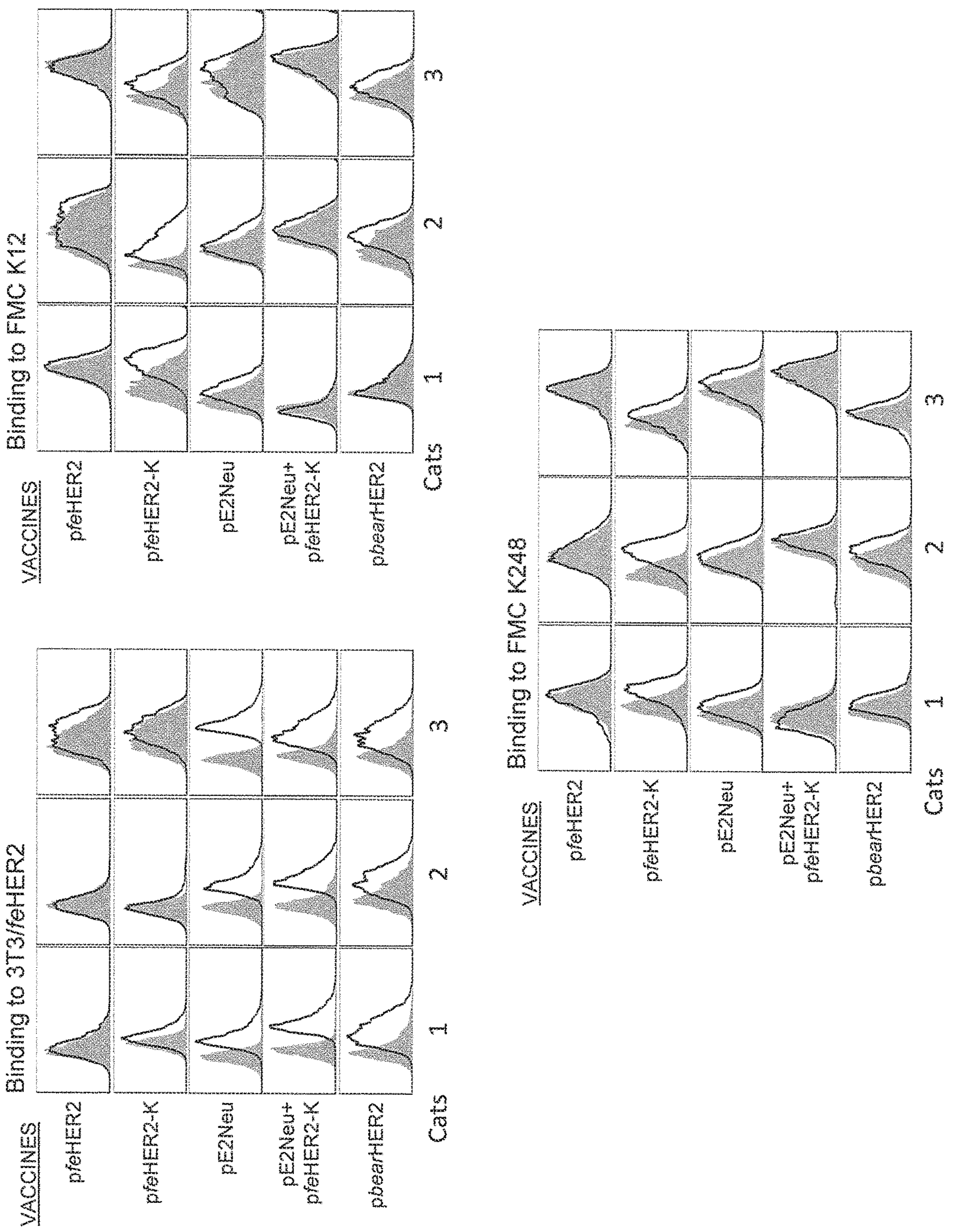
FIG. 10C shows the binding of immune sera to 3T3/feHER2 cells (top left panel), K12 tumor cells (top right panel) or K248 tumor cells (bottom panel),either prior to (shaded histogram) and two weeks after, the 4th vaccination (open histogram) with the indicated vaccines; each overlayed histogram represents an individual cat.

FIG. 10C shows the results of antibody binding experiments, in which immune sera were tested at 1:50-1:100 dilution, not only against 3T3 expressing only prefeHER2 (left panel), but also against feline mammary carcinoma cells of cell lines K12 (middle panel) and K248 (right panel), which express HER1, HER2, and HER3. Sera from cats immunized with pprefeHer2 ("pfeHER2") showed little binding to any of the test cells. Sera from cats immunized with pprefeHer2-Q141K ("pfeHER2-K") also showed little or low level binding to 3T3/feHER2, but they showed significant binding to K12 and K248 cells (FIG. 10C, middle and right panel, second line of each panel). Although other immune sera recognized 3T3/feHER2, they reacted minimally with K12 or K248 cells.

These findings indicate that vaccines including feline HER2 with a Q to K mutation at position 141 is sufficiently foreign to break tolerance to normal self HER2 in the cat model. The findings also suggest that vaccines including feline HER2 with a Q to K mutation at position 141 induce antibodies specific for epitopes whose expression is related to some combination of HER2, HER1 and/or HER3, a combination that is exposed naturally on feline mammary carcinoma cells.

The findings also indicate that prebearHER2, when administered as a heterologous vaccination to cats, is sufficiently foreign from feline HER2 to break tolerance, but sufficiently similar to induce antibodies that cross react with feline HER2.

FIGS. 12A-12C show the predicted 3D structure of feHER2-Q141K domains I-III using cartoon and space-filling models. The predicted effect of substituting Q with K at a.a. 141 is portrayed by an electrostatic surface model (SYBYL-X 2.1.1 software; Tripos), where the electropositive side chain of K is indicated by red and Q is shown in blue (FIG. 12C). It is hypothesized that feHER2-Q141K recapitulates a cryptic HER2 epitope naturally displayed when wild type feHER2 is heterodimerized or associated with other ERBB family members on a cell surface. Cats immunized with heterologous ppreE2Neu or pprebearHER2 produced antibodies that recognize dominant epitopes on wild type feHER2 as well as feHER2-Q141K expressed on 3T3 cells, but not the cryptic epitope exhibited by K12 or K248 cells. This seemingly subtle, but potentially critical difference in HER2 epitope recognition could only have been detected in vaccination experiments with the outbred cat system, wherein genetically un-manipulated cats naturally express HER1, 2, and 3.

T cell Responses of Cats to Substituted and Heterologous HER2 Vaccines

Cats were vaccinated with plasmids encoding prefeHER2-Q141K ("pfeHER2-K" in FIG. 13) or the heterologous non-substituted antigens prebearHER2 ("pbearHER2") or preE2neu ("pE2neu"), with combinations of these plasmids, as admixtures or as initial and booster vaccinations. The reactivity of the induced T cells to human HER2 was measured first. Immune PBMC were cultured with recombinant huHER2-Fc for three days before $IFN_\gamma$ ELISPOT analysis (FIG. 13A). The 6 cats receiving pE2Neu, with or without pfeHER2-K, responded to human HER2 at 130-750 SFU/$10^6$ PBMC, validating the effectiveness of DNA electrovaccination (FIG. 13A). pbearHER2 immune T cells also cross-reacted with human HER2, producing an average of ~160 SFU/$10^6$ PBMC. Vaccination with pfeHER2-K alone did not induce T cells that recognized human HER2.

IFN-γ T cell response to feHER2-Fc was measured to evaluate reactivity to self HER2. Of the 10 evaluated cats, three produced significant feHER2 specific T cell responses, with one cat each from the pfeHER2-K (~100 SFU per million cells), pE2Neu (~270 IFNγ spots) and pbearHER2 (~280 IFNγ spots) groups (FIG. 13B). The observed T cell responses indicate the immunogenic nature of both the heterologous bear and E2Neu and the Q-K substituted HER2 vaccines. The 30% response rate may reflect the heterogeneous genetic background of outbred cats, as in humans.

Three bi-weekly booster vaccinations were given to five cats that received pfeHER2-K or pfeHER2-K+pE2Neu (FIG. 13C). Only 1 of the 3 cats receiving the admixed vaccine converted from a non-responder to a responder after three boosters (~135 SFU/$10^6$ PBMC). Therefore, a total of 40% T cell response rate to self HER2 was achieved in healthy cats. Those cats initially receiving pE2Neu or pbearHER2 were boosted 3× with pfeHER2-K (FIG. 13D). Responses to recombinant human or feline HER2 did not increase, suggesting that cross-reactive T cells, not common epitopes in HER2 from pE2Neu or bear HER2, contributed to feline HER2 reactivity.

The cats tolerated the vaccination procedure without signs of pain or discomfort after they recovery from anesthesia. No adverse side effects were detected 6-12 months after the final vaccination and the cats continue to thrive.

Conclusion

Taken together, the experimental results disclosed in Example 3 validate a new vaccine design strategy of including a single residue substitution in a tumor self antigen. The results show that, in the feline mammary cancer test system, a feline HER2 antigenic polypeptide with a Q to K substitution at position 141 is sufficiently foreign to break tolerance, yet induces antibodies cross reactive with normal feline HER2, and with the HER2 molecules of humans and other species. Because the outbred cat system is a realistic system which reflects antigen and MHC diversity of natural human and animal populations, it is reasonably predictable that other species of HER2 including a Q to K substitution at position 141, or at an analogous position, will also be effective at immunizing against mammary carcinomas and other HER2 expressing cancers in other animal species, including humans.

The results of immunizations of cats with wild type bear HER2 validate the strategy of immunization of a host with HER2 that is heterologous, but relatively closely matched to self HER2. This indicates that bear HER2 is an effective antigen for the immunization and treatment of feline cancer hosts. Because of the similarity of bear, cat, and human HER2 (FIG. 6B), it is reasonably predictable that bear HER2 will be an effective antigen for immunizing humans, and possibly other mammals, against HER2-expressing tumor cells. This conclusion is further supported by the generalizability of results from the highly realistic, genetically diverse, outbred cat model.

Example 4

Additional Antigenic HER2 Polypeptides Including Amino Acid Substitutions

To further test the hypothesis that minimally altered variants of self HER2 can break tolerance and induce immunity to self HER2, an additional panel of substituted HER2 was generated. All of the substituted forms were based on the precursor form of human HER2 (prehumHER2).

Materials and Methods

Generation of Substituted Variants of Human HER2.

Figure 16:
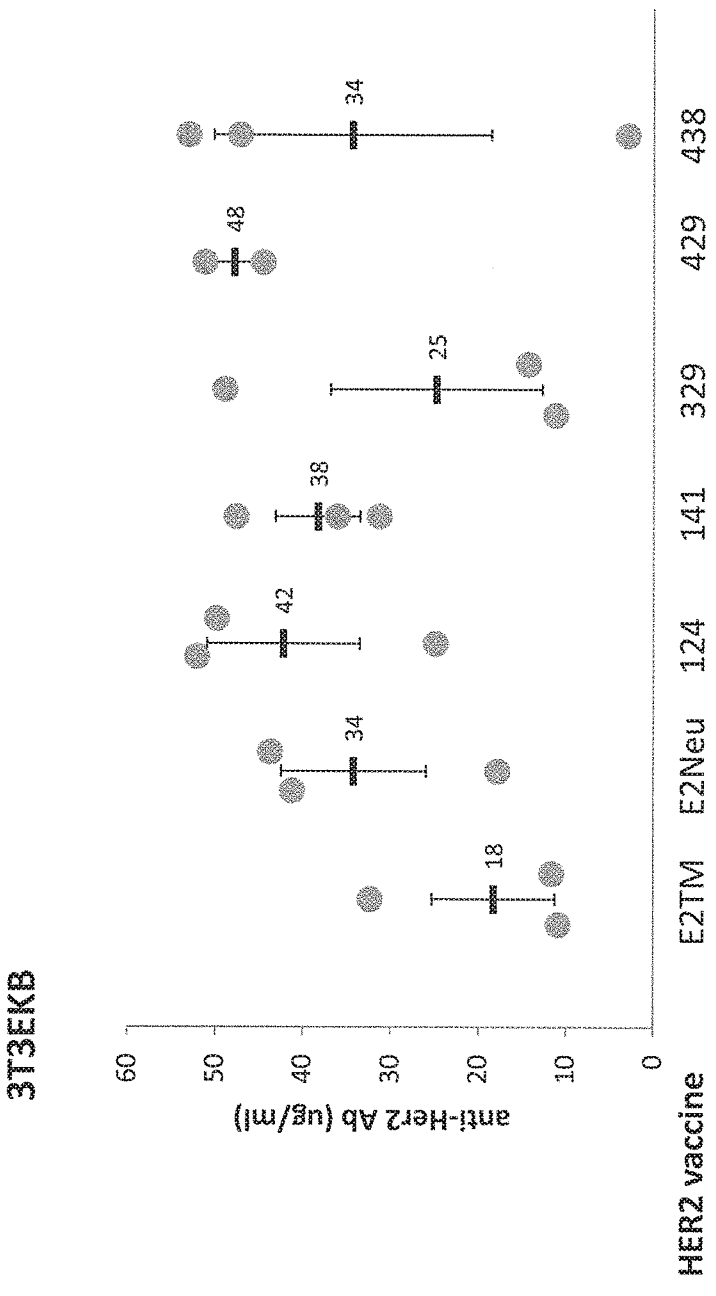
FIG. 16 shows binding of HER2 transgenic (HER2Tg) mouse immune serum to 3T3 EKB cells transfected to express WT human HER2.

Seven vaccine expression plasmids were constructed. Each encoded either a single point-mutated human precursor HER2 ECTM construct (pprehumHER2-Q141K, SEQ ID NO: 9; pprehumHER2-Q213K, SEQ ID NO: 84; pprehumHER2-Q239K, SEQ ID NO: 85; pprehumHER2-Q329K SEQ ID NO: 28; pprehumHER2-Q429R SEQ ID NO: 29; and pprehumHER2-N438D SEQ ID NO: 30); or a human precursor HER2 ECTM construct with 3 a.a. substitutions (pprehumHER2-NNT 124-126 DSG, SEQ ID NO: 85). The primer sequences for all constructs are listed in Table 3 below. For brevity, the constructs, and the polypeptides they encode, will be referred to in the following disclosure only by their substitutions, that is, respectively, Q141K, Q213K, Q239K, Q329K Q429R N438D, and NNT124DSG. In FIGS. 16 and 18, the terms are further abbreviated to, respectively, 141, 213, 239, 329, 429, 438, and 124.

TABLE 3

PCR primers for generating HER2 point variants

| Species | AA substitution | Primer sequence (5'->3'; reverse primer, ital.; mutant, lowercase) |
|---|---|---|
| Human | q141k | GCTGaAGCTTCGAAGCCTCACAGAG (SEQ ID NO: 87) |
| " | " | *TCCCGCAGGCCTCCTGGGGAGGC* (SEQ ID NO: 88) |
| " | q213k | TGAGGATTGTaAGAGCCTGAC (SEQ ID NO: 89) |
| " | " | *GAACTCTCTCCCCAGCAG* (SEQ ID NO: 90) |
| " | q239k | CTGCCATGAGaAGTGTGCTGC (SEQ ID NO: 91) |
| " | " | *CAGTCAGTGGGCAGTGGC* (SEQ ID NO: 92) |
| " | q320k | AAGAGGTGACAGCAGAGGATGGAAC (SEQ ID NO: 93) |
| " | " | *tGTTGTGCAGGGGGCAGACGAG* (SEQ ID NO: 94) |
| " | q329k | GGATGGAACAaAGCGGTGTGA (SEQ ID NO: 95) |
| " | " | *TCTGCTGTCACCTCTTGG* (SEQ ID NO: 96) |
| " | q429r | CCAGAACCTGagAGTAATCCGGG (SEQ ID NO: 97) |
| " | " | *AAGACGCTGAGGTCAGGC* (SEQ ID NO: 98) |
| " | n438d | AATTCTGCACgATGGCGCCTA (SEQ ID NO: 99) |
| " | " | CGTCCCCGGATTACTTGC (SEQ ID NO: 100) |
| " | nnt124dsg | ggcACACCTGTCACAGGGGCCTCCCCAG (SEQ ID NO: 101) |
| " | " | *actgtcCAGCGGGTCTCCATTGTCTAGCAC* (SEQ ID NO: 102) |
| Cat | q141k | GCGGGAGCTGaAGCTCCGAAG (SEQ ID NO: 103) |
| " | " | *AGCCCTCCTAGGGCAGCCCCTGTAG* (SEQ ID NO: 104) |
| " | r398q | TGAGCAGCTCcaAGTGTTTGAGGCTCTGGAG (SEQ ID NO: 105) |
| " | " | *GGCTGCAGGGGGGCAGTG* (SEQ ID NO: 106) |
| " | n421d | CAGCTTGCCTgACCTCAGTGTC (SEQ ID NO: 107) |
| " | " | *TCTGGCCACGCTGAGATG* (SEQ ID NO: 108) |

New England Biolab's Q5 Site-Directed Mutagenesis Kit was used with these primers to generate the variant vaccines, which were confirmed by DNA sequencing.

Stable HER2 expression of six gene constructs was confirmed in transiently transfected 3T3 cells by flow cytometry using anti-human HER2 moAbs Ab5 and N12 (FIGS. 14A and 14B). One construct, Q213K, was not expressed, and was removed from the test panel.

Electrovaccination of Mice and Cats

Mice were injected with an admix of 50 μg each of vaccine plasmid and plasmid encoding murine GM-CSF (pmuGM-CSF) in 50 μl PBS in the gastrocnemius muscle. Conductive gel was applied on the skin over the injection sites. Electroporation was conducted with NEPA21 electroporator (Napagene) using a tweezer electrode. Three 50 msec degenerating bipolar pulses of 100 V were administered at each site. Cats were injected with 1.5 mg each of HER2 vaccine plasmid and pfeGM-CSF in 1.5 mL PBS, divided equally over three injection sites in the biceps femoris or quadriceps. Two rounds of electroporation were applied to each site as described using a 1.5 cm2 caliper electrode (BTX).

Results

In vivo Expression of Substituted HER2 Polypeptides and Immune Activation in Wild Type (WT) BALB/c Mice The six verified constructs were advanced to vaccination tests as plasmid vaccines in wild type BALB/c mice. The plasmids pE2TM (prehumHER2) and pE2Neu (human HER2-rat neu hybrid ECTM) were employed as controls. There were 3 mice in each group. It was previously reported that pE2Neu induced significantly higher levels of anti-human HER2 Ab and T cell response in HER2 Tg mice than does pE2TM, showing the efficacy to overcome immune tolerance by incorporating heterologous neu sequence in ECD domains 3 and 4 (Jacob, et al., 2010). Because human HER2 with or without mutations are foreign proteins in WT mice, anti-HER2 antibody response is expected as long as the vaccine construct is expressed in vivo. Of the 6 mutants, five constructs except prehumHER2-Q239K induced anti-human HER2 Ab in at least one animal to show their successful expression in vivo and antibody induction after a single electrovaccination (FIG. 15).

Wild type BALB/c mice were electro-vaccinated i.m. with 60 μg HER2 construct+60 ug pmGMCSF divided in two sites. Serum was collected 3 weeks after immunization and binding to Her2-expressing SKOV3 cells was assessed by flow cytometry.

Of the 6 substituted polypeptides, all induced anti-human HER2 Ab in at least one animal (FIG. 15). This shows that the substituted polypeptides, prehumHER2-Q141K, prehumHER2-Q329K, prehumHER2-Q329K, prehumHER2-Q429R, prehumHER2-N438D, and prehumHER2-NNT124-126DSG were successfully expressed in vivo, and induced the expression of anti human-HER2 antibody after a single electrovaccination (FIG. 15).

Immune Activation in Human HER2 Transgenic (Tg) Mice

The five positive mutant constructs identified in WT BALB/c mice were advanced to human HER2 transgenic (Tg) mice (in BALB/c background). Mice received electrovaccinations twice, 2 wks apart, and immune sera were collected 2 wks after the final vaccination. Binding of immune sera to 3T3 cells that express human HER2, but not other human ERBB members, showed induction of anti-human HER2 antibodies by all 5 test vaccines as well as by control pE2TM or pE2Neu (FIG. 16).

The finer specificity of the immune sera was further tested with 5 human cancer cell lines. Breast cancer line SKBR3 and ovarian cancer line SKOV3 have amplified HER2 as shown by the binding to moAb Abs, N12, N29 and Herceptin (FIG. 17). They also express HER1 (EGFR). Three triple negative breast cancer cell lines SUM149, SUM159 and MDA MB231 show lower levels of HER2 expression. MDAMB231 has elevated HER1 (EGFR) expression.

All test immune sera except those from mice immunized with prehumHER2-NNT124DSG ("124") showed significant binding to the 5 human cancer cell lines (FIG. 18), indicating their immunogenic nature. To determine whether the substituted HER2 vaccines were more effective in overcoming immune tolerance than WT pE2TM, the change in their antibody level relative to pE2TM immune serum was calculated (FIG. 19). Of interest is that Q329K immune serum that showed comparable binding to SKOV3 as pE2TM immune serum. The same immune serum appears to bind MDA MB231 more effectively than pE2TM immune serum ($p<0.05$). Note that SKOV3 cells express high levels of HER2, moderate EGFR and no HER3 (see FIG. 3A). MDA MB231 cells express moderate levels of HER2, elevated HER1. It is hypothesized that HER2 epitopes on SKOV 3 and MDA-MB231 differ, and some unique HER2 epitopes on MDA MB231 are mimicked by HER2 Q329K. Perhaps MDA MB231 and K12/K248 cat mammary tumor cells share common HER2 structural features. Feline HER2 Q141K immune sera preferentially bind K12/K248, but minimally to 3T3 cells expressing feline HER2.

Discussion

It is proposed that an increased immune response to substituted HER2 vaccines is due to alteration of the amino acid charges or position of charges of HER2. The aa substitutions can be visualized by space-filling modeling (Protein Data Bank ID# 2a91; www.rcsb.org/;) 3D view of "The crystal structure of a truncated ErbB2 ectodomain reveals an active conformation, poised to interact with other ErbB receptors" (Garrett, et al., 2003). Amino acid substitutions on the outer surface of HER2 3D structure would presumably be directly accessible to B-cell receptors, and predispose to anti-HER2 antibody production. In contrast, the Q329K substitution which also increases the charge is beneath the surface, but may still trigger subtle changes in antigenicity.

Conclusion

The results indicate that prehumHER2-Q141K prehumHER2-Q329K, prehumHER2-Q429R, and prehumHER2-N438D, are effective antigens for breaking tolerance to self human HER2, as determined in the transgenic human HER2 mouse model. The finding that prehumHER2-Q141K breaks tolerance to self human HER2 reinforces the previously disclosed finding from the cat system, that prefeHER2-Q141K breaks tolerance to self feline HER2 (Example 3). The concordance of these two findings supports the generalizability of results from the outbred cat model to human HER2 immunobiology.

In addition, as previously stated, it is predictable that the mature forms of these substituted antigenic polypeptides, mhumHER2-Q119K, mhumHER2-Q407K, mhumHER2-Q429R, and mhumHER2-N438D are also effective as tolerance-breaking antigens. The lack of a signal peptide is expected to have no effect on the reactivity of the Q-K substitution epitope, which is over a hundred residues distant, in the ECD. Even if not processed onto the surface of a host cell, the mature forms of HER2 are nonetheless be available to antigen presenting cells upon apoptosis or necrosis of the expressing cells. Exemplary amino acid sequences of these substituted HER2 antigens are: mhumHER2-Q119K, SEQ ID NO: 3; mhumHER2-0407K, SEQ ID NO: 26; mhumHER2-Q429, SEQ ID NO: 29; and mhumHER2-N438D, SEQ ID NO: 30.

Finally, it is predictable that conservatively substituted variants of the substituted peptides of the present invention will also be effective antigens. For example, arginine can be substituted for lysine 141 in prehumHER2-Q141K and lysine 329 in prehumHER2-Q329K; lysine can be substituted for arginine 429 in prehumHER2-Q429R, and glutamic acid can be substituted for aspartic acid 438 prehumHER2-N438D.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE 4

| Amino acid and nucleotide sequences for substituted and wild type HER2 polypeptides |
|---|
| mfeHER2-Q119K, SEQ ID NO: 1 |
| 1 tqvctgtdmk lrlpaspeth ldmlrhlyqg cqvvqgnlel tylhanasls lqdiqevqg |
| 61 yvilahnqvk qvplqrlriv rgtqlfedny alavldngdp ldsgtpatga lgglrelkl |
| 121 rsltelikgg vliqrnpqlc hqdtilwkdi fhknnqlalm lidtnrsrac pcspackds |
| 181 hcwgassgdc qsltrtvcag gcarckgpqp tdccheqcaa gctgpkhsdc aclhfnhsg |
| 241 icelhcpalv tyntdtfesm pnpegrytfg ascvtacpyn ylstdvgsct vcplnnqev |
| 301 taedgtqrce kcskpcarvc yglgmehlre aravtsaniq efvgckkifg laflpesfe |
| 361 gdpasntapl qpeqlrvfea leeitgylyi sawpdslpnl svfqnlrvir rvlhdgays |
| 421 ltlqglgisw lglrslrelg sglalihrns rlcfvhtvpw dqlfrnphqa lhsanrped |
| 481 ecageglacy plcahghcwg pgptqcvncs qflrgqecve ecrvlqglpr yvkdrfclp |
| 541 chpecqpqng svtclgsead qcvacahykd ppfcvarcps gvkpdlsfmp wkfadeegt |
| 601 cqpcpincth scadldekgc paeqraspvt siiaavvgil lvvvvglvlg likrrrqki |
| 661 rkytm |
| mbearHER2-Q119K, SEQ ID NO: 2 |
| 1 tqvctgtdmk lrlpaspeth ldmlrhlyqa cqvvqgnlel tylpanasls lqdiqevqg |
| 61 yvliahsqvr qvplqrlriv rgtqlfedny alavldngep pkgdtsvaga pgglrelkl |
| 121 rslteilkgg vliqrnpqlc hqdtilwkdi fhknnqlalt lidtnrsrac pcspackdp |
| 181 hcwgassgdc qsltrtvcag gcarckgpkp tdccheqcaa gctgpkhsdc aclhfnhsg |
| 241 icelhcpalv tyntdtfesm pnpegrytfg ascvtacpyn ylstdvgsct vcplnnqev |
| 301 taedgtqrce kcsrpcarvc yglgmehlre aravtsaniq efagckkifg laflpesfe |
| 361 gdpasntapl qpeglrvfea leeitgylyi sawpdslpnl svfqnlrvir rvlhdgays |
| 421 ltlqglgisw lglrslrelg sglalihrna rlcfihtvpw eqlfrnphqa lhsanrpea |
| 481 ecvgeglacy plcahghcwg pgptqcvncs qflrgqecve ecrelhglpr yvkdryclp |
| 541 chpecrpqng svtcfgsead qcvacahykd ppscvarcps gvkpdlsfmp wkfadeegt |

TABLE 4 -continued

Amino acid and nucleotide sequences for substituted and wild type HER2 polypeptides 601 cqpcpincth scgdldergc paeqraspvt siiaavvgil lavvmglvlg likrrrqki
661 rkytm mhumHER2-Q119K, SEQ ID NO: 3
1 tqvctgtdmk lrlpaspeth ldmlrhlyqg cqvvqgnlel tylptnasls lqdiqevqg
61 yvliahnqvr qvplqrlriv rgtqlfedny alavldngdp lnnttpvtga pgglrelKl
121 rslteilkgg vliqrnpqlc yqdtilwkdi fhknnqlalt lidtnrsrac pcspmckgs
181 rcwgessedc qsltrtvcag gcarckgplp tdccheqcaa gctgpkhsdc aclhfnhsg
241 icelhcpalv tyntdtfesm pnpegrytfg ascvtacpyn ylstdvgsct vcplhnqev
301 taedgtqrce kcskpcarvc yglgmehlre vravtsaniq efagckkifg laflpesfd
361 gdpasntapl qpeqlqvfet leeitgylyi sawpdslpdl svfqnlqvir rilhngays
421 ltlqglgisw lglrslrelg sglalihhnt hlcfvhtvpw dqlfrnphqa lhtanrped
481 ecvgeglach qlcarghcwg pgptqcvncs qflrgqecve ecrvlqglpr yvnarhclp
541 chpecqpqng svtcfgpead qcvacahykd ppfcvarcps gvkpdlsymp wkfpdeega
601 cqpcpincth scvdlddkgc paeqrasplt siisavvgil lvvvlgvvfg likrrqqki
661 rkytm matouseHER2-Q120K, SEQ ID NO: 4
1 tqvctgtdmk lrlpaspeth ldmlrhlyqg cqvvqgnlel tylpanasls flqdiqevqg
61 ymliahnrvk hvplqrlriv rgtqlfedky alavldnrdp ldnvttaapg rtpeglrelk
121 lrslteilkg gvlirgnpql cyqdmvlwkd vlrknnqlap vdmdtnrsra cppcaptckd
181 nhcwgesped cqiltgtict sgcarckgrl ptdccheqca agctgpkhsd claclhfnhs
241 gicelhcpal ityntdtfes mlnpegrytf gascvttcpy nylstevgsc tlvcppnnqe
301 vtaedgtqrc ekcskpcagv cyglgmehlr garaitsdni qefagckkif gslaflpesf
361 dgnpssgvap lkpehlqvfe tleeitgyly isawpesfqd lsvfqnlrvi rgrilhdgay
421 sltlqglgih slglrslrel gsglalihrn thlcfvntvp wdqlfrnphq allhsgnrpe
481 eacgleglvc nslcarghcw gpgptqcvnc sqflrgqecv eecrvwkglp reyvrgkhcl
541 pchpecqpqn ssetcygsea dqceacahyk dssscvarcp sgvkpdlsym piwkypdeeg
601 icqpcpinct hscvdlderg cpaeqraspv tfiiatvvgv llfliivvvi gilikrrrqk
661 irkytm mratHER2-Q120K, SEQ ID NO: 5
1 tqvctgtdmk lrlpaspeth ldmlrhlyqg cqvvqgnlel tyvpanasls flqdiqevqg
61 ymliahnqvk rvplqrlriv rgtqlfedky alavldnrdp qdnvaastpg rtpeglrelk
121 lrslteilkg gvlirgnpql cyqdmvlwkd vfrknnqlap vdidtnrsra cppcapackd
181 nhcwgesped cqiltgtict sgcarckgrl ptdccheqca agctgpkhsd claclhfnhs
241 gicelhcpal vtyntdtfes mhnpegrytf gascvttcpy nylstevgsc tivcppnnqe
301 vtaedgtqrc ekcskpcarv cyglgmehlr garaitsdnv qefdgckkif gslaflpesf
361 dgdpssgiap lrpeqlqvfe tleeitgyly isawpdslrd lsvfqnlrii rgrilhdgay
421 sltlqglgih slglrslrel gsglalihrn ahlcfvhtvp wdqlfrnphq allhsgnrpe
481 edcgleglvc nslcahghcw gpgptqcvnc shflrgqecv eecrvwkglp reyvsdkrcl
541 pchpecqpqn ssetcfgsea dqcaacahyk dssscvarcp sgvkpdlsym piwkypdeeg
601 icqpcpinct hscvdlderg cpaeqraspv tfiiatvvgv llflilvvvv gilikrrrqk
661 irkytm mE2Neu-Q119K, SEQ ID NO: 6
1 tqvctgtdmk lrlpaspeth ldmlrhlyqg cqvvqgnlel tylptnasls flqdiqevqg
61 yvliahnqvr qvplqrlriv rgtqlfedny alavldngdp lnnttpvtga spgglrelkl
121 rslteilkgg vliqrnpqlc yqdtilwkdi fhknnqlalt lidtnrsrac hpcspmckgs
181 rcwgessedc qsltrtvcag gcarckgplp tdccheqcaa gctgpkhsdc laclhfnhsg
241 icelhcpalv tyntdtfesm pnpegrytfg ascvtacpyn ylstdvgsct lvcplhnqev
301 taedgtqrce kcskpcarvc yglgmehlre vravtsaniq efagckkifg slaflpesfd
361 gdpasntaef aplrpeqlqv fetleeitgy lyisawpdsl rdlsvfqnlr iirgrilhdg
421 aysltlqglg ihslglrslr elgsglalih rnahlcfvht vpwdqlfrnp hqallhsgnr
481 peedcglegl vcnslcahgh cwgpgptqcv ncshflrgqe cveecrvwkg lpreyvsdkr
541 clpchpecqp qnssetcfgs eadqcaacah ykdssscvar cpsgvkpdls ympiwkypde
601 egicqpcpin cthscvdlde rgcpaeqras pvtfiiatvv gvllflilvv vvgilikrrr
661 qkirkytm prefeHER2-Q141K, SEQ ID NO: 7
1 melaawcrwg lllallpsga tgtqvctgtd mklrlpaspe thldmlrhly qgcqvvqgnl
61 eltylhanas lsflqdiqev qgyvliahnq vkqvplqrlr ivrgtqlfed nyalavldng
121 dpldsgtpat gaalgglrel klrslteilk ggvliqrnpq lchqdtilwk difhknnqla
181 lmlidtnrsr acqpcspack dshcwgassg dcqsltrtvc aggcarckgp qptdccheqc
241 aagctgpkhs dclaclhfnh sgicelhcpa lvtyntdtfe smpnpegryt fgascvtacp
301 ynylstdvgs ctlvcplnnq evtaedgtqr cekcskpcar vcyglgmehl rearavtsan
361 iqefvgckki fgslaflpes fegdpasnta plqpeqlrvf ealeeitgyl yisawpdslp
421 nlsvfqnlry irgrvlhdga ysltlqglgi swlglrslre lgsglalihr nsrlcfvhtv
481 pwdqlfrnph qallhsanrp edecagegla cyplcahghc wgpgptqcvn csqflrgqec
541 veecrvlqgl preyvkdrfc lpchpecqpq ngsvtclgse adqcvacahy kdppfcvarc
601 psgvkpdlsf mpiwkfadee gtcqpcpinc thscadldek gcpaeqrasp vtsiiaavvg
661 illvvvvglv lgilikrrrq kirkytm prebearHER2-Q141K SEQ ID NO: 8
1 melaawcrwg lllallpsga agtqvctgtd mklrlpaspe thldmlrhly qacqvvqgnl
61 eltylpanas lsflqdiqev qgyvliahsq vrqvplqrlr ivrgtqlfed nyalavldng
121 eppkgdtsva gatpgglrel klrslteilk ggvliqrnpq lchqdtilwk difhknnqla TABLE 4 -continued Amino acid and nucleotide sequences for substituted and wild type HER2 polypeptides

```
181 ltlidtnrsr acqpcspack dphcwgassg dcqsltrtvc aggcarckgp kptdccheqc
241 aagctgpkhs dclaclhfnh sgicelhcpa lvtyntdtfe smpnpegryt fgascvtacp
301 ynylstdvgs ctlvcplnnq evtaedgtqr cekcsrpcar vcyglgmehl rearavtsan
361 igefagckki fgslaflpes fegdpasnta plqpeqlrvf ealeeitgyl yisawpdslp
421 nlsvfqnlrv irgrvlhdga ysltlqglgi swlglrslre lgsglalihr narlcfihtv
481 pweqlfrnph qallhsanrp eaecvgegla cyplcahghc wgpgptqcvn csqflrgqec
541 veecrelhgl preyvkdryc lpchpecrpq ngsvtcfgse adqcvacahy kdppscvarc
601 psgvkpdlsf mpiwkfadee gtcqpcpinc thscgdlder gcpaeqrasp vtsiiaavvg
661 illavvmglv lgilikrrrq kirkytm
```

prehumHER2-Q141K SEQ ID NO: 9

```
  1 melaalcrwg lllallppga astqvctgtd mklrlpaspe thldmlrhly qgcqvvqgnl
 61 eltylptnas lsflgdigev qgyvliahnq vrqvplqrlr ivrgtqlfed nyalavldng
121 dplnnttpvt gaspgglrel Klrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtqr cekcskpcar vcyglgmehl revravtsan
361 iqefagckki fgslaflpes fdgdpasnta plqpeqlqvf etleeitgyl yisawpdslp
421 dlsvfqnlqv irgrilhnga ysltlqglgi swlglrslre lgsglalihh nthlcfvhtv
481 pwdqlfrnph qallhtanrp edecvgegla chqlcarghc wgpgptqcvn csqflrggec
541 veecrvlqgl preyvnarhc lpchpecqpq ngsvtcfgpe adqcvacahy kdppfcvarc
601 psgvkpdlsy mpiwkfpdee gacqpcpinc thscvdlddk gcpaeqrasp ltsiisavvg
661 illvvvlgvv fgilikrrqq kirkytm
```

premouseHER2-Q142K, SEQ ID NO: 10

```
  1 melaawcrwg fllallspga agtqvctgtd mklrlpaspe thldmlrhly qgcqvvqgnl
 61 eltylpanas lsflqdiqev qgymliahnr vkhvplqrlr ivrgtqlfed kyalavldnr
121 dpldnvttaa pgrtpeglre lklrslteil kggvlirgnp qlcygdmvlw kdvlrknnql
181 apvdmdtnrs racppcaptc kdnhcwgesp edcqiltgti ctsgcarckg rlptdccheq
241 caagctgpkh sdclaclhfn hsgicelhcp alityntdtf esmlnpegry tfgascvttc
301 pynylstevg sctlvcppnn qevtaedgtq rcekcskpca gvcyglgmeh lrgaraitsd
361 niqefagckk ifgslaflpe sfdgnpssgv aplkpehlqv fetleeitgy lyisawpesf
421 qdlsvfqnlr virgrilhdg aysltlqglg ihslglrslr elgsglalih rnthlcfvnt
481 vpwdqlfrnp hqallhsgnr peeacglegl vcnslcargh cwgpgptqcv ncsqflrgqe
541 cveecrvwkg lpreyvrgkh clpchpecqp qnssetcygs eadqceacah ykdssscvar
601 cpsgvkpdls ympiwkypde egicqpcpin cthscvdlde rgcpaeqras pvtfiiatvv
661 gvllfliivv vigilikrrr qkirkytm
```

preratHER2-Q145K, SEQ ID NO: 11

```
  1 miimelaawc rwgfllallp pgiagtqvct gtdmklrlpa spethldmlr hlyggcqvvg
 61 gnleltyvpa naslsflqdi gevqgymlia hnqvkrvplq rlrivrgtql fedkyalavl
121 dnrdpqdnva astpgrtpeg lrelklrslt eilkggvlir gnpqlcyqdm vlwkdvfrkn
181 nqlapvdidt nrsracppca packdnhcwg espedcqilt gtictsgcar ckgrlptdcc
241 heqcaagctg pkhsdclacl hfnhsgicel hcpalvtynt dtfesmhnpe grytfgascv
301 ttcpynylst evgsctlvcp pnnqevtaed gtqrcekcsk pcarvcyglg mehlrgarai
361 tsdnvqefdg ckkifgslaf lpesfdgdps sgiaplrpeq lqvfetleei tgylyisawp
421 dslrdlsvfq nlriirgril hdgaysltlq glgihslglr slrelgsgla lihrnahlcf
481 vhtvpwdqlf rnphqallhs gnrpeedcgl eglvcnslca hghcwgpgpt qcvncshflr
541 gqecveecrv wkglpreyvs dkrclpchpe cqpqnssetc fgseadqcaa cahykdsssc
601 varcpsgvkp dlsympiwky pdeegicqpc pincthscvd ldergcpaeq raspvtfiia
661 tvvgvllfli lvvvvgilik rrrqkirkyt m
```

preE2Neu-Q141K SEQ ID NO: 12

```
  1 melaalcrwg lllallppga astqvctgtd mklrlpaspe thldmlrhly qgcqvvqgnl
 61 eltylptnas lsflqdiqev qgyvliahnq vrqvplqrlr ivrgtqlfed nyalavldng
121 dplnnttpvt gaspgglrel klrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtqr cekcskpcar vcyglgmehl revravtsan
361 iqefagckki fgslaflpes fdgdpasnta efaplrpeql qvfetleeit gylyisawpd
421 slrdlsvfqn lriirgrilh dgaysltlqg lgihslglrs lrelgsglal ihrnahlcfv
481 htvpwdqlfr nphqallhsg nrpeedcgle glvcnslcah ghcwgpgptq cvncshflrg
541 qecveecrvw kglpreyvsd krclpchpec qpqnssetcf gseadqcaac ahykdssscv
601 arcpsgvkpd lsympiwkyp deegicqpcp incthscvdl dergcpaeqr aspvtfiiat
661 vvgvllflil vvvvgilikr rrqkirkytm
```

mfeHER2-Q119K, SEQ ID NO: 13

```
  1 acccaagtgt gcaccggcac agacatgaag ctgcggctcc cagccagtcc cgagacccac
 61 ctggacatgc tccgccacct ctaccagggc tgtcaagtgg tacagggcaa cctggagctc
121 acctacctgc atgccaatgc cagcctctcc ttcctgcagg atatccagga ggtgcaaggc
181 tatgtgctca ttgcccacaa ccaagtgaaa caggtcccac tgcagaggct acgaatcgtg
241 cgaggcaccc agctctttga ggacaactac gccctggccg tgctggacaa cggagaccca
301 ctggacagtg gcacccctgc tacaggggct gccctaggag ggctgcggga gctgaagctc
361 cgaagcctca cagagatcct gaagggaggg gtcctcattc agcggaaccc gcagctctgc
421 caccaggaca cgattctgtg gaaggacatc ttccacaaga acaaccagct ggccctcatg
481 ctgatagaca ccaaccgctc tcgggcctgc caaccctgtt ctccagcttg taaagactcc
541 cactgctggg gagcaagttc cggggactgt cagagcttga ctcgaactgt ctgtgctggc
```

TABLE 4 -continued

Amino acid and nucleotide sequences for substituted and wild type HER2 polypeptides

```
 601 ggctgtgccc gctgcaaggg cccgcagccc accgactgct gccacgagca atgtgctgct
 661 ggctgcacgg gccccaagca ttctgactgc ctggcctgcc tccacttcaa ccacagtggc
 721 atctgtgagc tgcactgccc agccctggtc acctacaaca cggacacctt cgaatccatg
 781 cccaaccctg agggccgtta taccttcggt gccagctgtg tgactgcctg tccctacaac
 841 tacctgtcta cggacgtggg atcctgcacc ctggtctgtc ccctgaacaa ccaagaggtg
 901 acagctgagg atggaacaca gcggtgtgag aaatgcagca agccctgtgc ccgagtgtgc
 961 tacggcctag gcatggagca cctgcgggag gcgagggcag tcaccagtgc caacatccaa
1021 gaatttgtcg gctgcaagaa gatctttggg agcctggcgt ttctgccaga gagctttgag
1081 ggggacccag cctccaacac tgccccccctg cagcctgagc agctcagagt gtttgaggct
1141 ctggaggaga ttacaggtta cctgtacatc tcagcgtggc cagacagctt gcctaacctc
1201 agtgtcttcc agaacctcag agtgatccgg ggccgagttc tgcatgacgg tgcttactcg
1261 ctgacccttc aagggctggg catcagctgg ctggggctgc gctcgctgcg ggagctgggc
1321 agtgggctgg ccctcatcca ccgcaactcc cgcctctgct tcgtacacac ggtgccctgg
1381 gaccagctct tccggaaccc ccaccaggcc ctgctccaca gcgccaaccg gccagaggac
1441 gagtgcgcgg gtgagggcct ggcctgctat ccgctgtgtg cccacgggca ctgctggggt
1501 ccgggaccca cccagtgtgt caactgcagc cagttccttc ggggccagga gtgcgtggag
1561 gaatgccgag tattgcaggg gcttccccgg gagtatgtga aggataggtt ctgtctgcca
1621 tgccacccgg agtgtcagcc ccagaatggc tcagtgacct gcttgggctc ggaagctgac
1681 cagtgtgtgg cctgtgccca ctacaaggac cctcctttct gtgtggctcg ctgccccagt
1741 ggggtgaaac ctgacctctc cttcatgccc atctggaagt tcgcagatga ggagggcacg
1801 tgccagccat gccccatcaa ctgcacccac tcctgtgcgg acctggacga gaagggctgc
1861 cccgccgagc agagagccag ccctgtgacg tccatcattg ctgctgtggt gggcattctg
1921 ctggtcgtgg ttgtggggct ggtccttggc atcctaatca agcgaaggcg gcagaagatc
1981 cggaagtaca cgatg
```

mbearHER2-Q119K, SEQ ID NO: 14

```
   1 acccaagtgt gcaccggcac agacatgaag ctgcggctcc ctgccagtcc cgagacccac
  61 ctggatatgc tccgccacct ctaccaggcc tgtcaagtgg tacagggtaa cctggagctc
 121 acctacctgc ccgccaatgc cagcctgtcc ttcctgcagg atatccagga ggtacagggc
 181 tatgtgctca ttgctcacag ccaagtgaga caggtcccgc tgcagaggct ccgaatcgtg
 241 cgaggcaccc agctctttga ggacaactac gccctggccg tgctggacaa tggagagccg
 301 cccaaggggg acacctctgt ggcaggggct accccaggag ggctgcggga gctgaagctt
 361 cgaagcctca cagagatcct gaagggaggg gtcttgattc agcggaaccc acagctctgc
 421 caccaggaca cgattttgtg gaaggacatc ttccacaaga acaaccagct ggccctcacg
 481 ctgatagaca ccaaccgctc tcgggcctgc caaccctgtt ctccagcctg taaagacccc
 541 cactgctggg gagcaagttc cggggactgt cagagcttga cacgaaccgt ctgtgccggc
 601 ggctgtgccc gctgcaaggg cccaaaaccc actgactgct gccatgagca gtgcgcggct
 661 ggctgcacgg gccccaagca ctcggactgc ctggcctgcc ttcacttcaa ccacagtggc
 721 atctgtgagc tgcactgccc agccctggtc acctacaaca cggacacgtt cgaatccatg
 781 cccaaccctg agggccgata caccttcggt gccagctgtg tgaccgcctg tccctacaac
 841 tacctgtcca cggacgtggg atcctgcacc ctggtctgtc ccctgaacaa ccaagaggtg
 901 acggctgagg atggcaccca gcggtgtgag aaatgcagca gaccctgtgc ccgagtgtgc
 961 tatggtctgg gcatggagca cctgcgggag gcgagggcgg tcaccagcgc caacatccaa
1021 gagttcgccg gctgcaagaa gatctttggg agcctggcgt ttctgccaga gagcttcgag
1081 ggagacccag cctccaacac tgccccccctg cagcctgaac agctcagagt gttcgaggcc
1141 ctggaggaga tcacaggtta cctgtatatc tcagcgtggc cggacagctt gcctaacctc
1201 agtgtcttcc agaacctgcg agtaatccgg ggacgagttc tgcatgatgg cgcctactcg
1261 ctgaccctgc aagggctggg catcagctgg ctggggctgc gctcgctgcg ggaactgggc
1321 agcgggctgg ccctcatcca ccgcaacgcc cgcctctgct tcatccacac ggtgccctgg
1381 gagcagctct tccggaaccc ccaccaagcc ctgctgcaca gtgccaaccg gccggaggcc
1441 gagtgcgtgg gcgagggcct ggcctgctac ccgctgtgcg cccatgggca ctgctggggt
1501 ccggggccca cccagtgcgt caactgcagc caattccttc ggggccagga gtgcgtggag
1561 gaatgccgag aactgcacgg gctaccccgg gaatatgtga aggacagata ctgtctgcca
1621 tgccaccccg agtgtcggcc ccagaatggc tcagtgacct gctttgggtc ggaggctgac
1681 cagtgtgtgg cctgcgccca ctacaaggac cctccctcct gcgtggctcg ctgccccagt
1741 ggtgtgaaac ccgacctctc tttcatgccc atttggaagt ttgcagatga ggagggcaca
1801 tgccagccgt gccccatcaa ctgcacccac tcctgtgggg acctggacga gaggggctgc
1861 cccgccgaac agagagccag ccctgtgaca tccatcattg ccgctgtggt gggcattctg
1921 ctggccgtgg tcatggggct ggtcctcggc atcctgatca agcgaaggcg acagaagatc
1981 cggaagtaca cgatg
```

mhumHER2-Q119K, SEQ ID NO: 15

```
   1 acccaagtgt gcaccggcac agacatgaag ctgcggctcc ctgccagtcc cgagacccac
  61 ctggacatgc tccgccacct ctaccagggc tgccaggtgg tgcagggaaa cctggaactc
 121 acctacctgc ccaccaatgc cagcctgtcc ttcctgcagg atatccagga ggtgcagggc
 181 tacgtgctca tcgctcacaa ccaagtgagg caggtcccac tgcagaggct gcggattgtg
 241 cgaggcaccc agctctttga ggacaactat gccctggccg tgctagacaa tggagacccg
 301 ctgaacaata ccacccctgt cacaggggcc tccccaggag gcctgcggga gctgAagctt
 361 cgaagcctca cagagatctt gaaaggaggg gtcttgatcc agcggaaccc ccagctctgc
 421 taccaggaca cgattttgtg gaaggacatc ttccacaaga acaaccagct ggctctcaca
 481 ctgatagaca ccaaccgctc tcgggcctgc cacccctgtt ctccgatgtg taagggctcc
 541 cgctgctggg gagagagttc tgaggattgt cagagcctga cgcgcactgt ctgtgccggt
 601 ggctgtgccc gctgcaaggg gccactgccc actgactgct gccatgagca gtgtgctgcc
 661 ggctgcacgg gccccaagca ctctgactgc ctggcctgcc tccacttcaa ccacagtggc
 721 atctgtgagc tgcactgccc agccctggtc acctacaaca cagacacgtt tgagtccatg
 781 cccaatcccg agggccggta tacattcggc gccagctgtg tgactgcctg tccctacaac
 841 tacctttcta cggacgtggg atcctgcacc ctcgtctgcc ccctgcacaa ccaagaggtg
```

TABLE 4 -continued

Amino acid and nucleotide sequences for substituted and wild type HER2 polypeptides

```
 901 acagcagagg atggaacaca gcggtgtgag aagtgcagca agccctgtgc ccgagtgtgc
 961 tatggtctgg gcatggagca cttgcgagag gtgagggcag ttaccagtgc caatatccag
1021 gagtttgctg gctgcaagaa gatctttggg agcctggcat ttctgccgga gagctttgat
1081 ggggacccag cctccaacac tgccccgctc cagccagagc agctccaagt gtttgagact
1141 ctggaagaga tcacaggtta cctatacatc tcagcatggc cggacagcct gcctgacctc
1201 agcgtcttcc agaacctgca agtaatccgg ggacgaattc tgcacaatgg cgcctactcg
1261 ctgaccctgc aagggctggg catcagctgg ctggggctgc gctcactgag ggaactgggc
1321 agtggactgg ccctcatcca ccataacacc cacctctgct tcgtgcacac ggtgccctgg
1381 gaccagctct ttcggaaccc gcaccaagct ctgctccaca ctgccaaccg gccagaggac
1441 gagtgtgtgg gcgagggcct ggcctgccac cagctgtgcg cccgagggca ctgctggggt
1501 ccagggccca cccagtgtgt caactgcagc cagttccttc ggggccagga gtgcgtggag
1561 gaatgccgag tactgcaggg gctccccagg gagtatgtga atgccaggca ctgtttgccg
1621 tgccaccctg agtgtcagcc ccagaatggc tcagtgacct gttttggacc ggaggctgac
1681 cagtgtgtgg cctgtgccca ctataaggac cctcccttct gcgtggcccg ctgccccagc
1741 ggtgtgaaac ctgacctctc ctacatgccc atctggaagt ttccagatga ggagggcgca
1801 tgccagcctt gccccatcaa ctgcacccac tcctgtgtgg acctggatga caagggctgc
1861 cccgccgagc agagagccag ccctctgacg tccatcatct ctgcggtggt tggcattctg
1921 ctggtcgtgg tcttgggggt ggtctttggg atcctcatca agcgacggca gcagaagatc
1981 cggaagtaca cgatgtag
```

mmouseHER2-Q120K, SEQ ID NO: 16

```
   1 acccaagtgt gtaccggtac cgacatgaag ttgcgactcc ctgccagtcc tgagacccac
  61 ctggacatgc ttcgccacct ctaccagggc tgtcaggtgg tgcagggcaa tttggagctt
 121 acctacctgc ccgccaatgc cagcctctca ttcctgcagg acatccagga agtccaggga
 181 tacatgctca tcgctcacaa ccgagtgaaa cacgtcccac tgcagaggtt gcgcatcgtg
 241 agagggactc agctctttga ggacaagtat gccctggctg tgctagacaa ccgagaccct
 301 ttggacaacg tcaccaccgc cgccccaggc agaaccccag aagggctgcg ggagctgaag
 361 cttcgaagtc tcacagagat cttgaaggga ggagttttga tccgtgggaa ccctcagctc
 421 tgctaccagg acatggtttt gtggaaggat gtcctccgta agaataacca gctggctcct
 481 gtcgacatgg acaccaatcg ttcccgggcc tgtccacctt gtgccccaac ctgcaaagac
 541 aatcactgtt ggggtgagag tcctgaagac tgtcagatct tgactggcac catctgtact
 601 agtggctgtg cccggtgcaa gggccggctg cccactgact gttgccatga gcagtgtgct
 661 gcaggctgca cgggtcccaa gcattctgac tgcctggcct gcctccactt caatcatagt
 721 ggtatctgtg agctgcactg cccggccctc atcacctaca acacagacac cttcgagtcc
 781 atgctcaacc ctgagggtcg ctacaccttt ggtgccagct gtgtgaccac ctgcccctac
 841 aactacctct ccacggaagt gggatcctgc actctggtct gtcccccgaa caaccaagag
 901 gtcacagctg aggacggaac acagcggtgt gagaaatgca gcaagccctg tgctggagta
 961 tgctatggtc tgggcatgga gcacctccga ggggcgaggg ccatcaccag tgacaatatc
1021 caggagtttg ctggctgcaa gaagatcttt gggagcctgg catttttgcc ggagagcttt
1081 gatgggaacc cctcctccgg cgttgcccca ctgaagccag agcatctcca agtgttcgaa
1141 accctggagg agatcacagg ttacctatac atttcagcat ggccagagag cttccaagac
1201 ctcagtgtct tccagaacct tcgggtcatt cggggacgga ttctccatga tggtgcttac
1261 tcattgacgt tgcaaggcct ggggattcac tcactggggc tacgctcact gcgggagctg
1321 ggcagtggat tggctctcat tcaccgcaac acccatctct gctttgtaaa cactgtacct
1381 tgggaccagc tcttccggaa cccgcaccag gccctactcc acagtgggaa ccggccagaa
1441 gaggcatgtg gtcttgaggg cttggtctgt aactcactgt gtgcccgtgg gcactgctgg
1501 gggccagggc ccacccagtg tgtcaactgc agtcagttcc tccggggcca ggagtgtgtg
1561 gaggagtgcc gagtatggaa ggggctcccc agggagtatg tgaggggcaa gcactgtctg
1621 ccatgccacc ccgagtgtca gcctcaaaac agctcggaga cctgctatgg atcggaggct
1681 gaccagtgtg aggcttgtgc ccactacaag gactcatctt cctgtgtggc tcgctgcccc
1741 agtggtgtga agccagacct ctcctacatg cctatctgga agtacccgga tgaggagggc
1801 atatgtcagc catgccccat caactgcacc cactcatgtg tggacctgga cgaacgaggc
1861 tgcccagcag agcagagagc cagcccagtg acattcatca ttgcaactgt ggtgggcgtc
1921 ctgttgttcc tgatcatagt ggtggtcatt ggaatcctaa tcaaacgaag gcgacagaag
1981 atccggaagt ataccatg
```

mratHER2-Q120K, SEQ ID NO: 17

```
   1 acccaagtgt gtaccggcac agacatgaag ttgcggctcc ctgccagtcc tgagacccac
  61 ctggacatgc tccgccacct gtaccagggc tgtcaggtag tgcagggcaa cttggagctt
 121 acctacgtgc ctgccaatgc cagcctctca ttcctgcagg acatccagga agttcagggt
 181 tacatgctca tcgctcacaa ccaggtgaag cgcgtcccac tgcaaaggct gcgcatcgtg
 241 agagggaccc agctctttga ggacaagtat gccctggctg tgctagacaa ccgagatcct
 301 caggacaatg tcgccgcctc caccccaggc agaaccccag aggggctgcg ggagctgaag
 361 cttcgaagtc tcacagagat cctgaaggga ggagttttga tccgtgggaa ccctcagctc
 421 tgctaccagg acatggtttt gtggaaggac gtcttccgca agaataacca actggctcct
 481 gtcgatatag acaccaatcg ttcccgggcc tgtccacctt gtgcccccgc ctgcaaagac
 541 aatcactgtt ggggtgagag tccggaagac tgtcagatct tgactggcac catctgtacc
 601 agtggttgtg cccggtgcaa gggccggctg cccactgact gctgccatga gcagtgtgcc
 661 gcaggctgca cgggccccaa gcattctgac tgcctggcct gcctccactt caatcatagt
 721 ggtatctgtg agctgcactg cccagccctc gtcacctaca acacagacac ctttgagtcc
 781 atgcacaacc ctgagggtcg ctacaccttt ggtgccagct gcgtgaccac ctgcccctac
 841 aactacctgt ctacggaagt gggatcctgc actctggtgt gtcccccgaa taaccaagag
 901 gtcacagctg aggacggaac acagcgttgt gagaaatgca gcaagccctg tgctcgagtg
 961 tgctatggtc tgggcatgga gcaccttcga ggggcgaggg ccatcaccag tgacaatgtc
1021 caggagtttg atggctgcaa gaagatcttt gggagcctgg catttttgcc ggagagcttt
1081 gatggggacc cctcctccgg cattgctccg ctgaggcctg agcagctcca agtgttcgaa
1141 accctggagg agatcacagg ttacctgtac atctcagcat ggccagacag tctccgtgac
```

TABLE 4 -continued

Amino acid and nucleotide sequences for substituted and wild type HER2 polypeptides

```
1201 ctcagtgtct tccagaacct tcgaatcatt cggggacgga ttctccacga tggcgcgtac
1261 tcattgacac tgcaaggcct ggggatccac tcgctggggc tgcgctcact gcgggagctg
1321 ggcagtggat tggctctgat tcaccgcaac gcccatctct gctttgtaca cactgtacct
1381 tgggaccagc tcttccggaa cccacatcag gccctgctcc acagtgggaa ccggccggaa
1441 gaggattgtg gtctcgaggg cttggtctgt aactcactgt gtgcccacgg gcactgctgg
1501 gggccagggc ccacccagtg tgtcaactgc agtcatttcc ttcggggcca ggagtgtgtg
1561 gaggagtgcc gagtatggaa ggggctcccc cgggagtatg tgagtgacaa gcgctgtctg
1621 ccgtgtcacc ccgagtgtca gcctcaaaac agctcagaga cctgctttgg atcggaggct
1681 gatcagtgtg cagcctgcgc ccactacaag gactcgtcct cctgtgtggc tcgctgcccc
1741 agtggtgtga aaccggacct ctcctacatg cccatctgga agtacccgga tgaggagggc
1801 atatgccagc cgtgccccat caactgcacc cactcctgtg tggatctgga tgaacgaggc
1861 tgcccagcag agcagagagc cagcccggtg acattcatca ttgcaactgt agtgggcgtc
1921 ctgctgttcc tgatcttagt ggtggtcgtt ggaatcctaa tcaaacgaag gagacagaag
1981 atccggaagt atacgatg
```

mE2Neu-Q119K, SEQ ID NO: 18

```
   1 acccaagtgt gcaccggcac agacatgaag ctgcggctcc ctgccagtcc cgagacccac
  61 ctggacatgc tccgccacct ctaccagggc tgccaggtgg tgcagggaaa cctggaactc
 121 acctacctgc ccaccaatgc cagcctgtcc ttcctgcagg atatccagga ggtgcagggc
 181 tacgtgctca tcgctcacaa ccaagtgagg caggtcccac tgcagaggct gcggattgtg
 241 cgaggcaccc agctctttga ggacaactat gccctggccg tgctagacaa tggagacccg
 301 ctgaacaata ccacccctgt cacaggggcc tccccaggag gcctgcggga gctgaagctt
 361 cgaagcctca cagagatctt gaaaggaggg gtcttgatcc agcggaaccc ccagctctgc
 421 taccaggaca cgattttgtg gaaggacatc ttccacaaga acaaccagct ggctctcaca
 481 ctgatagaca ccaaccgctc tcgggcctgc cacccctgtt ctccgatgtg taagggctcc
 541 cgctgctggg gagagagttc tgaggattgt cagagcctga cgcgcactgt ctgtgccggt
 601 ggctgtgccc gctgcaaggg gccactgccc actgactgct gccatgagca gtgtgctgcc
 661 ggctgcacgg gccccaagca ctctgactgc ctggcctgcc tccacttcaa ccacagtggc
 721 atctgtgagc tgcactgccc agccctggtc acctacaaca cagacacgtt tgagtccatg
 781 cccaatcccg agggccggta tacattcggc gccagctgtg tgactgcctg tccctacaac
 841 tacctttcta cggacgtggg atcctgcacc ctcgtctgcc ccctgcacaa ccaagaggtg
 901 acagcagagg atggaacaca gcggtgtgag aagtgcagca agccctgtgc ccgagtgtgc
 961 tatggtctgg gcatggagca cttgcgagag gtgagggcag ttaccagtgc caatatccag
1021 gagtttgctg gctgcaagaa gatctttggg agcctggcat ttctgccgga gagctttgat
1081 ggggacccag cctccaacac tgccgaattc gctccgctga ggcctgagca gctccaagtg
1141 ttcgaaaccc tggaggagat cacaggttac ctgtacatct cagcatggcc agacagtctc
1201 cgtgacctca gtgtcttcca gaaccttcga atcattcggg gacggattct ccacgatggc
1261 gcgtactcat tgacactgca aggcctgggg atccactcgc tggggctgcg ctcactgcgg
1321 gagctgggca gtggattggc tctgattcac cgcaacgccc atctctgctt tgtacacact
1381 gtaccttggg accagctctt ccggaaccca catcaggccc tgctccacag tgggaaccgg
1441 ccggaagagg attgtggtct cgagggcttg gtctgtaact cactgtgtgc ccacgggcac
1501 tgctgggggc cagggcccac ccagtgtgtc aactgcagtc atttccttcg gggccaggag
1561 tgtgtggagg agtgccgagt atggaagggg ctcccccggg agtatgtgag tgacaagcgc
1621 tgtctgccgt gtcaccccga gtgtcagcct caaaacagct cagagacctg ctttggatcg
1681 gaggctgatc agtgtgcagc ctgcgcccac tacaaggact cgtcctcctg tgtggctcgc
1741 tgccccagtg gtgtgaaacc ggacctctcc tacatgccca tctggaagta cccggatgag
1801 gagggcatat gccagccgtg ccccatcaac tgcacccact cctgtgtgga tctggatgaa
1861 cgaggctgcc cagcagagca gagagccagc ccggtgacat tcatcattgc aactgtagtg
1921 ggcgtcctgc tgttcctgat cttagtggtg gtcgttggaa tcctaatcaa acgaaggaga
1981 cagaagatcc ggaagtatac gatg
```

prefeHER2-Q141, SEQ ID NO: 19

```
   1 atggagctgg cggcctggtg ccgctggggg ctcctcctcg ccctcctgcc ctccggagcc
  61 acgggcaccc aagtgtgcac cggcacagac atgaagctgc ggctcccagc cagtcccgag
 121 acccacctgg acatgctccg ccacctctac cagggctgtc aagtggtaca gggcaacctg
 181 gagctcacct acctgcatgc caatgccagc ctctccttcc tgcaggatat ccaggaggtg
 241 caaggctatg tgctcattgc ccacaaccaa gtgaaacagg tcccactgca gaggctacga
 301 atcgtgcgag gcacccagct ctttgaggac aactacgccc tggccgtgct ggacaacgga
 361 gacccactgg acagtggcac ccctgctaca ggggctgccc taggagggct gcgggagctg
 421 aagctccgaa gcctcacaga gatcctgaag ggaggggtcc tcattcagcg gaacccgcag
 481 ctctgccacc aggacacgat tctgtggaag gacatcttcc acaagaacaa ccagctggcc
 541 ctcatgctga tagacaccaa ccgctctcgg gcctgccaac cctgttctcc agcttgtaaa
 601 gactcccact gctggggagc aagttccggg gactgtcaga gcttgactcg aactgtctgt
 661 gctggcggct gtgcccgctg caagggcccg cagcccaccg actgctgcca cgagcaatgt
 721 gctgctggct gcacgggccc caagcattct gactgcctgg cctgcctcca cttcaaccac
 781 agtggcatct gtgagctgca ctgcccagcc ctggtcacct acaacacgga caccttcgaa
 841 tccatgccca accctgaggg ccgttatacc ttcggtgcca gctgtgtgac tgcctgtccc
 901 tacaactacc tgtctacgga cgtgggatcc tgcaccctgg tctgtcccct gaacaaccaa
 961 gaggtgacag ctgaggatgg aacacagcgg tgtgagaaat gcagcaagcc ctgtgcccga
1021 gtgtgctacg gcctaggcat ggagcacctg cgggaggcga gggcagtcac cagtgccaac
1081 atccaagaat ttgtcggctg caagaagatc tttgggagcc tggcgtttct gccagagagc
1141 tttgaggggg acccagcctc caacactgcc cccctgcagc ctgagcagct cagagtgttt
1201 gaggctctgg aggagattac aggttacctg tacatctcag cgtggccaga cagcttgcct
1261 aacctcagtg tcttccagaa cctcagagtg atccggggcc gagttctgca tgacggtgct
1321 tactcgctga cccttcaagg gctgggcatc agctggctgg ggctgcgctc gctgcgggag
1381 ctgggcagtg ggctggccct catccaccgc aactcccgcc tctgcttcgt acacacggtg
1441 ccctgggacc agctcttccg gaacccccac caggccctgc tccacagcgc caaccggcca
```

TABLE 4 -continued

Amino acid and nucleotide sequences for substituted and wild type HER2 polypeptides 1501 gaggacgagt gcgcgggtga gggcctggcc tgctatccgc tgtgtgccca cgggcactgc
1561 tggggtccgg gacccaccca gtgtgtcaac tgcagccagt tccttcgggg ccaggagtgc
1621 gtggaggaat gccgagtatt gcaggggctt ccccgggagt atgtgaagga taggttctgt
1681 ctgccatgcc acccggagtg tcagccccag aatggctcag tgacctgctt gggctcggaa
1741 gctgaccagt gtgtggcctg tgcccactac aaggaccctc ctttctgtgt ggctcgctgc
1801 cccagtgggg tgaaacctga cctctccttc atgcccatct ggaagttcgc agatgaggag
1861 ggcacgtgcc agccatgccc catcaactgc acccactcct gtgcggacct ggacgagaag
1921 ggctgccccg ccgagcagag agccagccct gtgacgtcca tcattgctgc tgtggtgggc
1981 attctgctgg tcgtggttgt ggggctggtc cttggcatcc taatcaagcg aaggcggcag
2041 aagatccgga agtacacgat g prebearHER2-Q141K, SEQ ID NO: 20

1 atggagctgg cggcctggtg ccgctggggg ctcctcctcg ccctcctgcc ctccggagcc
61 gcgggcaccc aagtgtgcac cggcacagac atgaagctgc ggctccctgc cagtcccgag
121 acccacctgg atatgctccg ccacctctac caggcctgtc aagtggtaca gggtaacctg
181 gagctcacct acctgcccgc caatgccagc ctgtccttcc tgcaggatat ccaggaggta
241 cagggctatg tgctcattgc tcacagccaa gtgagacagg tcccgctgca gaggctccga
301 atcgtgcgag gcacccagct ctttgaggac aactacgccc tggccgtgct ggacaatgga
361 gagccgccca agggggacac ctctgtggca ggggctaccc caggagggct gcgggagctg
421 aagcttcgaa gcctcacaga gatcctgaag ggaggggtct tgattcagcg gaacccacag
481 ctctgccacc aggacacgat tttgtggaag gacatcttcc acaagaacaa ccagctggcc
541 ctcacgctga tagacaccaa ccgctctcgg gcctgccaac cctgttctcc agcctgtaaa
601 gacccccact gctggggagc aagttccggg gactgtcaga gcttgacacg aaccgtctgt
661 gccggcggct gtgcccgctg caagggccca aaacccactg actgctgcca tgagcagtgc
721 gcggctggct gcacgggccc caagcactcg gactgcctgg cctgccttca cttcaaccac
781 agtggcatct gtgagctgca ctgcccagcc ctggtcacct acaacacgga cacgttcgaa
841 tccatgccca accctgaggg ccgatacacc ttcggtgcca gctgtgtgac cgcctgtccc
901 tacaactacc tgtccacgga cgtgggatcc tgcaccctgg tctgtcccct gaacaaccaa
961 gaggtgacgg ctgaggatgg cacccagcgg tgtgagaaat gcagcagacc ctgtgcccga
1021 gtgtgctatg gtctgggcat ggagcacctg cgggaggcga gggcggtcac cagcgccaac
1081 atccaagagt tcgccggctg caagaagatc tttgggagcc tggcgtttct gccagagagc
1141 ttcgagggag acccagcctc caacactgcc cccctgcagc ctgaacagct cagagtgttc
1201 gaggccctgg aggagatcac aggttacctg tatatctcag cgtggccgga cagcttgcct
1261 aacctcagtg tcttccagaa cctgcgagta atccggggac gagttctgca tgatggcgcc
1321 tactcgctga ccctgcaagg gctgggcatc agctggctgg ggctgcgctc gctgcgggaa
1381 ctgggcagcg ggctggccct catccaccgc aacgcccgcc tctgcttcat ccacacggtg
1441 ccctgggagc agctcttccg gaaccccccac caagccctgc tgcacagtgc caaccggccg
1501 gaggccgagt gcgtgggcga gggcctggcc tgctacccgc tgtgcgccca tgggcactgc
1561 tggggtccgg ggcccaccca gtgcgtcaac tgcagccaat tccttcgggg ccaggagtgc
1621 gtggaggaat gccgagaact gcacgggcta ccccgggaat atgtgaagga cagatactgt
1681 ctgccatgcc accccgagtg tcggccccag aatggctcag tgacctgctt tgggtcggag
1741 gctgaccagt gtgtggcctg cgcccactac aaggaccctc cctcctgcgt ggctcgctgc
1801 cccagtggtg tgaaacccga cctctctttc atgcccattt ggaagtttgc agatgaggag
1861 ggcacatgcc agccgtgccc catcaactgc acccactcct gtggggacct ggacgagagg
1921 ggctgccccg ccgaacagag agccagccct gtgacatcca tcattgccgc tgtggtgggc
1981 attctgctgg ccgtggtcat ggggctggtc ctcggcatcc tgatcaagcg aaggcgacag
2041 aagatccgga agtacacgat g prehumHER2-Q141K, SEQ ID NO: 21

1 atggagctgg cggccttgtg ccgctggggg ctcctcctcg ccctcttgcc ccccggagcc
61 gcgagcaccc aagtgtgcac cggcacagac atgaagctgc ggctccctgc cagtcccgag
121 acccacctgg acatgctccg ccacctctac cagggctgcc aggtggtgca gggaaacctg
181 gaactcacct acctgcccac caatgccagc ctgtccttcc tgcaggatat ccaggaggtg
241 cagggctacg tgctcatcgc tcacaaccaa gtgaggcagg tcccactgca gaggctgcgg
301 attgtgcgag gcacccagct ctttgaggac aactatgccc tggccgtgct agacaatgga
361 gacccgctga acaataccac ccctgtcaca ggggcctccc caggaggcct gcgggagctg
421 Aagcttcgaa gcctcacaga gatcttgaaa ggaggggtct tgatccagcg gaacccccag
481 ctctgctacc aggacacgat tttgtggaag gacatcttcc acaagaacaa ccagctggct
541 ctcacactga tagacaccaa ccgctctcgg gcctgccacc cctgttctcc gatgtgtaag
601 ggctcccgct gctggggaga gagttctgag gattgtcaga gcctgacgcg cactgtctgt
661 gccggtggct gtgcccgctg caaggggcca ctgcccactg actgctgcca tgagcagtgt
721 gctgccggct gcacgggccc caagcactct gactgcctgg cctgcctcca cttcaaccac
781 agtggcatct gtgagctgca ctgcccagcc ctggtcacct acaacacaga cacgtttgag
841 tccatgccca atcccgaggg ccggtataca ttcggcgcca gctgtgtgac tgcctgtccc
901 tacaactacc tttctacgga cgtgggatcc tgcaccctcg tctgccccct gcacaaccaa
961 gaggtgacag cagaggatgg aacacagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc ccgctccagc cagagcagct ccaagtgttt
1201 gagactctgg aagagatcac aggttaccta tacatctcag catggccgga cagcctgcct
1261 gacctcagcg tcttccagaa cctgcaagta atccggggac gaattctgca caatggcgcc
1321 tactcgctga ccctgcaagg gctgggcatc agctggctgg ggctgcgctc actgagggaa
1381 ctgggcagtg gactggccct catccaccat aacacccacc tctgcttcgt gcacacggtg
1441 ccctgggacc agctctttcg gaacccgcac caagctctgc tccacactgc caaccggcca
1501 gaggacgagt gtgtgggcga gggcctggcc tgccaccagc tgtgcgcccg agggcactgc
1561 tggggtccag ggcccaccca gtgtgtcaac tgcagccagt tccttcgggg ccaggagtgc
1621 gtggaggaat gccgagtact gcaggggctc cccagggagt atgtgaatgc caggcactgt TABLE 4 -continued

| Amino acid and nucleotide sequences for substituted and wild type HER2 polypeptides |
|---|
| 1681 ttgccgtgcc accctgagtg tcagccccag aatggctcag tgacctgttt tggaccggag |
| 1741 gctgaccagt gtgtggcctg tgcccactat aaggaccctc ccttctgcgt ggcccgctgc |
| 1801 cccagcggtg tgaaacctga cctctcctac atgcccatct ggaagtttcc agatgaggag |
| 1861 ggcgcatgcc agccttgccc catcaactgc acccactcct gtgtggacct ggatgacaag |
| 1921 ggctgccccg ccgagcagag agccagccct ctgacgtcca tcatctctgc ggtggttggc |
| 1981 attctgctgg tcgtggtctt gggggtggtc tttgggatcc tcatcaagcg acggcagcag |
| 2041 aagatccgga agtacacgat gtag |
| |
| premouseHER2-Q142K, SEQ ID NO: 22 |
| 1 atggagctgg cggcctggtg ccgttggggg ttcctcctcg ccctcctgtc ccccggagcc |
| 61 gcgggtaccc aagtgtgtac cggtaccgac atgaagttgc gactccctgc cagtcctgag |
| 121 acccacctgg acatgcttcg ccacctctac cagggctgtc aggtggtgca gggcaatttg |
| 181 gagcttacct acctgcccgc caatgccagc ctctcattcc tgcaggacat ccaggaagtc |
| 241 cagggataca tgctcatcgc tcacaaccga gtgaaacacg tcccactgca gaggttgcgc |
| 301 atcgtgagag ggactcagct ctttgaggac aagtatgccc tggctgtgct agacaaccga |
| 361 gaccctttgg acaacgtcac caccgccgcc ccaggcagaa ccccagaagg gctgcgggag |
| 421 ctgaagcttc gaagtctcac agagatcttg aagggaggag ttttgatccg tgggaaccct |
| 481 cagctctgct accaggacat ggttttgtgg aaggatgtcc tccgtaagaa taaccagctg |
| 541 gctcctgtcg acatggacac caatcgttcc cgggcctgtc caccttgtgc ccccaacctgc |
| 601 aaagacaatc actgttgggg tgagagtcct gaagactgtc agatcttgac tggcaccatc |
| 661 tgtactagtg gctgtgcccg gtgcaagggc cggctgccca ctgactgttg ccatgagcag |
| 721 tgtgctgcag gctgcacggg tcccaagcat tctgactgcc tggcctgcct ccacttcaat |
| 781 catagtggta tctgtgagct gcactgcccg gccctcatca cctacaacac agacaccttc |
| 841 gagtccatgc tcaaccctga gggtcgctac acctttggtg ccagctgtgt gaccacctgc |
| 901 ccctacaact acctctccac ggaagtggga tcctgcactc tggtctgtcc cccgaacaac |
| 961 caagaggtca cagctgagga cggaacacag cggtgtgaga aatgcagcaa gccctgtgct |
| 1021 ggagtatgct atggtctggg catggagcac ctccgagggg cgagggccat caccagtgac |
| 1081 aatatccagg agtttgctgg ctgcaagaag atctttggga gcctggcatt tttgccggag |
| 1141 agctttgatg ggaacccctc ctccggcgtt gccccactga agccagagca tctccaagtg |
| 1201 ttcgaaaccc tggaggagat cacaggttac ctatacattt cagcatggcc agagagcttc |
| 1261 caagacctca gtgtcttcca gaaccttcgg gtcattcggg gacggattct ccatgatggt |
| 1321 gcttactcat tgacgttgca aggcctgggg attcactcac tggggctacg ctcactgcgg |
| 1381 gagctgggca gtggattggc tctcattcac cgcaacaccc atctctgctt tgtaaacact |
| 1441 gtaccttggg accagctctt ccggaacccg caccaggccc tactccacag tgggaaccgg |
| 1501 ccagaagagg catgtggtct tgagggcttg gtctgtaact cactgtgtgc ccgtgggcac |
| 1561 tgctgggggc cagggcccac ccagtgtgtc aactgcagtc agttcctccg gggccaggag |
| 1621 tgtgtggagg agtgccgagt atggaagggg ctccccaggg agtatgtgag gggcaagcac |
| 1681 tgtctgccat gccaccccga gtgtcagcct caaaacagct cggagacctg ctatggatcg |
| 1741 gaggctgacc agtgtgaggc ttgtgcccac tacaaggact catcttcctg tgtggctcgc |
| 1801 tgccccagtg gtgtgaagcc agacctctcc tacatgccta tctggaagta cccggatgag |
| 1861 gagggcatat gtcagccatg ccccatcaac tgcacccact catgtgtgga cctggacgaa |
| 1921 cgaggctgcc cagcagagca gagagccagc ccagtgacat tcatcattgc aactgtggtg |
| 1981 ggcgtcctgt tgttcctgat catagtggtg gtcattggaa tcctaatcaa acgaaggcga |
| 2041 cagaagatcc ggaagtatac catg |
| |
| preratHER2-Q145K, SEQ ID NO: 23 |
| 1 atgatcatca tggagctggc ggcctggtgc cgctgggggt tcctcctcgc cctcctgccc |
| 61 cccggaatcg cgggcaccca agtgtgtacc ggcacagaca tgaagttgcg gctccctgcc |
| 121 agtcctgaga cccacctgga catgctccgc cacctgtacc agggctgtca ggtagtgcag |
| 181 ggcaacttgg agcttaccta cgtgcctgcc aatgccagcc tctcattcct gcaggacatc |
| 241 caggaagttc agggttacat gctcatcgct cacaaccagg tgaagcgcgt cccactgcaa |
| 301 aggctgcgca tcgtgagagg gacccagctc tttgaggaca agtatgccct ggctgtgcta |
| 361 gacaaccgag atcctcagga caatgtcgcc gcctccaccc caggcagaac cccagagggg |
| 421 ctgcgggagc tgaagcttcg aagtctcaca gagatcctga agggaggagt tttgatccgt |
| 481 gggaaccctc agctctgcta ccaggacatg gttttgtgga aggacgtctt ccgcaagaat |
| 541 aaccaactgg ctcctgtcga tatagacacc aatcgttccc gggcctgtcc accttgtgcc |
| 601 cccgcctgca aagacaatca ctgttggggt gagagtccgg aagactgtca gatcttgact |
| 661 ggcaccatct gtaccagtgg ttgtgcccgg tgcaagggcc ggctgcccac tgactgctgc |
| 721 catgagcagt gtgccgcagg ctgcacgggc cccaagcatt ctgactgcct ggcctgcctc |
| 781 cacttcaatc atagtggtat ctgtgagctg cactgcccag ccctcgtcac ctacaacaca |
| 841 gacacctttg agtccatgca caaccctgag ggtcgctaca cctttggtgc cagctgcgtg |
| 901 accacctgcc cctacaacta cctgtctacg gaagtgggat cctgcactct ggtgtgtccc |
| 961 ccgaataacc aagaggtcac agctgaggac ggaacacagc gttgtgagaa atgcagcaag |
| 1021 ccctgtgctc gagtgtgcta tggtctgggc atggagcacc ttcgaggggc gagggccatc |
| 1081 accagtgaca atgtccagga gtttgatggc tgcaagaaga tctttgggag cctggcattt |
| 1141 ttgccggaga gctttgatgg ggacccctcc tccggcattg ctccgctgag gcctgagcag |
| 1201 ctccaagtgt tcgaaaccct ggaggagatc acaggttacc tgtacatctc agcatggcca |
| 1261 gacagtctcc gtgacctcag tgtcttccag aaccttcgaa tcattcgggg acggattctc |
| 1321 cacgatggcg cgtactcatt gacactgcaa ggcctgggga tccactcgct ggggctgcgc |
| 1381 tcactgcggg agctgggcag tggattggct ctgattcacc gcaacgccca tctctgcttt |
| 1441 gtacacactg taccttggga ccagctcttc cggaacccac atcaggccct gctccacagt |
| 1501 gggaaccggc cggaagagga ttgtggtctc gagggcttgg tctgtaactc actgtgtgcc |
| 1561 cacgggcact gctgggggcc agggcccacc cagtgtgtca actgcagtca tttccttcgg |
| 1621 ggccaggagt gtgtggagga gtgccgagta tggaaggggc tcccccggga gtatgtgagt |
| 1681 gacaagcgct gtctgccgtg tcaccccgag tgtcagcctc aaaacagctc agagacctgc |
| 1741 tttggatcgg aggctgatca gtgtgcagcc tgcgcccact acaaggactc gtcctcctgt |
| 1801 gtggctcgct gccccagtgg tgtgaaaccg gacctctcct acatgcccat ctggaagtac |

TABLE 4 -continued

Amino acid and nucleotide sequences for substituted and wild type HER2 polypeptides

```
1861 ccggatgagg agggcatatg ccagccgtgc cccatcaact gcacccactc ctgtgtggat
1921 ctggatgaac gaggctgccc agcagagcag agagccagcc cggtgacatt catcattgca
1981 actgtagtgg gcgtcctgct gttcctgatc ttagtggtgg tcgttggaat cctaatcaaa
2041 cgaaggagac agaagatccg gaagtatacg atg
```

preE2Neu-Q141K, SEQ ID NO: 24

```
   1 atggagctgg cggccttgtg ccgctggggg ctcctcctcg ccctcttgcc ccccggagcc
  61 gcgagcaccc aagtgtgcac cggcacagac atgaagctgc ggctccctgc cagtcccgag
 121 acccacctgg acatgctccg ccacctctac cagggctgcc aggtggtgca gggaaacctg
 181 gaactcacct acctgcccac caatgccagc ctgtccttcc tgcaggatat ccaggaggtg
 241 cagggctacg tgctcatcgc tcacaaccaa gtgaggcagg tcccactgca gaggctgcgg
 301 attgtgcgag gcacccagct ctttgaggac aactatgccc tggccgtgct agacaatgga
 361 gacccgctga acaataccac ccctgtcaca ggggcctccc caggaggcct gcgggagctg
 421 aagcttcgaa gcctcacaga gatcttgaaa ggagggggtct tgatccagcg gaacccccag
 481 ctctgctacc aggacacgat tttgtggaag gacatcttcc acaagaacaa ccagctggct
 541 ctcacactga tagacaccaa ccgctctcgg gcctgccacc cctgttctcc gatgtgtaag
 601 ggctcccgct gctggggaga gagttctgag gattgtcaga gcctgacgcg cactgtctgt
 661 gccggtggct gtgcccgctg caaggggcca ctgcccactg actgctgcca tgagcagtgt
 721 gctgccggct gcacgggccc caagcactct gactgcctgg cctgcctcca cttcaaccac
 781 agtggcatct gtgagctgca ctgcccagcc ctggtcacct acaacacaga cacgtttgag
 841 tccatgccca atcccgaggg ccggtataca ttcggcgcca gctgtgtgac tgcctgtccc
 901 tacaactacc tttctacgga cgtgggatcc tgcaccctcg tctgccccct gcacaaccaa
 961 gaggtgacag cagaggatgg aacacagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc gaattcgctc cgctgaggcc tgagcagctc
1201 caagtgttcg aaaccctgga ggagatcaca ggttacctgt acatctcagc atggccagac
1261 agtctccgtg acctcagtgt cttccagaac cttcgaatca ttcggggacg gattctccac
1321 gatggcgcgt actcattgac actgcaaggc ctggggatcc actcgctggg gctgcgctca
1381 ctgcgggagc tgggcagtgg attggctctg attcaccgca acgcccatct ctgctttgta
1441 cacactgtac cttgggacca gctcttccgg aacccacatc aggccctgct ccacagtggg
1501 aaccggccgg aagaggattg tggtctcgag ggcttggtct gtaactcact gtgtgcccac
1561 gggcactgct gggggccagg gcccacccag tgtgtcaact gcagtcattt ccttcggggc
1621 caggagtgtg tggaggagtg ccgagtatgg aagggggctcc cccgggagta tgtgagtgac
1681 aagcgctgtc tgccgtgtca ccccgagtgt cagcctcaaa acagctcaga gacctgcttt
1741 ggatcggagg ctgatcagtg tgcagcctgc gcccactaca aggactcgtc ctcctgtgtg
1801 gctcgctgcc ccagtggtgt gaaaccggac ctctcctaca tgcccatctg gaagtacccg
1861 gatgaggagg gcatatgcca gccgtgcccc atcaactgca cccactcctg tgtggatctg
1921 gatgaacgag gctgcccagc agagcagaga gccagcccgg tgacattcat cattgcaact
1981 gtagtgggcg tcctgctgtt cctgatctta gtggtggtcg ttggaatcct aatcaaacga
2041 aggagacaga agatccggaa gtatacgatg
```

mhumHER2-Q307K, SEQ ID NO: 25

```
  1 tqvctgtdmk lrlpaspeth ldmlrhlyqg cqvvqgnlel tylptnasls flqdiqevqg
 61 yvliahnqvr qvplqrlriv rgtqlfedny alavldngdp lnnttpvtga spgglrelql
121 rslteilkgg vliqrnpqlc yqdtilwkdi fhknnqlalt lidtnrsrac hpcspmckgs
181 rcwgessedc qsltrtvcag gcarckgplp tdccheqcaa gctgpkhsdc laclhfnhsg
241 icelhcpalv tyntdtfesm pnpegrytfg ascvtacpyn ylstdvgsct lvcplhnqev
301 taedgtKrce kcskpcarvc yglgmehlre vravtsaniq efagckkifg slaflpesfd
361 gdpasntapl qpeqlqvfet leeitgylyi sawpdslpdl svfqnlqvir grilhngays
421 ltlqglgisw lglrslrelg sglalihhnt hlcfvhtvpw dqlfrnphqa llhtanrped
481 ecvgeglach qlcarghcwg pgptqcvncs qflrgqecve ecrvlqglpr eyvnarhclp
541 chpecqpqng svtcfgpead qcvacahykd ppfcvarcps gvkpdlsymp iwkfpdeega
601 cqpcpincth scvdlddkgc paeqrasplt siisavvgil lvvvlgvvfg ilikrrqqki
661 rkytm
```

mhumHER2-Q407R, SEQ ID NO: 26

```
  1 tqvctgtdmk lrlpaspeth ldmlrhlyqg cqvvqgnlel tylptnasls flqdiqevqg
 61 yvliahnqvr qvplqrlriv rgtqlfedny alavldngdp lnnttpvtga spgglrelql
121 rslteilkgg vliqrnpqlc yqdtilwkdi fhknnqlalt lidtnrsrac hpcspmckgs
181 rcwgessedc qsltrtvcag gcarckgplp tdccheqcaa gctgpkhsdc laclhfnhsg
241 icelhcpalv tyntdtfesm pnpegrytfg ascvtacpyn ylstdvgsct lvcplhnqev
301 taedgtqrce kcskpcarvc yglgmehlre vravtsaniq efagckkifg slaflpesfd
361 gdpasntapl qpeqlqvfet leeitgylyi sawpdslpdl svfqnlRvir grilhngays
421 ltlqglgisw lglrslrelg sglalihhnt hlcfvhtvpw dqlfrnphqa llhtanrped
481 ecvgeglach qlcarghcwg pgptqcvncs qflrgqecve ecrvlqglpr eyvnarhclp
541 chpecqpqng svtcfgpead qcvacahykd ppfcvarcps gvkpdlsymp iwkfpdeega
601 cqpcpincth scvdlddkgc paeqrasplt siisavvgil lvvvlgvvfg ilikrrqqki
661 rkytm
```

mhumHER2-N416D SEQ ID NO: 27

```
  1 tqvctgtdmk lrlpaspeth ldmlrhlyqg cqvvqgnlel tylptnasls flqdiqevqg
 61 yvliahnqvr qvplqrlriv rgtqlfedny alavldngdp lnnttpvtga spgglrelql
121 rslteilkgg vliqrnpqlc yqdtilwkdi fhknnqlalt lidtnrsrac hpcspmckgs
181 rcwgessedc qsltrtvcag gcarckgplp tdccheqcaa gctgpkhsdc laclhfnhsg
241 icelhcpalv tyntdtfesm pnpegrytfg ascvtacpyn ylstdvgsct lvcplhnqev
301 taedgtqrce kcskpcarvc yglgmehlre vravtsaniq efagckkifg slaflpesfd
```

TABLE 4 -continued

Amino acid and nucleotide sequences for substituted and wild type HER2 polypeptides 361 gdpasntapl qpeqlqvfet leeitgylyi sawpdslpdl svfqnlqvir grilhDgays
421 ltlqglgisw lglrslrelg sglalihhnt hlcfvhtvpw dqlfrnphqa llhtanrped
481 ecvgeglach qlcarghcwg pgptqcvncs qflrgqecve ecrvlqglpr eyvnarhclp
541 chpecqpqng svtcfgpead qcvacahykd ppfcvarcps gvkpdlsymp iwkfpdeega
601 cqpcpincth scvdlddkgc paeqrasplt siisavvgil lvvvlgvvfg ilikrrqqki
661 rkytm prehumHER2-Q329K, SEQ ID NO: 28
1 melaalcrwg lllallppga astqvctgtd mklrlpaspe thldmlrhly qgcqvvqgnl
61 eltylptnas lsflqdiqev qgyvliahnq vrqvplqrlr ivrgtqlfed nyalavldng
121 dplnnttpvt gaspgglrel qlrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtKr cekcskpcar vcyglgmehl revravtsan
361 iqefagckki fgslaflpes fdgdpasnta plqpeqlqvf etleeitgyl yisawpdslp
421 dlsvfqnlqv irgrilhnga ysltlqglgi swlglrslre lgsglalihh nthlcfvhtv
481 pwdqlfrnph qallhtanrp edecvgegla chqlcarghc wgpgptqcvn csqflrgqec
541 veecrvlqgl preyvnarhc lpchpecqpq ngsvtcfgpe adqcvacahy kdppfcvarc
601 psgvkpdlsy mpiwkfpdee gacqpcpinc thscvdlddk gcpaegrasp ltsiisavvg
661 illvvvlgvv fgilikrrqq kirkytm prehumHER2-Q429R, SEQ ID NO: 29
1 melaalcrwg lllallppga astqvctgtd mklrlpaspe thldmlrhly qgcqvvqgnl
61 eltylptnas lsflqdiqev qgyvliahnq vrqvplqrlr ivrgtqlfed nyalavldng
121 dplnnttpvt gaspgglrel qlrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtqr cekcskpcar vcyglgmehl revravtsan
361 iqefagckki fgslaflpes fdgdpasnta plqpeqlqvf etleeitgyl yisawpdslp
421 dlsvfqnlRv irgrilhnga ysltlqglgi swlglrslre lgsglalihh nthlcfvhtv
481 pwdqlfrnph qallhtanrp edecvgegla chqlcarghc wgpgptqcvn csqflrgqec
541 veecrvlqgl preyvnarhc lpchpecqpq ngsvtcfgpe adqcvacahy kdppfcvarc
601 psgvkpdlsy mpiwkfpdee gacqpcpinc thscvdlddk gcpaegrasp ltsiisavvg
661 illvvvlgvv fgilikrrqq kirkytm prehumHER2-N438D, SEQ ID NO: 30
1 melaalcrwg lllallppga astqvctgtd mklrlpaspe thldmlrhly qgcqvvqgnl
61 eltylptnas lsflqdiqev qgyvliahnq vrqvplqrlr ivrgtqlfed nyalavldng
121 dplnnttpvt gaspgglrel qlrslteilk ggvliqrnpq lcyqdtilwk difhknnqla
181 ltlidtnrsr achpcspmck gsrcwgesse dcqsltrtvc aggcarckgp lptdccheqc
241 aagctgpkhs dclaclhfnh sgicelhcpa lvtyntdtfe smpnpegryt fgascvtacp
301 ynylstdvgs ctlvcplhnq evtaedgtqr cekcskpcar vcyglgmehl revravtsan
361 igefagckki fgslaflpes fdgdpasnta plqpeqlqvf etleeitgyl yisawpdslp
421 dlsvfqnlqv irgrilhDga ysltlqglgi swlglrslre lgsglalihh nthlcfvhtv
481 pwdqlfrnph qallhtanrp edecvgegla chqlcarghc wgpgptqcvn csqflrgqec
541 veecrvlqgl preyvnarhc lpchpecqpq ngsvtcfgpe adqcvacahy kdppfcvarc
601 psgvkpdlsy mpiwkfpdee gacqpcpinc thscvdlddk gcpaeqrasp ltsiisavvg
661 illvvvlgvv fgilikrrqq kirkytm mhumHER24307K, SEQ ID NO: 31
1 acccaagtgt gcaccggcac agacatgaag ctgcggctcc ctgccagtcc cgagacccac
61 ctggacatgc tccgccacct ctaccagggc tgccaggtgg tgcagggaaa cctggaactc
121 acctacctgc ccaccaatgc cagcctgtcc ttcctgcagg atatccagga ggtgcagggc
181 tacgtgctca tcgctcacaa ccaagtgagg caggtcccac tgcagaggct gcggattgtg
241 cgaggcaccc agctctttga ggacaactat gccctggccg tgctagacaa tggagacccg
301 ctgaacaata ccacccctgt cacaggggcc tccccaggag gcctgcggga gctgcagctt
361 cgaagcctca cagagatctt gaaaggaggg gtcttgatcc agcggaaccc ccagctctgc
421 taccaggaca cgattttgtg gaaggacatc ttccacaaga acaaccagct ggctctcaca
481 ctgatagaca ccaaccgctc tcgggcctgc cacccctgtt ctccgatgtg taagggctcc
541 cgctgctggg gagagagttc tgaggattgt cagagcctga cgcgcactgt ctgtgccggt
601 ggctgtgccc gctgcaaggg gccactgccc actgactgct gccatgagca gtgtgctgcc
661 ggctgcacgg gccccaagca ctctgactgc ctggcctgcc tccacttcaa ccacagtggc
721 atctgtgagc tgcactgccc agccctggtc acctacaaca cagacacgtt tgagtccatg
781 cccaatcccg agggccggta tacattcggc gccagctgtg tgactgcctg tccctacaac
841 tacctttcta cggacgtggg atcctgcacc ctcgtctgcc ccctgcacaa ccaagaggtg
901 acagcagagg atggaacaAa gcggtgtgag aagtgcagca agccctgtgc ccgagtgtgc
961 tatggtctgg gcatggagca cttgcgagag gtgagggcag ttaccagtgc caatatccag
1021 gagtttgctg gctgcaagaa gatctttggg agcctggcat ttctgccgga gagctttgat
1081 ggggacccag cctccaacac tgccccgctc cagccagagc agctccaagt gtttgagact
1141 ctggaagaga tcacaggtta cctatacatc tcagcatggc cggacagcct gcctgacctc
1201 agcgtcttcc agaacctgca agtaatccgg ggacgaattc tgcacaatgg cgcctactcg
1261 ctgaccctgc aagggctggg catcagctgg ctggggctgc gctcactgag ggaactgggc
1321 agtggactgg ccctcatcca ccataacacc cacctctgct tcgtgcacac ggtgccctgg
1381 gaccagctct ttcggaaccc gcaccaagct ctgctccaca ctgccaaccg gccagaggac
1441 gagtgtgtgg gcgagggcct ggcctgccac cagctgtgcg cccgagggca ctgctggggt
1501 ccagggccca cccagtgtgt caactgcagc cagttccttc ggggccagga gtgcgtggag
1561 gaatgccgag tactgcaggg gctccccagg gagtatgtga atgccaggca ctgtttgccg TABLE 4 -continued

| Amino acid and nucleotide sequences for substituted and wild type HER2 polypeptides |
|---|
| 1621 tgccaccctg agtgtcagcc ccagaatggc tcagtgacct gttttggacc ggaggctgac |
| 1681 cagtgtgtgg cctgtgccca ctataaggac cctcccttct gcgtggcccg ctgccccagc |
| 1741 ggtgtgaaac ctgacctctc ctacatgccc atctggaagt ttccagatga ggagggcgca |
| 1801 tgccagcctt gccccatcaa ctgcacccac tcctgtgtgg acctggatga caagggctgc |
| 1861 cccgccgagc agagagccag ccctctgacg tccatcatct ctgcggtggt tggcattctg |
| 1921 ctggtcgtgg tcttgggggt ggtctttggg atcctcatca agcgacggca gcagaagatc |
| 1981 cggaagtaca cgatgtga |
| |
| mhumHER2-Q407R, SEQ ID NO: 32 |
| 1 acccaagtgt gcaccggcac agacatgaag ctgcggctcc ctgccagtcc cgagacccac |
| 61 ctggacatgc tccgccacct ctaccagggc tgccaggtgg tgcagggaaa cctggaactc |
| 121 acctacctgc ccaccaatgc cagcctgtcc ttcctgcagg atatccagga ggtgcagggc |
| 181 tacgtgctca tcgctcacaa ccaagtgagg caggtcccac tgcagaggct gcggattgtg |
| 241 cgaggcaccc agctctttga ggacaactat gccctggccg tgctagacaa tggagacccg |
| 301 ctgaacaata ccacccctgt cacaggggcc tccccaggag gcctgcggga gctgcagctt |
| 361 cgaagcctca cagagatctt gaaaggaggg gtcttgatcc agcggaaccc ccagctctgc |
| 421 taccaggaca cgattttgtg gaaggacatc ttccacaaga acaaccagct ggctctcaca |
| 481 ctgatagaca ccaaccgctc tcgggcctgc cacccctgtt ctccgatgtg taagggctcc |
| 541 cgctgctggg gagagagttc tgaggattgt cagagcctga cgcgcactgt ctgtgccggt |
| 601 ggctgtgccc gctgcaaggg gccactgccc actgactgct gccatgagca gtgtgctgcc |
| 661 ggctgcacgg gccccaagca ctctgactgc ctggcctgcc tccacttcaa ccacagtggc |
| 721 atctgtgagc tgcactgccc agccctggtc acctacaaca cagacacgtt tgagtccatg |
| 781 cccaatcccg agggccggta tacattcggc gccagctgtg tgactgcctg tccctacaac |
| 841 tacctttcta cggacgtggg atcctgcacc ctcgtctgcc ccctgcacaa ccaagaggtg |
| 901 acagcagagg atggaacaca gcggtgtgag aagtgcagca agccctgtgc ccgagtgtgc |
| 961 tatggtctgg gcatggagca cttgcgagag gtgagggcag ttaccagtgc caatatccag |
| 1021 gagtttgctg gctgcaagaa gatctttggg agcctggcat ttctgccgga gagctttgat |
| 1081 ggggacccag cctccaacac tgccccgctc cagccagagc agctccaagt gtttgagact |
| 1141 ctggaagaga tcacaggtta cctatacatc tcagcatggc cggacagcct gcctgacctc |
| 1201 agcgtcttcc agaacctgAG agtaatccgg ggacgaattc tgcacaatgg cgcctactcg |
| 1261 ctgaccctgc aagggctggg catcagctgg ctggggctgc gctcactgag ggaactgggc |
| 1321 agtggactgg ccctcatcca ccataacacc cacctctgct tcgtgcacac ggtgccctgg |
| 1381 gaccagctct ttcggaaccc gcaccaagct ctgctccaca ctgccaaccg gccagaggac |
| 1441 gagtgtgtgg gcgagggcct ggcctgccac cagctgtgcg cccgagggca ctgctggggt |
| 1501 ccagggccca cccagtgtgt caactgcagc cagttccttc ggggccagga gtgcgtggag |
| 1561 gaatgccgag tactgcaggg gctccccagg gagtatgtga atgccaggca ctgtttgccg |
| 1621 tgccaccctg agtgtcagcc ccagaatggc tcagtgacct gttttggacc ggaggctgac |
| 1681 cagtgtgtgg cctgtgccca ctataaggac cctcccttct gcgtggcccg ctgccccagc |
| 1741 ggtgtgaaac ctgacctctc ctacatgccc atctggaagt ttccagatga ggagggcgca |
| 1801 tgccagcctt gccccatcaa ctgcacccac tcctgtgtgg acctggatga caagggctgc |
| 1861 cccgccgagc agagagccag ccctctgacg tccatcatct ctgcggtggt tggcattctg |
| 1921 ctggtcgtgg tcttgggggt ggtctttggg atcctcatca agcgacggca gcagaagatc |
| 1981 cggaagtaca cgatgtga |
| |
| mhumHER2-N416D, SEQ ID NO: 33 |
| 1 acccaagtgt gcaccggcac agacatgaag ctgcggctcc ctgccagtcc cgagacccac |
| 61 ctggacatgc tccgccacct ctaccagggc tgccaggtgg tgcagggaaa cctggaactc |
| 121 acctacctgc ccaccaatgc cagcctgtcc ttcctgcagg atatccagga ggtgcagggc |
| 181 tacgtgctca tcgctcacaa ccaagtgagg caggtcccac tgcagaggct gcggattgtg |
| 241 cgaggcaccc agctctttga ggacaactat gccctggccg tgctagacaa tggagacccg |
| 301 ctgaacaata ccacccctgt cacaggggcc tccccaggag gcctgcggga gctgcagctt |
| 361 cgaagcctca cagagatctt gaaaggaggg gtcttgatcc agcggaaccc ccagctctgc |
| 421 taccaggaca cgattttgtg gaaggacatc ttccacaaga acaaccagct ggctctcaca |
| 481 ctgatagaca ccaaccgctc tcgggcctgc cacccctgtt ctccgatgtg taagggctcc |
| 541 cgctgctggg gagagagttc tgaggattgt cagagcctga cgcgcactgt ctgtgccggt |
| 601 ggctgtgccc gctgcaaggg gccactgccc actgactgct gccatgagca gtgtgctgcc |
| 661 ggctgcacgg gccccaagca ctctgactgc ctggcctgcc tccacttcaa ccacagtggc |
| 721 atctgtgagc tgcactgccc agccctggtc acctacaaca cagacacgtt tgagtccatg |
| 781 cccaatcccg agggccggta tacattcggc gccagctgtg tgactgcctg tccctacaac |
| 841 tacctttcta cggacgtggg atcctgcacc ctcgtctgcc ccctgcacaa ccaagaggtg |
| 901 acagcagagg atggaacaca gcggtgtgag aagtgcagca agccctgtgc ccgagtgtgc |
| 961 tatggtctgg gcatggagca cttgcgagag gtgagggcag ttaccagtgc caatatccag |
| 1021 gagtttgctg gctgcaagaa gatctttggg agcctggcat ttctgccgga gagctttgat |
| 1081 ggggacccag cctccaacac tgccccgctc cagccagagc agctccaagt gtttgagact |
| 1141 ctggaagaga tcacaggtta cctatacatc tcagcatggc cggacagcct gcctgacctc |
| 1201 agcgtcttcc agaacctgca agtaatccgg ggacgaattc tgcacGatgg cgcctactcg |
| 1261 ctgaccctgc aagggctggg catcagctgg ctggggctgc gctcactgag ggaactgggc |
| 1321 agtggactgg ccctcatcca ccataacacc cacctctgct tcgtgcacac ggtgccctgg |
| 1381 gaccagctct ttcggaaccc gcaccaagct ctgctccaca ctgccaaccg gccagaggac |
| 1441 gagtgtgtgg gcgagggcct ggcctgccac cagctgtgcg cccgagggca ctgctggggt |
| 1501 ccagggccca cccagtgtgt caactgcagc cagttccttc ggggccagga gtgcgtggag |
| 1561 gaatgccgag tactgcaggg gctccccagg gagtatgtga atgccaggca ctgtttgccg |
| 1621 tgccaccctg agtgtcagcc ccagaatggc tcagtgacct gttttggacc ggaggctgac |
| 1681 cagtgtgtgg cctgtgccca ctataaggac cctcccttct gcgtggcccg ctgccccagc |
| 1741 ggtgtgaaac ctgacctctc ctacatgccc atctggaagt ttccagatga ggagggcgca |
| 1801 tgccagcctt gccccatcaa ctgcacccac tcctgtgtgg acctggatga caagggctgc |
| 1861 cccgccgagc agagagccag ccctctgacg tccatcatct ctgcggtggt tggcattctg |

TABLE 4 -continued

Amino acid and nucleotide sequences for substituted and wild type HER2 polypeptides

```
1921 ctggtcgtgg tcttgggggt ggtctttggg atcctcatca agcgacggca gcagaagatc
1981 cggaagtaca cgatgtga
```

prehumHER2-Q329K, SEQ ID NO: 34

```
   1 atggagctgg cggccttgtg ccgctggggg ctcctcctcg ccctcttgcc ccccggagcc
  61 gcgagcaccc aagtgtgcac cggcacagac atgaagctgc ggctccctgc cagtcccgag
 121 acccacctgg acatgctccg ccacctctac cagggctgcc aggtggtgca gggaaacctg
 181 gaactcacct acctgcccac caatgccagc ctgtccttcc tgcaggatat ccaggaggtg
 241 cagggctacg tgctcatcgc tcacaaccaa gtgaggcagg tcccactgca gaggctgcgg
 301 attgtgcgag gcacccagct ctttgaggac aactatgccc tggccgtgct agacaatgga
 361 gacccgctga acaataccac ccctgtcaca ggggcctccc caggaggcct gcgggagctg
 421 cagcttcgaa gcctcacaga gatcttgaaa ggaggggtct tgatccagcg gaacccccag
 481 ctctgctacc aggacacgat tttgtggaag gacatcttcc acaagaacaa ccagctggct
 541 ctcacactga tagacaccaa ccgctctcgg gcctgccacc cctgttctcc gatgtgtaag
 601 ggctcccgct gctggggaga gagttctgag gattgtcaga gcctgacgcg cactgtctgt
 661 gccggtggct gtgcccgctg caaggggcca ctgcccactg actgctgcca tgagcagtgt
 721 gctgccggct gcacgggccc caagcactct gactgcctgg cctgcctcca cttcaaccac
 781 agtggcatct gtgagctgca ctgcccagcc ctggtcacct acaacacaga cacgtttgag
 841 tccatgccca atcccgaggg ccggtataca ttcggcgcca gctgtgtgac tgcctgtccc
 901 tacaactacc tttctacgga cgtgggatcc tgcaccctcg tctgccccct gcacaaccaa
 961 gaggtgacag cagaggatgg aacaAagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc ccgctccagc cagagcagct ccaagtgttt
1201 gagactctgg aagagatcac aggttaccta tacatctcag catggccgga cagcctgcct
1261 gacctcagcg tcttccagaa cctgcaagta atccggggac gaattctgca caatggcgcc
1321 tactcgctga ccctgcaagg gctgggcatc agctggctgg ggctgcgctc actgagggaa
1381 ctgggcagtg gactggccct catccaccat aacacccacc tctgcttcgt gcacacggtg
1441 ccctgggacc agctctttcg gaacccgcac caagctctgc tccacactgc caaccggcca
1501 gaggacgagt gtgtgggcga gggcctggcc tgccaccagc tgtgcgcccg agggcactgc
1561 tggggtccag ggcccaccca gtgtgtcaac tgcagccagt tccttcgggg ccaggagtgc
1621 gtggaggaat gccgagtact gcaggggctc cccagggagt atgtgaatgc caggcactgt
1681 ttgccgtgcc accctgagtg tcagccccag aatggctcag tgacctgttt tggaccggag
1741 gctgaccagt gtgtggcctg tgcccactat aaggaccctc ccttctgcgt ggcccgctgc
1801 cccagcggtg tgaaacctga cctctcctac atgcccatct ggaagtttcc agatgaggag
1861 ggcgcatgcc agccttgccc catcaactgc acccactcct gtgtggacct ggatgacaag
1921 ggctgccccg ccgagcagag agccagccct ctgacgtcca tcatctctgc ggtggttggc
1981 attctgctgg tcgtggtctt gggggtggtc tttgggatcc tcatcaagcg acggcagcag
2041 aagatccgga agtacacgat gtga
```

prehumHER2-Q429R, SEQ ID NO: 35

```
   1 atggagctgg cggccttgtg ccgctggggg ctcctcctcg ccctcttgcc ccccggagcc
  61 gcgagcaccc aagtgtgcac cggcacagac atgaagctgc ggctccctgc cagtcccgag
 121 acccacctgg acatgctccg ccacctctac cagggctgcc aggtggtgca gggaaacctg
 181 gaactcacct acctgcccac caatgccagc ctgtccttcc tgcaggatat ccaggaggtg
 241 cagggctacg tgctcatcgc tcacaaccaa gtgaggcagg tcccactgca gaggctgcgg
 301 attgtgcgag gcacccagct ctttgaggac aactatgccc tggccgtgct agacaatgga
 361 gacccgctga acaataccac ccctgtcaca ggggcctccc caggaggcct gcgggagctg
 421 cagcttcgaa gcctcacaga gatcttgaaa ggaggggtct tgatccagcg gaacccccag
 481 ctctgctacc aggacacgat tttgtggaag gacatcttcc acaagaacaa ccagctggct
 541 ctcacactga tagacaccaa ccgctctcgg gcctgccacc cctgttctcc gatgtgtaag
 601 ggctcccgct gctggggaga gagttctgag gattgtcaga gcctgacgcg cactgtctgt
 661 gccggtggct gtgcccgctg caaggggcca ctgcccactg actgctgcca tgagcagtgt
 721 gctgccggct gcacgggccc caagcactct gactgcctgg cctgcctcca cttcaaccac
 781 agtggcatct gtgagctgca ctgcccagcc ctggtcacct acaacacaga cacgtttgag
 841 tccatgccca atcccgaggg ccggtataca ttcggcgcca gctgtgtgac tgcctgtccc
 901 tacaactacc tttctacgga cgtgggatcc tgcaccctcg tctgccccct gcacaaccaa
 961 gaggtgacag cagaggatgg aacacagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc ccgctccagc cagagcagct ccaagtgttt
1201 gagactctgg aagagatcac aggttaccta tacatctcag catggccgga cagcctgcct
1261 gacctcagcg tcttccagaa cctgAGagta atccggggac gaattctgca caatggcgcc
1321 tactcgctga ccctgcaagg gctgggcatc agctggctgg ggctgcgctc actgagggaa
1381 ctgggcagtg gactggccct catccaccat aacacccacc tctgcttcgt gcacacggtg
1441 ccctgggacc agctctttcg gaacccgcac caagctctgc tccacactgc caaccggcca
1501 gaggacgagt gtgtgggcga gggcctggcc tgccaccagc tgtgcgcccg agggcactgc
1561 tggggtccag ggcccaccca gtgtgtcaac tgcagccagt tccttcgggg ccaggagtgc
1621 gtggaggaat gccgagtact gcaggggctc cccagggagt atgtgaatgc caggcactgt
1681 ttgccgtgcc accctgagtg tcagccccag aatggctcag tgacctgttt tggaccggag
1741 gctgaccagt gtgtggcctg tgcccactat aaggaccctc ccttctgcgt ggcccgctgc
1801 cccagcggtg tgaaacctga cctctcctac atgcccatct ggaagtttcc agatgaggag
1861 ggcgcatgcc agccttgccc catcaactgc acccactcct gtgtggacct ggatgacaag
1921 ggctgccccg ccgagcagag agccagccct ctgacgtcca tcatctctgc ggtggttggc
1981 attctgctgg tcgtggtctt gggggtggtc tttgggatcc tcatcaagcg acggcagcag
2041 aagatccgga agtacacgat gtga
```

TABLE 4 -continued

Amino acid and nucleotide sequences for substituted and wild type HER2 polypeptides prehumHER2-N438D SEQ ID NO: 36

```
   1 atggagctgg cggccttgtg ccgctggggg ctcctcctcg ccctcttgcc ccccggagcc
  61 gcgagcaccc aagtgtgcac cggcacagac atgaagctgc ggctccctgc cagtcccgag
 121 acccacctgg acatgctccg ccacctctac cagggctgcc aggtggtgca gggaaacctg
 181 gaactcacct acctgcccac caatgccagc ctgtccttcc tgcaggatat ccaggaggtg
 241 cagggctacg tgctcatcgc tcacaaccaa gtgaggcagg tcccactgca gaggctgcgg
 301 attgtgcgag gcacccagct ctttgaggac aactatgccc tggccgtgct agacaatgga
 361 gacccgctga acaataccac ccctgtcaca ggggcctccc caggaggcct gcgggagctg
 421 cagcttcgaa gcctcacaga gatcttgaaa ggaggggtct tgatccagcg gaacccccag
 481 ctctgctacc aggacacgat tttgtggaag gacatcttcc acaagaacaa ccagctggct
 541 ctcacactga tagacaccaa ccgctctcgg gcctgccacc cctgttctcc gatgtgtaag
 601 ggctcccgct gctggggaga gagttctgag gattgtcaga gcctgacgcg cactgtctgt
 661 gccggtggct gtgcccgctg caaggggcca ctgcccactg actgctgcca tgagcagtgt
 721 gctgccggct gcacgggccc caagcactct gactgcctgg cctgcctcca cttcaaccac
 781 agtggcatct gtgagctgca ctgcccagcc ctggtcacct acaacacaga cacgtttgag
 841 tccatgccca atcccgaggg ccggtataca ttcggcgcca gctgtgtgac tgcctgtccc
 901 tacaactacc tttctacgga cgtgggatcc tgcaccctcg tctgccccct gcacaaccaa
 961 gaggtgacag cagaggatgg aacacagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc ccgctccagc cagagcagct ccaagtgttt
1201 gagactctgg aagagatcac aggttaccta tacatctcag catggccgga cagcctgcct
1261 gacctcagcg tcttccagaa cctgcaagta atccggggac gaattctgca cGatggcgcc
1321 tactcgctga ccctgcaagg gctgggcatc agctggctgg ggctgcgctc actgagggaa
1381 ctgggcagtg gactggccct catccaccat aacacccacc tctgcttcgt gcacacggtg
1441 ccctgggacc agctctttcg gaacccgcac caagctctgc tccacactgc caaccggcca
1501 gaggacgagt gtgtgggcga gggcctggcc tgccaccagc tgtgcgcccg agggcactgc
1561 tggggtccag ggcccaccca gtgtgtcaac tgcagccagt tccttcgggg ccaggagtgc
1621 gtggaggaat gccgagtact gcaggggctc cccagggagt atgtgaatgc caggcactgt
1681 ttgccgtgcc accctgagtg tcagccccag aatggctcag tgacctgttt tggaccggag
1741 gctgaccagt gtgtggcctg tgcccactat aaggaccctc ccttctgcgt ggcccgctgc
1801 cccagcggtg tgaaacctga cctctcctac atgcccatct ggaagtttcc agatgaggag
1861 ggcgcatgcc agccttgccc catcaactgc acccactcct gtgtggacct ggatgacaag
1921 ggctgccccg ccgagcagag agccagccct ctgacgtcca tcatctctgc ggtggttggc
1981 attctgctgg tcgtggtctt gggggtggtc tttgggatcc tcatcaagcg acggcagcag
2041 aagatccgga agtacacgat gtga
```

prebearHER2, SEQ ID NO: 37

```
   1 melaawcrwg lllallpsga agtqvctgtd mklrlpaspe thldmlrhly qacqvvqgnl
  61 eltylpanas lsflqdiqev qgyvliahsq vrqvplqrlr ivrgtqlfed nyalavldng
 121 eppkgdtsva gatpgglrel qlrslteilk ggvliqrnpq lchqdtilwk difhknnqla
 181 ltlidtnrsr acqpcspack dphcwgassg dcqsltrtvc aggcarckgp kptdccheqc
 241 aagctgpkhs dclaclhfnh sgicelhcpa lvtyntdtfe smpnpegryt fgascvtacp
 301 ynylstdvgs ctlvcplnnq evtaedgtqr cekcsrpcar vcyglgmehl rearavtsan
 361 igefagckki fgslaflpes fegdpasnta plq8peqlrvf ealeeitgyl yisawpd-
     slp
 421 nlsvfqnlrv irgrvlhdga ysltlqglgi swlglrslre lgsglalihr narlcfihtv
 481 pweqlfrnph qallhsanrp eaecvgegla cyplcahghc wgpgptqcvn csqflrgqec
 541 veecrelhgl preyvkdryc lpchpecrpq ngsvtcfgse adqcvacahy kdppscvarc
 601 psgvkpdlsf mpiwkfadee gtcqpcpinc thscgdlder gcpaeqrasp vtsiiaavvg
 661 illavvmglv lgilikrrrq kirkytm
```

mbearHER2, SEQ ID NO: 38

```
   1 tqvctgtdmk lrlpaspeth ldmlrhlyqa cqvvqgnlel tylpanasls flqdiqevqg
  61 yvliahsqvr qvplqrlriv rgtqlfedny alavldngep pkgdtsvaga tpgglrelql
 121 rslteilkgg vliqrnpqlc hqdtilwkdi fhknnqlalt lidtnrsrac qpcspackdp
 181 hcwgassgdc qsltrtvcag gcarckgpkp tdccheqcaa gctgpkhsdc laclhfnhsg
 241 icelhcpalv tyntdtfesm pnpegrytfg ascvtacpyn ylstdvgsct lvcplnnqev
 301 taedgtqrce kcsrpcarvc yglgmehlre aravtsaniq efagckkifg slaflpesfe
 361 gdpasntapl qpeqlrvfea leeitgylyi sawpdslpnl svfqnlrvir grvlhdgays
 421 ltlqglgisw lglrslrelg sglalihrna rlcfihtvpw eqlfrnphqa llhsanrpea
 481 ecvgeglacy plcahghcwg pgptqcvncs qflrgqecve ecrelhglpr eyvkdryclp
 541 chpecrpqng svtcfgsead qcvacahykd ppscvarcps gvkpdlsfmp iwkfadeegt
 601 cqpcpincth scgdldergc paeqraspvt siiaavvgil lavvmglvlg ilikrrrqki
 661 rkytm
```

prefeHER2, SEQ ID NO: 39

```
   1 melaawcrwg lllallpsga tgtqvctgtd mklrlpaspe thldmlrhly qgcqvvqgnl
  61 eltylhanas lsflqdiqev qgyvliahnq vkqvplqrlr ivrgtqlfed nyalavldng
 121 dpldsgtpat gaalgglrel qlrslteilk ggvliqrnpq lchqdtilwk difhknnqla
 181 lmlidtnrsr acqpcspack dshcwgassg dcqsltrtvc aggcarckgp qptdccheqc
 241 aagctgpkhs dclaclhfnh sgicelhcpa lvtyntdtfe smpnpegryt fgascvtacp
 301 ynylstdvgs ctlvcplnnq evtaedgtqr cekcskpcar vcyglgmehl rearavtsan
 361 iqefvgckki fgslaflpes fegdpasnta plqpeqlrvf ealeeitgyl yisawpdslp
 421 nlsvfqnlrv irgrvlhdga ysltlqglgi swlglrslre lgsglalihr nsrlcfvhtv
 481 pwdqlfrnph qallhsanrp edecagegla cyplcahghc wgpgptqcvn csqflrgqec
 541 veecrvlqgl preyvkdrfc lpchpecqpq ngsvtclgse adqcvacahy kdppfcvarc
```

TABLE 4 -continued

Amino acid and nucleotide sequences for substituted and wild type HER2 polypeptides 601 psgvkpdlsf mpiwkfadee gtcqpcpinc thscadldek gcpaeqrasp vtsiiaavvg
661 illvvvvglv lgilikrrrq kirkytm mfeHER2 SEQ ID NO: 40
1 tqvctgtdmk lrlpaspeth ldmlrhlyqg cqvvqgnlel tylhanasls flqdiqevqg
61 yvliahnqvk qvplqrlriv rgtqlfedny alavldngdp ldsgtpatga algglrelql
121 rslteilkgg vliqrnpqlc hqdtilwkdi fhknnqlalm lidtnrsrac qpcspackds
181 hcwgassgdc qsltrtvcag gcarckgpqp tdccheqcaa gctgpkhsdc laclhfnhsg
241 icelhcpalv tyntdtfesm pnpegrytfg ascvtacpyn ylstdvgsct lvcplnnqev
301 taedgtqrce kcskpcarvc yglgmehlre aravtsaniq efvgckkifg slaflpesfe
361 gdpasntapl qpeqlrvfea leeitgylyi sawpdslpnl svfqnlrvir grvlhdgays
421 ltlqglgisw lglrslrelg sglalihrns rlcfvhtvpw dqlfrnphqa llhsanrped
481 ecageglacy plcahghcwg pgptqcvncs qflrgqecve ecrvlqglpr eyvkdrfclp
541 chpecqpqng svtclgsead qcvacahykd ppfcvarcps gvkpdlsfmp iwkfadeegt
601 cqpcpincth scadldekgc paeqraspvt siiaavvgil lvvvvglvlg ilikrrrqki
661 rkytm prebearHER2, SEQ ID NO: 41
1 atggagctgg cggcctggtg ccgctggggg ctcctcctcg ccctcctgcc ctccggagcc
61 gcgggcaccc aagtgtgcac cggcacagac atgaagctgc ggctccctgc cagtcccgag
121 acccacctgg atatgctccg ccacctctac caggcctgtc aagtggtaca gggtaacctg
181 gagctcacct acctgcccgc caatgccagc ctgtccttcc tgcaggatat ccaggaggta
241 cagggctatg tgctcattgc tcacagccaa gtgagacagg tcccgctgca gaggctccga
301 atcgtgcgag gcacccagct ctttgaggac aactacgccc tggccgtgct ggacaatgga
361 gagccgccca agggggacac ctctgtggca ggggctaccc caggagggct gcgggagctg
421 cagcttcgaa gcctcacaga gatcctgaag ggaggggtct tgattcagcg gaacccacag
481 ctctgccacc aggacacgat tttgtggaag gacatcttcc acaagaacaa ccagctggcc
541 ctcacgctga tagacaccaa ccgctctcgg gcctgccaac cctgttctcc agcctgtaaa
601 gacccccact gctggggagc aagttccggg gactgtcaga gcttgacacg aaccgtctgt
661 gccggcggct gtgcccgctg caagggccca aaacccactg actgctgcca tgagcagtgc
721 gcggctggct gcacgggccc caagcactcg gactgcctgg cctgccttca cttcaaccac
781 agtggcatct gtgagctgca ctgcccagcc ctggtcacct acaacacgga cacgttcgaa
841 tccatgccca accctgaggg ccgatacacc ttcggtgcca gctgtgtgac cgcctgtccc
901 tacaactacc tgtccacgga cgtgggatcc tgcaccctgg tctgtcccct gaacaaccaa
961 gaggtgacgg ctgaggatgg cacccagcgg tgtgagaaat gcagcagacc ctgtgcccga
1021 gtgtgctatg gtctgggcat ggagcacctg cgggaggcga gggcggtcac cagcgccaac
1081 atccaagagt tcgccggctg caagaagatc tttgggagcc tggcgtttct gccagagagc
1141 ttcgagggag acccagcctc caacactgcc cccctgcagc ctgaacagct cagagtgttc
1201 gaggccctgg aggagatcac aggttacctg tatatctcag cgtggccgga cagcttgcct
1261 aacctcagtg tcttccagaa cctgcgagta atccggggac gagttctgca tgatggcgcc
1321 tactcgctga ccctgcaagg gctgggcatc agctggctgg ggctgcgctc gctgcgggaa
1381 ctgggcagcg ggctggccct catccaccgc aacgcccgcc tctgcttcat ccacacggtg
1441 ccctgggagc agctcttccg gaacccccac caagccctgc tgcacagtgc caaccggccg
1501 gaggccgagt gcgtgggcga gggcctggcc tgctacccgc tgtgcgccca tgggcactgc
1561 tggggtccgg ggcccaccca gtgcgtcaac tgcagccaat tccttcgggg ccaggagtgc
1621 gtggaggaat gccgagaact gcacgggcta ccccgggaat atgtgaagga cagatactgt
1681 ctgccatgcc accccgagtg tcggccccag aatggctcag tgacctgctt tgggtcggag
1741 gctgaccagt gtgtggcctg cgcccactac aaggaccctc cctcctgcgt ggctcgctgc
1801 cccagtggtg tgaaacccga cctctctttc atgcccattt ggaagtttgc agatgaggag
1861 ggcacatgcc agccgtgccc catcaactgc acccactcct gtggggacct ggacgagagg
1921 ggctgccccg ccgaacagag agccagccct gtgacatcca tcattgccgc tgtggtgggc
1981 attctgctgg ccgtggtcat ggggctggtc ctcggcatcc tgatcaagcg aaggcgacag
2041 aagatccgga agtacacgat g mbearHER2 SEQ ID NO: 42
1 acccaagtgt gcaccggcac agacatgaag ctgcggctcc ctgccagtcc cgagacccac
61 ctggatatgc tccgccacct ctaccaggcc tgtcaagtgg tacagggtaa cctggagctc
121 acctacctgc ccgccaatgc cagcctgtcc ttcctgcagg atatccagga ggtacagggc
181 tatgtgctca ttgctcacag ccaagtgaga caggtcccgc tgcagaggct ccgaatcgtg
241 cgaggcaccc agctctttga ggacaactac gccctggccg tgctggacaa tggagagccg
301 cccaaggggg acacctctgt ggcaggggct accccaggag ggctgcggga gctgcagctt
361 cgaagcctca cagagatcct gaagggaggg gtcttgattc agcggaaccc acagctctgc
421 caccaggaca cgattttgtg gaaggacatc ttccacaaga acaaccagct ggccctcacg
481 ctgatagaca ccaaccgctc tcgggcctgc caaccctgtt ctccagcctg taaagacccc
541 cactgctggg gagcaagttc cggggactgt cagagcttga cacgaaccgt ctgtgccggc
601 ggctgtgccc gctgcaaggg cccaaaaccc actgactgct gccatgagca gtgcgcggct
661 ggctgcacgg gccccaagca ctcggactgc ctggcctgcc ttcacttcaa ccacagtggc
721 atctgtgagc tgcactgccc agccctggtc acctacaaca cggacacgtt cgaatccatg
781 cccaaccctg agggccgata caccttcggt gccagctgtg tgaccgcctg tccctacaac
841 tacctgtcca cggacgtggg atcctgcacc ctggtctgtc ccctgaacaa ccaagaggtg
901 acggctgagg atggcaccca gcggtgtgag aaatgcagca gaccctgtgc ccgagtgtgc
961 tatggtctgg gcatggagca cctgcgggag gcgagggcgg tcaccagcgc caacatccaa
1021 gagttcgccg gctgcaagaa gatctttggg agcctggcgt ttctgccaga gagcttcgag
1081 ggagacccag cctccaacac tgcccccctg cagcctgaac agctcagagt gttcgaggcc
1141 ctggaggaga tcacaggtta cctgtatatc tcagcgtggc cggacagctt gcctaacctc
1201 agtgtcttcc agaacctgcg agtaatccgg ggacgagttc tgcatgatgg cgcctactcg
1261 ctgaccctgc aagggctggg catcagctgg ctggggctgc gctcgctgcg ggaactgggc TABLE 4 -continued Amino acid and nucleotide sequences for substituted and wild type HER2 polypeptides

```
1321 agcgggctgg ccctcatcca ccgcaacgcc cgcctctgct tcatccacac ggtgccctgg
1381 gagcagctct tccggaaccc ccaccaagcc ctgctgcaca gtgccaaccg gccggaggcc
1441 gagtgcgtgg gcgagggcct ggcctgctac ccgctgtgcg cccatgggca ctgctggggt
1501 ccggggccca cccagtgcgt caactgcagc caattccttc ggggccagga gtgcgtggag
1561 gaatgccgag aactgcacgg gctaccccgg gaatatgtga aggacagata ctgtctgcca
1621 tgccaccccg agtgtcggcc ccagaatggc tcagtgacct gctttgggtc ggaggctgac
1681 cagtgtgtgg cctgcgccca ctacaaggac cctccctcct gcgtggctcg ctgccccagt
1741 ggtgtgaaac ccgacctctc tttcatgccc atttggaagt ttgcagatga ggagggcaca
1801 tgccagccgt gccccatcaa ctgcacccac tcctgtgggg acctggacga gaggggctgc
1861 cccgccgaac agagagccag ccctgtgaca tccatcattg ccgctgtggt gggcattctg
1921 ctggccgtgg tcatggggct ggtcctcggc atcctgatca agcgaaggcg acagaagatc
1981 cggaagtaca cgatg
```

prefeHER2, SEQ ID NO: 43

```
   1 atggagctgg cggcctggtg ccgctggggg ctcctcctcg ccctcctgcc ctccggagcc
  61 acgggcaccc aagtgtgcac cggcacagac atgaagctgc ggctcccagc cagtcccgag
 121 acccacctgg acatgctccg ccacctctac cagggctgtc aagtggtaca gggcaacctg
 181 gagctcacct acctgcatgc caatgccagc ctctccttcc tgcaggatat ccaggaggtg
 241 caaggctatg tgctcattgc ccacaaccaa gtgaaacagg tcccactgca gaggctacga
 301 atcgtgcgag gcacccagct ctttgaggac aactacgccc tggccgtgct ggacaacgga
 361 gacccactgg acagtggcac ccctgctaca ggggctgccc taggagggct gcgggagctg
 421 cagctccgaa gcctcacaga gatcctgaag ggaggggtcc tcattcagcg gaacccgcag
 481 ctctgccacc aggacacgat tctgtggaag gacatcttcc acaagaacaa ccagctggcc
 541 ctcatgctga tagacaccaa ccgctctcgg gcctgccaac cctgttctcc agcttgtaaa
 601 gactcccact gctggggagc aagttccggg gactgtcaga gcttgactcg aactgtctgt
 661 gctggcggct gtgcccgctg caagggcccg cagcccaccg actgctgcca cgagcaatgt
 721 gctgctggct gcacgggccc caagcattct gactgcctgg cctgcctcca cttcaaccac
 781 agtggcatct gtgagctgca ctgcccagcc ctggtcacct acaacacgga caccttcgaa
 841 tccatgccca accctgaggg ccgttatacc ttcggtgcca gctgtgtgac tgcctgtccc
 901 tacaactacc tgtctacgga cgtgggatcc tgcaccctgg tctgtcccct gaacaaccaa
 961 gaggtgacag ctgaggatgg aacacagcgg tgtgagaaat gcagcaagcc ctgtgcccga
1021 gtgtgctacg gcctaggcat ggagcacctg cgggaggcga gggcagtcac cagtgccaac
1081 atccaagaat ttgtcggctg caagaagatc tttgggagcc tggcgtttct gccagagagc
1141 tttgaggggg acccagcctc caacactgcc cccctgcagc ctgagcagct cagagtgttt
1201 gaggctctgg aggagattac aggttacctg tacatctcag cgtggccaga cagcttgcct
1261 aacctcagtg tcttccagaa cctcagagtg atccggggcc gagttctgca tgacggtgct
1321 tactcgctga cccttcaagg gctgggcatc agctggctgg ggctgcgctc gctgcgggag
1381 ctgggcagtg ggctggccct catccaccgc aactcccgcc tctgcttcgt acacacggtg
1441 ccctgggacc agctcttccg gaacccccac caggccctgc tccacagcgc caaccggcca
1501 gaggacgagt gcgcgggtga gggcctggcc tgctatccgc tgtgtgccca cgggcactgc
1561 tggggtccgg gacccaccca gtgtgtcaac tgcagccagt tccttcgggg ccaggagtgc
1621 gtggaggaat gccgagtatt gcaggggctt ccccgggagt atgtgaagga taggttctgt
1681 ctgccatgcc acccggagtg tcagccccag aatggctcag tgacctgctt gggctcggaa
1741 gctgaccagt gtgtggcctg tgcccactac aaggaccctc ctttctgtgt ggctcgctgc
1801 cccagtgggg tgaaacctga cctctccttc atgcccatct ggaagttcgc agatgaggag
1861 ggcacgtgcc agccatgccc catcaactgc acccactcct gtgcggacct ggacgagaag
1921 ggctgccccg ccgagcagag agccagccct gtgacgtcca tcattgctgc tgtggtgggc
1981 attctgctgg tcgtggttgt ggggctggtc cttggcatcc taatcaagcg aaggcggcag
2041 aagatccgga agtacacgat g
```

mfeHER2, SEQ ID NO: 44

```
   1 acccaagtgt gcaccggcac agacatgaag ctgcggctcc cagccagtcc cgagacccac
  61 ctggacatgc tccgccacct ctaccagggc tgtcaagtgg tacagggcaa cctggagctc
 121 acctacctgc atgccaatgc cagcctctcc ttcctgcagg atatccagga ggtgcaaggc
 181 tatgtgctca ttgcccacaa ccaagtgaaa caggtcccac tgcagaggct acgaatcgtg
 241 cgaggcaccc agctctttga ggacaactac gccctggccg tgctggacaa cggagaccca
 301 ctggacagtg gcacccctgc tacaggggct gccctaggag ggctgcggga gctgcagctc
 361 cgaagcctca cagagatcct gaagggaggg gtcctcattc agcggaaccc gcagctctgc
 421 caccaggaca cgattctgtg gaaggacatc ttccacaaga acaaccagct ggccctcatg
 481 ctgatagaca ccaaccgctc tcgggcctgc caaccctgtt ctccagcttg taaagactcc
 541 cactgctggg gagcaagttc cggggactgt cagagcttga ctcgaactgt ctgtgctggc
 601 ggctgtgccc gctgcaaggg cccgcagccc accgactgct gccacgagca atgtgctgct
 661 ggctgcacgg gccccaagca ttctgactgc ctggcctgcc tccacttcaa ccacagtggc
 721 atctgtgagc tgcactgccc agccctggtc acctacaaca cggacacctt cgaatccatg
 781 cccaaccctg agggccgtta taccttcggt gccagctgtg tgactgcctg tccctacaac
 841 tacctgtcta cggacgtggg atcctgcacc ctggtctgtc ccctgaacaa ccaagaggtg
 901 acagctgagg atggaacaca gcggtgtgag aaatgcagca agccctgtgc ccgagtgtgc
 961 tacggcctag gcatggagca cctgcgggag gcgagggcag tcaccagtgc caacatccaa
1021 gaatttgtcg gctgcaagaa gatctttggg agcctggcgt ttctgccaga gagctttgag
1081 ggggacccag cctccaacac tgcccccctg cagcctgagc agctcagagt gtttgaggct
1141 ctggaggaga ttacaggtta cctgtacatc tcagcgtggc cagacagctt gcctaacctc
1201 agtgtcttcc agaacctcag agtgatccgg ggccgagttc tgcatgacgg tgcttactcg
1261 ctgacccttc aagggctggg catcagctgg ctggggctgc gctcgctgcg ggagctgggc
1321 agtgggctgg ccctcatcca ccgcaactcc cgcctctgct tcgtacacac ggtgccctgg
1381 gaccagctct tccggaaccc ccaccaggcc ctgctccaca gcgccaaccg gccagaggac
1441 gagtgcgcgg gtgagggcct ggcctgctat ccgctgtgtg cccacgggca ctgctggggt
1501 ccgggaccca cccagtgtgt caactgcagc cagttccttc ggggccagga gtgcgtggag
```

TABLE 4 -continued

| Amino acid and nucleotide sequences for substituted and wild type HER2 polypeptides |
|---|
| 1561 gaatgccgag tattgcaggg gcttccccgg gagtatgtga aggataggtt ctgtctgcca |
| 1621 tgccacccgg agtgtcagcc ccagaatggc tcagtgacct gcttgggctc ggaagctgac |
| 1681 cagtgtgtgg cctgtgccca ctacaaggac cctccttttct gtgtggctcg ctgccccagt |
| 1741 ggggtgaaac ctgacctctc cttcatgccc atctggaagt tcgcagatga ggagggcacg |
| 1801 tgccagccat gccccatcaa ctgcacccac tcctgtgcgg acctggacga gaagggctgc |
| 1861 cccgccgagc agagagccag ccctgtgacg tccatcattg ctgctgtggt gggcattctg |
| 1921 ctggtcgtgg ttgtggggct ggtccttggc atcctaatca agcgaaggcg gcagaagatc |
| 1981 cggaagtaca cgatg |
| |
| prehumHER2, SEQ ID NO: 45 |
| 1 melaalcrwg lllallppga astqvctgtd mklrlpaspe thldmlrhly qgcqvvqgnl |
| 61 eltylptnas lsflqdiqev qgyvliahnq vrqvplqrlr ivrgtqlfed nyalavldng |
| 121 dplnnttpvt gaspgglrel qlrslteilk ggvliqrnpq lcyqdtilwk difhknnqla |
| 181 ltlidtnrsr achpcspmck gsrcwgesse dcqsltrtvc aggcarckgp lptdccheqc |
| 241 aagctgpkhs dclaclhfnh sgicelhcpa lvtyntdtfe smpnpegryt fgascvtacp |
| 301 ynylstdvgs ctlvcplhnq evtaedgtqr cekcskpcar vcyglgmehl revravtsan |
| 361 iqefagckki fgslaflpes fdgdpasnta plqpeqlqvf etleeitgyl yisawpdslp |
| 421 dlsvfqnlqv irgrilhnga ysltlqglgi swlglrslre lgsglalihh nthlcfvhtv |
| 481 pwdqlfrnph qallhtanrp edecvgegla chqlcarghc wgpgptqcvn csqflrgqec |
| 541 veecrvlqgl preyvnarhc lpchpecqpq ngsvtcfgpe adqcvacahy kdppfcvarc |
| 601 psgvkpdlsy mpiwkfpdee gacqpcpinc thscvdlddk gcpaeqrasp ltsiisavvg |
| 661 illvvvlgvv fgilikrrqq kirkytm |
| |
| mhumHER2, SEQ ID NO: 46 |
| 1 tqvctgtdmk lrlpaspeth ldmlrhlyqg cqvvqgnlel tylptnasls flqdiqevqg |
| 61 yvliahnqvr qvplqrlriv rgtqlfedny alavldngdp lnnttpvtga spgglrelql |
| 121 rslteilkgg vliqrnpqlc yqdtilwkdi fhknnqlalt lidtnrsrac hpcspmckgs |
| 181 rcwgessedc qsltrtvcag gcarckgplp tdccheqcaa gctgpkhsdc laclhfnhsg |
| 241 icelhcpalv tyntdtfesm pnpegrytfg ascvtacpyn ylstdvgsct lvcplhnqev |
| 301 taedgtqrce kcskpcarvc yglgmehlre vravtsaniq efagckkifg slaflpesfd |
| 361 gdpasntapl qpeqlqvfet leeitgylyi sawpdslpdl svfqnlqvir grilhngays |
| 421 ltlqglgisw lglrslrelg sglalihhnt hlcfvhtvpw dqlfrnphqa llhtanrped |
| 481 ecvgeglach qlcarghcwg pgptqcvncs qflrgqecve ecrvlqglpr eyvnarhclp |
| 541 chpecqpqng svtcfgpead qcvacahykd ppfcvarcps gvkpdlsymp iwkfpdeega |
| 601 cqpcpincth scvdlddkgc paeqrasplt siisavvgil lvvvlgvvfg ilikrrqqki |
| 661 rkytm |
| |
| premouseHER2, SEQ ID NO: 47 |
| 1 melaawcrwg fllallspga agtqvctgtd mklrlpaspe thldmlrhly qgcqvvqgnl |
| 61 eltylpanas lsflqdiqev qgymliahnr vkhvplqrlr ivrgtqlfed kyalavldnr |
| 121 dpldnvttaa pgrtpeglre lqlrslteil kggvlirgnp qlcyqdmvlw kdvlrknnql |
| 181 apvdmdtnrs racppcaptc kdnhcwgesp edcqiltgti ctsgcarckg rlptdccheq |
| 241 caagctgpkh sdclaclhfn hsgicelhcp alityntdtf esmlnpegry tfgascvttc |
| 301 pynylstevg sctlvcppnn qevtaedgtq rcekcskpca gvcyglgmeh lrgaraitsd |
| 361 niqefagckk ifgslaflpe sfdgnpssgv aplkpehlqv fetleeitgy lyisawpesf |
| 421 qdlsvfqnlr virgrilhdg aysltlqglg ihslglrslr elgsglalih rnthlcfvnt |
| 481 vpwdqlfrnp hqallhsgnr peeacglegl vcnslcargh cwgpgptqcv ncsqflrgqe |
| 541 cveecrvwkg lpreyvrgkh clpchpecqp qnssetcygs eadqceacah ykdssscvar |
| 601 cpsgvkpdls ympiwkypde egicqpcpin cthscvdlde rgcpaeqras pvtfiiatvv |
| 661 gvllfliivv vigilikrrr qkirkytm |
| |
| mmouseHER2, SEQ ID NO: 48 |
| 1 tqvctgtdmk lrlpaspeth ldmlrhlyqg cqvvqgnlel tylpanasls flqdiqevqg |
| 61 ymliahnrvk hvplqrlriv rgtqlfedky alavldnrdp ldnvttaapg rtpeglrelq |
| 121 lrslteilkg gvlirgnpql cyqdmvlwkd vlrknnqlap vdmdtnrsra cppcaptckd |
| 181 nhcwgesped cqiltgtict sgcarckgrl ptdccheqca agctgpkhsd claclhfnhs |
| 241 gicelhcpal ityntdtfes mlnpegrytf gascvttcpy nylstevgsc tlvcppnnqe |
| 301 vtaedgtqrc ekcskpcagv cyglgmehlr garaitsdni qefagckkif gslaflpesf |
| 361 dgnpssgvap lkpehlqvfe tleeitgyly isawpesfqd lsvfqnlrvi rgrilhdgay |
| 421 sltlqglgih slglrslrel gsglalihrn thlcfvntvp wdqlfrnphq allhsgnrpe |
| 481 eacgleglvc nslcarghcw gpgptqcvnc sqflrgqecv eecrvwkglp reyvrgkhcl |
| 541 pchpecqpqn ssetcygsea dqceacahyk dssscvarcp sgvkpdlsym piwkypdeeg |
| 601 icqpcpinct hscvdlderg cpaeqraspv tfiiatvvgv llfliivvvi gilikrrrqk |
| 661 irkytm |
| |
| preratHER2, SEQ ID NO: 49 |
| 1 miimelaawc rwgfllallp pgiagtqvct gtdmklrlpa spethldmlr hlyqgcqvvq |
| 61 gnleltyvpa naslsflqdi qevqgymlia hnqvkrvplq rlrivrgtql fedkyalavl |
| 121 dnrdpqdnva astpgrtpeg lrelqlrslt eilkggvlir gnpqlcyqdm vlwkdvfrkn |
| 181 nqlapvdidt nrsracppca packdnhcwg espedcqilt gtictsgcar ckgrlptdcc |
| 241 heqcaagctg pkhsdclacl hcpalvtynt dtfesmhnpe grytfgascv |
| 301 ttcpynylst evgsctlvcp pnnqevtaed gtqrcekcsk pcarvcyglg mehlrgarai |
| 361 tsdnvqefdg ckkifgslaf lpesfdgdps sgiaplrpeq lqvfetleei tgylyisawp |
| 421 dslrdlsvfq nlriirgril hdgaysltlq glgihslglr slrelgsgla lihrnahlcf |
| 481 vhtvpwdqlf rnphqallhs gnrpeedcgl eglvcnslca hghcwgpgpt qcvncshflr |

TABLE 4 -continued

Amino acid and nucleotide sequences for substituted and wild type HER2 polypeptides

```
 541 gqecveecry wkglpreyvs dkrclpchpe cqpqnssetc fgseadqcaa cahykdsssc
 601 varcpsgvkp dlsympiwky pdeegicqpc pincthscvd ldergcpaeq raspvtfiia
 661 tvvgvllfli lvvvvgilik rrrqkirkyt m

mratHER2, SEQ ID NO: 50
   1 tqvctgtdmk lrlpaspeth ldmlrhlyqg cqvvqgnlel tyvpanasls flqdiqevqg
  61 ymliahnqvk rvplqrlriv rgtqlfedky alavldnrdp qdnvaastpg rtpeglrelq
 121 lrslteilkg gvlirgnpql cyqdmvlwkd vfrknnqlap vdidtnrsra cppcapackd
 181 nhcwgesped cqiltgtict sgcarckgrl ptdccheqca agctgpkhsd claclhfnhs
 241 gicelhcpal vtyntdtfes mhnpegrytf gascvttcpy nylstevgsc tlvcppnnqe
 301 vtaedgtqrc ekcskpcarv cyglgmehlr garaitsdnv qefdgckkif gslaflpesf
 361 dgdpssgiap lrpeqlqvfe tleeitgyly isawpdslrd lsvfqnlrii rgrilhdgay
 421 sltlqglgih slglrslrel gsglalihrn ahlcfvhtvp wdqlfrnphq allhsgnrpe
 481 edcgleglvc nslcahghcw gpgptqcvnc shflrgqecv eecrvwkglp reyvsdkrcl
 541 pchpecqpqn ssetcfgsea dqcaacahyk dssscvarcp sgvkpdlsym piwkypdeeg
 601 icqpcpinct hscvdlderg cpaeqraspv tfiiatvvgv llflilvvvv gilikrrrqk
 661 irkytm

Precursor: preE2Neu SEQ ID NO: 51
   1 melaalcrwg lllallppga astqvctgtd mklrlpaspe thldmlrhly qgcqvvqgnl
  61 eltylptnas lsflqdiqev qgyvliahnq vrqvplqrlr ivrgtqlfed nyalavldng
 121 dplnnttpvt gaspgglrel qlrslteilk ggvliqrnpq lcyqdtilwk difhknnqla
 181 ltlidtnrsr achpcspmck gsrcwgesse dcqsltrtvc aggcarckgp lptdccheqc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta efaplrpeql qvfetleeit gylyisawpd
 421 slrdlsvfqn lriirgrilh dgaysltlqg lgihslglrs lrelgsglal ihrnahlcfv
 481 htvpwdqlfr nphqallhsg nrpeedcgle glvcnslcah ghcwgpgptq cvncshflrg
 541 qecveecrvw kglpreyvsd krclpchpec qpqnssetcf gseadqcaac ahykdssscv
 601 arcpsgvkpd lsympiwkyp deegicqpcp incthscvdl dergcpaeqr aspvtfiiat
 661 vvgvllflil vvvvgilikr rrqkirkytm

mE2Neu, SEQ ID NO: 52
   1 tqvctgtdmk lrlpaspeth ldmlrhlyqg cqvvqgnlel tylptnasls flqdiqevqg
  61 yvliahnqvr qvplqrlriv rgtqlfedny alavldngdp lnnttpvtga spgglrelql
 121 rslteilkgg vliqrnpqlc yqdtilwkdi fhknnqlalt lidtnrsrac hpcspmckgs
 181 rcwgessedc qsltrtvcag gcarckgplp tdccheqcaa gctgpkhsdc laclhfnhsg
 241 icelhcpalv tyntdtfesm pnpegrytfg ascvtacpyn ylstdvgsct lvcplhnqev
 301 taedgtqrce kcskpcarvc yglgmehlre vravtsaniq efagckkifg slaflpesfd
 361 gdpasntaef aplrpeqlqv fetleeitgy lyisawpdsl rdlsvfqnlr iirgrilhdg
 421 aysltlqglg ihslglrslr elgsglalih rnahlcfvht vpwdqlfrnp hqallhsgnr
 481 peedcglegl vcnslcahgh cwgpgptqcv ncshflrgqe cveecrvwkg lpreyvsdkr
 541 clpchpecqp qnssetcfgs eadqcaacah ykdssscvar cpsgvkpdls ympiwkypde
 601 egicqpcpin cthscvdlde rgcpaeqras pvtfiiatvv gvllflilvv vvgilikrrr
 661 qkirkytm

prehumHER2, SEQ ID NO: 53
   1 atggagctgg cggccttgtg ccgctggggg ctcctcctcg ccctcttgcc ccccggagcc
  61 gcgagcaccc aagtgtgcac cggcacagac atgaagctgc ggctccctgc cagtcccgag
 121 acccacctgg acatgctccg ccacctctac cagggctgcc aggtggtgca gggaaacctg
 181 gaactcacct acctgcccac caatgccagc ctgtccttcc tgcaggatat ccaggaggtg
 241 cagggctacg tgctcatcgc tcacaaccaa gtgaggcagg tcccactgca gaggctgcgg
 301 attgtgcgag gcacccagct ctttgaggac aactatgccc tggccgtgct agacaatgga
 361 gacccgctga acaataccac ccctgtcaca ggggcctccc caggaggcct gcgggagctg
 421 cagcttcgaa gcctcacaga gatcttgaaa ggaggggtct tgatccagcg gaacccccag
 481 ctctgctacc aggacacgat tttgtggaag gacatcttcc acaagaacaa ccagctggct
 541 ctcacactga tagacaccaa ccgctctcgg gcctgccacc cctgttctcc gatgtgtaag
 601 ggctcccgct gctggggaga gagttctgag gattgtcaga gcctgacgcg cactgtctgt
 661 gccggtggct gtgcccgctg caagggggcca ctgcccactg actgctgcca tgagcagtgt
 721 gctgccggct gcacgggccc caagcactct gactgcctgg cctgcctcca cttcaaccac
 781 agtggcatct gtgagctgca ctgcccagcc ctggtcacct acaacacaga cacgtttgag
 841 tccatgccca atcccgaggg ccggtataca ttcggcgcca gctgtgtgac tgcctgtccc
 901 tacaactacc tttctacgga cgtgggatcc tgcaccctcg tctgccccct gcacaaccaa
 961 gaggtgacag cagaggatgg aacacagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc ccgctccagc cagagcagct ccaagtgttt
1201 gagactctgg aagagatcac aggttaccta tacatctcag catggccgga cagcctgcct
1261 gacctcagcg tcttccagaa cctgcaagta atccggggac gaattctgca caatggcgcc
1321 tactcgctga ccctgcaagg gctgggcatc agctggctgg ggctgcgctc actgagggaa
1381 ctgggcagtg gactggccct catccaccat aacacccacc tctgcttcgt gcacacggtg
1441 ccctgggacc agctctttcg gaacccgcac caagctctgc tccacactgc caaccggcca
1501 gaggacgagt gtgtgggcga gggcctggcc tgccaccagc tgtgcgcccg agggcactgc
1561 tggggtccag ggcccaccca gtgtgtcaac tgcagccagt tccttcgggg ccaggagtgc
1621 gtggaggaat gccgagtact gcaggggctc cccagggagt atgtgaatgc caggcactgt
1681 ttgccgtgcc accctgagtg tcagccccag aatggctcag tgacctgttt tggaccggag
1741 gctgaccagt gtgtggcctg tgcccactat aaggaccctc ccttctgcgt ggcccgctgc
```

TABLE 4 -continued

Amino acid and nucleotide sequences for substituted and wild type HER2 polypeptides

```
1801 cccagcggtg tgaaacctga cctctcctac atgcccatct ggaagtttcc agatgaggag
1861 ggcgcatgcc agccttgccc catcaactgc acccactcct gtgtggacct ggatgacaag
1921 ggctgccccg ccgagcagag agccagccct ctgacgtcca tcatctctgc ggtggttggc
1981 attctgctgg tcgtggtctt gggggtggtc tttgggatcc tcatcaagcg acggcagcag
2041 aagatccgga agtacacgat gtga
```

mhumHER2, SEQ ID NO: 54

```
   1 acccaagtgt gcaccggcac agacatgaag ctgcggctcc ctgccagtcc cgagacccac
  61 ctggacatgc tccgccacct ctaccagggc tgccaggtgg tgcagggaaa cctggaactc
 121 acctacctgc ccaccaatgc cagcctgtcc ttcctgcagg atatccagga ggtgcagggc
 181 tacgtgctca tcgctcacaa ccaagtgagg caggtcccac tgcagaggct gcggattgtg
 241 cgaggcaccc agctctttga ggacaactat gccctggccg tgctagacaa tggagacccg
 301 ctgaacaata ccacccctgt cacaggggcc tccccaggag gcctgcggga gctgcagctt
 361 cgaagcctca cagagatctt gaaaggaggg gtcttgatcc agcggaaccc ccagctctgc
 421 taccaggaca cgattttgtg gaaggacatc ttccacaaga acaaccagct ggctctcaca
 481 ctgatagaca ccaaccgctc tcgggcctgc caccoctgtt ctccgatgtg taagggctcc
 541 cgctgctggg gagagagttc tgaggattgt cagagcctga cgcgcactgt ctgtgccggt
 601 ggctgtgccc gctgcaaggg gccactgccc actgactgct gccatgagca gtgtgctgcc
 661 ggctgcacgg gccccaagca ctctgactgc ctggcctgcc tccacttcaa ccacagtggc
 721 atctgtgagc tgcactgccc agccctggtc acctacaaca cagacacgtt tgagtccatg
 781 cccaatcccg agggccggta tacattcggc gccagctgtg tgactgcctg tccctacaac
 841 tacctttcta cggacgtggg atcctgcacc ctcgtctgcc ccctgcacaa ccaagaggtg
 901 acagcagagg atggaacaca gcggtgtgag aagtgcagca agccctgtgc ccgagtgtgc
 961 tatggtctgg gcatggagca cttgcgagag gtgagggcag ttaccagtgc caatatccag
1021 gagtttgctg gctgcaagaa gatctttggg agcctggcat ttctgccgga gagctttgat
1081 ggggacccag cctccaacac tgccccgctc cagccagagc agctccaagt gtttgagact
1141 ctggaagaga tcacaggtta cctatacatc tcagcatggc cggacagcct gcctgacctc
1201 agcgtcttcc agaacctgca agtaatccgg ggacgaattc tgcacaatgg cgcctactcg
1261 ctgaccctgc aagggctggg catcagctgg ctggggctgc gctcactgag ggaactgggc
1321 agtggactgg ccctcatcca ccataacacc cacctctgct tcgtgcacac ggtgccctgg
1381 gaccagctct ttcggaaccc gcaccaagct ctgctccaca ctgccaaccg gccagaggac
1441 gagtgtgtgg gcgagggcct ggcctgccac cagctgtgcg cccgagggca ctgctggggt
1501 ccagggccca cccagtgtgt caactgcagc cagttccttc ggggccagga gtgcgtggag
1561 gaatgccgag tactgcaggg gctccccagg gagtatgtga atgccaggca ctgtttgccg
1621 tgccaccctg agtgtcagcc ccagaatggc tcagtgacct gttttggacc ggaggctgac
1681 cagtgtgtgg cctgtgccca ctataaggac cctcccttct gcgtggcccg ctgccccagc
1741 ggtgtgaaac ctgacctctc ctacatgccc atctggaagt ttccagatga ggagggcgca
1801 tgccagcctt gccccatcaa ctgcacccac tcctgtgtgg acctggatga caagggctgc
1861 cccgccgagc agagagccag ccctctgacg tccatcatct ctgcggtggt tggcattctg
1921 ctggtcgtgg tcttgggggt ggtctttggg atcctcatca agcgacggca gcagaagatc
1981 cggaagtaca cgatgtga
```

premouseHER2, SEQ ID NO: 55

```
   1 atggagctgg cggcctggtg ccgttggggg ttcctcctcg ccctcctgtc ccccggagcc
  61 gcgggtaccc aagtgtgtac cggtaccgac atgaagttgc gactccctgc cagtcctgag
 121 acccacctgg acatgcttcg ccacctctac cagggctgtc aggtggtgca gggcaatttg
 181 gagcttacct acctgcccgc caatgccagc ctctcattcc tgcaggacat ccaggaagtc
 241 cagggataca tgctcatcgc tcacaaccga gtgaaacacg tcccactgca gaggttgcgc
 301 atcgtgagag ggactcagct ctttgaggac aagtatgccc tggctgtgct agacaaccga
 361 gaccctttgg acaacgtcac caccgccgcc ccaggcagaa ccccagaagg gctgcgggag
 421 ctgcagcttc gaagtctcac agagatcttg aagggaggag ttttgatccg tgggaaccct
 481 cagctctgct accaggacat ggttttgtgg aaggatgtcc tccgtaagaa taaccagctg
 541 gctcctgtcg acatggacac caatcgttcc cgggcctgtc caccttgtgc ccccaacctgc
 601 aaagacaatc actgttgggg tgagagtcct gaagactgtc agatcttgac tggcaccatc
 661 tgtactagtg gctgtgcccg gtgcaagggc cggctgccca ctgactgttg ccatgagcag
 721 tgtgctgcag gctgcacggg tcccaagcat tctgactgcc tggcctgcct ccacttcaat
 781 catagtggta tctgtgagct gcactgcccg gccctcatca cctacaacac agacaccttc
 841 gagtccatgc tcaaccctga gggtcgctac acctttggtg ccagctgtgt gaccacctgc
 901 ccctacaact acctctccac ggaagtggga tcctgcactc tggtctgtcc cccgaacaac
 961 caagaggtca cagctgagga cggaacacag cggtgtgaga aatgcagcaa gccctgtgct
1021 ggagtatgct atggtctggg catggagcac ctccgagggg cgagggccat caccagtgac
1081 aatatccagg agtttgctgg ctgcaagaag atctttggga gcctggcatt tttgccggag
1141 agctttgatg ggaacccctc ctccggcgtt gccccactga agccagagca tctccaagtg
1201 ttcgaaaccc tggaggagat cacaggttac ctatacattt cagcatggcc agagagcttc
1261 caagacctca gtgtcttcca gaaccttcgg gtcattcggg gacggattct ccatgatggt
1321 gcttactcat tgacgttgca aggcctgggg attcactcac tggggctacg ctcactgcgg
1381 gagctgggca gtggattggc tctcattcac cgcaacaccc atctctgctt tgtaaacact
1441 gtaccttggg accagctctt ccggaacccg caccaggccc tactccacag tgggaaccgg
1501 ccagaagagg catgtggtct tgagggcttg gtctgtaact cactgtgtgc ccgtgggcac
1561 tgctgggggc cagggcccac ccagtgtgtc aactgcagtc agttcctccg ggccaggag
1621 tgtgtggagg agtgccgagt atggaagggg ctccccaggg agtatgtgag ggcaagcac
1681 tgtctgccat gccaccccga gtgtcagcct caaaacagct cggagacctg ctatggatcg
1741 gaggctgacc agtgtgaggc ttgtgcccac tacaaggact catcttcctg tgtggctcgc
1801 tgccccagtg gtgtgaagcc agacctctcc tacatgccta tctggaagta cccggatgag
1861 gagggcatat gtcagccatg ccccatcaac tgcacccact catgtgtgga cctggacgaa
1921 cgaggctgcc cagcagagca gagagccagc ccagtgacat tcatcattgc aactgtggtg
1981 ggcgtcctgt tgttcctgat catagtggtg gtcattggaa tcctaatcaa acgaaggcga
```

TABLE 4 -continued

Amino acid and nucleotide sequences for substituted and wild type HER2 polypeptides

```
2041 cagaagatcc ggaagtatac catg

mmouseHER2, SEQ ID NO: 56
   1 acccaagtgt gtaccggtac cgacatgaag ttgcgactcc ctgccagtcc tgagacccac
  61 ctggacatgc ttcgccacct ctaccagggc tgtcaggtgg tgcagggcaa tttggagctt
 121 acctacctgc ccgccaatgc cagcctctca ttcctgcagg acatccagga agtccaggga
 181 tacatgctca tcgctcacaa ccgagtgaaa cacgtcccac tgcagaggtt gcgcatcgtg
 241 agagggactc agctctttga ggacaagtat gccctggctg tgctagacaa ccgagaccct
 301 ttggacaacg tcaccaccgc cgccccaggc agaaccccag aagggctgcg ggagctgcag
 361 cttcgaagtc tcacagagat cttgaaggga ggagttttga tccgtgggaa ccctcagctc
 421 tgctaccagg acatggtttt gtggaaggat gtcctccgta agaataacca gctggctcct
 481 gtcgacatgg acaccaatcg ttcccgggcc tgtccacctt gtgccccaac ctgcaaagac
 541 aatcactgtt ggggtgagag tcctgaagac tgtcagatct tgactggcac catctgtact
 601 agtggctgtg cccggtgcaa gggccggctg cccactgact gttgccatga gcagtgtgct
 661 gcaggctgca cgggtcccaa gcattctgac tgcctggcct gcctccactt caatcatagt
 721 ggtatctgtg agctgcactg cccggccctc atcacctaca acacagacac cttcgagtcc
 781 atgctcaacc ctgagggtcg ctacaccttt ggtgccagct gtgtgaccac ctgcccctac
 841 aactacctct ccacggaagt gggatcctgc actctggtct gtcccccgaa caaccaagag
 901 gtcacagctg aggacggaac acagcggtgt gagaaatgca gcaagccctg tgctggagta
 961 tgctatggtc tgggcatgga gcacctccga ggggcgaggg ccatcaccag tgacaatatc
1021 caggagtttg ctggctgcaa gaagatcttt gggagcctgg catttttgcc ggagagcttt
1081 gatgggaacc cctcctccgg cgttgcccca ctgaagccag agcatctcca agtgttcgaa
1141 accctggagg agatcacagg ttacctatac atttcagcat ggccagagag cttccaagac
1201 ctcagtgtct tccagaacct tcgggtcatt cggggacgga ttctccatga tggtgcttac
1261 tcattgacgt tgcaaggcct ggggattcac tcactggggc tacgctcact gcgggagctg
1321 ggcagtggat tggctctcat tcaccgcaac acccatctct gctttgtaaa cactgtacct
1381 tgggaccagc tcttccggaa cccgcaccag gccctactcc acagtgggaa ccggccagaa
1441 gaggcatgtg gtcttgaggg cttggtctgt aactcactgt gtgcccgtgg gcactgctgg
1501 gggccagggc ccacccagtg tgtcaactgc agtcagttcc tccggggcca ggagtgtgtg
1561 gaggagtgcc gagtatggaa ggggctcccc agggagtatg tgaggggcaa gcactgtctg
1621 ccatgccacc ccgagtgtca gcctcaaaac agctcggaga cctgctatgg atcggaggct
1681 gaccagtgtg aggcttgtgc ccactacaag gactcatctt cctgtgtggc tcgctgcccc
1741 agtggtgtga agccagacct ctcctacatg cctatctgga agtacccgga tgaggagggc
1801 atatgtcagc catgccccat caactgcacc cactcatgtg tggacctgga cgaacgaggc
1861 tgcccagcag agcagagagc cagcccagtg acattcatca ttgcaactgt ggtgggcgtc
1921 ctgttgttcc tgatcatagt ggtggtcatt ggaatcctaa tcaaacgaag gcgacagaag
1981 atccggaagt ataccatg

preratHER2, SEQ ID NO: 57
   1 atgatcatca tggagctggc ggcctggtgc cgctgggggt tcctcctcgc cctcctgccc
  61 cccggaatcg cgggcaccca agtgtgtacc ggcacagaca tgaagttgcg gctccctgcc
 121 agtcctgaga cccacctgga catgctccgc cacctgtacc agggctgtca ggtagtgcag
 181 ggcaacttgg agcttaccta cgtgcctgcc aatgccagcc tctcattcct gcaggacatc
 241 caggaagttc agggttacat gctcatcgct cacaaccagg tgaagcgcgt cccactgcaa
 301 aggctgcgca tcgtgagagg gacccagctc tttgaggaca agtatgccct ggctgtgcta
 361 gacaaccgag atcctcagga caatgtcgcc gcctccaccc caggcagaac cccagagggg
 421 ctgcgggagc tgcagcttcg aagtctcaca gagatcctga agggaggagt tttgatccgt
 481 gggaaccctc agctctgcta ccaggacatg gttttgtgga aggacgtctt ccgcaagaat
 541 aaccaactgg ctcctgtcga tatagacacc aatcgttccc gggcctgtcc accttgtgcc
 601 cccgcctgca aagacaatca ctgttggggt gagagtccgg aagactgtca gatcttgact
 661 ggcaccatct gtaccagtgg ttgtgcccgg tgcaagggcc ggctgcccac tgactgctgc
 721 catgagcagt gtgccgcagg ctgcacgggc cccaagcatt ctgactgcct ggcctgcctc
 781 cacttcaatc atagtggtat ctgtgagctg cactgcccag ccctcgtcac ctacaacaca
 841 gacacctttg agtccatgca caaccctgag ggtcgctaca cctttggtgc cagctgcgtg
 901 accacctgcc cctacaacta cctgtctacg gaagtgggat cctgcactct ggtgtgtccc
 961 ccgaataacc aagaggtcac agctgaggac ggaacacagc gttgtgagaa atgcagcaag
1021 ccctgtgctc gagtgtgcta tggtctgggc atggagcacc ttcgaggggc gagggccatc
1081 accagtgaca atgtccagga gtttgatggc tgcaagaaga tctttgggag cctggcattt
1141 ttgccggaga gctttgatgg ggacccctcc tccggcattg ctccgctgag gcctgagcag
1201 ctccaagtgt tcgaaaccct ggaggagatc acaggttacc tgtacatctc agcatggcca
1261 gacagtctcc gtgacctcag tgtcttccag aaccttcgaa tcattcgggg acggattctc
1321 cacgatggcg cgtactcatt gacactgcaa ggcctgggga tccactcgct ggggctgcgc
1381 tcactgcggg agctgggcag tggattggct ctgattcacc gcaacgccca tctctgcttt
1441 gtacacactg taccttggga ccagctcttc cggaacccac atcaggccct gctccacagt
1501 gggaaccggc cggaagagga ttgtggtctc gagggcttgg tctgtaactc actgtgtgcc
1561 cacgggcact gctgggggcc agggcccacc cagtgtgtca actgcagtca tttccttcgg
1621 ggccaggagt gtgtggagga gtgccgagta tggaaggggc tcccccggga gtatgtgagt
1681 gacaagcgct gtctgccgtg tcaccccgag tgtcagcctc aaaacagctc agagacctgc
1741 tttggatcgg aggctgatca gtgtgcagcc tgcgcccact acaaggactc gtcctcctgt
1801 gtggctcgct gccccagtgg tgtgaaaccg gacctctcct acatgcccat ctggaagtac
1861 ccggatgagg agggcatatg ccagccgtgc cccatcaact gcacccactc ctgtgtggat
1921 ctggatgaac gaggctgccc agcagagcag agagccagcc cggtgacatt catcattgca
1981 actgtagtgg gcgtcctgct gttcctgatc ttagtggtgg tcgttggaat cctaatcaaa
2041 cgaaggagac agaagatccg gaagtatacg atg
```

TABLE 4 -continued

| Amino acid and nucleotide sequences for substituted and wild type HER2 polypeptides |
|---|

mratHER2, SEQ ID NO: 58

1 acccaagtgt gtaccggcac agacatgaag ttgcggctcc ctgccagtcc tgagacccac
61 ctggacatgc tccgccacct gtaccagggc tgtcaggtag tgcagggcaa cttggagctt
121 acctacgtgc ctgccaatgc cagcctctca ttcctgcagg acatccagga agttcagggt
181 tacatgctca tcgctcacaa ccaggtgaag cgcgtcccac tgcaaaggct gcgcatcgtg
241 agagggaccc agctctttga ggacaagtat gccctggctg tgctagacaa ccgagatcct
301 caggacaatg tcgccgcctc caccccaggc agaaccccag aggggctgcg ggagctgcag
361 cttcgaagtc tcacagagat cctgaaggga ggagttttga tccgtgggaa ccctcagctc
421 tgctaccagg acatggtttt gtggaaggac gtcttccgca agaataacca actggctcct
481 gtcgatatag acaccaatcg ttcccgggcc tgtccacctt gtgcccccgc ctgcaaagac
541 aatcactgtt ggggtgagag tccggaagac tgtcagatct tgactggcac catctgtacc
601 agtggttgtg cccggtgcaa gggccggctg cccactgact gctgccatga gcagtgtgcc
661 gcaggctgca cgggccccaa gcattctgac tgcctggcct gcctccactt caatcatagt
721 ggtatctgtg agctgcactg cccagccctc gtcacctaca acacagacac ctttgagtcc
781 atgcacaacc ctgagggtcg ctacaccttt ggtgccagct gcgtgaccac ctgcccctac
841 aactacctgt ctacggaagt gggatcctgc actctggtgt gtcccccgaa taaccaagag
901 gtcacagctg aggacggaac acagcgttgt gagaaatgca gcaagccctg tgctcgagtg
961 tgctatggtc tgggcatgga gcaccttcga ggggcgaggg ccatcaccag tgacaatgtc
1021 caggagtttg atggctgcaa gaagatcttt gggagcctgg cattttgcc ggagagcttt
1081 gatggggacc cctcctccgg cattgctccg ctgaggcctg agcagctcca agtgttcgaa
1141 accctggagg agatcacagg ttacctgtac atctcagcat ggccagacag tctccgtgac
1201 ctcagtgtct tccagaacct tcgaatcatt cggggacgga ttctccacga tggcgcgtac
1261 tcattgacac tgcaaggcct ggggatccac tcgctggggc tgcgctcact gcgggagctg
1321 ggcagtggat tggctctgat tcaccgcaac gcccatctct gctttgtaca cactgtacct
1381 tgggaccagc tcttccggaa cccacatcag gccctgctcc acagtgggaa ccggccggaa
1441 gaggattgtg gtctcgaggg cttggtctgt aactcactgt gtgcccacgg gcactgctgg
1501 gggccagggc ccacccagtg tgtcaactgc agtcatttcc ttcggggcca ggagtgtgtg
1561 gaggagtgcc gagtatggaa ggggctcccc cgggagtatg tgagtgacaa gcgctgtctg
1621 ccgtgtcacc ccgagtgtca gcctcaaaac agctcagaga cctgctttgg atcggaggct
1681 gatcagtgtg cagcctgcgc ccactacaag gactcgtcct cctgtgtggc tcgctgcccc
1741 agtggtgtga aaccggacct ctcctacatg cccatctgga agtacccgga tgaggagggc
1801 atatgccagc cgtgccccat caactgcacc cactcctgtg tggatctgga tgaacgaggc
1861 tgcccagcag agcagagagc cagcccggtg acattcatca ttgcaactgt agtgggcgtc
1921 ctgctgttcc tgatcttagt ggtggtcgtt ggaatcctaa tcaaacgaag gagacagaag
1981 atccggaagt atacgatg preE2Neu, SEQ ID NO: 59

1 atggagctgg cggccttgtg ccgctggggg ctcctcctcg ccctcttgcc ccccggagcc
61 gcgagcaccc aagtgtgcac cggcacagac atgaagctgc ggctccctgc cagtcccgag
121 acccacctgg acatgctccg ccacctctac cagggctgcc aggtggtgca gggaaacctg
181 gaactcacct acctgcccac caatgccagc ctgtccttcc tgcaggatat ccaggaggtg
241 cagggctacg tgctcatcgc tcacaaccaa gtgaggcagg tcccactgca gaggctgcgg
301 attgtgcgag gcacccagct ctttgaggac aactatgccc tggccgtgct agacaatgga
361 gacccgctga acaataccac ccctgtcaca ggggcctccc caggaggcct gcgggagctg
421 cagcttcgaa gcctcacaga gatcttgaaa ggaggggtct tgatccagcg gaacccccag
481 ctctgctacc aggacacgat tttgtggaag gacatcttcc acaagaacaa ccagctggct
541 ctcacactga tagacaccaa ccgctctcgg gcctgccacc cctgttctcc gatgtgtaag
601 ggctcccgct gctggggaga gagttctgag gattgtcaga gcctgacgcg cactgtctgt
661 gccggtggct gtgcccgctg caaggggcca ctgcccactg actgctgcca tgagcagtgt
721 gctgccggct gcacgggccc caagcactct gactgcctgg cctgcctcca cttcaaccac
781 agtggcatct gtgagctgca ctgcccagcc ctggtcacct acaacacaga cacgtttgag
841 tccatgccca atcccgaggg ccggtataca ttcggcgcca gctgtgtgac tgcctgtccc
901 tacaactacc tttctacgga cgtgggatcc tgcaccctcg tctgccccct gcacaaccaa
961 gaggtgacag cagaggatgg aacacagcgg tgtgagaagt gcagcaagcc ctgtgcccga
1021 gtgtgctatg gtctgggcat ggagcacttg cgagaggtga gggcagttac cagtgccaat
1081 atccaggagt ttgctggctg caagaagatc tttgggagcc tggcatttct gccggagagc
1141 tttgatgggg acccagcctc caacactgcc gaattcgctc cgctgaggcc tgagcagctc
1201 caagtgttcg aaaccctgga ggagatcaca ggttacctgt acatctcagc atggccagac
1261 agtctccgtg acctcagtgt cttccagaac cttcgaatca ttcggggacg gattctccac
1321 gatggcgcgt actcattgac actgcaaggc ctggggatcc actcgctggg gctgcgctca
1381 ctgcgggagc tgggcagtgg attggctctg attcaccgca acgcccatct ctgctttgta
1441 cacactgtac cttgggacca gctcttccgg aacccacatc aggccctgct ccacagtggg
1501 aaccggccgg aagaggattg tggtctcgag ggcttggtct gtaactcact gtgtgcccac
1561 gggcactgct gggggccagg gcccacccag tgtgtcaact gcagtcattt ccttcggggc
1621 caggagtgtg tggaggagtg ccgagtatgg aaggggctcc cccgggagta tgtgagtgac
1681 aagcgctgtc tgccgtgtca ccccgagtgt cagcctcaaa acagctcaga gacctgcttt
1741 ggatcggagg ctgatcagtg tgcagcctgc gcccactaca aggactcgtc ctcctgtgtg
1801 gctcgctgcc ccagtggtgt gaaaccggac ctctcctaca tgcccatctg gaagtacccg
1861 gatgaggagg gcatatgcca gccgtgcccc atcaactgca cccactcctg tgtggatctg
1921 gatgaacgag gctgcccagc agagcagaga gccagcccgg tgacattcat cattgcaact
1981 gtagtgggcg tcctgctgtt cctgatctta gtggtggtcg ttggaatcct aatcaaacga
2041 aggagacaga agatccggaa gtatacgatg mE2Neu, SEQ ID NO: 60

1 acccaagtgt gcaccggcac agacatgaag ctgcggctcc ctgccagtcc cgagacccac
61 ctggacatgc tccgccacct ctaccagggc tgccaggtgg tgcagggaaa cctggaactc TABLE 4 -continued Amino acid and nucleotide sequences for substituted and wild type HER2 polypeptides

```
 121 acctacctgc ccaccaatgc cagcctgtcc ttcctgcagg atatccagga ggtgcagggc
 181 tacgtgctca tcgctcacaa ccaagtgagg caggtcccac tgcagaggct gcggattgtg
 241 cgaggcaccc agctctttga ggacaactat gccctggccg tgctagacaa tggagacccg
 301 ctgaacaata ccacccctgt cacaggggcc tccccaggag gcctgcggga gctgcagctt
 361 cgaagcctca cagagatctt gaaaggaggg gtcttgatcc agcggaaccc ccagctctgc
 421 taccaggaca cgattttgtg gaaggacatc ttccacaaga acaaccagct ggctctcaca
 481 ctgatagaca ccaaccgctc tcgggcctgc cacccctgtt ctccgatgtg taagggctcc
 541 cgctgctggg gagagagttc tgaggattgt cagagcctga cgcgcactgt ctgtgccggt
 601 ggctgtgccc gctgcaaggg gccactgccc actgactgct gccatgagca gtgtgctgcc
 661 ggctgcacgg gccccaagca ctctgactgc ctggcctgcc tccacttcaa ccacagtggc
 721 atctgtgagc tgcactgccc agccctggtc acctacaaca cagacacgtt tgagtccatg
 781 cccaatcccg agggccggta tacattcggc gccagctgtg tgactgcctg tccctacaac
 841 tacctttcta cggacgtggg atcctgcacc ctcgtctgcc ccctgcacaa ccaagaggtg
 901 acagcagagg atggaacaca gcggtgtgag aagtgcagca agccctgtgc ccgagtgtgc
 961 tatggtctgg gcatggagca cttgcgagag gtgagggcag ttaccagtgc caatatccag
1021 gagtttgctg gctgcaagaa gatctttggg agcctggcat ttctgccgga gagctttgat
1081 ggggacccag cctccaacac tgccgaattc gctccgctga ggcctgagca gctccaagtg
1141 ttcgaaaccc tggaggagat cacaggttac ctgtacatct cagcatggcc agacagtctc
1201 cgtgacctca gtgtcttcca gaaccttcga atcattcggg gacggattct ccacgatggc
1261 gcgtactcat tgacactgca aggcctgggg atccactcgc tggggctgcg ctcactgcgg
1321 gagctgggca gtggattggc tctgattcac cgcaacgccc atctctgctt tgtacacact
1381 gtaccttggg accagctctt ccggaaccca catcaggccc tgctccacag tgggaaccgg
1441 ccggaagagg attgtggtct cgagggcttg gtctgtaact cactgtgtgc ccacgggcac
1501 tgctggggc  cagggcccac ccagtgtgtc aactgcagtc atttccttcg gggccaggag
1561 tgtgtggagg agtgccgagt atggaagggg ctcccccggg agtatgtgag tgacaagcgc
1621 tgtctgccgt gtcaccccga gtgtcagcct caaaacagct cagagacctg ctttggatcg
1681 gaggctgatc agtgtgcagc ctgcgcccac tacaaggact cgtcctcctg tgtggctcgc
1741 tgccccagtg gtgtgaaacc ggacctctcc tacatgccca tctggaagta cccggatgag
1801 gagggcatat gccagccgtg ccccatcaac tgcacccact cctgtgtgga tctggatgaa
1861 cgaggctgcc cagcagagca gagagccagc ccggtgacat tcatcattgc aactgtagtg
1921 ggcgtcctgc tgttcctgat cttagtggtg gtcgttggaa tcctaatcaa acgaaggaga
1981 cagaagatcc ggaagtatac gatg
```

pprehumHER2-Q213K, SEQ ID NO: 84

```
   1 melaalcrwg lllallppga astqvctgtd mklrlpaspe thldmlrhly qgcqvvqgnl
  61 eltylptnas lsflqdiqev qgyvliahnq vrqvplqrlr ivrgtqlfed nyalavldng
 121 dplnnttpvt gaspgglrel qlrslteilk ggvliqrnpq lcyqdtilwk difhknnqla
 181 ltlidtnrsr achpcspmck gsrcwgesse dcKsltrtvc aggcarckgp lptdccheqc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph qallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gcpaeqrasp ltsiisavvg
 661 illvvvlgvv fgilikrrqq kirkytm
```

pprehumHER2-Q239K, SEQ ID NO: 85

```
   1 melaalcrwg lllallppga astqvctgtd mklrlpaspe thldmlrhly qgcqvvqgnl
  61 eltylptnas lsflqdiqev qgyvliahnq vrqvplqrlr ivrgtqlfed nyalavldng
 121 dplnnttpvt gaspgglrel qlrslteilk ggvliqrnpq lcyqdtilwk difhknnqla
 181 ltlidtnrsr achpcspmck gsrcwgesse dcqsltrtvc aggcarckgp lptdccheKc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph qallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gcpaeqrasp ltsiisavvg
 661 illvvvlgvv fgilikrrqq kirkytm
```

pprehumHER2-NNT 124-126 DSG, SEQ ID NO: 86

```
   1 melaalcrwg lllallppga astqvctgtd mklrlpaspe thldmlrhly qgcqvvqgnl
  61 eltylptnas lsflqdiqev qgyvliahnq vrqvplqrlr ivrgtqlfed nyalavldng
 121 dplDSGtpvt gaspgglrel qlrslteilk ggvliqrnpq lcyqdtilwk difhknnqla
 181 ltlidtnrsr achpcspmck gsrcwgesse dcqsltrtvc aggcarckgp lptdccheqc
 241 aagctgpkhs dclaclhfnh sgicelhcpa lvtyntdtfe smpnpegryt fgascvtacp
 301 ynylstdvgs ctlvcplhnq evtaedgtqr cekcskpcar vcyglgmehl revravtsan
 361 iqefagckki fgslaflpes fdgdpasnta plqpeqlqvf etleeitgyl yisawpdslp
 421 dlsvfqnlqv irgrilhnga ysltlqglgi swlglrslre lgsglalihh nthlcfvhtv
 481 pwdqlfrnph qallhtanrp edecvgegla chqlcarghc wgpgptqcvn csqflrgqec
 541 veecrvlqgl preyvnarhc lpchpecqpq ngsvtcfgpe adqcvacahy kdppfcvarc
 601 psgvkpdlsy mpiwkfpdee gacqpcpinc thscvdlddk gcpaeqrasp ltsiisavvg
 661 illvvvlgvv fgilikrrqq kirkytm
```

REFERENCES CITED

Carmen S, Jermutus L. Concepts in antibody phage display. Brief Funct Genomic Proteomic. 2002; 1: 189-203

Cobleigh, M. A., C. L. Vogel, D. Tripathy, N. J. Robert, S. Scholl, L. Fehrnbacher, J. M. Wolter, V. Paton, S. Shak, G. Lieberman, D. J. Slamon. 1999. Multinational study of the efficacy and safety of humanized anti-HER2 monoclonal antibody in women who have HER2-overexpressing metastatic breast cancer that has progressed after chemotherapy for metastatic disease. J. Clin. Oncol. 17: 2639.

Colombo M P, Piconese S. Regulatory-T-cell inhibition versus depletion: the right choice in cancer immunotherapy. Nat Rev Cancer. 2007; 7: 880-7.

De Maria R, Olivero M, lussich S, Nakaichi M, Murata T, Biolatti B, et al. Spontaneous feline mammary carcinoma is a model of HER2 overexpressing poor prognosis human breast cancer. Cancer Research. 2005; 65(3): 907-12.

Disis, M., E. Calenoff, G. McLaughlin, A. E. Murphy, W. Chen, B. Groner, M. Jeschke, N. Lydon, E. McGlynn, R. B. Livingston, et al 1994. Existent T cell and antibody immunity to Her-2/neu protein in patients with breast cancer. Cancer Res. 54: 16.

Drebin J A, Stern D F, Link V C, Weinberg R A, Greene M I. Monoclonal antibodies identify a cell-surface antigen associated with an activated cellular oncogene. Nature. 1984; 312(5994): 545-8.

Fisk, B., B. W. Anderson, K. R. Gravitt, C. A. O'Brian, A. P. Kudelka, J. L. Murray, J. T. Wharton, C. G. loannides. 1997. Identification of naturally processed human ovarian peptides recognized by tumor-associated cytotoxic T lymphocytes. Cancer Res. 57: 87.

Garrett T P, McKern N M, Lou M, Elleman T C, Adams T E, Lovrecz G O, et al. The crystal structure of a truncated ErbB2 ectodomain reveals an active conformation, poised to interact with other ErbB receptors. Mol Cell 2003; 11: 495-505.

Gibson H M, Mishra A, Chan D V, Hake T S, Porcu P, Wong H K. Impaired proteasome function activates GATA3 in T cells and upregulates CTLA-4: relevance for Sezary syndrome. The Journal of investigative dermatology. 2013; 133(1): 249-57.

Gimenez F, Hecht S, Craig L E, Legendre A M. Early detection, aggressive therapy: optimizing the management of feline mammary masses. Journal of feline medicine and Surgery. 2010; 12(3): 214-24.

Gostring L, Maim M, Hoiden-Guthenberg I, Frejd F Y, Stahl S, Lofblom J, et al. Cellular effects of HER3-specific affibody molecules. PloS one. 2012; 7(6): e40023.

Green, M. R. and Sambrook, J. Molecular Cloning: A Laboratory Manual (Fourth Edition). Cold Spring Harbor Laboratory, Cold Spring Harbor, 2012.

Hammers C M, Stanley J R. Antibody Phage Display: Techniques and Applications. J Invest Dermatol 2014; 134: e17

Harlow E and Lane D. Antibodies: A Laboratory Manual. Cold Spring Harbor Laboratory, Cold Spring Harbor, 1988.

Harrop R, John J, Carroll M W. Recombinant viral vectors: Cancer vaccines. Adv. Drug Deliv. Rev. 2006; 58: 931-947

Hayden D W, Nielsen S W. Feline mammary tumours. The Journal of small animal practice. 1971; 12(12): 687-98.

Hudziak R M, Lewis G D, Winget M, Fendly B M, Shepard H M, Ullrich A. p 185HER2 monoclonal antibody has antiproliferative effects in vitro and sensitizes human breast tumor cells to tumor necrosis factor. Molecular and cellular biology. 1989; 9(3): 1165-72.

Jacob J, Radkevich O, Forni G, Zielinski J, Shim D, Jones R F, et al. Activity of DNA vaccines encoding self or heterologous Her-2/neu in Her-2 or neu transgenic mice. Cell lmmunol. 2006; 240(2): 96-106.

Jacob J B, Kong Y C, Meroueh C, Snower D P, David C S, Ho Y S, et al. Control of Her-2 tumor immunity and thyroid autoimmunity by MHC and regulatory T cells. Cancer research. 2007; 67(14): 7020-7.

Jacob J B, Quaglino E, Radkevich-Brown O, Jones R F, Piechocki M P, Reyes J D, et al. Combining human and rat sequences in her-2 DNA vaccines blunts immune tolerance and drives antitumor immunity. Cancer Research. 2010; 70(1): 119-28.

Kobayashi, H., M. Wood, Y. Song, E. Appella, E. Celis. 2000. Defining promiscuous MHC class II helper T-cell epitopes for the HER2/neu tumor antigen. Cancer Res. 60: 5228.

Konthur Z. and Walter G. Automation of phage display for high throughput antibody development. Drug Discovery Today: Targets 2002 1: 30-36.

McKenzie S J, Marks P J, Lam T, Morgan J, Panicali D L, Trimpe K L, et al. Generation and characterization of monoclonal antibodies specific for the human neu oncogene product, p 185. Oncogene. 1989; 4(5): 543-8.

Minke J M, Schuuring E, van den Berghe R, Stolwijk J A, Boonstra J, Cornelisse C, et al. Isolation of two distinct epithelial cell lines from a single feline mammary carcinoma with different tumorigenic potential in nude mice and expressing different levels of epidermal growth factor receptors. Cancer Research. 1991; 51(15): 4028-37.

Modiano J F, Kokai Y, Weiner D B, Pykett M J, Nowell P C, Lyttle C R. Progesterone augments proliferation induced by epidermal growth factor in a feline mammary adenocarcinoma cell line. Journal of cellular biochemistry. 1991; 45(2): 196-206.

Mullikin J C, Hansen N F, Shen L, Ebling H, Donahue W F, Tao W, et al. Light whole genome sequence for SNP discovery across domestic cat breeds. BMC genomics. 2010; 11: 406.

Munson L, Moresco A. Comparative pathology of mammary gland cancers in domestic and wild animals. Breast disease. 2007; 28: 7-21.

Olayioye, M. A. Update on HER-2 as a target for cancer therapy: Intracellular signaling pathways of ErbB2/HER-2 and family members. Breast Cancer Res 2001, 3: 385-389.

Pandey, H. Hybridoma technology for production of monoclonal antibodies. Int. J. Pharmaceutical Sci. Rev. and Res. 2010, 1: 88-94.

Peoples, G. E., P. S. Goedegebuure, R. Smith, D. C. Linehan, I. Yoshino, T. J. Eberlein. 1995. Breast and ovarian cancer-specific cytotoxic T lymphocytes recognize the same Her-2/neu-derived peptide. Proc. Nat. Acad. Sci. USA 92: 432.

Piechocki, M. P, Pilon, S. A., Wei W. Z. Complementary Antitumor Immunity Induced by Plasmid DNA Encoding Secreted and Cytoplasmic Human ErbB-2. J. Immunol. 2001, 167: 3367-3374

Radkevich-Brown O, Jacob J, Kershaw M, Wei W Z. Genetic regulation of the response to Her-2 DNA vaccination in human Her-2 transgenic mice. Cancer Research. 2009; 69(1): 212-8.

Roskoski R Jr. The ErbB/HER family of protein-tyrosine kinases and cancer. Pharmacolog Res 2014; 79: 34-74

Slamon, D. J., W. Godolphin, L. A. Jones, J. A. Holt, S. G. Wong, D. E. Keith, W. J. Levin, S. G. Stuart, J. Udove, A. Ullrich, M. F. Press. 1989. Studies of the HER-2/neu proto-oncogene in human breast and ovarian cancer. Science 244: 707.

Soares M, Correia J, Rodrigues P, Simoes M, de Matos A, Ferreira F. Feline HER2 protein expression levels and gene status in feline mammary carcinoma: optimization of immunohistochemistry (IHC) and in situ hybridization (ISH) techniques. Microscopy and microanalysis: the official journal of Microscopy Society of America, Microbeam Analysis Society, Microscopical Society of Canada. 2013; 19(4): 876-82.

Stancovski I, Hurwitz E, Leitner O, Ullrich A, Yarden Y, Sela M. Mechanistic aspects of the opposing effects of monoclonal antibodies to the ERBB2 receptor on tumor growth. Proceedings of the National Academy of Sciences of the United States of America. 1991; 88(19): 8691-5.

Tzahar, E., Y. Yarden. 1998. The ErbB-2/HER2 oncogenic receptor of adenocarcinomas: from orphanhood to multiple stromal ligands. Biochem. Biophys. Acta. 1377: M25. Medline Vassaux G, Nitcheu J, Jezzard S, Lemoine N R. Bacterial gene therapy strategies. J. Pathol. 2006; 208: 290-298.

Wei W-Z, Morris G P, Kong, Y-C. Anti-tumor immunity and autoimmunity: a balancing act of regulatory T cells. Cancer Immunol Immunother 2004; 53: 73-78.

Witton, C. J., Structure of HER receptors and intracellular localisation of downstream effector elements gives insight into mechanism of tumour growth promotion. Breast Cancer Res 2003, 5: 206-207.

Yu, D., M. C. Hung. 2000. Overexpression of ErbB2 in cancer and ErbB2-targeting strategies. Oncogene 19: 6115.

What is claimed is:

1. A gene expression construct comprising a nucleic acid sequence encoding an antigenic polypeptide of the HER2 of an animal species, said antigenic polypeptide comprising at least the extracellular domain of HER2, including an amino acid substitution of glutamine for lysine (Q-K) or for a conservative amino acid of K, said gene construct additionally including at least one promoter operatively linked to said nucleic acid sequence encoding a HER2 polypeptide, for expression of said antigenic peptide in a living cell, wherein said nucleic acid sequence additionally encodes the signal peptide of HER2 (precursor HER2), and said amino acid substitution of glutamine for lysine (Q-K) or for a conservative amino acid of K, is encoded at amino acid 141 of precursor feline HER2, wherein said nucleic acid sequence encoding an antigenic polypeptide is selected from the group consisting of nucleic acid sequences encoding precursor feline HER2, and wherein said amino acid substitution is encoded at amino acid 141 (prefeHER2-Q141K); precursor bear HER2, wherein said substitution is encoded at amino acid 141 (prebearHER2-Q141K); precursor human HER2, wherein said substitution is encoded at amino acid 141 (prehumHER2-Q141K); precursor mouse HER2, wherein said substitution is encoded at amino acid 142 (premouseHER2-Q142K); precursor rat HER2, wherein said substitution is encoded at amino acid 145 (preratHER2-Q145K); and precursor human rat chimeric HER2, wherein said substitution is encoded at amino acid 141 (mE2Neu-Q141K), wherein said nucleotide sequence encoding prefe-HER2-Q141K includes SEQ ID NO: 19; said nucleotide sequence encoding prebearHER2-Q141K includes SEQ ID NO: 20; said nucleotide sequence encoding prehumHER2-Q141K includes SEQ ID NO: 21; said nucleotide sequence encoding premouseHER2-Q142K includes SEQ ID NO: 22; said nucleotide sequence encoding preratHER2-Q145K includes SEQ ID NO: 23; and said nucleotide sequence encoding mE2Neu-Q141K includes SEQ ID NO: 24.

2. The gene construct according to claim 1, wherein said promoter is the cytomegalovirus (CMV) promoter.

3. A vaccine composition for inducing immunity to HER2 in a mammalian subject, comprising an effective amount of a gene expression construct according to claim 1, and an effective amount of an adjuvant.

4. The vaccine composition according to claim 3, wherein said adjuvant is granulocyte macrophage colony stimulating factor (GM-CSF).

5. The vaccine composition according to claim 4, wherein said GM-CSF adjuvant is an expression vector comprising GM-CSF polynucleotide and capable of expressing GM-CSF in a mammalian subject.

6. The vaccine composition according to claim 4, wherein said GM-CSF adjuvant is GM-CSF protein.

* * * * *